(12) United States Patent
Saxinger

(10) Patent No.: US 7,304,127 B2
(45) Date of Patent: Dec. 4, 2007

(54) POLYPEPTIDES THAT BIND HIV GP120 AND RELATED NUCLEIC ACIDS, ANTIBODIES, COMPOSITIONS, AND METHODS OF USE

(75) Inventor: Carl Saxinger, Bethesda, MD (US)

(73) Assignee: United States of America as represented by the Secretary, Department of Health and Human Services, Washington, DC (US)

( * ) Notice: Subject to any disclaimer, the term of this patent is extended or adjusted under 35 U.S.C. 154(b) by 60 days.

(21) Appl. No.: 10/084,813

(22) Filed: Feb. 27, 2002

(65) Prior Publication Data

US 2003/0068615 A1    Apr. 10, 2003

Related U.S. Application Data

(63) Continuation of application No. PCT/US00/23505, filed on Aug. 25, 2000.

(60) Provisional application No. 60/151,270, filed on Aug. 27, 1999.

(51) Int. Cl.
*A61K 38/00* (2006.01)
(52) U.S. Cl. .................................................. 530/326
(58) Field of Classification Search ................ 530/350, 530/326
See application file for complete search history.

(56) References Cited

U.S. PATENT DOCUMENTS 6,448,375 B1 * 9/2002 Samson et al. ............. 530/350

FOREIGN PATENT DOCUMENTS

| WO | WO91/02714 | 3/1991 |
|---|---|---|
| WO | WO97/35881 | 10/1997 |
| WO | WO97/44055 | 11/1997 |
| WO | WO97/45543 | 12/1997 |
| WO | WO97/47318 | 12/1997 |
| WO | WO98/00538 | 1/1998 |
| WO | WO98/01757 | 1/1998 |
| WO | WO98/15569 | 4/1998 |
| WO | WO99/43711 | 9/1999 |

OTHER PUBLICATIONS

Chan et al., *Journal of Virology* 73(3): 2350-2358 (Mar. 1999).
Farzan et al., *Journal of Virology* 72(2): 1160-1164 (Feb. 1988).
Shapira-Nahor et al., *Cellular Immunology* 128:101-117 (1990).

* cited by examiner

*Primary Examiner*—Jeffrey S. Parkin
(74) *Attorney, Agent, or Firm*—Leydig, Voit & Mayer, Ltd.

(57) ABSTRACT

The present invention provides, among other things, a polypeptide that binds with the gp120 envelope protein of HIV, in particular HIV-1, under physiological conditions, a nucleic acid that encodes such a polypeptide and can be expressed in a cell, a composition comprising such a polypeptide or nucleic acid or an antibody and a carrier therefor, a composition comprising a solid support matrix to which is attached an above-described polypeptide or an anti-antibody to a specified polypeptide sequence, a method of making an antibody to gp120, and a method of removing HIV from a bodily fluid.

18 Claims, 24 Drawing Sheets

|  |  |  | Formula | MW |
|---|---|---|---|---|
| E-2560 | | H-Val-OH | $C_5H_{11}NO_2$ | 117.15 |
| E-3250 | | H-[$^{15}$N]Val-OH | $C_5H_{11}{}^{15}NO_2$ | 118.15 |
| F-2180 | | H-D-Val-OH | $C_5H_{11}NO_2$ | 117.15 |
| F-3025 | | H-DL-Val-OH | $C_5H_{11}NO_2$ | 117.15 |
| E-3510 | | H-Val-ally ester p-tosylate | $C_8H_{16}NO_2 \cdot C_7H_8O_3S$ | 330.43 |
| E-2565 | | H-Val-NH$_2 \cdot$ HBr | $C_5H_{12}N_7O \cdot$ HBr | 197.08 |
| E-2570 | | H-Val-NH$_2 \cdot$ HCl | $C_5H_{12}N_2O \cdot$ HCl | 152.63 |
| E-2585 | | H-Val-NHtBu | $C_9H_{20}N_2O$ | 172.27 |
| E-2600 | | H-Val-p-nitrobenzyl ester $\cdot$ HBr | $C_{12}H_{16}N_2O_4 \cdot$ HBr | 333.19 |
| E-2590 | | H-Val-OtBu $\cdot$ HCl | $C_9H_{19}NO_2 \cdot$ HCl | 209.72 |
| F-3170 | | H-D-Val-OtBu $\cdot$ HCl | $C_9H_{19}NO_2 \cdot$ HCl | 209.72 |
| E-2575 | | H-Val-OBzL $\cdot$ HCl | $C_{12}H_{12}NO_2 \cdot$ HCl | 243.74 |
| E-2580 | | H-Val-OBzL $\cdot$ p-tosylate | $C_{12}H_{17}NO_2 \cdot C_7H_8O_3S$ | 379.48 |
| F-3500 | | H-D-Val-OBzL $\cdot$ p-tosylate | $C_{12}H_{17}NO_2 \cdot C_7H_8O_3S$ | 379.48 |
| E-1825 | | H-Val-OEt $\cdot$ HCl | $C_7H_{15}NO_2 \cdot$ HCl | 181.65 |
| E-2595 | | H-Val-OMe $\cdot$ HCl | $C_6H_{13}NO_2 \cdot$ HCl | 167.64 |
| F-3160 | | H-D-Val-OMe $\cdot$ HCl | $C_6H_{13}NO_2 \cdot$ HCl | 167.64 |
| C-3700 | | Z-N-Me-Val-OH | $C_{14}H_{19}NO_4$ | 265.31 |
| C-2805 | | Z-Val-OH | $C_{13}H_{17}NO_4$ | 251.28 |
| C-2810 | | Z-D-Val-OH | $C_{13}H_{17}NO_4$ | 251.28 |
| C-2815 | | Z-Val-NHtBu | $C_{12}H_{26}N_2O_3$ | 306.41 |
| C-2830 | | Z-Val-ONp | $C_{19}H_{20}N_2O_4$ | 372.38 |
| C-2820 | | Z-Val-OSu | $C_{17}H_{20}N_2O_4$ | 348.36 |
| C-2825 | | Z-D-Val-OSu | $C_{17}H_{20}N_2O_4$ | 348.36 |

Fig. 1A

Special Amino Acids and Amino Acid Derivatives

| | |
|---|---|
| F-1190 | H-Abu-OH |
| F-2440 | H-Abu-NH$_2$ · HCl |
| F-3035 | H-Abu-OtBu · HCl |
| F-3755 | H-γ-Abu-OtBu · HCl |
| E-2660 | Ac-p-aminohippuric acid |
| F-1015 | Ac-p-amino-Phe-OMe |
| F-2275 | Ac-p-bromo-DL-Phe-OH |
| F-3265 | Ac-p-Bz-D-Phe-OH [Ac-D-Bpa-OH] |
| M-1935 | Ac-Cys(farnesyl)-OH |
| F-2930 | Ac-Cys(farnesyl)-OMe |
| F-1020 | Ac-Dob(Boc)-OH |
| F-3175 | Ac-4,5 dehydro-Leu-OH |
| F-1030 | Ac-3,5-dinitro-Tyr-OEt |
| F-1010 | DL-2-Acetylamino-6-N-Boc-amino-4-hexynoic acid · DCHA |
| F-2295 | Ac-p-fluoro-DL-Phe-OH |
| F-3015 | Ac-p-iodo-D-Phe-OH |
| F-2940 | Ac-Met(O)-OH |
| F-2305 | Ac-5-Me-DL-Trp-OH |
| F-2420 | Ac-D-2-Nal-OH |
| F-1080 | Ac-DL-propargyl-Gly-OEt |
| E-3060 | H-Aib-OtBu |
| F-1160 | H-allo-Ile-OH |
| F-1165 | H-D-allo-Ile-OH |
| F-1170 | H-DL-allo-Ile-OH |

Fig. 1B

| | |
|---|---|
| F-1175 | H-allo-Thr-OH |
| F-1180 | H-D-allo-Thr-OH |
| F-2635 | H-DL-allo-Thr-OH |
| F-2545 | H-allo-Thr-OMe · HCl |
| F-2540 | H-allo-Thr(tBu)-OH |
| F-2560 | L-α-Aminoadipic acid [L-2-Aminohexanedioic acid] |
| F-2575 | D-α-Aminoadipic acid [D-2-Aminohexanedioic acid] |
| F-1185 | DL-α-Aminoadipic acid [DL-2-Aminohexanedioic acid] |
| F-3150 | L-2-Aminoadipic acid-δ-2-butyl ester [L-2-Aminohexanedioic acid-δ-2-butyl ester |
| F-3130 | L-α-Aminoadipic acid-δ-methyl ester · HCl [L-2-Aminohexanedioic acid-δ-methyl ester · HCl |
| F-3800 | 1-Aminocyclopropane-1-carbohydroxamic acid · HCl |
| F-3805 | 1-Aminocyclopropane-1-carboxylic acid |
| F-1200 | H-4-Amino-3,5-diodo-Phe-OH |
| F-1205 | 7-Aminoheptanoic acid |
| F-3480 | 4-Amino-1-methylimidazole-2-carboxylic acid-ethyl ester · HCl |
| F-3485 | 4-Amino-1-methylpyrrole-2-carboxylic acid methyl ester · HCl |
| F-1225 | H-p-Amino-Phe-OH · HCl |
| F-2855 | H-p-Amino-D-Phe-OH · HCl |
| F-1230 | H-p-Amino-DL-Phe-OH |
| F-1235 | DL-α-Aminopimelic acid [DL-2-Aminoheptanedioic acid] |
| H-3605 | 4-Aminopiperidine-4-carboxylic acid [H-Pip-OH] |
| F-2740 | L-2-Aminosuberic acid [L-2-Aminooctanedioic acid/H-Asu-OH] |

Fig. 1C

| | |
|---|---|
| F-3315 | D-α-Aminosuberic acid<br>[D-2-Aminooctanedioic acid/H-D-Asu-OH] |
| F-3305 | DL-α-Aminosuberic acid<br>[DL-2-Aminooctanedioic acid/H-DL-Asu-OH] |
| F3675 | H-3-Amino-Tyr-OH • 2 HCl<br>[5-Aminopentanoic acid-benzyl ester • p-tosylate] |
| E-1700 | n-Aminovaleric acid-benzyl ester • p-tosylate<br>[5-Aminopentanoic acid-benzyl ester • p-tosylate] |
| F-1281 | L-Azetidine-2-carboxylic acid |
| F-2285 | Azetidine-3-carboxylic acid |
| F3075 | H-p-Azido-Phe-OH |
| F-2490 | H-ß-(3-Benzothienyl)-Ala-OH |
| F-2485 | H-ß-(3-Benzathienyl)-D-Ala-OH |
| F-1215 | Bestatin<br>[(2S,3R)-3Amino-2-hydroxy-4-phenylbutanoyl-L-leucine] |
| F-2630 | S-[2,3-Bis(palmitoyloxy)-(2RS)-propyl]-N-palmitoyl-(R)-Cys-OH |
| A-1135 | Boc-Abu-OH |
| A-1175 | Boc-D-Abu-OH |
| A-1140 | Boc-γ-Abu-OH |
| A-1145 | Boc-Abu-ONp |
| A-3240 | Boc-Abz-OH |
| A-2800 | Boc-4-Abz-OH |
| A-4300 | Boc-4-Abz-Osu |
| A2015 | Boc-Aib-OH |
| A3825 | Boc-Aib-Osu |
| A-3345 | Boc-allo-Ile-OH |
| A-3735 | Boc-D-allo-Ile-OH |
| A-1150 | Boc-ε-aminocaproic acid |
| A-1155 | Boc-ε-aminocaproic acid-Osu |

Fig. 1D

| | |
|---|---|
| A-1160 | Boc-4-amino-3,5-diiodo-Phe-OH |
| A-1175 | Boc-7-aminoheptanoic acid |
| A-1185 | Boc-p-amino-Phe-OH |
| A-2980 | Boc-p-amino-D-Phe-OH |
| A-3975 | Boc-p-amino-Phe(Fmoc)-OH |
| A-4065 | Boc-p-amino-D-Phe(Fmoc)-OH |
| A-1455 | Boc-p-amino-Phe(Z)-OH |
| A-4370 | 1-Boc-4-aminopiperidine-4-carboxylic acid [H-Pip(Boc)-OH] |
| A-3310 | Boc-11-aminoundecanoic acid |
| A-3405 | Boc-ö-aminovaleric acid [Boc-5-aminopentanoic acid] |
| A-3S70 | Boc-p-azido-Phe-OH |
| A-4200 | Boc-p-azido-D-Phe-OH |
| A-3540 | Boc-ß-(3-benzothienyl)-Ala-OH |
| A-3695 | Boc-p-bromo-Phe-OH |
| A-4205 | Boc-p-bromo-D-Phe-OH |
| A-4490 | Boc-p-tBu-Phe-OH |
| A-4485 | Boc-p-tBu-D-Phe-OH |
| A-3295 | Boc-p-Bz-Phe-OH [Boc-Bpa-OH] |
| A-3S60 | Boc-p-Bz-D-Phe-OH [Boc-D-Bpa-OH] |
| A-4325 | Boc-p-carboxy-Phe(OtBu)-OH • DCHA |
| A-3860 | Boc-ß-chloro-Ala-OH |
| A-1525 | Boc-p-chloro-Phe-OH |
| A-2655 | Boc-p-chloro-D-Phe-OH |
| A-1535 | Boc-ß-cyano-Ala-OH |

Fig. 1E

| | |
|---|---|
| A-1540 | Boc-ß-cyano-D-Ala-OH |
| A-4375 | Boc-p-cyano-Phe-OH |
| A-3760 | Boc-ß-cyclohexyl-Ala-OH |
| A-3840 | Boc-ß-cyclohexyl-D-Ala-OH |
| A-2960 | Boc-ß-cyclohexyl-Ala-OH • DCHA |
| A-2920 | Boc-ß-cyclohexyl-D-Ala-OH • DCHA |
| A-4465 | Boc-cyclohexyl-Gly-OH |
| A-4470 | Boc-cyclohexyl-D-Gly-OH |
| A-3340 | N-Boc-cyclohexylstatine [N-Boc-(3S,4S)-4-amino-5-cyclohexyl-3-hydroxypentanoic acid] |
| A-4150 | Boc-ß-cyclopropyl-Ala-OH |
| A-3215 | Boc-Dab-OH |
| A-4215 | Boc-D-Dab-OH |
| A-4415 | Boc-Dab-OtBu • HCl |
| A-4125 | Boc-Dab-(Aloc)-OH |
| A-3480 | Boc-Dab-(Boc)-OH • DCHA |
| A-3820 | Boc-Dab-(Fmoc)-OH |
| A-4230 | Boc-D-Dab(Fmoc)-OH |
| A-2905 | Boc-Dab(Z)-OH • DCHA |
| A-4260 | Boc-D-Dab(Z)-OH • DCHA |
| A-3220 | Boc-Dap-OH |
| A-3890 | Boc-D-Dap-OH |
| A-4115 | Boc-Dap(Aloc)-OH |
| A-3475 | Boc-Dap(Boc)-OH • DCHA |
| A-4130 | Boc-Dap(bromoacetyl)-OH |
| A-4290 | Boc-Dap(Dnp)-OH |
| A-4295 | Boc-Dap(Dnp)-OSu |

Fig. 1F

| | |
|---|---|
| A-3880 | Boc-Dap(Fmoc)-OH |
| A-4235 | Boc-D-Dap(Fmoc)-OH |
| A-3000 | Boc-Dap(Z)-OH · DCHA |
| A-4265 | Boc-D-Dap(Z)-OH · DCHA |
| A-3485 | Boc-4,5-dehydro-Leu-OH · DCHA |
| A-1550 | Boc-3,4-dehydro-Pro-OH |
| A-1555 | Boc-3,5-dibromo-Tyr-OH |
| A-4220 | Boc-3,5-dibromo-D-Tyr-OH |
| A-4045 | Boc-3,4-dichloro-D-Phe-OH |
| A-1580 | Boc-3,5-diiodo-Tyr-OH |
| A-4225 | Boc-3,5-diiodo-D-Tyr-OH |
| A-1590 | Boc-3,5-diiodo-Tyr-OMe |
| A-1585 | Boc-3,5-diiodo-Tyr-OSu |
| A-1410 | Boc-3,5-diiodo-Tyr(3'-bromo-Bzl)-OH |
| A-2570 | Boc-3,5-diiodo-Tyr(2',6'-dichloro-Bzl)-OH |
| A-3065 | Boc-p-fluoro-Phe-OH |
| A-2835 | Boc-p-fluoro-D-Phe-OH |
| A-1605 | Boc-p-fluoro-DL-Phe-OH |
| A-4320 | Boc-α-(Fmoc-amino)-Gly-OH [Fmoc-α-(Boc-amino) Gly-OH] |
| A-4040 | Boc-Homoarg-OH · HCl |
| A-3775 | Boc-Homoarg(Et)$_2$-OH |
| A-3780 | Boc-D-Homoarg(Et)$_2$-OH |
| A-3935 | Boc-Homoarg(NO$_2$)-OH |
| A-3465 | Boc-Homocit-OH |
| A-2870 | Boc-D-Homocit-OH |
| A-3420 | Boc-Homocys(Mbzl)-OH |

Fig. 1G

| | |
|---|---|
| A-4255 | Boc-D-Homocys(Mbzl)-OH |
| A-3610 | Boc-Homocys(Trt)-OH |
| A-1190 | Boc-Homophe-OH |
| A-1195 | Boc-D-Homophe-OH |
| A-2830 | Boc-Homopro-OH |
| A-3125 | Boc-D-Homopro-OH |
| A-4165 | Boc-7-hydroxy-Tic-OH |
| A-4170 | Boc-7-hydroxy-D-Tic-OH |
| A-1800 | Boc-p-iodo-Phe-OH |
| A-3640 | Boc-p-iodo-D-Phe-OH |
| A-1805 | Boc-p-iodo-DL-Phe-OH |
| A-3815 | Boc-isonipecotic acid [Boc-piperidine-4-carboxylic acid] |
| A-3715 | Boc-N-Me-Abz-OH |
| A-2025 | Boc-N-Me-allo-Ile-OH |
| A-3730 | Boc-N-Me-D-allo-Ile-OH |
| A-2880 | Boc-N-Me-p-chloro-D-Phe-OH |
| A-2070 | Boc-N-Me-p-nitro-Phe-OH · DCHA |
| A-4495 | Boc-p-Me-Phe-OH |
| A-4500 | Boc-p-Me-D-Phe-OH |
| A-1965 | Boc-Met(O)-OH |
| A-2885 | Boc-Met($O_2$)-OH |
| A-4145 | Boc-α-Me-DL-Val-OH |
| A-3225 | Boc-1-Nal-OH |
| A-4305 | Boc-D-1-Nal-OH |
| A-2850 | Boc-2-Nal-OH |
| A-2575 | Boc-D-2-Nal-OH |

Fig. 1H

| | |
|---|---|
| A-3110 | Boc-Neopentylgly-OH |
| A-4210 | Boc-D-Neopentylgly-OH |
| A-2125 | Boc-p-nitro-Phe-OH |
| A-2130 | Boc-p-nitro-D-Phe-OH |
| A-3645 | Boc-Oic-OH<br>[Boc-L-octohydroindole-2-carboxylic acid] |
| A-2965 | Boc-Pen(Acm)-OH |
| A-2970 | Boc-D-Pen(Acm)-OH |
| A-3660 | Boc-Pen(Mbzl)-OH · DCHA |
| A-3665 | Boc-D-Pen(Mbzl)-OH · DCHA |
| A-2900 | Boc-Pen(Mob)-OH |
| A-3990 | Boc-D-Pen(Mob)-OH |
| A-3650 | Boc-Pen(NPys)-OH |
| A-3655 | Boc-D-Pen(NPys)-OH |
| A-3850 | Boc-Pen(Trt)-OH |
| A-3855 | Boc-D-Pen(Trt)-OH |
| A-3915 | Boc-pentafluoro-Phe-OH |
| A-3960 | Boc-pentafluoro-D-Phe-OH |
| A-4385 | Boc-p-phenyl-Phe-OH<br>[Boc-β-(4-biphenyl)-Ala-OH; Boc-Bip-OH] |
| A-4390 | Boc-p-phenyl-D-Phe-OH<br>[Boc-β-(4-biphenyl)-D-Ala-OH; Boc-D-Bip-OH] |
| A-4100 | N-Boc-phenylstatine<br>[N-Boc-(3S,4S)-4-amino-3-hydroxy-5-phenylpentanoic acid] |
| B-3115 | 1-Boc-piperidine-4-Fmoc-amino-4-carboxylic acid<br>[Fmoc-Pip(Boc)-OH] |
| A-3745 | Boc-β-(3-pyridyl)-Ala-OH |
| A-2855 | Boc-β-(3-pyridyl)-D-Ala-OH |
| A-4395 | Boc-β-(2-quinolyl)-Ala-OH |
| A-4400 | Boc-β-(2-quinolyl)-D-Ala-OH |

Fig. 1I

| | |
|---|---|
| A-1180 | N-Boc-statine<br>[N-Boc-(3S,4S)-4-amino-3-hydroxy-6-methylheptanoic acid] |
| A-3945 | Boc-L-thiazolidine-4-carboxylic acid<br>[Boc-L-thioproline] |
| A-3940 | Boc-D-thiazolidine-4-carboxylic acid<br>[Boc-D-thioproline] |
| A-2290 | Boc-β-(2-thienyl)-Ala-OH |
| A-2295 | Boc-β-(2-thienyl)-D-Ala-OH |
| A-2300 | Boc-β-(2-thienyl)-DL-Ala-OH |
| A-3700 | Boc-L-thiocitrulline-OtBu |
| A-4360 | Boc-Thionoala-1-(6-nitro)benzotriazolide |
| A-4345 | Boc-Thionoleu-1-(6-nitro)benzotriazolide |
| A-4355 | Boc-Thionophe-1-(6-nitro)benzotriazolide |
| A-4365 | Boc-Thionoser(Bzl)-1-(6-nitro)benzotriazolide |
| A-4350 | Boc-Thionoval-1-(6-nitro)benzotriazolide |
| A-3070 | Boc-Tic-OH |
| A-3075 | Boc-D-Tic-OH |
| A-4090 | Boc-D-Tpi-OH<br>[Boc-D-1,2,3,4-tetrahydronoharman-3-carboxylic acid] |
| F-1305 | H-p-Bromo-Phe-OH |
| F-3700 | H-p-Bromo-D-Phe-OH |
| F-1310 | H-p-Bromo-DL-Phe-OH |
| F-3790 | H-p-tBu-Phe-OH |
| F-3795 | H-p-tBu-D-Phe-OH |
| F-3250 | n-Butyloxycarbonyl-Dap-OH |
| F-2800 | H-p-Bz-Phe-OH<br>[H-Bpa-OH] |
| F-2810 | H-p-Bz-D-Phe-OH<br>[H-D-Bpa-OH] |

Fig. 1J

| | |
|---|---|
| F-2345 | Carbamoyl-DL-Ala-OH |
| F-1375 | Carbamoyl-β-Ala-OH |
| M-2240 | Carbamoyl-Asp-OH · magnesium salt |
| F-2430 | Carbamoyl-Leu-OH |
| Q-1140 | β-Carboline-3-carboxylic acid-ethyl ester |
| Q-1145 | β-Carboline-3-carboxylic acid-propyl ester |
| F-3590 | H-p-Carboxy-Phe-OH |
| F-3585 | H-p-Carboxy-Phe(OtBu)-OH |
| F-2700 | L-Carnitine [(R)-β-Hydroxy-γ-(trimethylammonio)butyrate] |
| F-1425 | H-β-Chloro-Ala-OH |
| F-1430 | H-β-Chloro-Ala-OH · HCl |
| F-1435 | H-β-Chloro-D-Ala-OH · HCl |
| F-1440 | H-β-Chloro-DL-Ala-OH |
| F-2325 | H-β-Chloro-DL-Ala-OH · HCl |
| F-3380 | H-β-Chloro-Ala-NHOH |
| F-3465 | H-β-Chloro-Ala-OMe · HCl |
| F-1445 | H-p-Chloro-Phe-OH |
| F-2520 | H-p-Chloro-D-Phe-OH |
| F-1450 | H-p-Chloro-DL-Phe-OH |
| F-2690 | H-p-Cloro-D-Phe-OMe · HCl |
| F-1455 | H-p-Chloro-DL-Phe-OMe · HCl |
| F-1460 | H-β-Cyano-Ala-OH |
| F-3610 | H-p-Cyano-Phe-OH |
| F-2500 | H-β-Cyclohexyl-Ala-OH · HCl |
| F-2505 | H-β-Cyclohexyl-D-Ala-OH · HCl |
| F-3760 | H-Cyclohexyl-Gly-OH · salt |
| F-3765 | H-Cyclohexyl-D-Gly-OH · salt |

Fig. 1K

| | |
|---|---|
| F-2830 | Cyclohexylstatine<br>[(3S,4S)-4-Amino-5-cyclohexyl-3-hydroxypentanoic acid] |
| F-1470 | H-β-(1-Cyclopentenyl)-DL-Ala-OH |
| F-1465 | H-β-(1-Cyclopentenyl)-DL-Ala-OH |
| F-3470 | H-β-Cyclopropyl-Ala-OH |
| F-1475 | L-Cycloserine |
| F-1480 | D-Cycloserine |
| F-1485 | DL-Cycloserine |
| F-3050 | H-Dob-OH · 2 HCl |
| F-3055 | H-D-Dob-OH · 2 HCl |
| A-3305 | H-Dob(Boc)-OH |
| E-3360 | H-Dob(Boc)-OMe · HCl |
| F-3040 | H-Dop-OH · HCl |
| F-3045 | H-D-Dop-OH · HCl |
| F-3420 | H-Dop(Boc)-OMe · HCl |
| F-2985 | H-4,5-Dehydro-Leu-OH |
| F-2970 | H-trans-4,5-Dehydro-Lys-OH<br>[DL-trans-2,6-Diamino-4-hexenoic acid] |
| F-1490 | H-3,4 Dehydro-Pro-OH |
| F-2705 | H-3,4-Dehydro-DL-Pro-OH |
| F-1495 | H-3,4-Dehydro-Pro-NH$_2$ · HCl |
| F-1500 | H-3,4-Dehydro-Pro-OMe · HCl |
| F-1505 | 2,6-Diaminopimelic (LL,DD and Meso)<br>[2,6-Diaminoheptanedioic acid] |
| F-1510 | H-6-Diazo-5-oxo-Nle-OH<br>[L-DON] |
| F-2185 | H-6-Diazo-5-oxo-D-Nle-OH<br>[D-DON] |

Fig. 1L

| | |
|---|---|
| F-1520 | H-3,5-Dibromo-Tyr-OH |
| F-3395 | H-3,4-Dichloro-Phe-OH |
| F-3400 | H-3,4-Dichloro-D-Phe-OH |
| F-3695 | H-β,β,Dicyclohexyl-DL-Ala-OH |
| F-2395 | H-α-Difluoro-Me-DL-Orn-OH [DFMO] |
| F-1525 | H-β-(3,4-Dihydroxyphenyl)-DL-Ser-OH [DL-Threo-DOPS] |
| F-3460 | H-2,5-Diiodo-His-OH · HCL |
| F-2225 | H-3,5-Diiodo-Tyr-OH |
| F-3005 | H-3,5-Diiodo-D-Tyr-OH |
| E-2385 | H-3,5-Diiodo-Tyr-OMe · HCL |
| M-1925 | FA-Cys(farnesyl)-OH |
| M-1920 | FA-Cys(farnesyl)-OMe |
| F-2530 | H-β-Fluoro-DL-Ala-OH |
| F-3285 | H-m-Fluoro-Phe-OH |
| F-3290 | H-m-Fluoro-D-Phe-OH |
| F-2135 | H-m-Fluoro-DL-Phe-OH |
| F-1530 | H-p-Fluoro-Phe-OH |
| F-2320 | H-p-Fluoro-D-Phe-OH |
| F-1535 | H-p-Fluoro-DL-Phe-OH |
| F-3820 | H-p-Fluoro-Phe-OEt · HCL |
| F-3295 | H-m-Fluoro-D-Phe-OMe · HCL |
| F-1540 | H-p-Fluoro-DL-Phe-OMe · HCL |
| B-1780 | Fmoc-Abu-OH |
| B-2920 | Fmoc-D-Abu-OH |
| B-1910 | Fmoc-γ-Abu-OH |

Fig. 1M

| | |
|---|---|
| B-3260 | Fmoc-Abz-OH |
| B-2985 | Fmoc-4-Abz-OH |
| B-1860 | Fmoc-Aib-OH |
| B-2880 | Fmoc-allo-Ile-OH |
| B-2230 | Fmoc-D-allo-Ile-OH |
| B-3100 | Fmoc-allo-Thr-OH |
| B-3090 | Fmoc-D-allo-Thr-OH |
| B-1815 | Fmoc-allo-Thr(tBu)-OH |
| B-1810 | Fmoc-allo-Thr(tBu)-Odhbt |
| B-3280 | Fmoc-α-allyl-DL-Gly-OH [Fmoc-DL-2-amino-4-pentanoic acid] |
| B-2440 | Fmoc-L-α-aminoadipic acid-δ-t-butyl ester [Fmoc-L-2-aminohexanedioic acid-δ-t-butyl ester] |
| B-1560 | Fmoc-ε-aminocoproic acid |
| B-3310 | 2-(Fmoc-amino)-3-(2,2-dimethyl-4H-benzol[1,3]dioxin-6-yl)-propionic acid |
| B-2070 | Fmoc-p-amino-Phe-OH |
| B-1995 | Fmoc-p-amino-Phe-(Boc)-OH |
| B-2930 | Fmoc-p-amino-D-Phe-(Boc)-OH |
| B-2360 | Fmoc-p-azido-Phe-OH |
| B-2830 | Fmoc-β-(3-benzothienyl)-Ala-OH |
| B-3320 | Fmoc-p-tBu-Phe-OH |
| B-3325 | Fmoc-p-tBu-D-Phe-OH |
| B-2220 | Fmoc-p-Bz-Phe-OH [Fmoc-Bpa-OH] |
| B-2340 | Fmoc-p-Bz-D-Phe-OH [Fmoc-D-Bpa-OH] |
| B-3070 | Fmoc-p-carboxy-Phe(OtBu)-OH |
| B-2115 | Fmoc-p-chloro-Phe-OH |

Fig. 1N

| | |
|---|---|
| B-1900 | Fmoc-p-chloro-D-Phe-OH |
| B-3125 | Fmoc-p-cyano-Phe-OH |
| B-1975 | Fmoc-ß-cyclohexyl-Ala-OH |
| B-2345 | Fmoc-ß-cyclohexyl-D-Ala-OH |
| B-3270 | Fmoc-cyclohexyl-Gly-OH |
| B-3275 | Fmoc-cyclohexyl-D-Gly-OH |
| B-2905 | Fmoc-ß-cyclopropyl-Ala-OH |
| B-3120 | Fmoc-Cys(Boc-3-aminopropyl)-OH |
| B-2300 | Fmoc-Dab-OH |
| B-2365 | Fmoc-D-Dab-OH |
| B-2860 | Fmoc-Dab-(Adpoc)-OH |
| B-2850 | Fmoc-Dab-(aloc)-OH |
| B-1800 | Fmoc-Dab-(Boc)-OH |
| B-2960 | Fmoc-D-Dab(Boc)-OH |
| B-2270 | Fmoc-D-Dab(Fmoc)-OH |
| B-3250 | Fmoc-Dab(Z)-OH |
| B-2385 | Fmoc-Dap-OH |
| B-3055 | Fmoc-D-Dap-OH |
| B-2865 | Fmoc-Dap(Adpoc)-OH |
| B-2845 | Fmoc-Dap(Aloc)-OH |
| B-2380 | Fmoc-Dap(Boc)-OH |
| B-2965 | Fmoc-D-Dap(Boc)-OH |
| B-2995 | Fmoc-Dap(Dnp)-OH |
| B-2265 | Fmoc-Dap(Fmoc)-OH |
| B-2255 | Fmoc-4,5-dehydro-Leu-OH |
| B-1660 | Fmoc-3,4-dehydro-Pro-OH |

Fig. 10

| | |
|---|---|
| B-1275 | Fmoc-3,5-dibromo-Tyr-OH |
| B-1285 | Fmoc-3,5-Diiodo-Tyr-OH |
| B-3265 | Fmoc-3,5,dinitro-Tyr-OH |
| B-2595 | Fmoc-m-fluoro-Phe-OH |
| B-2835 | Fmoc-p-fluoro-Phe-OH |
| B-3210 | Fmoc-p-fluoro-D-Phe-OH |
| B-1550 | Fmoc-p-fluoro-DL-Phe-OH |
| B-3130 | Fmoc-Homoarg(Pmc)-OH |
| B-2250 | Fmoc-Homocit-OH |
| B-2390 | Fmoc-D-Homocit-OH |
| B-2405 | Fmoc-Homocys(Trt)-OH |
| B-1535 | Fmoc-Homophe-OH |
| B-2810 | Fmoc-D-Homophe-OH |
| B-2285 | Fmoc-Homopro-OH |
| B-2290 | Fmoc-D-Homopro-OH |
| B-2750 | Fmoc-p-iodo-Phe-OH |
| B-1740 | Fmoc-3-iodo-Tyr-OH |
| B-3190 | Fmoc-isonipecotic acid |
| B-2590 | Fmoc-DL-Isoser-OH |
| B-3335 | Fmoc-p-Me-Phe-OH |
| B-3330 | Fmoc-p-Me-D-Phe-OH |
| B-2130 | Fmoc-Met(O)-OH |
| B-1905 | Fmoc-Met($O_2$)-OH |
| B-1965 | Fmoc-1-Nal-OH |
| B-3020 | Fmoc-D-1-Nal-OH |
| B-2100 | Fmoc-2-Nal-OH |

Fig. 1P

| | |
|---|---|
| B-1950 | Fmoc-D-2-Nal-OH |
| B-2690 | Fmoc-m-nitro-p-hydroxy-Phe-OH<br>[Fmoc-m-nitro-Tyr-OH] |
| B-1395 | Fmoc-p-nitro-Phe-OH |
| B-2350 | Fmoc-p-nitro-D-Phe-OH |
| B-2690 | Fmoc-m-nitro-Tyr-OH<br>[Fmoc-m-nitro-p-hydroxy-Phe-OH] |
| B-2425 | Fmoc-Oic-OH<br>[Fmoc-L-actahydroindole-2-carboxylic acid] |
| B-1885 | Fmoc-Pen(Acm)-OH |
| B-1915 | Fmoc-D-Pen(Acm)-OH |
| B-1545 | Fmoc-D-Pen(Bzl)-OH |
| B-2315 | Fmoc-Pen-(Trt)-OH |
| B-2320 | Fmoc-D-Pen(Trt)-OH |
| B-3155 | Fmoc-p-phenyl-Phe-OH<br>[Fmoc-ß-(4-biphenyl)-Ala-OH; Fmoc-Bip-OH] |
| B-3160 | Fmoc-p-phenyl-D-Phe-OH<br>[Fmoc-ß-(4-biphenyl)-D-Ala-OH; Fmoc-D-Bip-OH] |
| B-3195 | 1-Fmoc-piperidine-4-Fmoc-amino-4-carboxylic acid<br>[Fmoc-Pip(Fmoc)-OH] |
| B-3175 | Fmoc-4-piperidylacetic acid<br>[Fmoc-4-carboxymethyl-piperidine] |
| B-2005 | Fmoc-ß-(3-pyridyl)-Ala-OH |
| B-2040 | Fmoc-ß-(3-pyridyl)-D-Ala-OH |
| B-3165 | Fmoc-ß-(2-quinolyl)-Ala-OH |
| B-3170 | Fmoc-ß-(2-quinolyl)-D-Ala-OH |
| B-1665 | Fmoc-ß-(2-thienyl)-Ala-OH |
| B-2120 | Fmoc-ß-(2-thienyl)-D-Ala-OH |
| B-1920 | Fmoc-Tic-OH |
| B-1925 | Fmoc-D-Tic-OH |

Fig. 1Q

| | |
|---|---|
| B-2470 | Fmoc-Tyr(PO$_3$H$_2$)-OH |
| B-1990 | Fmoc-Tyr(PO$_3$Me$_2$)-OH |
| B-2275 | Fmoc-D-Tyr(PO$_3$Me$_2$)-OH |
| E-2870 | Glutaryl-Leu-OH · 2DCHA |
| G-4490 | Hippuryl-Cys(2-aminoethyl)-OH [Bz-Gly-Cys(2-aminoethyl)-OH; BZ-Gly-4-thia-Lys-OH] |
| F-3815 | H-α-Homoethyl-Gly-OH |
| F-2780 | H-Homoarg-OH |
| F-2995 | H-Homocit-OH |
| F-2735 | H-D-Homocit-OH |
| F-1610 | H-Homophe-OH |
| F-1615 | H-D-Homophe-OH |
| F-1620 | H-DL-Homophe-OH |
| F-1625 | H-Homopro-OH |
| F-1630 | H-D-Homopro-OH |
| F-2915 | H-DL-Homopro-OH |
| F-2465 | H-Homopro-OMe · HCl |
| F-3125 | H-D-Homopro-OMe · HCl |
| F-3330 | H-(2S,4S)-γ-Hydroxy-Glu-OH |
| F-3335 | H-(2S,4R)-γ-Hydroxy-Glu-OH |
| Q-1420 | o-Hydroxyhippuric acid [Salicyluric acid] |
| E-2655 | p-Hydroxyhippuric acid |
| F-1650 | H-DL-δ-Hydroxy-DL-Lys-OH · HCl |
| F-2335 | H-DL-δ-Hydroxy-DL-Lys(Boc)-OH |
| F-3685 | H-α-Hydroxy-nor-L-arginine [L-2-Amino-(4-2'-hydroxyguanidino) butyric acid] |
| F-2935 | H-7-Hydroxy-Tic-OH |

Fig. 1R

| | |
|---|---|
| F-2990 | H-7-Hydroxy-D-Tic-OH |
| F-1665 | H-p-Iodo-Phe-OH |
| F-1670 | H-p-Iodo-D-Phe-OH |
| F-1675 | H-p-Iodo-DL-Phe-OH |
| F-3350 | H-m-Iodo-Tyr-OH |
| F-1695 | H-DL-Isoser-OH<br>[H-DL-β-Amino-α-hydroxypropionic acid] |
| F-1195 | Lysinoalanine-2 HCl (diastereomeric mixture: LL + LD)<br>H-Lys(DL-2-amino-2-carboxyethyl)-OH · 2HCl |
| F-1765 | N-Me-Aib-OH |
| F-1760 | N-Me-allo-Ile-Obzl · P-tosylate |
| F-1795 | H-α-Me-DL-His-OH · 2HCl |
| Q-1585 | Melphalan-methyl ester · 2HCl<br>[H-p-Dl(2-chloroethyl)amino-Phe-OMe · 2HCl] |
| F-1800 | H-α-Me-DL-Leu-OH |
| F-1780 | N-Me-p-nitro-Phe-OH |
| E-3150 | H-α-Me-Phe-OH |
| F-3115 | H-α-Me-D-Phe-OH |
| F-1805 | H-α-Me-DL-Phe-OH |
| F-2805 | H-α-Me-DL-Phe-OMe · HCl |
| F-3780 | H-p-Me-Phe-OH |
| F-3785 | H-p-Me-D-Phe-OH |
| F-3440 | H-α-Me-Pro-OH |
| F-3615 | H-2-Mercapto-His-OH |
| F-3620 | H-2-Mercapto-His-OMe |
| M-2345 | H-β-(7-Methoxycoumarin-4yl)-Ala-OH<br>[L-2-Amino-3-(7-methoxycoumarin-4-yl)-propionic acid] |
| F-3810 | 1-Methylaminocyclopropone-1-carboxylic acid |

Fig. 1S

| | |
|---|---|
| F-1815 | H-γ-Methylene-DL-Glu-OH |
| Q-1645 | (2-Methyl-1-indolyl)acetic · DCHA |
| F-3180 | S-Methyl-L-thiocitrulline · acetate |
| F-2945 | H-Met(O)-OH |
| F-2895 | H-Met($O_2$)-OH |
| F-1810 | H-α-Me-DL-Trp-OH |
| F-2240 | H-α-Me-DL-Trp-OMe |
| F-1820 | H-1-Me-DL-Trp-OH |
| F-3535 | H-α-Me-Val-OH |
| F-3540 | H-α-Me-D-Val-OH |
| F-3355 | H-α-Me-DL-Val-OH |
| F-2550 | Myristoyl-Gly-OH |
| F-1840 | H-1-Nal-OH |
| F-1845 | H-D-1-Nal-OH |
| F-1850 | H-DL-1-Nal-OH |
| F-1855 | H-2-Nal-OH |
| F-1860 | H-D-2-Nal-OH |
| F-1865 | H-DL-2-Nal-OH |
| F-3710 | H-2-Nal-Obzl · salt |
| F-1315 | H-Neopentylgly-OH |
| F-1320 | H-D-Neopentylgly-OH |
| F-1325 | H-DL-Neopentylgly-O |
| F-3340 | H-m-Nitro-p-hydroxy-Phe-OH [H-m-Nitro-Tyr-OH] |
| F-1895 | H-p-Nitro-Phe-OH |
| F-1900 | H-p-Nitro-D-Phe-OH |
| F-1905 | H-p-Nitro-DL-Phe-OH |

Fig. 1T

| | |
|---|---|
| F-1910 | H-p-Nitro-Phe-OMe · HCl |
| F-3340 | H-m-Nitro-Tyr-OH<br>[H-m-Nitro-p-hydroxy-Phe-OH] |
| F-3105 | H-Oic-OH<br>[L-Octahydroindole-2-carboxylic acid] |
| F-2515 | H-Pan-OH |
| F-3065 | H-Pan(Trt)-OH |
| F-3645 | H-β-Phenyl-Phe-OH<br>[H-β-(4-Biphenyl)-Ala-OH; H-Bip-OH |
| F-3650 | H-p-Phenyl-D-Phe-OH<br>[H-β-(4-Biphenyl)-D-Ala-OH; H-D-Bip-OH |
| F-2040 | H-Propargyl-Gly-OH |
| F-2900 | H-D-Propargyl-Gly-OH |
| F-2860 | H-DL-Propargyl-Gly-OH |
| F-2075 | H-Propargyl-Gly-OMe · HCl |
| F-2825 | H-β-(2-Pyridyl)-Ala-OH |
| F-2790 | H-β-(2-Pyridyl)-D-Ala-OH |
| F-2825 | H-β-(2-Pyridyl)-DL-Ala-OH |
| F-3195 | H-β-(3-Pyridyl)-Ala-OH |
| F-2640 | H-β-(3-Pyridyl)-D-Ala-OH |
| F-3705 | H-β-(3-Pyridyl)-DL-Ala-OH |
| F-3655 | H-β-(2-Quinolyl)-Ala-OH |
| F-3660 | H-β-(2-Quinolyl)-D-Ala-OH |
| F-2030 | H-Ser($PO_3H_2$)-OH |
| F-2035 | H-D-Ser($PO_3H_2$)-OH |
| F-3365 | H-Ser($SO_3H$)-OH |
| F-3370 | H-D-Ser($SO_3H$)-OH |

Fig. 1U

| | |
|---|---|
| F-1220 | Statine<br>[(3S,4S)-4-Amino-3-hydroxy-6-methylheptanoic acid] |
| F-3665 | L-4,5,6,7-Tetrahydra-1H-imidazo(4,5-c)pyridine-6-carboxylic acid |
| Q-1535 | L-Thiozoldin-2-one-4-carboxlic acid<br>[L-2-Oxothiozolidine-4-carboxlic acid] |
| F-2955 | H-β-(2-Thiozolyl)-DL-Ala-OH |
| F-2110 | H-β-(2-Thienyl)-Ala-OH |
| F-2115 | H-β-(2-Thienyl)-D-Ala-OH |
| N-1150 | H-β-(2-Thienyl)-DL-Ala-OH |
| F-2120 | H-β-(2-Thienyl)-DL-Ser-OH |
| N-1195 | DL-Thiorphan<br>[(DL-3-Mercapto-2-benzylproponoyl)-Gly-OH] |
| F-2460 | L-Thyronine<br>[H-p-(p-Hydroxypheonoxy)-Phe-OH] |
| F-2405 | DL-Thyronine<br>[H-p-(p-Hydroxyphenoxy)-DL-Phe-OH] |
| F-2580 | H-Tic-OH |
| F-2585 | H-D-Tic-OH |
| F-3310 | H-D-Tic-OtBu · HCl |
| Q-1700 | H-Tpi-OH<br>[L-1,2,3,4-Tetrahydronorharman-3-carboxlic acid] |
| F-3225 | H-β-(1,2,4-Triozol-1yl)-DL-Ala-OH |
| F-3670 | H-β-(Ureido)-Ala-OH<br>[H-β-((Aminocarbonyl)amino)-Ala-OH; L-Albizziine] |
| C-1260 | Z-Abu-OH |
| C-3160 | Z-γ-Abu-OH |
| C-1265 | Z-Abu-OSu |
| C-3350 | Z-3-Abz-OSu |
| C-3680 | Z-Aib-OH |

Fig. 1V

| | |
|---|---|
| C-3390 | Z-allo-Thr(tBu)-OH · DCHA |
| C-3385 | Z-L-α-aminoadipic acid<br>[Z-L-2-aminohexanedioic acid] |
| C-3790 | Z-L-2-aminoadipic acid-δ-t-butyl ester · DCHA<br>[Z-L-2-aminohexanedioic acid]-δ-t-butyl ester · DCHA] |
| C-1270 | Z-ε-aminocaproic acid |
| C-3975 | Z-p-carboxy-Phe(OtBu)-OH |
| C-3920 | Z-β-cyclohexyl-D-Ala-OH · DCHA |
| C-3705 | Z-Dob-OH |
| C-3770 | Z-D-Dob-OH |
| C-3510 | Z-Dob(Boc)-OH · DCHA |
| C-3765 | Z-D-Dob-(Boc)-OH · DCHA |
| C-3690 | Z-Dob(Z)-OH |
| C-3315 | Z-Dop-OH |
| C-3755 | Z-D-Dop-OH |
| C-3685 | Z-Dop(Boc)-OH · DCHA |
| C-3760 | Z-D-Dop(Boc)-OH |
| C-3695 | Z-Dop(Z)-OH |
| C-1535 | Z-dehydro-Ala-OH |
| C-1540 | Z-dehydro-Ala-OMe |
| C-3525 | Z-p-fluoro-Phe-OH |
| C-3965 | Z—D-Homocit-OH<br>[Z-α-amino-ε-uneidocaproic acid] |
| C-1275 | Z-Homophe-OH |
| C-1280 | Z-D-Homophe-OH |
| C-3010 | Z-1-Nal-OH |
| C3950 | Z-D-1-Nal-OH |
| C-3500 | Z-2-Nal-OH |

Fig. 1W

| | |
|---|---|
| C-2255 | Z-D-2-Nal-OH |
| C-2260 | Z-Neopentylgly-OH • DCHA |
| C-2265 | Z-D-Neopenlylgly-OH |
| C-4030 | Z-p-phenyl—Phe-OH<br>[Z-ß-(4-biphenyl)-Ala-OH; Z-Bip-OH] |
| C-4035 | Z-p-phenyl-D-Phe-OH<br>[Z-ß-(4-biphenyl)-D-Ala-OH;Z-D-Bip-OH] |
| C-3870 | Z-D-Tic-OH |

Fig. 1X

SEQUENCE LISTING

<160> NUMBER OF SEQ ID NOS: 1242

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: "Xaa" is a variable amino acid.
<220> FEATURE:
<221> NAME/KEY: misc_feature
<222> LOCATION: (7)..(8)
<223> OTHER INFORMATION: "Xaa" is a variable amino acid.

<400> SEQUENCE: 1

Tyr Asp Ile Xaa Tyr Tyr Xaa Xaa Glu
1 5

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: "Xaa" is a variable amino acid.
<220> FEATURE:
<221> NAME/KEY: misc_feature
<222> LOCATION: (7)..(8)
<223> OTHER INFORMATION: "Xaa" is a variable amino acid.

<400> SEQUENCE: 2

Tyr Asp Ile Xaa Tyr Tyr Xaa Xaa Glu
1 5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 3

Tyr Asp Ile Asn Tyr Tyr Thr Ser Glu
 1               5

<210> SEQ ID NO 4
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: "Xaa" is a variable amino acid.
<220> FEATURE:
<221> NAME/KEY: misc_feature
<222> LOCATION: (4)..(6)
<223> OTHER INFORMATION: "Xaa" is a variable amino acid.
<220> FEATURE:
<221> NAME/KEY: misc_feature
<222> LOCATION: (8)..(8)
<223> OTHER INFORMATION: "Xaa" is a variable amino acid.
<220> FEATURE:
<221> NAME/KEY: misc_feature
<222> LOCATION: (13)..(13)
<223> OTHER INFORMATION: "Xaa" is a variable amino acid.
<220> FEATURE:
<221> NAME/KEY: misc_feature
<222> LOCATION: (16)..(17)
<223> OTHER INFORMATION: "Xaa" is a variable amino acid.

<400> SEQUENCE: 4

Xaa Xaa Tyr Xaa Xaa Xaa Ser Xaa Ile Tyr Asp Ile Xaa Tyr Tyr Xaa
 1               5                  10                  15

Xaa Glu

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 5

Met Asp Tyr Gln Val Ser Ser Pro Ile Tyr Asp Ile Asn Tyr Tyr Thr
 1               5                  10                  15

Ser Glu

<210> SEQ ID NO 6
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" is a variable amino acid.
<220> FEATURE:
<221> NAME/KEY: misc_feature
<222> LOCATION: (3)..(3)
<223> OTHER INFORMATION: "Xaa" is a variable amino acid.

```
<220> FEATURE:
<221> NAME/KEY: misc_feature
<222> LOCATION: (5)..(5)
<223> OTHER INFORMATION: "Xaa" is a variable amino acid.
<220> FEATURE:
<221> NAME/KEY: misc_feature
<222> LOCATION: (8)..(10)
<223> OTHER INFORMATION: "Xaa" is a variable amino acid.
<220> FEATURE:
<221> NAME/KEY: misc_feature
<222> LOCATION: (13)..(15)
<223> OTHER INFORMATION: "Xaa" is a variable amino acid.

<400> SEQUENCE: 6

Xaa Glu Xaa Ile Xaa Ile Tyr Xaa Xaa Xaa Asn Tyr Xaa Xaa Xaa
 1               5                  10                  15

<210> SEQ ID NO 7
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: "Xaa" is a variable amino acid.
<220> FEATURE:
<221> NAME/KEY: misc_feature
<222> LOCATION: (4)..(4)
<223> OTHER INFORMATION: "Xaa" is a variable amino acid.
<220> FEATURE:
<221> NAME/KEY: misc_feature
<222> LOCATION: (7)..(9)
<223> OTHER INFORMATION: "Xaa" is a variable amino acid.

<400> SEQUENCE: 7

Glu Xaa Ile Xaa Ile Tyr Xaa Xaa Xaa Asn Tyr
 1               5                  10

<210> SEQ ID NO 8
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: "Xaa" is a variable amino acid.
<220> FEATURE:
<221> NAME/KEY: misc_feature
<222> LOCATION: (3)
<223> OTHER INFORMATION: "Xaa" is a variable amino acid.
<220> FEATURE:
<221> NAME/KEY: misc_feature
<222> LOCATION: (5)
<223> OTHER INFORMATION: "Xaa" is a variable amino acid.
<220> FEATURE:
<221> NAME/KEY: misc_feature
<222> LOCATION: (8)..(10)
<223> OTHER INFORMATION: "Xaa" is a variable amino acid.
<220> FEATURE:
<221> NAME/KEY: misc_feature
<222> LOCATION: (13)..(15)
<223> OTHER INFORMATION: "Xaa" is a variable amino acid.

<400> SEQUENCE: 8

Xaa Glu Xaa Ile Xaa Ile Tyr Xaa Xaa Xaa Asn Tyr Xaa Xaa Xaa
 1               5                  10                  15

<210> SEQ ID NO 9
<211> LENGTH: 15
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)
<223> OTHER INFORMATION: "Xaa" is a variable amino acid.
<220> FEATURE:
<221> NAME/KEY: misc_feature
<222> LOCATION: (13)..(15)
<223> OTHER INFORMATION: "Xaa" is a variable amino acid.

<400> SEQUENCE: 9

Xaa Glu Gly Ile Ser Ile Tyr Thr Ser Asp Asn Tyr Xaa Xaa Xaa
 1               5                  10                  15

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 10

Glu His Gln Ala Phe Leu Gln Phe Ser
 1               5

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 11

Leu Pro Pro Leu Tyr Ser Leu Val Phe Ile Phe Gly Phe Val Gly Asn
 1               5                  10                  15

Met Leu

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: binding
      peptide

<400> SEQUENCE: 12

Gln Trp Asp Phe Gly Asn Thr Met Cys Gln Leu Leu Thr Gly Leu Tyr
 1               5                  10                  15

Phe Ile Gly Phe Phe Ser
                20

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 13

Ser Gln Tyr Gln Phe Trp Lys Asn Phe Gln Thr Leu Lys Ile Val Ile
 1               5                  10                  15
```

Leu Gly

```
<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: binding
      peptide

<400> SEQUENCE: 14

Ala Pro Tyr Asn Ile Val Leu Leu Asn Thr Phe Gln Glu Phe Phe
  1               5                  10                  15

Gly Leu Asn Asn Cys Ser
             20

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 15

Tyr Ala Phe Val Gly Glu Lys Phe Arg Asn Tyr Leu Leu Val Phe Phe
  1               5                  10                  15

Gln Lys

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 16

Leu Leu Leu Thr Ile Pro Asp Phe Ile Phe Ala Asn Val Ser Glu Ala
  1               5                  10                  15

Asp Asp

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 17

Val Val Phe Gln Phe Gln His Ile Met Val Gly Leu Ile Leu Pro Gly
  1               5                  10                  15

Ile Val

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 18

Ile Asp Ser Phe Ile Leu Leu Glu Ile Ile Lys Gln Gly Cys Glu Phe
```

```
                1               5                  10                  15
Glu Asn

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 19

Leu Val Ile Ser Ile Phe Tyr His Lys Leu Gln Ser Leu Thr Asp Val
  1               5                  10                  15

Phe Leu

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 20

Pro Phe Trp Ala Tyr Ala Gly Ile His Glu Trp Val Phe Gly Gln Val
  1               5                  10                  15

Met Cys

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 21

Glu Ala Ile Ser Thr Val Val Leu Ala Thr Gln Met Thr Leu Gly Phe
  1               5                  10                  15

Phe Leu

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 22

Leu Thr Met Ile Val Cys Tyr Ser Val Ile Ile Lys Thr Leu Leu His
  1               5                  10                  15

Ala Gly

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: binding
      peptide

<400> SEQUENCE: 23
```

```
Met Ala Val Phe Leu Leu Thr Gln Met Pro Phe Asn Leu Met Lys Phe
 1               5                  10                  15

Ile Arg Ser Thr His Trp
                20

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 24

His Trp Glu Tyr Tyr Ala Met Thr Ser Phe His Tyr Thr Ile Met Val
 1               5                  10                  15

Thr Glu

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 25

Ala Cys Leu Asn Pro Val Leu Tyr Ala Phe Val Ser Leu Lys Phe Arg
 1               5                  10                  15

Lys Asn

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 26

Ser Lys Thr Phe Ser Ala Ser His Asn Val Glu Ala Thr Ser Met Phe
 1               5                  10                  15

Gln Leu

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 27

Asp Thr Tyr Ile Cys Glu Val Glu Asp
 1               5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 28
```

Glu Val Gln Leu Leu Val Phe Gly Leu Thr Ala Asn Ser Asp
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 29

Thr His Leu Leu Gln Gly Gln Ser Leu Thr Leu Thr Leu Glu Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 30

Gly Glu Gln Val Glu Phe Ser Phe Pro Leu Ala Phe Thr Val Glu
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 31

Met Asp Tyr Gln Val Ser Ser Pro Ile Tyr Asp Ile Asn Tyr Tyr Thr
1               5                   10                  15

Ser Glu

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 32

Val Ser Ser Pro Ile Tyr Asp Ile Asn Tyr Tyr Thr Ser Glu Pro Cys
1               5                   10                  15

Gln Lys

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 33

Ile Tyr Asp Ile Asn Tyr Tyr Thr Ser Glu Pro Cys Gln Lys Ile Asn
1               5                   10                  15

Val Lys

```
<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 34

Asn Tyr Tyr Thr Ser Glu Pro Cys Gln Lys Ile Asn Val Lys Gln Ile
 1               5                  10                  15

Ala Ala

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 35

Ser Glu Pro Cys Gln Lys Ile Asn Val Lys Gln Ile Ala Ala Arg Leu
 1               5                  10                  15

Leu Pro

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 36

Gln Lys Ile Asn Val Lys Gln Ile Ala Ala Arg Leu Leu Pro Pro Leu
 1               5                  10                  15

Tyr Ser

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 37

Val Lys Gln Ile Ala Ala Arg Leu Leu Pro Pro Leu Tyr Ser Leu Val
 1               5                  10                  15

Phe Ile

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 38

Ala Ala Arg Leu Leu Pro Pro Leu Tyr Ser Leu Val Phe Ile Phe Gly
 1               5                  10                  15

Phe Val
```

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 39

Leu Pro Pro Leu Tyr Ser Leu Val Phe Ile Phe Gly Phe Val Gly Asn
1               5                   10                  15

Met Leu

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 40

Tyr Ser Leu Val Phe Ile Phe Gly Phe Val Gly Asn Met Leu Val Ile
1               5                   10                  15

Leu Ile

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 41

Phe Ile Phe Gly Phe Val Gly Asn Met Leu Val Ile Leu Ile Leu Ile
1               5                   10                  15

Asn Cys

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 42

Phe Val Gly Asn Met Leu Val Ile Leu Ile Leu Ile Asn Cys Lys Arg
1               5                   10                  15

Leu Lys

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 43

Met Leu Val Ile Leu Ile Leu Ile Asn Cys Lys Arg Leu Lys Ser Met
1               5                   10                  15

Thr Asp

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 44

Leu Ile Leu Ile Asn Cys Lys Arg Leu Lys Ser Met Thr Asp Ile Tyr
 1               5                  10                  15

Leu Leu

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 45

Asn Cys Lys Arg Leu Lys Ser Met Thr Asp Ile Tyr Leu Leu Asn Leu
 1               5                  10                  15

Ala Ile

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 46

Leu Lys Ser Met Thr Asp Ile Tyr Leu Leu Asn Leu Ala Ile Ser Asp
 1               5                  10                  15

Leu Phe

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 47

Thr Asp Ile Tyr Leu Leu Asn Leu Ala Ile Ser Asp Leu Phe Phe Leu
 1               5                  10                  15

Leu Thr

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 48

Leu Leu Asn Leu Ala Ile Ser Asp Leu Phe Phe Leu Leu Thr Val Pro
 1               5                  10                  15

Phe Trp

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 49

Ala Ile Ser Asp Leu Phe Phe Leu Leu Thr Val Pro Phe Trp Ala His
 1               5                  10                  15

Tyr Ala

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 50

Leu Phe Phe Leu Leu Thr Val Pro Phe Trp Ala His Tyr Ala Ala Ala
 1               5                  10                  15

Gln Trp

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 51

Leu Thr Val Pro Phe Trp Ala His Tyr Ala Ala Ala Gln Trp Asp Phe
 1               5                  10                  15

Gly Asn

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 52

Phe Trp Ala His Tyr Ala Ala Ala Gln Trp Asp Phe Gly Asn Thr Met
 1               5                  10                  15

Cys Gln

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 53

Tyr Ala Ala Ala Gln Trp Asp Phe Gly Asn Thr Met Cys Gln Leu Leu

```
                1               5                  10                 15
Thr Gly

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 54

Gln Trp Asp Phe Gly Asn Thr Met Cys Gln Leu Leu Thr Gly Leu Tyr
  1               5                  10                 15
Phe Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 55

Gly Asn Thr Met Cys Gln Leu Leu Thr Gly Leu Tyr Phe Ile Gly Phe
  1               5                  10                 15
Phe Ser

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 56

Cys Gln Leu Leu Thr Gly Leu Tyr Phe Ile Gly Phe Phe Ser Gly Ile
  1               5                  10                 15
Phe Phe

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 57

Thr Gly Leu Tyr Phe Ile Gly Phe Phe Ser Gly Ile Phe Phe Ile Ile
  1               5                  10                 15
Leu Leu

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 58
```

Phe Ile Gly Phe Phe Ser Gly Ile Phe Phe Ile Ile Leu Leu Thr Ile
 1               5                  10                  15
Asp Arg

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 59

Phe Ser Gly Ile Phe Phe Ile Ile Leu Leu Thr Ile Asp Arg Tyr Leu
 1               5                  10                  15
Ala Val

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 60

Phe Phe Ile Ile Leu Leu Thr Ile Asp Arg Tyr Leu Ala Val Val His
 1               5                  10                  15
Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 61

Leu Leu Thr Ile Asp Arg Tyr Leu Ala Val Val His Ala Val Phe Ala
 1               5                  10                  15
Leu Lys

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 62

Asp Arg Tyr Leu Ala Val Val His Ala Val Phe Ala Leu Lys Ala Arg
 1               5                  10                  15
Thr Val

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 63

Ala Val Val His Ala Val Phe Ala Leu Lys Ala Arg Thr Val Thr Phe
1               5                   10                  15

Gly Val

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 64

Ala Val Phe Ala Leu Lys Ala Arg Thr Val Thr Phe Gly Val Val Thr
1               5                   10                  15

Ser Val

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 65

Leu Lys Ala Arg Thr Val Thr Phe Gly Val Val Thr Ser Val Ile Thr
1               5                   10                  15

Trp Val

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 66

Thr Val Thr Phe Gly Val Val Thr Ser Val Ile Thr Trp Val Val Ala
1               5                   10                  15

Val Phe

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 67

Gly Val Val Thr Ser Val Ile Thr Trp Val Val Ala Val Phe Ala Ser
1               5                   10                  15

Leu Pro

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 68

Ser Val Ile Thr Trp Val Ala Val Phe Ala Ser Leu Pro Gly Ile
 1               5                  10                  15

Ile Phe

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 69

Trp Val Val Ala Val Phe Ala Ser Leu Pro Gly Ile Ile Phe Thr Arg
 1               5                  10                  15

Ser Gln

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 70

Val Phe Ala Ser Leu Pro Gly Ile Ile Phe Thr Arg Ser Gln Lys Glu
 1               5                  10                  15

Gly Leu

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 71

Leu Pro Gly Ile Ile Phe Thr Arg Ser Gln Lys Glu Gly Leu His Tyr
 1               5                  10                  15

Thr Cys

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 72

Ile Phe Thr Arg Ser Gln Lys Glu Gly Leu His Tyr Thr Cys Ser Ser
 1               5                  10                  15

His Phe

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: binding
      peptide
```

<400> SEQUENCE: 73

Ser Gln Lys Glu Gly Leu His Tyr Thr Cys Ser Ser His Phe Pro Tyr
 1               5                  10                  15

Ser Gln

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 74

Gly Leu His Tyr Thr Cys Ser Ser His Phe Pro Tyr Ser Gln Tyr Gln
 1               5                  10                  15

Phe Trp

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 75

Gly Leu His Tyr Thr Cys Ser Ser His Phe Pro Tyr Ser Gln Tyr Gln
 1               5                  10                  15

Phe Trp

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 76

His Phe Pro Tyr Ser Gln Tyr Gln Phe Trp Lys Asn Phe Gln Thr Leu
 1               5                  10                  15

Lys Ile

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 77

Ser Gln Tyr Gln Phe Trp Lys Asn Phe Gln Thr Leu Lys Ile Val Ile
 1               5                  10                  15

Leu Gly

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: binding -continued peptide

<400> SEQUENCE: 78

Phe Trp Lys Asn Phe Gln Thr Leu Lys Ile Val Ile Leu Gly Leu Val
  1               5                  10                  15

Leu Pro

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 79

Phe Gln Thr Leu Lys Ile Val Ile Leu Gly Leu Val Leu Pro Leu Leu
  1               5                  10                  15

Val Met

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 80

Lys Ile Val Ile Leu Gly Leu Val Leu Pro Leu Leu Val Met Val Ile
  1               5                  10                  15

Cys Tyr

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 81

Leu Gly Leu Val Leu Pro Leu Leu Val Met Val Ile Cys Tyr Ser Gly
  1               5                  10                  15

Ile Leu

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 82

Leu Pro Leu Leu Val Met Val Ile Cys Tyr Ser Gly Ile Leu Lys Thr
  1               5                  10                  15

Leu Leu

<210> SEQ ID NO 83
<211> LENGTH: 18
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 83

Val Met Val Ile Cys Tyr Ser Gly Ile Leu Lys Thr Leu Leu Arg Cys
 1               5                  10                  15

Arg Asn

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 84

Cys Tyr Ser Gly Ile Leu Lys Thr Leu Leu Arg Cys Arg Asn Glu Lys
 1               5                  10                  15

Lys Arg

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 85

Ile Leu Lys Thr Leu Leu Arg Cys Arg Asn Glu Lys Lys Arg His Arg
 1               5                  10                  15

Ala Val

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 86

Leu Leu Arg Cys Arg Asn Glu Lys Lys Arg His Arg Ala Val Arg Leu
 1               5                  10                  15

Ile Phe

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 87

Arg Asn Glu Lys Lys Arg His Arg Ala Val Arg Leu Ile Phe Thr Ile
 1               5                  10                  15

Met Ile

<210> SEQ ID NO 88
<211> LENGTH: 18
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 88

Lys Arg His Arg Ala Val Arg Leu Ile Phe Thr Ile Met Ile Val Tyr
 1               5                  10                  15

Phe Leu

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 89

Ala Val Arg Leu Ile Phe Thr Ile Met Ile Val Tyr Phe Leu Phe Trp
 1               5                  10                  15

Ala Pro

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 90

Ile Phe Thr Ile Met Ile Val Tyr Phe Leu Phe Trp Ala Pro Tyr Asn
 1               5                  10                  15

Ile Val

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 91

Met Ile Val Tyr Phe Leu Phe Trp Ala Pro Tyr Asn Ile Val Leu Leu
 1               5                  10                  15

Leu Asn

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 92

Phe Leu Phe Trp Ala Pro Tyr Asn Ile Val Leu Leu Leu Asn Thr Phe
 1               5                  10                  15

Gln Glu

<210> SEQ ID NO 93
<211> LENGTH: 18
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 93

Ala Pro Tyr Asn Ile Val Leu Leu Leu Asn Thr Phe Gln Glu Phe Phe
 1               5                  10                  15

Gly Leu

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 94

Ile Val Leu Leu Leu Asn Thr Phe Gln Glu Phe Phe Gly Leu Asn Asn
 1               5                  10                  15

Cys Ser

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 95

Leu Asn Thr Phe Gln Glu Phe Phe Gly Leu Asn Asn Cys Ser Ser Ser
 1               5                  10                  15

Asn Arg

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 96

Gln Glu Phe Phe Gly Leu Asn Asn Cys Ser Ser Ser Asn Arg Leu Asp
 1               5                  10                  15

Gln Ala

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 97

Gly Leu Asn Asn Cys Ser Ser Ser Asn Arg Leu Asp Gln Ala Met Gln
 1               5                  10                  15

Val Thr

<210> SEQ ID NO 98
<211> LENGTH: 18
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 98

Cys Ser Ser Ser Asn Arg Leu Asp Gln Ala Met Gln Val Thr Glu Thr
 1               5                  10                  15

Leu Gly

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 99

Asn Arg Leu Asp Gln Ala Met Gln Val Thr Glu Thr Leu Gly Met Thr
 1               5                  10                  15

His Cys

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 100

Gln Ala Met Gln Val Thr Glu Thr Leu Gly Met Thr His Cys Cys Ile
 1               5                  10                  15

Asn Pro

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 101

Val Thr Glu Thr Leu Gly Met Thr His Cys Cys Ile Asn Pro Ile Ile
 1               5                  10                  15

Tyr Ala

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 102

Leu Gly Met Thr His Cys Cys Ile Asn Pro Ile Ile Tyr Ala Phe Val
 1               5                  10                  15

Gly Glu

<210> SEQ ID NO 103
```

```
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 103

His Cys Cys Ile Asn Pro Ile Ile Tyr Ala Phe Val Gly Glu Lys Phe
 1               5                  10                  15

Arg Asn

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 104

Asn Pro Ile Ile Tyr Ala Phe Val Gly Glu Lys Phe Arg Asn Tyr Leu
 1               5                  10                  15

Leu Val

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 105

Tyr Ala Phe Val Gly Glu Lys Phe Arg Asn Tyr Leu Leu Val Phe Phe
 1               5                  10                  15

Gln Lys

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 106

Gly Glu Lys Phe Arg Asn Tyr Leu Leu Val Phe Phe Gln Lys His Ile
 1               5                  10                  15

Ala Lys

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 107

Arg Asn Tyr Leu Leu Val Phe Phe Gln Lys His Ile Ala Lys Arg Phe
 1               5                  10                  15

Cys Lys
```

```
<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 108

Leu Val Phe Phe Gln Lys His Ile Ala Lys Arg Phe Cys Lys Cys Cys
 1               5                  10                  15

Ser Ile

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 109

Gln Lys His Ile Ala Lys Arg Phe Cys Lys Cys Cys Ser Ile Phe Gln
 1               5                  10                  15

Gln Glu

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 110

Ala Lys Arg Phe Cys Lys Cys Cys Ser Ile Phe Gln Gln Glu Ala Pro
 1               5                  10                  15

Glu Arg

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 111

Cys Lys Cys Cys Ser Ile Phe Gln Gln Glu Ala Pro Glu Arg Ala Ser
 1               5                  10                  15

Ser Val

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 112

Ser Ile Phe Gln Gln Glu Ala Pro Glu Arg Ala Ser Ser Val Tyr Thr
 1               5                  10                  15

Arg Ser
```

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 113

Gln Glu Ala Pro Glu Arg Ala Ser Ser Val Tyr Thr Arg Ser Thr Gly
 1               5                  10                  15

Glu Gln

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 114

Glu Arg Ala Ser Ser Val Tyr Thr Arg Ser Thr Gly Glu Gln Glu Ile
 1               5                  10                  15

Ser Val

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: binding
      peptide

<400> SEQUENCE: 115

Ser Val Tyr Thr Arg Ser Thr Gly Glu Gln Glu Ile Ser Val Gly Leu
 1               5                  10                  15

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 116

Met Glu Gly Ile Ser Ile Tyr Thr Ser Asp Asn Tyr Thr Glu Glu Met
 1               5                  10                  15

Gly Ser

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 117

Ser Ile Tyr Thr Ser Asp Asn Tyr Thr Glu Glu Met Gly Ser Gly Asp
 1               5                  10                  15

Tyr Asp

```
<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 118

Ser Asp Asn Tyr Thr Glu Glu Met Gly Ser Gly Asp Tyr Asp Ser Met
  1               5                  10                  15

Lys Glu

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 119

Thr Glu Glu Met Gly Ser Gly Asp Tyr Asp Ser Met Lys Glu Pro Cys
  1               5                  10                  15

Phe Arg

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 120

Gly Ser Gly Asp Tyr Asp Ser Met Lys Glu Pro Cys Phe Arg Glu Glu
  1               5                  10                  15

Asn Ala

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 121

Tyr Asp Ser Met Lys Glu Pro Cys Phe Arg Glu Glu Asn Ala Asn Phe
  1               5                  10                  15

Asn Lys

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 122

Lys Glu Pro Cys Phe Arg Glu Glu Asn Ala Asn Phe Asn Lys Ile Phe
  1               5                  10                  15

Leu Pro
```

```
<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 123

Phe Arg Glu Glu Asn Ala Asn Phe Asn Lys Ile Phe Leu Pro Thr Ile
 1               5                  10                  15

Tyr Ser

<210> SEQ ID NO 124
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 124

Asn Ala Asn Phe Asn Lys Ile Phe Leu Pro Thr Ile Tyr Ser Ile Ile
 1               5                  10                  15

Phe Leu

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 125

Asn Lys Ile Phe Leu Pro Thr Ile Tyr Ser Ile Ile Phe Leu Thr Gly
 1               5                  10                  15

Ile Val

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 126

Leu Pro Thr Ile Tyr Ser Ile Ile Phe Leu Thr Gly Ile Val Gly Asn
 1               5                  10                  15

Gly Leu

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 127

Tyr Ser Ile Ile Phe Leu Thr Gly Ile Val Gly Asn Gly Leu Val Ile
 1               5                  10                  15

Leu Val
```

-continued

```
<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 128

Phe Leu Thr Gly Ile Val Gly Asn Gly Leu Val Ile Leu Val Met Gly
 1               5                  10                  15

Tyr Gln

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 129

Ile Val Gly Asn Gly Leu Val Ile Leu Val Met Gly Tyr Gln Lys Lys
 1               5                  10                  15

Leu Arg

<210> SEQ ID NO 130
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 130

Gly Leu Val Ile Leu Val Met Gly Tyr Gln Lys Lys Leu Arg Ser Met
 1               5                  10                  15

Thr Asp

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 131

Leu Val Met Gly Tyr Gln Lys Lys Leu Arg Ser Met Thr Asp Lys Tyr
 1               5                  10                  15

Arg Leu

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 132

Tyr Gln Lys Lys Leu Arg Ser Met Thr Asp Lys Tyr Arg Leu His Leu
 1               5                  10                  15
```

Ser Val

```
<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 133
```

Leu Arg Ser Met Thr Asp Lys Tyr Arg Leu His Leu Ser Val Ala Asp
 1               5                  10                  15

Leu Leu

```
<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 134
```

Thr Asp Lys Tyr Arg Leu His Leu Ser Val Ala Asp Leu Leu Phe Val
 1               5                  10                  15

Ile Thr

```
<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 135
```

Arg Leu His Leu Ser Val Ala Asp Leu Leu Phe Val Ile Thr Leu Pro
 1               5                  10                  15

Phe Trp

```
<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 136
```

Ser Val Ala Asp Leu Leu Phe Val Ile Thr Leu Pro Phe Trp Ala Val
 1               5                  10                  15

Asp Ala

```
<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 137
```

Leu Leu Phe Val Ile Thr Leu Pro Phe Trp Ala Val Asp Ala Val Ala
 1               5                  10                  15

```
Asn Trp

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 138

Ile Thr Leu Pro Phe Trp Ala Val Asp Ala Val Ala Asn Trp Tyr Phe
 1               5                  10                  15

Gly Asn

<210> SEQ ID NO 139
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 139

Phe Trp Ala Val Asp Ala Val Ala Asn Trp Tyr Phe Gly Asn Phe Leu
 1               5                  10                  15

Cys Lys

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 140

Asp Ala Val Ala Asn Trp Tyr Phe Gly Asn Phe Leu Cys Lys Ala Val
 1               5                  10                  15

His Val

<210> SEQ ID NO 141
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 141

Asn Trp Tyr Phe Gly Asn Phe Leu Cys Lys Ala Val His Val Ile Tyr
 1               5                  10                  15

Thr Val

<210> SEQ ID NO 142
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 142

Gly Asn Phe Leu Cys Lys Ala Val His Val Ile Tyr Thr Val Asn Leu
```

```
                1               5                  10                 15
Tyr Ser

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 143

Cys Lys Ala Val His Val Ile Tyr Thr Val Asn Leu Tyr Ser Ser Val
  1               5                  10                 15

Leu Ile

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 144

His Val Ile Tyr Thr Val Asn Leu Tyr Ser Ser Val Leu Ile Leu Ala
  1               5                  10                 15

Phe Ile

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 145

Thr Val Asn Leu Tyr Ser Ser Val Leu Ile Leu Ala Phe Ile Ser Leu
  1               5                  10                 15

Asp Arg

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 146

Tyr Ser Ser Val Leu Ile Leu Ala Phe Ile Ser Leu Asp Arg Tyr Leu
  1               5                  10                 15

Ala Ile

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 147
```

-continued

Leu Ile Leu Ala Phe Ile Ser Leu Asp Arg Tyr Leu Ala Ile Val His
1               5                   10                  15
Ala Thr

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 148

Phe Ile Ser Leu Asp Arg Tyr Leu Ala Ile Val His Ala Thr Asn Ser
1               5                   10                  15
Gln Arg

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 149

Asp Arg Tyr Leu Ala Ile Val His Ala Thr Asn Ser Gln Arg Pro Arg
1               5                   10                  15
Lys Leu

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 150

Ala Ile Val His Ala Thr Asn Ser Gln Arg Pro Arg Lys Leu Leu Ala
1               5                   10                  15
Glu Lys

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 151

Ala Thr Asn Ser Gln Arg Pro Arg Lys Leu Leu Ala Glu Lys Val Val
1               5                   10                  15
Tyr Val

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 152

```
Gln Arg Pro Arg Lys Leu Leu Ala Glu Lys Val Val Tyr Val Gly Val
  1               5                  10                  15

Trp Ile
```

<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 153

```
Lys Leu Leu Ala Glu Lys Val Val Tyr Val Gly Val Trp Ile Pro Ala
  1               5                  10                  15

Leu Leu
```

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 154

```
Glu Lys Val Val Tyr Val Gly Val Trp Ile Pro Ala Leu Leu Leu Thr
  1               5                  10                  15

Ile Pro
```

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 155

```
Tyr Val Gly Val Trp Ile Pro Ala Leu Leu Leu Thr Ile Pro Asp Phe
  1               5                  10                  15

Ile Phe
```

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 156

```
Trp Ile Pro Ala Leu Leu Leu Thr Ile Pro Asp Phe Ile Phe Ala Asn
  1               5                  10                  15

Val Ser
```

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 157

Leu Leu Leu Thr Ile Pro Asp Phe Ile Phe Ala Asn Val Ser Glu Ala
 1               5                  10                  15

Asp Asp

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 158

Ile Pro Asp Phe Ile Phe Ala Asn Val Ser Glu Ala Asp Asp Arg Tyr
 1               5                  10                  15

Ile Cys

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 159

Ile Phe Ala Asn Val Ser Glu Ala Asp Asp Arg Tyr Ile Cys Asp Arg
 1               5                  10                  15

Phe Tyr

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 160

Val Ser Glu Ala Asp Asp Arg Tyr Ile Cys Asp Arg Phe Tyr Pro Asn
 1               5                  10                  15

Asp Leu

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 161

Asp Asp Arg Tyr Ile Cys Asp Arg Phe Tyr Pro Asn Asp Leu Trp Val
 1               5                  10                  15

Val Val

<210> SEQ ID NO 162
<211> LENGTH: 18
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 162

Ile Cys Asp Arg Phe Tyr Pro Asn Asp Leu Trp Val Val Val Phe Gln
 1               5                  10                  15

Phe Gln

<210> SEQ ID NO 163
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 163

Phe Tyr Pro Asn Asp Leu Trp Val Val Val Phe Gln Phe Gln His Ile
 1               5                  10                  15

Met Val

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 164

Asp Leu Trp Val Val Val Phe Gln Phe Gln His Ile Met Val Gly Leu
 1               5                  10                  15

Ile Leu

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 165

Val Val Phe Gln Phe Gln His Ile Met Val Gly Leu Ile Leu Pro Gly
 1               5                  10                  15

Ile Val

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 166

Phe Gln His Ile Met Val Gly Leu Ile Leu Pro Gly Ile Val Ile Leu
 1               5                  10                  15

Ser Cys

<210> SEQ ID NO 167
<211> LENGTH: 18
<212> TYPE: PRT
<213> ORGANISM: Artificial Sequence
<220> FEATURE:
<223> OTHER INFORMATION: Description of Artificial Sequence: binding
``` peptide

<400> SEQUENCE: 167

Met Val Gly Leu Ile Leu Pro Gly Ile Val Ile Leu Ser Cys Tyr Cys
 1               5                   10                  15

Ile Ile

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 168

Ile Leu Pro Gly Ile Val Ile Leu Ser Cys Tyr Cys Ile Ile Ile Ser
 1               5                   10                  15

Lys Leu

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 169

Ile Val Ile Leu Ser Cys Tyr Cys Ile Ile Ile Ser Lys Leu Ser His
 1               5                   10                  15

Ser Lys

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 170

Ser Cys Tyr Cys Ile Ile Ile Ser Lys Leu Ser His Ser Lys Gly His
 1               5                   10                  15

Gln Lys

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 171

Ile Ile Ile Ser Lys Leu Ser His Ser Lys Gly His Gln Lys Arg Lys
 1               5                   10                  15

Ala Leu

<210> SEQ ID NO 172
<211> LENGTH: 18
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 172

Lys Leu Ser His Ser Lys Gly His Gln Lys Arg Lys Ala Leu Lys Thr
 1               5                  10                  15

Thr Val

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 173

Ser Lys Gly His Gln Lys Arg Lys Ala Leu Lys Thr Thr Val Ile Leu
 1               5                  10                  15

Ile Leu

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 174

Gln Lys Arg Lys Ala Leu Lys Thr Thr Val Ile Leu Ile Leu Ala Phe
 1               5                  10                  15

Phe Ala

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 175

Ala Leu Lys Thr Thr Val Ile Leu Ile Leu Ala Phe Phe Ala Cys Trp
 1               5                  10                  15

Leu Pro

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 176

Thr Val Ile Leu Ile Leu Ala Phe Phe Ala Cys Trp Leu Pro Tyr Tyr
 1               5                  10                  15

Ile Gly

<210> SEQ ID NO 177
<211> LENGTH: 18
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 177

Ile Leu Ala Phe Phe Ala Cys Trp Leu Pro Tyr Tyr Ile Gly Ile Ser
 1               5                  10                  15

Ile Asp

<210> SEQ ID NO 178
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 178

Phe Ala Cys Trp Leu Pro Tyr Tyr Ile Gly Ile Ser Ile Asp Ser Phe
 1               5                  10                  15

Ile Leu

<210> SEQ ID NO 179
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 179

Leu Pro Tyr Tyr Ile Gly Ile Ser Ile Asp Ser Phe Ile Leu Leu Glu
 1               5                  10                  15

Ile Ile

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 180

Ile Gly Ile Ser Ile Asp Ser Phe Ile Leu Leu Glu Ile Ile Lys Gln
 1               5                  10                  15

Gly Cys

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 181

Ile Asp Ser Phe Ile Leu Leu Glu Ile Ile Lys Gln Gly Cys Glu Phe
 1               5                  10                  15

Glu Asn

<210> SEQ ID NO 182
<211> LENGTH: 18
<212> TYPE: PRT
```

<213> ORGANISM: Artificial Sequence
<220> FEATURE:
<223> OTHER INFORMATION: Description of Artificial Sequence: binding peptide

<400> SEQUENCE: 182

Ile Leu Leu Glu Ile Ile Lys Gln Gly Cys Glu Phe Glu Asn Thr Val
 1               5                  10                  15
His Lys

<210> SEQ ID NO 183
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 183

Ile Ile Lys Gln Gly Cys Glu Phe Glu Asn Thr Val His Lys Trp Ile
 1               5                  10                  15
Ser Ile

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 184

Gly Cys Glu Phe Glu Asn Thr Val His Lys Trp Ile Ser Ile Thr Glu
 1               5                  10                  15
Ala Leu

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 185

Glu Asn Thr Val His Lys Trp Ile Ser Ile Thr Glu Ala Leu Ala Phe
 1               5                  10                  15
Phe His

<210> SEQ ID NO 186
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 186

His Lys Trp Ile Ser Ile Thr Glu Ala Leu Ala Phe Phe His Cys Cys
 1               5                  10                  15
Leu Asn

<210> SEQ ID NO 187
<211> LENGTH: 18

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 187

Ser Ile Thr Glu Ala Leu Ala Phe Phe His Cys Cys Leu Asn Pro Ile
 1               5                  10                  15

Leu Tyr

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 188

Ala Leu Ala Phe Phe His Cys Cys Leu Asn Pro Ile Leu Tyr Ala Phe
 1               5                  10                  15

Leu Gly

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 189

Phe His Cys Cys Leu Asn Pro Ile Leu Tyr Ala Phe Leu Gly Ala Lys
 1               5                  10                  15

Phe Lys

<210> SEQ ID NO 190
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 190

Leu Asn Pro Ile Leu Tyr Ala Phe Leu Gly Ala Lys Phe Lys Thr Ser
 1               5                  10                  15

Ala Gln

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 191

Leu Tyr Ala Phe Leu Gly Ala Lys Phe Lys Thr Ser Ala Gln His Ala
 1               5                  10                  15

Leu Thr

<210> SEQ ID NO 192
```

```
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 192

Leu Gly Ala Lys Phe Lys Thr Ser Ala Gln His Ala Leu Thr Ser Val
 1               5                  10                  15

Ser Arg

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 193

Phe Lys Thr Ser Ala Gln His Ala Leu Thr Ser Val Ser Arg Gly Ser
 1               5                  10                  15

Ser Leu

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 194

Ala Gln His Ala Leu Thr Ser Val Ser Arg Gly Ser Ser Leu Lys Ile
 1               5                  10                  15

Leu Ser

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 195

Leu Thr Ser Val Ser Arg Gly Ser Ser Leu Lys Ile Leu Ser Lys Gly
 1               5                  10                  15

Lys Arg

<210> SEQ ID NO 196
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 196

Ser Arg Gly Ser Ser Leu Lys Ile Leu Ser Lys Gly Lys Arg Gly Gly
 1               5                  10                  15

His Ser
```

```
<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 197

Ser Leu Lys Ile Leu Ser Lys Gly Lys Arg Gly Gly His Ser Ser Val
 1               5                  10                  15

Ser Thr

<210> SEQ ID NO 198
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 198

Leu Ser Lys Gly Lys Arg Gly Gly His Ser Ser Val Ser Thr Glu Ser
 1               5                  10                  15

Glu Ser

<210> SEQ ID NO 199
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 199

Lys Arg Gly Gly His Ser Ser Val Ser Thr Glu Ser Glu Ser Ser Ser
 1               5                  10                  15

Phe His

<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: binding
      peptide

<400> SEQUENCE: 200

His Ser Ser Val Ser Thr Glu Ser Glu Ser Ser Phe His Ser Ser
 1               5                  10                  15

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 201

Met Ala Glu His Asp Tyr His Glu Asp Tyr Gly Phe Ser Ser Phe Asn
 1               5                  10                  15

Asp Ser
```

```
<210> SEQ ID NO 202
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 202

Asp Tyr His Glu Asp Tyr Gly Phe Ser Ser Phe Asn Asp Ser Ser Gln
 1               5                  10                  15

Glu Glu

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 203

Asp Tyr Gly Phe Ser Ser Phe Asn Asp Ser Ser Gln Glu Glu His Gln
 1               5                  10                  15

Ala Phe

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 204

Ser Ser Phe Asn Asp Ser Ser Gln Glu Glu His Gln Ala Phe Leu Gln
 1               5                  10                  15

Phe Ser

<210> SEQ ID NO 205
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 205

Asp Ser Ser Gln Glu Glu His Gln Ala Phe Leu Gln Phe Ser Lys Val
 1               5                  10                  15

Phe Leu

<210> SEQ ID NO 206
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 206

Glu Glu His Gln Ala Phe Leu Gln Phe Ser Lys Val Phe Leu Pro Cys
 1               5                  10                  15

Met Tyr
```

```
<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 207

Ala Phe Leu Gln Phe Ser Lys Val Phe Leu Pro Cys Met Tyr Leu Val
 1               5                  10                  15

Val Phe

<210> SEQ ID NO 208
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 208

Phe Ser Lys Val Phe Leu Pro Cys Met Tyr Leu Val Val Phe Val Cys
 1               5                  10                  15

Gly Leu

<210> SEQ ID NO 209
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 209

Phe Leu Pro Cys Met Tyr Leu Val Val Phe Val Cys Gly Leu Val Gly
 1               5                  10                  15

Asn Ser

<210> SEQ ID NO 210
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 210

Met Tyr Leu Val Val Phe Val Cys Gly Leu Val Gly Asn Ser Leu Val
 1               5                  10                  15

Leu Val

<210> SEQ ID NO 211
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 211

Val Phe Val Cys Gly Leu Val Gly Asn Ser Leu Val Leu Val Ile Ser
 1               5                  10                  15

Ile Phe
```

```
<210> SEQ ID NO 212
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 212

Gly Leu Val Gly Asn Ser Leu Val Leu Val Ile Ser Ile Phe Tyr His
 1               5                  10                  15

Lys Leu

<210> SEQ ID NO 213
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 213

Asn Ser Leu Val Leu Val Ile Ser Ile Phe Tyr His Lys Leu Gln Ser
 1               5                  10                  15

Leu Thr

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 214

Leu Val Ile Ser Ile Phe Tyr His Lys Leu Gln Ser Leu Thr Asp Val
 1               5                  10                  15

Phe Leu

<210> SEQ ID NO 215
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 215

Ile Phe Tyr His Lys Leu Gln Ser Leu Thr Asp Val Phe Leu Val Asn
 1               5                  10                  15

Leu Pro

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 216

Lys Leu Gln Ser Leu Thr Asp Val Phe Leu Val Asn Leu Pro Leu Ala
 1               5                  10                  15
```

Asp Leu

<210> SEQ ID NO 217
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 217

Leu Thr Asp Val Phe Leu Val Asn Leu Pro Leu Ala Asp Leu Val Phe
 1               5                  10                  15

Val Cys

<210> SEQ ID NO 218
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 218

Phe Leu Val Asn Leu Pro Leu Ala Asp Leu Val Phe Val Cys Thr Leu
 1               5                  10                  15

Pro Phe

<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 219

Leu Pro Leu Ala Asp Leu Val Phe Val Cys Thr Leu Pro Phe Trp Ala
 1               5                  10                  15

Tyr Ala

<210> SEQ ID NO 220
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 220

Asp Leu Val Phe Val Cys Thr Leu Pro Phe Trp Ala Tyr Ala Gly Ile
 1               5                  10                  15

His Glu

<210> SEQ ID NO 221
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 221

Val Cys Thr Leu Pro Phe Trp Ala Tyr Ala Gly Ile His Glu Trp Val
 1               5                  10                  15

Phe Gly

<210> SEQ ID NO 222
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 222

Pro Phe Trp Ala Tyr Ala Gly Ile His Glu Trp Val Phe Gly Gln Val
 1               5                  10                  15

Met Cys

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 223

Pro Phe Trp Ala Tyr Ala Gly Ile His Glu Trp Val Phe Gly Gln Val
 1               5                  10                  15

Met Cys

<210> SEQ ID NO 224
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 224

His Glu Trp Val Phe Gly Gln Val Met Cys Lys Ser Leu Leu Gly Ile
 1               5                  10                  15

Tyr Thr

<210> SEQ ID NO 225
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 225

Phe Gly Gln Val Met Cys Lys Ser Leu Leu Gly Ile Tyr Thr Ile Asn
 1               5                  10                  15

Phe Tyr

<210> SEQ ID NO 226
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 226

Met Cys Lys Ser Leu Leu Gly Ile Tyr Thr Ile Asn Phe Tyr Thr Ser

Met Leu

<210> SEQ ID NO 227
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 227

Leu Leu Gly Ile Tyr Thr Ile Asn Phe Tyr Thr Ser Met Leu Ile Leu
 1               5                  10                  15
Thr Cys

<210> SEQ ID NO 228
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 228

Tyr Thr Ile Asn Phe Tyr Thr Ser Met Leu Ile Leu Thr Cys Ile Thr
 1               5                  10                  15
Val Asp

<210> SEQ ID NO 229
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 229

Phe Tyr Thr Ser Met Leu Ile Leu Thr Cys Ile Thr Val Asp Arg Phe
 1               5                  10                  15
Ile Val

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 230

Met Leu Ile Leu Thr Cys Ile Thr Val Asp Arg Phe Ile Val Val Val
 1               5                  10                  15
Lys Ala

<210> SEQ ID NO 231
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 231

-continued

```
Thr Cys Ile Thr Val Asp Arg Phe Ile Val Val Lys Ala Thr Lys
1               5                   10                  15

Ala Tyr
```

<210> SEQ ID NO 232
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 232

```
Val Asp Arg Phe Ile Val Val Lys Ala Thr Lys Ala Tyr Asn Gln
1               5                   10                  15

Gln Ala
```

<210> SEQ ID NO 233
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 233

```
Ile Val Val Val Lys Ala Thr Lys Ala Tyr Asn Gln Gln Ala Lys Arg
1               5                   10                  15

Met Thr
```

<210> SEQ ID NO 234
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 234

```
Lys Ala Thr Lys Ala Tyr Asn Gln Gln Ala Lys Arg Met Thr Trp Gly
1               5                   10                  15

Lys Val
```

<210> SEQ ID NO 235
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 235

```
Ala Tyr Asn Gln Gln Ala Lys Arg Met Thr Trp Gly Lys Val Thr Ser
1               5                   10                  15

Leu Leu
```

<210> SEQ ID NO 236
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 236

```
Gln Ala Lys Arg Met Thr Trp Gly Lys Val Thr Ser Leu Leu Ile Trp
 1               5                  10                  15

Val Ile
```

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 237

```
Met Thr Trp Gly Lys Val Thr Ser Leu Leu Ile Trp Val Ile Ser Leu
 1               5                  10                  15

Leu Val
```

<210> SEQ ID NO 238
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 238

```
Lys Val Thr Ser Leu Leu Ile Trp Val Ile Ser Leu Leu Val Ser Leu
 1               5                  10                  15

Pro Gln
```

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 239

```
Leu Leu Ile Trp Val Ile Ser Leu Leu Val Ser Leu Pro Gln Ile Ile
 1               5                  10                  15

Tyr Gly
```

<210> SEQ ID NO 240
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 240

```
Val Ile Ser Leu Leu Val Ser Leu Pro Gln Ile Ile Tyr Gly Asn Val
 1               5                  10                  15

Phe Asn
```

<210> SEQ ID NO 241
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 241

Leu Val Ser Leu Pro Gln Ile Ile Tyr Gly Asn Val Phe Asn Leu Asp
  1               5                  10                  15

Lys Leu

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 242

Pro Gln Ile Ile Tyr Gly Asn Val Phe Asn Leu Asp Lys Leu Ile Cys
  1               5                  10                  15

Gly Tyr

<210> SEQ ID NO 243
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 243

Tyr Gly Asn Val Phe Asn Leu Asp Lys Leu Ile Cys Gly Tyr His Asp
  1               5                  10                  15

Glu Ala

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 244

Phe Asn Leu Asp Lys Leu Ile Cys Gly Tyr His Asp Glu Ala Ile Ser
  1               5                  10                  15

Thr Val

<210> SEQ ID NO 245
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 245

Lys Leu Ile Cys Gly Tyr His Asp Glu Ala Ile Ser Thr Val Val Leu
  1               5                  10                  15

Ala Thr

<210> SEQ ID NO 246
<211> LENGTH: 18
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 246

Gly Tyr His Asp Glu Ala Ile Ser Thr Val Val Leu Ala Thr Gln Met
 1               5                  10                  15
Thr Leu

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 247

Glu Ala Ile Ser Thr Val Val Leu Ala Thr Gln Met Thr Leu Gly Phe
 1               5                  10                  15
Phe Leu

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 248

Thr Val Val Leu Ala Thr Gln Met Thr Leu Gly Phe Phe Leu Pro Leu
 1               5                  10                  15
Leu Thr

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 249

Ala Thr Gln Met Thr Leu Gly Phe Phe Leu Pro Leu Leu Thr Met Ile
 1               5                  10                  15
Val Cys

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 250

Thr Leu Gly Phe Phe Leu Pro Leu Leu Thr Met Ile Val Cys Tyr Ser
 1               5                  10                  15
Val Ile

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: binding
```

-continued peptide

<400> SEQUENCE: 251

Phe Leu Pro Leu Leu Thr Met Ile Val Cys Tyr Ser Val Ile Ile Lys
 1              5                   10               15

Thr Leu

<210> SEQ ID NO 252
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 252

Leu Thr Met Ile Val Cys Tyr Ser Val Ile Ile Lys Thr Leu Leu His
 1              5                   10               15

Ala Gly

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 253

Val Cys Tyr Ser Val Ile Ile Lys Thr Leu Leu His Ala Gly Gly Phe
 1              5                   10               15

Gln Lys

<210> SEQ ID NO 254
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 254

Val Ile Ile Lys Thr Leu Leu His Ala Gly Gly Phe Gln Lys His Arg
 1              5                   10               15

Ser Leu

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 255

Thr Leu Leu His Ala Gly Gly Phe Gln Lys His Arg Ser Leu Lys Ile
 1              5                   10               15

Ile Phe

<210> SEQ ID NO 256
<211> LENGTH: 18
<212> TYPE: PRT
<213> ORGANISM: Artificial Sequence
<220> FEATURE:

<223> OTHER INFORMATION: Description of Artificial Sequence: binding
      peptide

<400> SEQUENCE: 256

Ala Gly Gly Phe Gln Lys His Arg Ser Leu Lys Ile Ile Phe Leu Val
 1               5                   10                  15

Met Ala

<210> SEQ ID NO 257
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 257

Gln Lys His Arg Ser Leu Lys Ile Ile Phe Leu Val Met Ala Val Phe
 1               5                   10                  15

Leu Leu

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 258

Ser Leu Lys Ile Ile Phe Leu Val Met Ala Val Phe Leu Leu Thr Gln
 1               5                   10                  15

Met Pro

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 259

Ile Phe Leu Val Met Ala Val Phe Leu Leu Thr Gln Met Pro Phe Asn
 1               5                   10                  15

Leu Met

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 260

Met Ala Val Phe Leu Leu Thr Gln Met Pro Phe Asn Leu Met Lys Phe
 1               5                   10                  15

Ile Arg

<210> SEQ ID NO 261
<211> LENGTH: 18
<212> TYPE: PRT
<213> ORGANISM: Artificial Sequence -continued

```
<220> FEATURE:
<223> OTHER INFORMATION: Description of Artificial Sequence: binding
      peptide

<400> SEQUENCE: 261

Leu Leu Thr Gln Met Pro Phe Asn Leu Met Lys Phe Ile Arg Ser Thr
1               5                   10                  15

His Trp

<210> SEQ ID NO 262
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 262

Met Pro Phe Asn Leu Met Lys Phe Ile Arg Ser Thr His Trp Glu Tyr
1               5                   10                  15

Tyr Ala

<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 263

Leu Met Lys Phe Ile Arg Ser Thr His Trp Glu Tyr Tyr Ala Met Thr
1               5                   10                  15

Ser Phe

<210> SEQ ID NO 264
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 264

Ile Arg Ser Thr His Trp Glu Tyr Tyr Ala Met Thr Ser Phe His Tyr
1               5                   10                  15

Thr Ile

<210> SEQ ID NO 265
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 265

His Trp Glu Tyr Tyr Ala Met Thr Ser Phe His Tyr Thr Ile Met Val
1               5                   10                  15

Thr Glu

<210> SEQ ID NO 266
<211> LENGTH: 18
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 266

Tyr Ala Met Thr Ser Phe His Tyr Thr Ile Met Val Thr Glu Ala Ile
 1               5                   10                  15

Ala Tyr

<210> SEQ ID NO 267
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 267

Ser Phe His Tyr Thr Ile Met Val Thr Glu Ala Ile Ala Tyr Leu Arg
 1               5                   10                  15

Ala Cys

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 268

Thr Ile Met Val Thr Glu Ala Ile Ala Tyr Leu Arg Ala Cys Leu Asn
 1               5                   10                  15

Pro Val

<210> SEQ ID NO 269
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 269

Thr Glu Ala Ile Ala Tyr Leu Arg Ala Cys Leu Asn Pro Val Leu Tyr
 1               5                   10                  15

Ala Phe

<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 270

Ala Tyr Leu Arg Ala Cys Leu Asn Pro Val Leu Tyr Ala Phe Val Ser
 1               5                   10                  15

Leu Lys

<210> SEQ ID NO 271
<211> LENGTH: 18
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 271

Ala Cys Leu Asn Pro Val Leu Tyr Ala Phe Val Ser Leu Lys Phe Arg
 1               5                  10                  15

Lys Asn

<210> SEQ ID NO 272
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 272

Pro Val Leu Tyr Ala Phe Val Ser Leu Lys Phe Arg Lys Asn Phe Trp
 1               5                  10                  15

Lys Leu

<210> SEQ ID NO 273
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 273

Ala Phe Val Ser Leu Lys Phe Arg Lys Asn Phe Trp Lys Leu Val Lys
 1               5                  10                  15

Asp Ile

<210> SEQ ID NO 274
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 274

Leu Lys Phe Arg Lys Asn Phe Trp Lys Leu Val Lys Asp Ile Gly Cys
 1               5                  10                  15

Leu Pro

<210> SEQ ID NO 275
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 275

Lys Asn Phe Trp Lys Leu Val Lys Asp Ile Gly Cys Leu Pro Tyr Leu
 1               5                  10                  15

Gly Val

<210> SEQ ID NO 276
```

<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 276

Lys Leu Val Lys Asp Ile Gly Cys Leu Pro Tyr Leu Gly Val Ser His
 1               5                  10                  15

Gln Trp

<210> SEQ ID NO 277
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 277

Asp Ile Gly Cys Leu Pro Tyr Leu Gly Val Ser His Gln Trp Lys Ser
 1               5                  10                  15

Ser Glu

<210> SEQ ID NO 278
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 278

Leu Pro Tyr Leu Gly Val Ser His Gln Trp Lys Ser Ser Glu Asp Asn
 1               5                  10                  15

Ser Lys

<210> SEQ ID NO 279
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 279

Gly Val Ser His Gln Trp Lys Ser Ser Glu Asp Asn Ser Lys Thr Phe
 1               5                  10                  15

Ser Ala

<210> SEQ ID NO 280
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 280

Gln Trp Lys Ser Ser Glu Asp Asn Ser Lys Thr Phe Ser Ala Ser His
 1               5                  10                  15

Asn Val

```
<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 281

Ser Glu Asp Asn Ser Lys Thr Phe Ser Ala Ser His Asn Val Glu Ala
 1               5                  10                  15

Thr Ser

<210> SEQ ID NO 282
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 282

Ser Lys Thr Phe Ser Ala Ser His Asn Val Glu Ala Thr Ser Met Phe
 1               5                  10                  15

Gln Leu

<210> SEQ ID NO 283
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 283

Met Asn Arg Gly Val Pro Phe Arg His Leu Leu Leu Val Leu Gln Leu
 1               5                  10                  15

Ala Leu Leu Pro Ala
             20

<210> SEQ ID NO 284
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 284

Pro Phe Arg His Leu Leu Leu Val Leu Gln Leu Ala Leu Leu Pro Ala
 1               5                  10                  15

Ala Thr Gln Gly Lys
             20

<210> SEQ ID NO 285
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 285

Leu Leu Val Leu Gln Leu Ala Leu Leu Pro Ala Ala Thr Gln Gly Lys
 1               5                  10                  15
```

-continued

Lys Val Val Leu Gly
                20

<210> SEQ ID NO 286
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 286

Leu Ala Leu Leu Pro Ala Ala Thr Gln Gly Lys Lys Val Val Leu Gly
 1               5                  10                  15

Lys Lys Gly Asp Thr
                20

<210> SEQ ID NO 287
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 287

Ala Ala Thr Gln Gly Lys Lys Val Val Leu Gly Lys Lys Gly Asp Thr
 1               5                  10                  15

Val Glu Leu Thr Cys
                20

<210> SEQ ID NO 288
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 288

Lys Lys Val Val Leu Gly Lys Lys Gly Asp Thr Val Glu Leu Thr Cys
 1               5                  10                  15

Thr Ala Ser Gln Lys
                20

<210> SEQ ID NO 289
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 289

Gly Lys Lys Gly Asp Thr Val Glu Leu Thr Cys Thr Ala Ser Gln Lys
 1               5                  10                  15

Lys Ser Ile Gln Phe
                20

<210> SEQ ID NO 290
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 290

Thr Val Glu Leu Thr Cys Thr Ala Ser Gln Lys Lys Ser Ile Gln Phe
1               5                   10                  15

His Trp Lys Asn Ser
            20

<210> SEQ ID NO 291
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 291

Cys Thr Ala Ser Gln Lys Lys Ser Ile Gln Phe His Trp Lys Asn Ser
1               5                   10                  15

Asn Gln Ile Lys Ile
            20

<210> SEQ ID NO 292
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 292

Lys Lys Ser Ile Gln Phe His Trp Lys Asn Ser Asn Gln Ile Lys Ile
1               5                   10                  15

Leu Gly Asn Gln Gly
            20

<210> SEQ ID NO 293
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 293

Phe His Trp Lys Asn Ser Asn Gln Ile Lys Ile Leu Gly Asn Gln Gly
1               5                   10                  15

Ser Phe Leu Thr Lys
            20

<210> SEQ ID NO 294
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 294

Ser Asn Gln Ile Lys Ile Leu Gly Asn Gln Gly Ser Phe Leu Thr Lys
1               5                   10                  15

Gly Pro Ser Lys Leu
            20

<210> SEQ ID NO 295

```
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 295

Ile Leu Gly Asn Gln Gly Ser Phe Leu Thr Lys Gly Pro Ser Lys Leu
 1               5                  10                  15

Asn Asp Arg Ala Asp
            20

<210> SEQ ID NO 296
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 296

Gly Ser Phe Leu Thr Lys Gly Pro Ser Lys Leu Asn Asp Arg Ala Asp
 1               5                  10                  15

Ser Arg Arg Ser Leu
            20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 297

Lys Gly Pro Ser Lys Leu Asn Asp Arg Ala Asp Ser Arg Arg Ser Leu
 1               5                  10                  15

Trp Asp Gln Gly Asn
            20

<210> SEQ ID NO 298
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 298

Leu Asn Asp Arg Ala Asp Ser Arg Arg Ser Leu Trp Asp Gln Gly Asn
 1               5                  10                  15

Phe Pro Leu Ile Ile
            20

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 299

Asp Ser Arg Arg Ser Leu Trp Asp Gln Gly Asn Phe Pro Leu Ile Ile
 1               5                  10                  15
```

```
Lys Asn Leu Lys Ile
                20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 300

Leu Trp Asp Gln Gly Asn Phe Pro Leu Ile Ile Lys Asn Leu Lys Ile
  1               5                  10                  15

Glu Asp Ser Asp Thr
                20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 301

Asn Phe Pro Leu Ile Ile Lys Asn Leu Lys Ile Glu Asp Ser Asp Thr
  1               5                  10                  15

Tyr Ile Cys Glu Val
                20

<210> SEQ ID NO 302
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 302

Ile Lys Asn Leu Lys Ile Glu Asp Ser Asp Thr Tyr Ile Cys Glu Val
  1               5                  10                  15

Glu Asp Gln Lys Glu
                20

<210> SEQ ID NO 303
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 303

Ile Glu Asp Ser Asp Thr Tyr Ile Cys Glu Val Glu Asp Gln Lys Glu
  1               5                  10                  15

Glu Val Gln Leu Leu
                20

<210> SEQ ID NO 304
<211> LENGTH: 21
<212> TYPE: PRT
<213> ORGANISM: Artificial Sequence
<220> FEATURE:
<223> OTHER INFORMATION: Description of Artificial Sequence: binding
```

-continued

```
peptide

<400> SEQUENCE: 304

Thr Tyr Ile Cys Glu Val Glu Asp Gln Lys Glu Glu Val Gln Leu Leu
 1               5                  10                  15

Val Phe Gly Leu Thr
            20

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 305

Val Glu Asp Gln Lys Glu Glu Val Gln Leu Leu Val Phe Gly Leu Thr
 1               5                  10                  15

Ala Asn Ser Asp Thr
            20

<210> SEQ ID NO 306
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 306

Glu Glu Val Gln Leu Leu Val Phe Gly Leu Thr Ala Asn Ser Asp Thr
 1               5                  10                  15

His Leu Leu Gln Gly
            20

<210> SEQ ID NO 307
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 307

Leu Val Phe Gly Leu Thr Ala Asn Ser Asp Thr His Leu Leu Gln Gly
 1               5                  10                  15

Gln Ser Leu Thr Leu
            20

<210> SEQ ID NO 308
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 308

Thr Ala Asn Ser Asp Thr His Leu Leu Gln Gly Gln Ser Leu Thr Leu
 1               5                  10                  15

Thr Leu Glu Ser Pro
            20
```

<210> SEQ ID NO 309
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 309

Thr His Leu Leu Gln Gly Gln Ser Leu Thr Leu Thr Leu Glu Ser Pro
 1               5                  10                  15

Pro Gly Ser Ser Pro
             20

<210> SEQ ID NO 310
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 310

Gly Gln Ser Leu Thr Leu Thr Leu Glu Ser Pro Pro Gly Ser Ser Pro
 1               5                  10                  15

Ser Val Gln Cys Arg
             20

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 311

Leu Thr Leu Glu Ser Pro Pro Gly Ser Ser Pro Ser Val Gln Cys Arg
 1               5                  10                  15

Ser Pro Arg Gly Lys
             20

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 312

Pro Pro Gly Ser Ser Pro Ser Val Gln Cys Arg Ser Pro Arg Gly Lys
 1               5                  10                  15

Asn Ile Gln Gly Gly
             20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 313

Pro Ser Val Gln Cys Arg Ser Pro Arg Gly Lys Asn Ile Gln Gly Gly

```
                1               5                  10                 15
Lys Thr Leu Ser Val
                20

<210> SEQ ID NO 314
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 314

Arg Ser Pro Arg Gly Lys Asn Ile Gln Gly Gly Lys Thr Leu Ser Val
 1               5                  10                  15

Ser Gln Leu Glu Leu
                20

<210> SEQ ID NO 315
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 315

Lys Asn Ile Gln Gly Gly Lys Thr Leu Ser Val Ser Gln Leu Glu Leu
 1               5                  10                  15

Gln Asp Ser Gly Thr
                20

<210> SEQ ID NO 316
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 316

Gly Lys Thr Leu Ser Val Ser Gln Leu Glu Leu Gln Asp Ser Gly Thr
 1               5                  10                  15

Trp Thr Cys Thr Val
                20

<210> SEQ ID NO 317
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 317

Val Ser Gln Leu Glu Leu Gln Asp Ser Gly Thr Trp Thr Cys Thr Val
 1               5                  10                  15

Leu Gln Asn Gln Lys
                20

<210> SEQ ID NO 318
<211> LENGTH: 21
<212> TYPE: PRT
<213> ORGANISM: Artificial Sequence
<220> FEATURE:
```

```
<223> OTHER INFORMATION: Description of Artificial Sequence: binding
      peptide

<400> SEQUENCE: 318

Leu Gln Asp Ser Gly Thr Trp Thr Cys Thr Val Leu Gln Asn Gln Lys
 1               5                  10                  15

Lys Val Glu Phe Lys
            20

<210> SEQ ID NO 319
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 319

Thr Trp Thr Cys Thr Val Leu Gln Asn Gln Lys Lys Val Glu Phe Lys
 1               5                  10                  15

Ile Asp Ile Val Val
            20

<210> SEQ ID NO 320
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 320

Val Leu Gln Asn Gln Lys Lys Val Glu Phe Lys Ile Asp Ile Val Val
 1               5                  10                  15

Leu Ala Phe Gln Lys
            20

<210> SEQ ID NO 321
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 321

Lys Lys Val Glu Phe Lys Ile Asp Ile Val Val Leu Ala Phe Gln Lys
 1               5                  10                  15

Ala Ser Ser Ile Val
            20

<210> SEQ ID NO 322
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 322

Lys Ile Asp Ile Val Val Leu Ala Phe Gln Lys Ala Ser Ser Ile Val
 1               5                  10                  15

Tyr Lys Lys Glu Gly
            20
```

```
<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 323

Val Leu Ala Phe Gln Lys Ala Ser Ser Ile Val Tyr Lys Lys Glu Gly
 1               5                  10                  15

Glu Gln Val Glu Phe
            20

<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 324

Lys Ala Ser Ser Ile Val Tyr Lys Lys Glu Gly Glu Gln Val Glu Phe
 1               5                  10                  15

Ser Phe Pro Leu Ala
            20

<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 325

Val Tyr Lys Lys Glu Gly Glu Gln Val Glu Phe Ser Phe Pro Leu Ala
 1               5                  10                  15

Phe Thr Val Glu Lys
            20

<210> SEQ ID NO 326
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 326

Gly Glu Gln Val Glu Phe Ser Phe Pro Leu Ala Phe Thr Val Glu Lys
 1               5                  10                  15

Leu Thr Gly Ser Gly
            20

<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 327
```

```
Phe Ser Phe Pro Leu Ala Phe Thr Val Glu Lys Leu Thr Gly Ser Gly
 1               5                  10                  15

Glu Leu Trp Trp Gln
            20

<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 328

Ala Phe Thr Val Glu Lys Leu Thr Gly Ser Gly Glu Leu Trp Trp Gln
 1               5                  10                  15

Ala Glu Arg Ala Ser
            20

<210> SEQ ID NO 329
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 329

Lys Leu Thr Gly Ser Gly Glu Leu Trp Trp Gln Ala Glu Arg Ala Ser
 1               5                  10                  15

Ser Ser Lys Ser Trp
            20

<210> SEQ ID NO 330
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 330

Gly Glu Leu Trp Trp Gln Ala Glu Arg Ala Ser Ser Ser Lys Ser Trp
 1               5                  10                  15

Ile Thr Phe Asp Leu
            20

<210> SEQ ID NO 331
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 331

Gln Ala Glu Arg Ala Ser Ser Ser Lys Ser Trp Ile Thr Phe Asp Leu
 1               5                  10                  15

Lys Asn Lys Glu Val
            20

<210> SEQ ID NO 332
<211> LENGTH: 21
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 332

Ser Ser Ser Lys Ser Trp Ile Thr Phe Asp Leu Lys Asn Lys Glu Val
 1               5                  10                  15

Ser Val Lys Arg Val
            20

<210> SEQ ID NO 333
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 333

Trp Ile Thr Phe Asp Leu Lys Asn Lys Glu Val Ser Val Lys Arg Val
 1               5                  10                  15

Thr Gln Asp Pro Lys
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 334

Leu Lys Asn Lys Glu Val Ser Val Lys Arg Val Thr Gln Asp Pro Lys
 1               5                  10                  15

Leu Gln Met Gly Lys
            20

<210> SEQ ID NO 335
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 335

Val Ser Val Lys Arg Val Thr Gln Asp Pro Lys Leu Gln Met Gly Lys
 1               5                  10                  15

Lys Leu Pro Leu His
            20

<210> SEQ ID NO 336
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 336

Val Thr Gln Asp Pro Lys Leu Gln Met Gly Lys Lys Leu Pro Leu His
 1               5                  10                  15

Leu Thr Leu Pro Gln
            20
```

<210> SEQ ID NO 337
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 337

Lys Leu Gln Met Gly Lys Lys Leu Pro Leu His Leu Thr Leu Pro Gln
 1               5                  10                  15

Ala Leu Pro Gln Tyr
            20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 338

Lys Lys Leu Pro Leu His Leu Thr Leu Pro Gln Ala Leu Pro Gln Tyr
 1               5                  10                  15

Ala Gly Ser Gly Asn
            20

<210> SEQ ID NO 339
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 339

His Leu Thr Leu Pro Gln Ala Leu Pro Gln Tyr Ala Gly Ser Gly Asn
 1               5                  10                  15

Leu Thr Leu Ala Leu
            20

<210> SEQ ID NO 340
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 340

Gln Ala Leu Pro Gln Tyr Ala Gly Ser Gly Asn Leu Thr Leu Ala Leu
 1               5                  10                  15

Glu Ala Lys Thr Gly
            20

<210> SEQ ID NO 341
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 341

```
Tyr Ala Gly Ser Gly Asn Leu Thr Leu Ala Leu Glu Ala Lys Thr Gly
 1               5                  10                  15

Lys Leu His Gln Glu
            20

<210> SEQ ID NO 342
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 342

Asn Leu Thr Leu Ala Leu Glu Ala Lys Thr Gly Lys Leu His Gln Glu
 1               5                  10                  15

Val Asn Leu Val Val
            20

<210> SEQ ID NO 343
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 343

Leu Glu Ala Lys Thr Gly Lys Leu His Gln Glu Val Asn Leu Val Val
 1               5                  10                  15

Met Arg Ala Thr Gln
            20

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 344

Gly Lys Leu His Gln Glu Val Asn Leu Val Val Met Arg Ala Thr Gln
 1               5                  10                  15

Leu Gln Lys Asn Leu
            20

<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 345

Glu Val Asn Leu Val Val Met Arg Ala Thr Gln Leu Gln Lys Asn Leu
 1               5                  10                  15

Thr Cys Glu Val Trp
            20

<210> SEQ ID NO 346
<211> LENGTH: 21
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 346

Val Met Arg Ala Thr Gln Leu Gln Lys Asn Leu Thr Cys Glu Val Trp
 1               5                  10                  15

Gly Pro Thr Ser Pro
            20

<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 347

Gln Leu Gln Lys Asn Leu Thr Cys Glu Val Trp Gly Pro Thr Ser Pro
 1               5                  10                  15

Lys Leu Met Leu Ser
            20

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 348

Leu Thr Cys Glu Val Trp Gly Pro Thr Ser Pro Lys Leu Met Leu Ser
 1               5                  10                  15

Leu Lys Leu Glu Asn
            20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 349

Trp Gly Pro Thr Ser Pro Lys Leu Met Leu Ser Leu Lys Leu Glu Asn
 1               5                  10                  15

Lys Glu Ala Lys Val
            20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 350

Pro Lys Leu Met Leu Ser Leu Lys Leu Glu Asn Lys Glu Ala Lys Val
 1               5                  10                  15

Ser Lys Arg Glu Lys
```

```
                    20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 351

Ser Leu Lys Leu Glu Asn Lys Glu Ala Lys Val Ser Lys Arg Glu Lys
 1               5                  10                  15

Ala Val Trp Val Leu
            20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 352

Asn Lys Glu Ala Lys Val Ser Lys Arg Glu Lys Ala Val Trp Val Leu
 1               5                  10                  15

Asn Pro Glu Ala Gly
            20

<210> SEQ ID NO 353
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 353

Val Ser Lys Arg Glu Lys Ala Val Trp Val Leu Asn Pro Glu Ala Gly
 1               5                  10                  15

Met Trp Gln Cys Leu
            20

<210> SEQ ID NO 354
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 354

Lys Ala Val Trp Val Leu Asn Pro Glu Ala Gly Met Trp Gln Cys Leu
 1               5                  10                  15

Leu Ser Asp Ser Gly
            20

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: binding
      peptide
```

-continued

```
<400> SEQUENCE: 355

Leu Asn Pro Glu Ala Gly Met Trp Gln Cys Leu Leu Ser Asp Ser Gly
 1               5                  10                  15

Gln Val Leu Leu Glu
            20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 356

Gly Met Trp Gln Cys Leu Leu Ser Asp Ser Gly Gln Val Leu Leu Glu
 1               5                  10                  15

Ser Asn Ile Lys Val
            20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 357

Leu Leu Ser Asp Ser Gly Gln Val Leu Leu Glu Ser Asn Ile Lys Val
 1               5                  10                  15

Leu Pro Thr Trp Ser
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 358

Gly Gln Val Leu Leu Glu Ser Asn Ile Lys Val Leu Pro Thr Trp Ser
 1               5                  10                  15

Thr Pro Val Gln Pro
            20

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 359

Glu Ser Asn Ile Lys Val Leu Pro Thr Trp Ser Thr Pro Val Gln Pro
 1               5                  10                  15

Met Ala Leu Ile Val
            20

<210> SEQ ID NO 360
<211> LENGTH: 21
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 360

Val Leu Pro Thr Trp Ser Thr Pro Val Gln Pro Met Ala Leu Ile Val
 1               5                  10                  15

Leu Gly Gly Val Ala
            20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 361

Ser Thr Pro Val Gln Pro Met Ala Leu Ile Val Leu Gly Gly Val Ala
 1               5                  10                  15

Gly Leu Leu Leu Phe
            20

<210> SEQ ID NO 362
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 362

Pro Met Ala Leu Ile Val Leu Gly Gly Val Ala Gly Leu Leu Leu Phe
 1               5                  10                  15

Ile Gly Leu Gly Ile
            20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 363

Val Leu Gly Gly Val Ala Gly Leu Leu Leu Phe Ile Gly Leu Gly Ile
 1               5                  10                  15

Phe Phe Cys Val Arg
            20

<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 364

Ala Gly Leu Leu Leu Phe Ile Gly Leu Gly Ile Phe Phe Cys Val Arg
 1               5                  10                  15
```

Cys Arg His Arg Arg
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 365

Phe Ile Gly Leu Gly Ile Phe Phe Cys Val Arg Cys Arg His Arg Arg
1               5                   10                  15

Arg Gln Ala Glu Arg
            20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 366

Ile Phe Phe Cys Val Arg Cys Arg His Arg Arg Gln Ala Glu Arg
1               5                   10                  15

Met Ser Gln Ile Lys
            20

<210> SEQ ID NO 367
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 367

Arg Cys Arg His Arg Arg Arg Gln Ala Glu Arg Met Ser Gln Ile Lys
1               5                   10                  15

Arg Leu Leu Ser Glu
            20

<210> SEQ ID NO 368
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 368

Arg Arg Gln Ala Glu Arg Met Ser Gln Ile Lys Arg Leu Leu Ser Glu
1               5                   10                  15

Lys Lys Thr Cys Gln
            20

<210> SEQ ID NO 369
<211> LENGTH: 21
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 369

Arg Met Ser Gln Ile Lys Arg Leu Leu Ser Glu Lys Lys Thr Cys Gln
 1               5                  10                  15

Cys Pro His Arg Phe
            20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 370

Lys Arg Leu Leu Ser Glu Lys Lys Thr Cys Gln Cys Pro His Arg Phe
 1               5                  10                  15

Gln Lys Thr Cys Ser
            20

<210> SEQ ID NO 371
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 371

Glu Lys Lys Thr Cys Gln Cys Pro His Arg Phe Gln Lys Thr Cys Ser
 1               5                  10                  15

Pro Ile

<210> SEQ ID NO 372
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 372

Met Asp Tyr Gln Val Ser Ser Pro Ile Tyr Asp Ile Asn Tyr Tyr Thr
 1               5                  10                  15

Ser Glu

<210> SEQ ID NO 373
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 373

Asp Tyr Gln Val Ser Ser Pro Ile Tyr Asp Ile Asn Tyr Tyr Thr Ser
 1               5                  10                  15

Glu Pro

<210> SEQ ID NO 374
<211> LENGTH: 18
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 374

Tyr Gln Val Ser Ser Pro Ile Tyr Asp Ile Asn Tyr Tyr Thr Ser Glu
 1               5                  10                  15

Pro Cys

<210> SEQ ID NO 375
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 375

Gln Val Ser Ser Pro Ile Tyr Asp Ile Asn Tyr Tyr Thr Ser Glu Pro
 1               5                  10                  15

Cys Gln

<210> SEQ ID NO 376
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 376

Val Ser Ser Pro Ile Tyr Asp Ile Asn Tyr Tyr Thr Ser Glu Pro Cys
 1               5                  10                  15

Gln Lys

<210> SEQ ID NO 377
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 377

Ser Ser Pro Ile Tyr Asp Ile Asn Tyr Tyr Thr Ser Glu Pro Cys Gln
 1               5                  10                  15

Lys Ile

<210> SEQ ID NO 378
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 378

Ser Pro Ile Tyr Asp Ile Asn Tyr Tyr Thr Ser Glu Pro Cys Gln Lys
 1               5                  10                  15

Ile Asn

<210> SEQ ID NO 379
<211> LENGTH: 18
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 379

Pro Ile Tyr Asp Ile Asn Tyr Tyr Thr Ser Glu Pro Cys Gln Lys Ile
 1               5                  10                  15
Asn Val

<210> SEQ ID NO 380
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 380

Ile Tyr Asp Ile Asn Tyr Tyr Thr Ser Glu Pro Cys Gln Lys Ile Asn
 1               5                  10                  15
Val Lys

<210> SEQ ID NO 381
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 381

Tyr Asp Ile Asn Tyr Tyr Thr Ser Glu Pro Cys Gln Lys Ile Asn Val
 1               5                  10                  15
Lys Gln

<210> SEQ ID NO 382
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 382

Asp Ile Asn Tyr Tyr Thr Ser Glu Pro Cys Gln Lys Ile Asn Val Lys
 1               5                  10                  15
Gln Ile

<210> SEQ ID NO 383
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 383

Ile Asn Tyr Tyr Thr Ser Glu Pro Cys Gln Lys Ile Asn Val Lys Gln
 1               5                  10                  15
Ile Ala

<210> SEQ ID NO 384
<211> LENGTH: 18
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 384

Asn Tyr Tyr Thr Ser Glu Pro Cys Gln Lys Ile Asn Val Lys Gln Ile
 1               5                   10                  15
Ala Ala

<210> SEQ ID NO 385
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 385

Tyr Tyr Thr Ser Glu Pro Cys Gln Lys Ile Asn Val Lys Gln Ile Ala
 1               5                   10                  15
Ala Arg

<210> SEQ ID NO 386
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 386

Tyr Thr Ser Glu Pro Cys Gln Lys Ile Asn Val Lys Gln Ile Ala
 1               5                   10                  15

<210> SEQ ID NO 387
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 387

Thr Ser Glu Pro Cys Gln Lys Ile Asn Val Lys Gln Ile Ala Ala
 1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 388

Ser Glu Pro Cys Gln Lys Ile Asn Val Lys Gln Ile Ala Ala Arg
 1               5                   10                  15

<210> SEQ ID NO 389
<211> LENGTH: 12
<212> TYPE: PRT
<213> ORGANISM: Artificial Sequence
<220> FEATURE:
<223> OTHER INFORMATION: Description of Artificial Sequence: binding
```

-continued

```
          peptide

<400> SEQUENCE: 389

Glu Pro Cys Gln Lys Ile Asn Val Lys Gln Ile Ala
 1               5                  10

<210> SEQ ID NO 390
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 390

Pro Cys Gln Lys Ile Asn Val Lys Gln Ile Ala Ala
 1               5                  10

<210> SEQ ID NO 391
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 391

Cys Gln Lys Ile Asn Val Lys Gln Ile Ala Ala Arg
 1               5                  10

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 392

Gln Lys Ile Asn Val Lys Gln Ile Ala
 1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 393

Lys Ile Asn Val Lys Gln Ile Ala Ala
 1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 394

Ile Asn Val Lys Gln Ile Ala Ala Arg
 1               5

<210> SEQ ID NO 395
```

```
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 395

Met Glu Gly Ile Ser Ile Tyr Thr Ser Asp Asn Tyr Thr Glu Glu Met
 1               5                  10                  15

Gly Ser

<210> SEQ ID NO 396
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 396

Glu Gly Ile Ser Ile Tyr Thr Ser Asp Asn Tyr Thr Glu Glu Met Gly
 1               5                  10                  15

Ser Gly

<210> SEQ ID NO 397
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 397

Gly Ile Ser Ile Tyr Thr Ser Asp Asn Tyr Thr Glu Glu Met Gly Ser
 1               5                  10                  15

Gly Asp

<210> SEQ ID NO 398
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 398

Ile Ser Ile Tyr Thr Ser Asp Asn Tyr Thr Glu Glu Met Gly Ser Gly
 1               5                  10                  15

Asp Tyr

<210> SEQ ID NO 399
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 399

Ser Ile Tyr Thr Ser Asp Asn Tyr Thr Glu Glu Met Gly Ser Gly Asp
 1               5                  10                  15

Tyr Asp
```

```
<210> SEQ ID NO 400
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 400

Ile Tyr Thr Ser Asp Asn Tyr Thr Glu Glu Met Gly Ser Gly Asp Tyr
 1               5                  10                  15

Asp Ser

<210> SEQ ID NO 401
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 401

Tyr Thr Ser Asp Asn Tyr Thr Glu Glu Met Gly Ser Gly Asp Tyr Asp
 1               5                  10                  15

Ser Met

<210> SEQ ID NO 402
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 402

Thr Ser Asp Asn Tyr Thr Glu Glu Met Gly Ser Gly Asp Tyr Asp Ser
 1               5                  10                  15

Met Lys

<210> SEQ ID NO 403
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 403

Ser Asp Asn Tyr Thr Glu Glu Met Gly Ser Gly Asp Tyr Asp Ser Met
 1               5                  10                  15

Lys Glu

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 404

Asp Asn Tyr Thr Glu Glu Met Gly Ser Gly Asp Tyr Asp Ser Met Lys
 1               5                  10                  15

Glu Pro
```

-continued

```
<210> SEQ ID NO 405
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 405

Asn Tyr Thr Glu Glu Met Gly Ser Gly Asp Tyr Asp Ser Met Lys Glu
 1               5                  10                  15

Pro Cys

<210> SEQ ID NO 406
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 406

Tyr Thr Glu Glu Met Gly Ser Gly Asp Tyr Asp Ser Met Lys Glu Pro
 1               5                  10                  15

Cys Phe

<210> SEQ ID NO 407
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 407

Thr Glu Glu Met Gly Ser Gly Asp Tyr Asp Ser Met Lys Glu Pro Cys
 1               5                  10                  15

Phe Arg

<210> SEQ ID NO 408
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 408

Glu Glu Met Gly Ser Gly Asp Tyr Asp Ser Met Lys Glu Pro Cys Phe
 1               5                  10                  15

Arg Glu

<210> SEQ ID NO 409
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 409

Glu Met Gly Ser Gly Asp Tyr Asp Ser Met Lys Glu Pro Cys Phe Arg
 1               5                  10                  15

Glu Glu
```

```
<210> SEQ ID NO 410
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 410

Met Gly Ser Gly Asp Tyr Asp Ser Met Lys Glu Pro Cys Phe Arg Glu
 1               5                  10                  15

Glu Asn

<210> SEQ ID NO 411
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 411

Gly Ser Gly Asp Tyr Asp Ser Met Lys Glu Pro Cys Phe Arg Glu Glu
 1               5                  10                  15

Asn Ala

<210> SEQ ID NO 412
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 412

Ser Gly Asp Tyr Asp Ser Met Lys Glu Pro Cys Phe Arg Glu Glu Asn
 1               5                  10                  15

Ala Asn

<210> SEQ ID NO 413
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 413

Gly Asp Tyr Asp Ser Met Lys Glu Pro Cys Phe Arg Glu Glu Asn Ala
 1               5                  10                  15

Asn Phe

<210> SEQ ID NO 414
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 414

Asp Tyr Asp Ser Met Lys Glu Pro Cys Phe Arg Glu Glu Asn Ala Asn
 1               5                  10                  15
```

Phe Asn

<210> SEQ ID NO 415
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 415

Tyr Asp Ser Met Lys Glu Pro Cys Phe Arg Glu Glu Asn Ala Asn Phe
 1               5                  10                  15

Asn Lys

<210> SEQ ID NO 416
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 416

Asp Ser Met Lys Glu Pro Cys Phe Arg Glu Glu Asn Ala Asn Phe Asn
 1               5                  10                  15

Lys Ile

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 417

Ser Met Lys Glu Pro Cys Phe Arg Glu Glu Asn Ala Asn Phe Asn
 1               5                  10                  15

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 418

Met Lys Glu Pro Cys Phe Arg Glu Glu Asn Ala Asn Phe Asn Lys
 1               5                  10                  15

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 419

Lys Glu Pro Cys Phe Arg Glu Glu Asn Ala Asn Phe Asn Lys Ile
 1               5                  10                  15

<210> SEQ ID NO 420
<211> LENGTH: 12

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 420

Glu Pro Cys Phe Arg Glu Glu Asn Ala Asn Phe Asn
 1               5                  10

<210> SEQ ID NO 421
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 421

Pro Cys Phe Arg Glu Glu Asn Ala Asn Phe Asn Lys
 1               5                  10

<210> SEQ ID NO 422
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 422

Cys Phe Arg Glu Glu Asn Ala Asn Phe Asn Lys Ile
 1               5                  10

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 423

Arg Glu Glu Asn Ala Asn Phe Asn Lys
 1               5

<210> SEQ ID NO 424
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 424

Met Ala Glu His Asp Tyr His Glu Asp Tyr Gly Phe Ser Ser Phe Asn
 1               5                  10                  15

Asp Ser

<210> SEQ ID NO 425
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 425
```

Ala Glu His Asp Tyr His Glu Asp Tyr Gly Phe Ser Ser Phe Asn Asp
1               5                   10                  15

Ser Ser

<210> SEQ ID NO 426
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 426

Glu His Asp Tyr His Glu Asp Tyr Gly Phe Ser Ser Phe Asn Asp Ser
1               5                   10                  15

Ser Gln

<210> SEQ ID NO 427
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 427

His Asp Tyr His Glu Asp Tyr Gly Phe Ser Ser Phe Asn Asp Ser Ser
1               5                   10                  15

Gln Glu

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 428

Asp Tyr His Glu Asp Tyr Gly Phe Ser Ser Phe Asn Asp Ser Ser Gln
1               5                   10                  15

Glu Glu

<210> SEQ ID NO 429
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 429

Tyr His Glu Asp Tyr Gly Phe Ser Ser Phe Asn Asp Ser Ser Gln Glu
1               5                   10                  15

Glu His

<210> SEQ ID NO 430
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 430

His Glu Asp Tyr Gly Phe Ser Ser Phe Asn Asp Ser Ser Gln Glu Glu
 1               5                   10                  15

His Gln

<210> SEQ ID NO 431
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 431

Glu Asp Tyr Gly Phe Ser Ser Phe Asn Asp Ser Ser Gln Glu Glu His
 1               5                   10                  15

Gln Ala

<210> SEQ ID NO 432
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 432

Asp Tyr Gly Phe Ser Ser Phe Asn Asp Ser Ser Gln Glu Glu His Gln
 1               5                   10                  15

Ala Phe

<210> SEQ ID NO 433
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 433

Tyr Gly Phe Ser Ser Phe Asn Asp Ser Ser Gln Glu Glu His Gln Ala
 1               5                   10                  15

Phe Leu

<210> SEQ ID NO 434
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 434

Gly Phe Ser Ser Phe Asn Asp Ser Ser Gln Glu Glu His Gln Ala Phe
 1               5                   10                  15

Leu Gln

<210> SEQ ID NO 435
<211> LENGTH: 18
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 435

Phe Ser Ser Phe Asn Asp Ser Ser Gln Glu Glu His Gln Ala Phe Leu
 1               5                  10                  15

Gln Phe

<210> SEQ ID NO 436
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 436

Ser Ser Phe Asn Asp Ser Ser Gln Glu Glu His Gln Ala Phe Leu Gln
 1               5                  10                  15

Phe Ser

<210> SEQ ID NO 437
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 437

Ser Phe Asn Asp Ser Ser Gln Glu Glu His Gln Ala Phe Leu Gln Phe
 1               5                  10                  15

Ser Lys

<210> SEQ ID NO 438
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 438

Phe Asn Asp Ser Ser Gln Glu Glu His Gln Ala Phe Leu Gln Phe Ser
 1               5                  10                  15

Lys Val

<210> SEQ ID NO 439
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 439

Asn Asp Ser Ser Gln Glu Glu His Gln Ala Phe Leu Gln Phe Ser
 1               5                  10                  15

<210> SEQ ID NO 440
<211> LENGTH: 15
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 440

Asp Ser Ser Gln Glu Glu His Gln Ala Phe Leu Gln Phe Ser Lys
 1               5                  10                  15

<210> SEQ ID NO 441
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 441

Ser Ser Gln Glu Glu His Gln Ala Phe Leu Gln Phe Ser Lys Val
 1               5                  10                  15

<210> SEQ ID NO 442
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 442

Ser Gln Glu Glu His Gln Ala Phe Leu Gln Phe Ser
 1               5                  10

<210> SEQ ID NO 443
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 443

Gln Glu Glu His Gln Ala Phe Leu Gln Phe Ser Lys
 1               5                  10

<210> SEQ ID NO 444
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 444

Glu Glu His Gln Ala Phe Leu Gln Phe Ser Lys Val
 1               5                  10

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 445

Glu His Gln Ala Phe Leu Gln Phe Ser
 1               5

<210> SEQ ID NO 446
<211> LENGTH: 9
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 446

His Gln Ala Phe Leu Gln Phe Ser Lys
 1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 447

Gln Ala Phe Leu Gln Phe Ser Lys Val
 1               5

<210> SEQ ID NO 448
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 448

Met Asp Tyr Gln Val Ser Ser Pro Ile Tyr Asp Ile Asn Tyr Tyr Thr
 1               5                  10                  15

Ser Glu

<210> SEQ ID NO 449
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 449

Ala Asp Tyr Gln Val Ser Ser Pro Ile Tyr Asp Ile Asn Tyr Tyr Thr
 1               5                  10                  15

Ser Glu

<210> SEQ ID NO 450
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 450

Met Ala Tyr Gln Val Ser Ser Pro Ile Tyr Asp Ile Asn Tyr Tyr Thr
 1               5                  10                  15

Ser Glu

<210> SEQ ID NO 451
<211> LENGTH: 18
<212> TYPE: PRT
<213> ORGANISM: Artificial Sequence
<220> FEATURE:
<223> OTHER INFORMATION: Description of Artificial Sequence: binding
```

<400> SEQUENCE: 451

Met Asp Ala Gln Val Ser Ser Pro Ile Tyr Asp Ile Asn Tyr Tyr Thr
1               5                   10                  15

Ser Glu

<210> SEQ ID NO 452
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 452

Met Asp Tyr Ala Val Ser Ser Pro Ile Tyr Asp Ile Asn Tyr Tyr Thr
1               5                   10                  15

Ser Glu

<210> SEQ ID NO 453
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 453

Met Asp Tyr Gln Ala Ser Ser Pro Ile Tyr Asp Ile Asn Tyr Tyr Thr
1               5                   10                  15

Ser Glu

<210> SEQ ID NO 454
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 454

Met Asp Tyr Gln Val Ala Ser Pro Ile Tyr Asp Ile Asn Tyr Tyr Thr
1               5                   10                  15

Ser Glu

<210> SEQ ID NO 455
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 455

Met Asp Tyr Gln Val Ser Ala Pro Ile Tyr Asp Ile Asn Tyr Tyr Thr
1               5                   10                  15

Ser Glu

<210> SEQ ID NO 456
<211> LENGTH: 18
<212> TYPE: PRT
<213> ORGANISM: Artificial Sequence
<220> FEATURE:

-continued

```
<223> OTHER INFORMATION: Description of Artificial Sequence: binding
      peptide

<400> SEQUENCE: 456

Met Asp Tyr Gln Val Ser Ser Ala Ile Tyr Asp Ile Asn Tyr Tyr Thr
 1               5                  10                  15

Ser Glu

<210> SEQ ID NO 457
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 457

Met Asp Tyr Gln Val Ser Ser Pro Ala Tyr Asp Ile Asn Tyr Tyr Thr
 1               5                  10                  15

Ser Glu

<210> SEQ ID NO 458
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 458

Met Asp Tyr Gln Val Ser Ser Pro Ile Ala Asp Ile Asn Tyr Tyr Thr
 1               5                  10                  15

Ser Glu

<210> SEQ ID NO 459
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 459

Met Asp Tyr Gln Val Ser Ser Pro Ile Tyr Ala Ile Asn Tyr Tyr Thr
 1               5                  10                  15

Ser Glu

<210> SEQ ID NO 460
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 460

Met Asp Tyr Gln Val Ser Ser Pro Ile Tyr Asp Ala Asn Tyr Tyr Thr
 1               5                  10                  15

Ser Glu

<210> SEQ ID NO 461
<211> LENGTH: 18
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 461

Met Asp Tyr Gln Val Ser Ser Pro Ile Tyr Asp Ile Ala Tyr Tyr Thr
1               5                   10                  15

Ser Glu

<210> SEQ ID NO 462
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 462

Met Asp Tyr Gln Val Ser Ser Pro Ile Tyr Asp Ile Asn Ala Tyr Thr
1               5                   10                  15

Ser Glu

<210> SEQ ID NO 463
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 463

Met Asp Tyr Gln Val Ser Ser Pro Ile Tyr Asp Ile Asn Tyr Ala Thr
1               5                   10                  15

Ser Glu

<210> SEQ ID NO 464
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 464

Met Asp Tyr Gln Val Ser Ser Pro Ile Tyr Asp Ile Asn Tyr Tyr Ala
1               5                   10                  15

Ser Glu

<210> SEQ ID NO 465
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 465

Met Asp Tyr Gln Val Ser Ser Pro Ile Tyr Asp Ile Asn Tyr Tyr Thr
1               5                   10                  15

Ala Glu

<210> SEQ ID NO 466
<211> LENGTH: 18
<212> TYPE: PRT
```

<213> ORGANISM: Artificial Sequence
<220> FEATURE:
<223> OTHER INFORMATION: Description of Artificial Sequence: binding
      peptide

<400> SEQUENCE: 466

Met Asp Tyr Gln Val Ser Ser Pro Ile Tyr Asp Ile Asn Tyr Tyr Thr
 1               5                  10                  15
Ser Ala

<210> SEQ ID NO 467
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 467

Met Glu Gly Ile Ser Ile Tyr Thr Ser Asp Asn Tyr Thr Glu Glu Met
 1               5                  10                  15
Gly Ser

<210> SEQ ID NO 468
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 468

Ala Glu Gly Ile Ser Ile Tyr Thr Ser Asp Asn Tyr Thr Glu Glu Met
 1               5                  10                  15
Gly Ser

<210> SEQ ID NO 469
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 469

Met Ala Gly Ile Ser Ile Tyr Thr Ser Asp Asn Tyr Thr Glu Glu Met
 1               5                  10                  15
Gly Ser

<210> SEQ ID NO 470
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 470

Met Glu Ala Ile Ser Ile Tyr Thr Ser Asp Asn Tyr Thr Glu Glu Met
 1               5                  10                  15
Gly Ser

<210> SEQ ID NO 471
<211> LENGTH: 18

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 471

Met Glu Gly Ala Ser Ile Tyr Thr Ser Asp Asn Tyr Thr Glu Glu Met
 1               5                  10                  15

Gly Ser

<210> SEQ ID NO 472
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 472

Met Glu Gly Ile Ala Ile Tyr Thr Ser Asp Asn Tyr Thr Glu Glu Met
 1               5                  10                  15

Gly Ser

<210> SEQ ID NO 473
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 473

Met Glu Gly Ile Ser Ala Tyr Thr Ser Asp Asn Tyr Thr Glu Glu Met
 1               5                  10                  15

Gly Ser

<210> SEQ ID NO 474
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 474

Met Glu Gly Ile Ser Ile Ala Thr Ser Asp Asn Tyr Thr Glu Glu Met
 1               5                  10                  15

Gly Ser

<210> SEQ ID NO 475
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 475

Met Glu Gly Ile Ser Ile Tyr Ala Ser Asp Asn Tyr Thr Glu Glu Met
 1               5                  10                  15

Gly Ser

<210> SEQ ID NO 476
```

```
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 476

Met Glu Gly Ile Ser Ile Tyr Thr Ala Asp Asn Tyr Thr Glu Glu Met
 1               5                  10                  15

Gly Ser

<210> SEQ ID NO 477
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 477

Met Glu Gly Ile Ser Ile Tyr Thr Ser Ala Asn Tyr Thr Glu Glu Met
 1               5                  10                  15

Gly Ser

<210> SEQ ID NO 478
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 478

Met Glu Gly Ile Ser Ile Tyr Thr Ser Asp Ala Tyr Thr Glu Glu Met
 1               5                  10                  15

Gly Ser

<210> SEQ ID NO 479
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 479

Met Glu Gly Ile Ser Ile Tyr Thr Ser Asp Asn Ala Thr Glu Glu Met
 1               5                  10                  15

Gly Ser

<210> SEQ ID NO 480
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 480

Met Glu Gly Ile Ser Ile Tyr Thr Ser Asp Asn Tyr Ala Glu Glu Met
 1               5                  10                  15

Gly Ser
```

<210> SEQ ID NO 481
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 481

Met Glu Gly Ile Ser Ile Tyr Thr Ser Asp Asn Tyr Thr Ala Glu Met
 1               5                  10                  15
Gly Ser

<210> SEQ ID NO 482
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 482

Met Glu Gly Ile Ser Ile Tyr Thr Ser Asp Asn Tyr Thr Glu Ala Met
 1               5                  10                  15
Gly Ser

<210> SEQ ID NO 483
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 483

Met Glu Gly Ile Ser Ile Tyr Thr Ser Asp Asn Tyr Thr Glu Glu Ala
 1               5                  10                  15
Gly Ser

<210> SEQ ID NO 484
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 484

Met Glu Gly Ile Ser Ile Tyr Thr Ser Asp Asn Tyr Thr Glu Glu Met
 1               5                  10                  15
Ala Ser

<210> SEQ ID NO 485
<211> LENGTH: 18
<212> TYPE: PRT
<213> ORGANISM: Artificial Sequence
<220> FEATURE:
<223> OTHER INFORMATION: Description of Artificial Sequence: binding peptide

<400> SEQUENCE: 485

Met Glu Gly Ile Ser Ile Tyr Thr Ser Asp Asn Tyr Thr Glu Glu Met
 1               5                  10                  15
Gly Ala

```
<210> SEQ ID NO 486
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 486

Glu Glu His Gln Ala Phe Leu Gln Phe Ser Lys Val Phe Leu Pro Cys
 1               5                  10                  15

Met Tyr

<210> SEQ ID NO 487
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 487

Ala Glu His Gln Ala Phe Leu Gln Phe Ser Lys Val Phe Leu Pro Cys
 1               5                  10                  15

Met Tyr

<210> SEQ ID NO 488
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 488

Glu Ala His Gln Ala Phe Leu Gln Phe Ser Lys Val Phe Leu Pro Cys
 1               5                  10                  15

Met Tyr

<210> SEQ ID NO 489
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 489

Glu Glu Ala Gln Ala Phe Leu Gln Phe Ser Lys Val Phe Leu Pro Cys
 1               5                  10                  15

Met Tyr

<210> SEQ ID NO 490
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 490

Glu Glu His Ala Ala Phe Leu Gln Phe Ser Lys Val Phe Leu Pro Cys
 1               5                  10                  15

Met Tyr
```

<210> SEQ ID NO 491
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 491

Glu Glu His Gln Ala Phe Leu Gln Phe Ser Lys Val Phe Leu Pro Cys
 1               5                  10                  15

Met Tyr

<210> SEQ ID NO 492
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 492

Glu Glu His Gln Ala Ala Leu Gln Phe Ser Lys Val Phe Leu Pro Cys
 1               5                  10                  15

Met Tyr

<210> SEQ ID NO 493
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 493

Glu Glu His Gln Ala Phe Ala Gln Phe Ser Lys Val Phe Leu Pro Cys
 1               5                  10                  15

Met Tyr

<210> SEQ ID NO 494
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 494

Glu Glu His Gln Ala Phe Leu Ala Phe Ser Lys Val Phe Leu Pro Cys
 1               5                  10                  15

Met Tyr

<210> SEQ ID NO 495
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 495

Glu Glu His Gln Ala Phe Leu Gln Ala Ser Lys Val Phe Leu Pro Cys
 1               5                  10                  15

Met Tyr

<210> SEQ ID NO 496
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 496

Glu Glu His Gln Ala Phe Leu Gln Phe Ala Lys Val Phe Leu Pro Cys
 1               5                  10                  15

Met Tyr

<210> SEQ ID NO 497
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 497

Glu Glu His Gln Ala Phe Leu Gln Phe Ser Ala Val Phe Leu Pro Cys
 1               5                  10                  15

Met Tyr

<210> SEQ ID NO 498
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 498

Glu Glu His Gln Ala Phe Leu Gln Phe Ser Lys Ala Phe Leu Pro Cys
 1               5                  10                  15

Met Tyr

<210> SEQ ID NO 499
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 499

Glu Glu His Gln Ala Phe Leu Gln Phe Ser Lys Val Ala Leu Pro Cys
 1               5                  10                  15

Met Tyr

<210> SEQ ID NO 500
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 500

Glu Glu His Gln Ala Phe Leu Gln Phe Ser Lys Val Phe Ala Pro Cys
 1               5                  10                  15

Met Tyr

<210> SEQ ID NO 501
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 501

Glu Glu His Gln Ala Phe Leu Gln Phe Ser Lys Val Phe Leu Ala Cys
 1               5                  10                  15
Met Tyr

<210> SEQ ID NO 502
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 502

Glu Glu His Gln Ala Phe Leu Gln Phe Ser Lys Val Phe Leu Pro Ala
 1               5                  10                  15
Met Tyr

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 503

Glu Glu His Gln Ala Phe Leu Gln Phe Ser Lys Val Phe Leu Pro Cys
 1               5                  10                  15
Ala Tyr

<210> SEQ ID NO 504
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 504

Glu Glu His Gln Ala Phe Leu Gln Phe Ser Lys Val Phe Leu Pro Cys
 1               5                  10                  15
Met Ala

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 505

Asp Thr Tyr Ile Cys Glu Val Glu Asp

```
<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 506

Lys Glu Glu Val Gln Leu Leu Val Phe
 1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 507

Glu Glu Val Gln Leu Leu Val Phe Gly
 1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 508

Glu Val Gln Leu Leu Val Phe Gly Leu
 1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 509

Glu Gln Val Glu Phe Ser Phe Pro Leu
 1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 510

Gln Val Glu Phe Ser Phe Pro Leu Ala
 1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: binding
```

-continued

```
peptide

<400> SEQUENCE: 511

Val Glu Phe Ser Phe Pro Leu Ala Phe
1               5

<210> SEQ ID NO 512
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 512

Cys Glu Val Glu Asp Gln Lys Glu Glu Val Gln Leu Leu Val Phe
1               5                   10                  15

<210> SEQ ID NO 513
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 513

Glu Val Glu Asp Gln Lys Glu Glu Val Gln Leu Leu Val Phe Gly
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 514

Val Glu Asp Gln Lys Glu Glu Val Gln Leu Leu Val Phe Gly Leu
1               5                   10                  15

<210> SEQ ID NO 515
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 515

Glu Asp Gln Lys Glu Glu Val Gln Leu Leu Val Phe Gly Leu Thr
1               5                   10                  15

<210> SEQ ID NO 516
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 516

Asp Gln Lys Glu Glu Val Gln Leu Leu Val Phe Gly Leu Thr Ala
1               5                   10                  15

<210> SEQ ID NO 517
```

-continued

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 517

Gln Lys Glu Glu Val Gln Leu Leu Val Phe Gly Leu Thr Ala Asn
 1               5                  10                  15

<210> SEQ ID NO 518
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 518

Lys Glu Glu Val Gln Leu Leu Val Phe Gly Leu Thr Ala Asn Ser
 1               5                  10                  15

<210> SEQ ID NO 519
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 519

Glu Glu Val Gln Leu Leu Val Phe Gly Leu Thr Ala Asn Ser Asp
 1               5                  10                  15

<210> SEQ ID NO 520
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 520

Glu Val Gln Leu Leu Val Phe Gly Leu Thr Ala Asn Ser Asp Thr
 1               5                  10                  15

<210> SEQ ID NO 521
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 521

Asp Thr His Leu Leu Gln Gly Gln Ser Leu Thr Leu Thr Leu Glu
 1               5                  10                  15

<210> SEQ ID NO 522
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 522
```

Thr His Leu Leu Gln Gly Gln Ser Leu Thr Leu Thr Leu Glu Ser
1               5                  10                 15

<210> SEQ ID NO 523
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 523

His Leu Leu Gln Gly Gln Ser Leu Thr Leu Thr Leu Glu Ser Pro
1               5                  10                 15

<210> SEQ ID NO 524
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 524

Lys Lys Glu Gly Glu Gln Val Glu Phe Ser Phe Pro Leu Ala Phe
1               5                  10                 15

<210> SEQ ID NO 525
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 525

Lys Glu Gly Glu Gln Val Glu Phe Ser Phe Pro Leu Ala Phe Thr
1               5                  10                 15

<210> SEQ ID NO 526
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 526

Glu Gly Glu Gln Val Glu Phe Ser Phe Pro Leu Ala Phe Thr Val
1               5                  10                 15

<210> SEQ ID NO 527
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 527

Gly Glu Gln Val Glu Phe Ser Phe Pro Leu Ala Phe Thr Val Glu
1               5                  10                 15

<210> SEQ ID NO 528
<211> LENGTH: 15
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 528

Glu Gln Val Glu Phe Ser Phe Pro Leu Ala Phe Thr Val Glu Lys
 1               5                  10                  15

<210> SEQ ID NO 529
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 529

Gln Val Glu Phe Ser Phe Pro Leu Ala Phe Thr Val Glu Lys Leu
 1               5                  10                  15

<210> SEQ ID NO 530
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 530

Ile Glu Asp Ser Asp Thr Tyr Ile Cys Glu Val Glu
 1               5                  10

<210> SEQ ID NO 531
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 531

Glu Asp Gln Lys Glu Glu Val Gln Leu Leu Val Phe
 1               5                  10

<210> SEQ ID NO 532
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 532

Asp Gln Lys Glu Glu Val Gln Leu Leu Val Phe Gly
 1               5                  10

<210> SEQ ID NO 533
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 533

Gln Lys Glu Glu Val Gln Leu Leu Val Phe Gly Leu
 1               5                  10
```

```
<210> SEQ ID NO 534
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 534

Lys Glu Glu Val Gln Leu Leu Val Phe Gly Leu Thr
 1               5                  10

<210> SEQ ID NO 535
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 535

Glu Glu Val Gln Leu Leu Val Phe Gly Leu Thr Ala
 1               5                  10

<210> SEQ ID NO 536
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 536

Glu Val Gln Leu Leu Val Phe Gly Leu Thr Ala Asn
 1               5                  10

<210> SEQ ID NO 537
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 537

Leu Leu Gln Gly Gln Ser Leu Thr Leu Thr Leu Glu
 1               5                  10

<210> SEQ ID NO 538
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 538

Glu Gly Glu Gln Val Glu Phe Ser Phe Pro Leu Ala
 1               5                  10

<210> SEQ ID NO 539
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 539
```

```
Gly Glu Gln Val Glu Phe Ser Phe Pro Leu Ala Phe
 1               5                  10
```

<210> SEQ ID NO 540
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 540

```
Glu Gln Val Glu Phe Ser Phe Pro Leu Ala Phe Thr
 1               5                  10
```

<210> SEQ ID NO 541
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 541

```
Gln Val Glu Phe Ser Phe Pro Leu Ala Phe Thr Val
 1               5                  10
```

<210> SEQ ID NO 542
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 542

```
Asp Thr Tyr Ile Cys Glu Val Glu Asp Gln Lys Glu Glu Val Gln Leu
 1               5                  10                  15

Leu Val
```

<210> SEQ ID NO 543
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 543

```
Thr Tyr Ile Cys Glu Val Glu Asp Gln Lys Glu Glu Val Gln Leu Leu
 1               5                  10                  15

Val Phe
```

<210> SEQ ID NO 544
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 544

```
Tyr Ile Cys Glu Val Glu Asp Gln Lys Glu Glu Val Gln Leu Leu Val
 1               5                  10                  15

Phe Gly
```

<210> SEQ ID NO 545
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 545

Ile Cys Glu Val Glu Asp Gln Lys Glu Glu Val Gln Leu Leu Val Phe
 1               5                  10                  15

Gly Leu

<210> SEQ ID NO 546
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 546

Cys Glu Val Glu Asp Gln Lys Glu Glu Val Gln Leu Leu Val Phe Gly
 1               5                  10                  15

Leu Thr

<210> SEQ ID NO 547
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 547

Glu Val Glu Asp Gln Lys Glu Glu Val Gln Leu Leu Val Phe Gly Leu
 1               5                  10                  15

Thr Ala

<210> SEQ ID NO 548
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 548

Val Glu Asp Gln Lys Glu Glu Val Gln Leu Leu Val Phe Gly Leu Thr
 1               5                  10                  15

Ala Asn

<210> SEQ ID NO 549
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 549

Glu Asp Gln Lys Glu Glu Val Gln Leu Leu Val Phe Gly Leu Thr Ala
 1               5                  10                  15

Asn Ser

<210> SEQ ID NO 550
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 550

Asp Gln Lys Glu Glu Val Gln Leu Leu Val Phe Gly Leu Thr Ala Asn
 1               5                  10                  15

Ser Asp

<210> SEQ ID NO 551
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 551

Gln Lys Glu Glu Val Gln Leu Leu Val Phe Gly Leu Thr Ala Asn Ser
 1               5                  10                  15

Asp Thr

<210> SEQ ID NO 552
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 552

Ala Asn Ser Asp Thr His Leu Leu Gln Gly Gln Ser Leu Thr Leu Thr
 1               5                  10                  15

Leu Glu

<210> SEQ ID NO 553
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 553

Asn Ser Asp Thr His Leu Leu Gln Gly Gln Ser Leu Thr Leu Thr Leu
 1               5                  10                  15

Glu Ser

<210> SEQ ID NO 554
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 554

Ser Asp Thr His Leu Leu Gln Gly Gln Ser Leu Thr Leu Thr Leu Glu
 1               5                  10                  15

Ser Pro

<210> SEQ ID NO 555
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 555

Ile Val Tyr Lys Lys Glu Gly Glu Gln Val Glu Phe Ser Phe Pro Leu
 1               5                  10                  15

Ala Phe

<210> SEQ ID NO 556
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 556

Val Tyr Lys Lys Glu Gly Glu Gln Val Glu Phe Ser Phe Pro Leu Ala
 1               5                  10                  15

Phe Thr

<210> SEQ ID NO 557
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 557

Tyr Lys Lys Glu Gly Glu Gln Val Glu Phe Ser Phe Pro Leu Ala Phe
 1               5                  10                  15

Thr Val

<210> SEQ ID NO 558
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 558

Lys Lys Glu Gly Glu Gln Val Glu Phe Ser Phe Pro Leu Ala Phe Thr
 1               5                  10                  15

Val Glu

<210> SEQ ID NO 559
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 559

Lys Glu Gly Glu Gln Val Glu Phe Ser Phe Pro Leu Ala Phe Thr Val

```
                1               5                  10                 15
Glu Lys

<210> SEQ ID NO 560
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 560

Glu Gly Glu Gln Val Glu Phe Ser Phe Pro Leu Ala Phe Thr Val Glu
  1               5                  10                 15

Lys Leu

<210> SEQ ID NO 561
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 561

Gly Glu Gln Val Glu Phe Ser Phe Pro Leu Ala Phe Thr Val Glu Lys
  1               5                  10                 15

Leu Thr

<210> SEQ ID NO 562
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 562

Gly Asn Phe Pro Leu Ile Ile Lys Asn Leu Lys Ile Glu Asp Ser Asp
  1               5                  10                 15

Thr Tyr Ile Cys Glu
            20

<210> SEQ ID NO 563
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 563

Asn Phe Pro Leu Ile Ile Lys Asn Leu Lys Ile Glu Asp Ser Asp Thr
  1               5                  10                 15

Tyr Ile Cys Glu Val
            20

<210> SEQ ID NO 564
<211> LENGTH: 21
<212> TYPE: PRT
<213> ORGANISM: Artificial Sequence
<220> FEATURE:
<223> OTHER INFORMATION: Description of Artificial Sequence: binding
      peptide
```

-continued

```
<400> SEQUENCE: 564

Phe Pro Leu Ile Ile Lys Asn Leu Lys Ile Glu Asp Ser Asp Thr Tyr
  1               5                  10                  15

Ile Cys Glu Val Glu
            20

<210> SEQ ID NO 565
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 565

Pro Leu Ile Ile Lys Asn Leu Lys Ile Glu Asp Ser Asp Thr Tyr Ile
  1               5                  10                  15

Cys Glu Val Glu Asp
            20

<210> SEQ ID NO 566
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 566

Leu Ile Ile Lys Asn Leu Lys Ile Glu Asp Ser Asp Thr Tyr Ile Cys
  1               5                  10                  15

Glu Val Glu Asp Gln
            20

<210> SEQ ID NO 567
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 567

Ile Ile Lys Asn Leu Lys Ile Glu Asp Ser Asp Thr Tyr Ile Cys Glu
  1               5                  10                  15

Val Glu Asp Gln Lys
            20

<210> SEQ ID NO 568
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 568

Ile Lys Asn Leu Lys Ile Glu Asp Ser Asp Thr Tyr Ile Cys Glu Val
  1               5                  10                  15

Glu Asp Gln Lys Glu
            20

<210> SEQ ID NO 569
<211> LENGTH: 21
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 569

Lys Asn Leu Lys Ile Glu Asp Ser Asp Thr Tyr Ile Cys Glu Val Glu
 1               5                  10                  15

Asp Gln Lys Glu Glu
            20

<210> SEQ ID NO 570
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 570

Leu Lys Ile Glu Asp Ser Asp Thr Tyr Ile Cys Glu Val Glu Asp Gln
 1               5                  10                  15

Lys Glu Glu Val Gln
            20

<210> SEQ ID NO 571
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 571

Lys Ile Glu Asp Ser Asp Thr Tyr Ile Cys Glu Val Glu Asp Gln Lys
 1               5                  10                  15

Glu Glu Val Gln Leu
            20

<210> SEQ ID NO 572
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 572

Ile Glu Asp Ser Asp Thr Tyr Ile Cys Glu Val Glu Asp Gln Lys Glu
 1               5                  10                  15

Glu Val Gln Leu Leu
            20

<210> SEQ ID NO 573
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 573

Glu Asp Ser Asp Thr Tyr Ile Cys Glu Val Glu Asp Gln Lys Glu Glu
 1               5                  10                  15
```

-continued

```
Val Gln Leu Leu Val
            20

<210> SEQ ID NO 574
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 574

Asp Ser Asp Thr Tyr Ile Cys Glu Val Glu Asp Gln Lys Glu Glu Val
 1               5                  10                  15

Gln Leu Leu Val Phe
            20

<210> SEQ ID NO 575
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 575

Ser Asp Thr Tyr Ile Cys Glu Val Glu Asp Gln Lys Glu Glu Val Gln
 1               5                  10                  15

Leu Leu Val Phe Gly
            20

<210> SEQ ID NO 576
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 576

Asp Thr Tyr Ile Cys Glu Val Glu Asp Gln Lys Glu Glu Val Gln Leu
 1               5                  10                  15

Leu Val Phe Gly Leu
            20

<210> SEQ ID NO 577
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 577

Thr Tyr Ile Cys Glu Val Glu Asp Gln Lys Glu Glu Val Gln Leu Leu
 1               5                  10                  15

Val Phe Gly Leu Thr
            20

<210> SEQ ID NO 578
<211> LENGTH: 21
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 578

Tyr Ile Cys Glu Val Glu Asp Gln Lys Glu Val Gln Leu Leu Val
 1               5                  10                  15

Phe Gly Leu Thr Ala
            20

<210> SEQ ID NO 579
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 579

Ile Cys Glu Val Glu Asp Gln Lys Glu Val Gln Leu Leu Val Phe
 1               5                  10                  15

Gly Leu Thr Ala Asn
            20

<210> SEQ ID NO 580
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 580

Cys Glu Val Glu Asp Gln Lys Glu Val Gln Leu Leu Val Phe Gly
 1               5                  10                  15

Leu Thr Ala Asn Ser
            20

<210> SEQ ID NO 581
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 581

Phe Gly Leu Thr Ala Asn Ser Asp Thr His Leu Leu Gln Gly Gln Ser
 1               5                  10                  15

Leu Thr Leu Thr Leu
            20

<210> SEQ ID NO 582
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 582

Gly Leu Thr Ala Asn Ser Asp Thr His Leu Leu Gln Gly Gln Ser Leu
 1               5                  10                  15

Thr Leu Thr Leu Glu
            20

<210> SEQ ID NO 583
```

```
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 583
```

Leu Thr Ala Asn Ser Asp Thr His Leu Leu Gln Gly Gln Ser Leu Thr
 1               5                  10                  15

Leu Thr Leu Glu Ser
            20

```
<210> SEQ ID NO 584
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 584
```

Thr Ala Asn Ser Asp Thr His Leu Leu Gln Gly Gln Ser Leu Thr Leu
 1               5                  10                  15

Thr Leu Glu Ser Pro
            20

```
<210> SEQ ID NO 585
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 585
```

Phe Gln Lys Ala Ser Ser Ile Val Tyr Lys Lys Glu Gly Glu Gln Val
 1               5                  10                  15

Glu Phe Ser Phe Pro
            20

```
<210> SEQ ID NO 586
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 586
```

Gln Lys Ala Ser Ser Ile Val Tyr Lys Lys Glu Gly Glu Gln Val Glu
 1               5                  10                  15

Phe Ser Phe Pro Leu
            20

```
<210> SEQ ID NO 587
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 587
```

Lys Ala Ser Ser Ile Val Tyr Lys Lys Glu Gly Glu Gln Val Glu Phe
 1               5                  10                  15

Ser Phe Pro Leu Ala
            20

<210> SEQ ID NO 588
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 588

Ala Ser Ser Ile Val Tyr Lys Lys Glu Gly Glu Gln Val Glu Phe Ser
 1               5                  10                  15

Phe Pro Leu Ala Phe
            20

<210> SEQ ID NO 589
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 589

Ser Ser Ile Val Tyr Lys Lys Glu Gly Glu Gln Val Glu Phe Ser Phe
 1               5                  10                  15

Pro Leu Ala Phe Thr
            20

<210> SEQ ID NO 590
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 590

Ser Ile Val Tyr Lys Lys Glu Gly Glu Gln Val Glu Phe Ser Phe Pro
 1               5                  10                  15

Leu Ala Phe Thr Val
            20

<210> SEQ ID NO 591
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 591

Ile Val Tyr Lys Lys Glu Gly Glu Gln Val Glu Phe Ser Phe Pro Leu
 1               5                  10                  15

Ala Phe Thr Val Glu
            20

<210> SEQ ID NO 592
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 592

Phe Ser Phe Pro Leu Ala Phe Thr Val Glu Lys Leu Thr Gly Ser Gly
 1               5                  10                  15

Glu Leu Trp Trp Gln
            20

<210> SEQ ID NO 593
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 593

Ser Phe Pro Leu Ala Phe Thr Val Glu Lys Leu Thr Gly Ser Gly Glu
 1               5                  10                  15

Leu Trp Trp Gln Ala
            20

<210> SEQ ID NO 594
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 594

Phe Pro Leu Ala Phe Thr Val Glu Lys Leu Thr Gly Ser Gly Glu Leu
 1               5                  10                  15

Trp Trp Gln Ala Glu
            20

<210> SEQ ID NO 595
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 595

Pro Leu Ala Phe Thr Val Glu Lys Leu Thr Gly Ser Gly Glu Leu Trp
 1               5                  10                  15

Trp Gln Ala Glu Arg
            20

<210> SEQ ID NO 596
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 596

Leu Ala Phe Thr Val Glu Lys Leu Thr Gly Ser Gly Glu Leu Trp Trp
 1               5                  10                  15

Gln Ala Glu Arg Ala
            20

-continued

```
<210> SEQ ID NO 597
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 597

Leu Trp Asp Gln Gly Asn Phe Pro Leu Ile Ile Lys Asn Leu Lys Ile
 1               5                  10                  15

Glu Asp Ser Asp Thr
            20

<210> SEQ ID NO 598
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 598

Trp Asp Gln Gly Asn Phe Pro Leu Ile Ile Lys Asn Leu Lys Ile Glu
 1               5                  10                  15

Asp Ser Asp Thr Tyr
            20

<210> SEQ ID NO 599
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 599

Asp Gln Gly Asn Phe Pro Leu Ile Ile Lys Asn Leu Lys Ile Glu Asp
 1               5                  10                  15

Ser Asp Thr Tyr Ile
            20

<210> SEQ ID NO 600
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 600

Gln Gly Asn Phe Pro Leu Ile Ile Lys Asn Leu Lys Ile Glu Asp Ser
 1               5                  10                  15

Asp Thr Tyr Ile Cys
            20

<210> SEQ ID NO 601
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 601

Gly Asn Phe Pro Leu Ile Ile Lys Asn Leu Lys Ile Glu Asp Ser Asp
```

```
                1               5              10              15

Thr Tyr Ile Cys Glu
            20

<210> SEQ ID NO 602
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 602

Asn Phe Pro Leu Ile Ile Lys Asn Leu Lys Ile Glu Asp Ser Asp Thr
  1               5              10              15

Tyr Ile Cys Glu Val
            20

<210> SEQ ID NO 603
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 603

Phe Pro Leu Ile Ile Lys Asn Leu Lys Ile Glu Asp Ser Asp Thr Tyr
  1               5              10              15

Ile Cys Glu Val Glu
            20

<210> SEQ ID NO 604
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 604

Pro Leu Ile Ile Lys Asn Leu Lys Ile Glu Asp Ser Asp Thr Tyr Ile
  1               5              10              15

Cys Glu Val Glu Asp
            20

<210> SEQ ID NO 605
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 605

Leu Ile Ile Lys Asn Leu Lys Ile Glu Asp Ser Asp Thr Tyr Ile Cys
  1               5              10              15

Glu Val Glu Asp Gln
            20

<210> SEQ ID NO 606
<211> LENGTH: 21
<212> TYPE: PRT
<213> ORGANISM: Artificial Sequence
<220> FEATURE:
```

```
<223> OTHER INFORMATION: Description of Artificial Sequence: binding
      peptide

<400> SEQUENCE: 606

Ile Ile Lys Asn Leu Lys Ile Glu Asp Ser Asp Thr Tyr Ile Cys Glu
 1               5                  10                  15

Val Glu Asp Gln Lys
            20

<210> SEQ ID NO 607
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 607

Ile Lys Asn Leu Lys Ile Glu Asp Ser Asp Thr Tyr Ile Cys Glu Val
 1               5                  10                  15

Glu Asp Gln Lys Glu
            20

<210> SEQ ID NO 608
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 608

Lys Asn Leu Lys Ile Glu Asp Ser Asp Thr Tyr Ile Cys Glu Val Glu
 1               5                  10                  15

Asp Gln Lys Glu Glu
            20

<210> SEQ ID NO 609
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 609

Asn Leu Lys Ile Glu Asp Ser Asp Thr Tyr Ile Cys Glu Val Glu Asp
 1               5                  10                  15

Gln Lys Glu Glu Val
            20

<210> SEQ ID NO 610
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 610

Leu Lys Ile Glu Asp Ser Asp Thr Tyr Ile Cys Glu Val Glu Asp Gln
 1               5                  10                  15

Lys Glu Glu Val Gln
            20
```

```
<210> SEQ ID NO 611
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 611

Lys Ile Glu Asp Ser Asp Thr Tyr Ile Cys Glu Val Glu Asp Gln Lys
  1               5                  10                  15

Glu Glu Val Gln Leu
             20

<210> SEQ ID NO 612
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 612

Ile Glu Asp Ser Asp Thr Tyr Ile Cys Glu Val Glu Asp Gln Lys Glu
  1               5                  10                  15

Glu Val Gln Leu Leu
             20

<210> SEQ ID NO 613
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 613

Glu Asp Ser Asp Thr Tyr Ile Cys Glu Val Glu Asp Gln Lys Glu Glu
  1               5                  10                  15

Val Gln Leu Leu Val
             20

<210> SEQ ID NO 614
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 614

Asp Ser Asp Thr Tyr Ile Cys Glu Val Glu Asp Gln Lys Glu Glu Val
  1               5                  10                  15

Gln Leu Leu Val Phe
             20

<210> SEQ ID NO 615
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 615
```

Ser Asp Thr Tyr Ile Cys Glu Val Glu Asp Gln Lys Glu Glu Val Gln
 1               5                  10                  15

Leu Leu Val Phe Gly
            20

<210> SEQ ID NO 616
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 616

Asp Thr Tyr Ile Cys Glu Val Glu Asp Gln Lys Glu Glu Val Gln Leu
 1               5                  10                  15

Leu Val Phe Gly Leu
            20

<210> SEQ ID NO 617
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 617

Thr Tyr Ile Cys Glu Val Glu Asp Gln Lys Glu Glu Val Gln Leu Leu
 1               5                  10                  15

Val Phe Gly Leu Thr
            20

<210> SEQ ID NO 618
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 618

Tyr Ile Cys Glu Val Glu Asp Gln Lys Glu Glu Val Gln Leu Leu Val
 1               5                  10                  15

Phe Gly Leu Thr Ala
            20

<210> SEQ ID NO 619
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 619

Ile Cys Glu Val Glu Asp Gln Lys Glu Glu Val Gln Leu Leu Val Phe
 1               5                  10                  15

Gly Leu Thr Ala Asn
            20

<210> SEQ ID NO 620
<211> LENGTH: 21
<212> TYPE: PRT
<213> ORGANISM: Artificial Sequence -continued

```
<220> FEATURE:
<223> OTHER INFORMATION: Description of Artificial Sequence: binding
      peptide

<400> SEQUENCE: 620

Cys Glu Val Glu Asp Gln Lys Glu Glu Val Gln Leu Leu Val Phe Gly
  1               5                  10                  15

Leu Thr Ala Asn Ser
             20

<210> SEQ ID NO 621
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 621

Glu Val Glu Asp Gln Lys Glu Glu Val Gln Leu Leu Val Phe Gly Leu
  1               5                  10                  15

Thr Ala Asn Ser Asp
             20

<210> SEQ ID NO 622
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 622

Val Glu Asp Gln Lys Glu Glu Val Gln Leu Leu Val Phe Gly Leu Thr
  1               5                  10                  15

Ala Asn Ser Asp Thr
             20

<210> SEQ ID NO 623
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 623

Glu Asp Gln Lys Glu Glu Val Gln Leu Leu Val Phe Gly Leu Thr Ala
  1               5                  10                  15

Asn Ser Asp Thr His
             20

<210> SEQ ID NO 624
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 624

Asp Gln Lys Glu Glu Val Gln Leu Leu Val Phe Gly Leu Thr Ala Asn
  1               5                  10                  15

Ser Asp Thr His Leu
             20
```

<210> SEQ ID NO 625
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 625

Gln Lys Glu Glu Val Gln Leu Leu Val Phe Gly Leu Thr Ala Asn Ser
 1               5                  10                  15

Asp Thr His Leu Leu
            20

<210> SEQ ID NO 626
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 626

Lys Glu Glu Val Gln Leu Leu Val Phe Gly Leu Thr Ala Asn Ser Asp
 1               5                  10                  15

Thr His Leu Leu Gln
            20

<210> SEQ ID NO 627
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 627

Glu Glu Val Gln Leu Leu Val Phe Gly Leu Thr Ala Asn Ser Asp Thr
 1               5                  10                  15

His Leu Leu Gln Gly
            20

<210> SEQ ID NO 628
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 628

Glu Val Gln Leu Leu Val Phe Gly Leu Thr Ala Asn Ser Asp Thr His
 1               5                  10                  15

Leu Leu Gln Gly Gln
            20

<210> SEQ ID NO 629
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 629

-continued

```
Val Gln Leu Leu Val Phe Gly Leu Thr Ala Asn Ser Asp Thr His Leu
  1               5                  10                  15

Leu Gln Gly Gln Ser
             20

<210> SEQ ID NO 630
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 630

Gln Leu Leu Val Phe Gly Leu Thr Ala Asn Ser Asp Thr His Leu Leu
  1               5                  10                  15

Gln Gly Gln Ser Leu
             20

<210> SEQ ID NO 631
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 631

Leu Leu Val Phe Gly Leu Thr Ala Asn Ser Asp Thr His Leu Leu Gln
  1               5                  10                  15

Gly Gln Ser Leu Thr
             20

<210> SEQ ID NO 632
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 632

Leu Val Phe Gly Leu Thr Ala Asn Ser Asp Thr His Leu Leu Gln Gly
  1               5                  10                  15

Gln Ser Leu Thr Leu
             20

<210> SEQ ID NO 633
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 633

Val Phe Gly Leu Thr Ala Asn Ser Asp Thr His Leu Leu Gln Gly Gln
  1               5                  10                  15

Ser Leu Thr Leu Thr
             20

<210> SEQ ID NO 634
<211> LENGTH: 21
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 634

Phe Gly Leu Thr Ala Asn Ser Asp Thr His Leu Leu Gln Gly Gln Ser
 1               5                  10                  15

Leu Thr Leu Thr Leu
            20

<210> SEQ ID NO 635
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 635

Gly Leu Thr Ala Asn Ser Asp Thr His Leu Leu Gln Gly Gln Ser Leu
 1               5                  10                  15

Thr Leu Thr Leu Glu
            20

<210> SEQ ID NO 636
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 636

Leu Thr Ala Asn Ser Asp Thr His Leu Leu Gln Gly Gln Ser Leu Thr
 1               5                  10                  15

Leu Thr Leu Glu Ser
            20

<210> SEQ ID NO 637
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 637

Thr Ala Asn Ser Asp Thr His Leu Leu Gln Gly Gln Ser Leu Thr Leu
 1               5                  10                  15

Thr Leu Glu Ser Pro
            20

<210> SEQ ID NO 638
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 638

Thr Trp Thr Cys Thr Val Leu Gln Asn Gln Lys Lys Val Glu Phe Lys
 1               5                  10                  15

Ile Asp Ile Val Val
```

<210> SEQ ID NO 639
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 639

Trp Thr Cys Thr Val Leu Gln Asn Gln Lys Lys Val Glu Phe Lys Ile
 1               5                  10                  15

Asp Ile Val Val Leu
            20

<210> SEQ ID NO 640
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 640

Thr Cys Thr Val Leu Gln Asn Gln Lys Lys Val Glu Phe Lys Ile Asp
 1               5                  10                  15

Ile Val Val Leu Ala
            20

<210> SEQ ID NO 641
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 641

Cys Thr Val Leu Gln Asn Gln Lys Lys Val Glu Phe Lys Ile Asp Ile
 1               5                  10                  15

Val Val Leu Ala Phe
            20

<210> SEQ ID NO 642
<211> LENGTH: 21
<212> TYPE: PRT
<213> ORGANISM: Artificial Sequence
<220> FEATURE:
<223> OTHER INFORMATION: Description of Artificial Sequence: binding peptide

<400> SEQUENCE: 642

Thr Val Leu Gln Asn Gln Lys Lys Val Glu Phe Lys Ile Asp Ile Val
 1               5                  10                  15

Val Leu Ala Phe Gln
            20

<210> SEQ ID NO 643
<211> LENGTH: 21
<212> TYPE: PRT
<213> ORGANISM: Artificial Sequence
<220> FEATURE:
<223> OTHER INFORMATION: Description of Artificial Sequence: binding peptide

```
<400> SEQUENCE: 643

Val Leu Gln Asn Gln Lys Lys Val Glu Phe Lys Ile Asp Ile Val Val
 1               5                  10                  15

Leu Ala Phe Gln Lys
            20

<210> SEQ ID NO 644
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 644

Leu Gln Asn Gln Lys Lys Val Glu Phe Lys Ile Asp Ile Val Val Leu
 1               5                  10                  15

Ala Phe Gln Lys Ala
            20

<210> SEQ ID NO 645
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 645

Gln Asn Gln Lys Lys Val Glu Phe Lys Ile Asp Ile Val Val Leu Ala
 1               5                  10                  15

Phe Gln Lys Ala Ser
            20

<210> SEQ ID NO 646
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 646

Asn Gln Lys Lys Val Glu Phe Lys Ile Asp Ile Val Val Leu Ala Phe
 1               5                  10                  15

Gln Lys Ala Ser Ser
            20

<210> SEQ ID NO 647
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 647

Gln Lys Lys Val Glu Phe Lys Ile Asp Ile Val Val Leu Ala Phe Gln
 1               5                  10                  15

Lys Ala Ser Ser Ile
            20

<210> SEQ ID NO 648
<211> LENGTH: 21
```

<212> TYPE: PRT
<213> ORGANISM: Artificial Sequence
<220> FEATURE:
<223> OTHER INFORMATION: Description of Artificial Sequence: binding
peptide

<400> SEQUENCE: 648

Lys Lys Val Glu Phe Lys Ile Asp Ile Val Val Leu Ala Phe Gln Lys
1               5                   10                  15

Ala Ser Ser Ile Val
            20

<210> SEQ ID NO 649
<211> LENGTH: 21
<212> TYPE: PRT
<213> ORGANISM: Artificial Sequence
<220> FEATURE:
<223> OTHER INFORMATION: Description of Artificial Sequence: binding
peptide

<400> SEQUENCE: 649

Lys Val Glu Phe Lys Ile Asp Ile Val Val Leu Ala Phe Gln Lys Ala
1               5                   10                  15

Ser Ser Ile Val Tyr
            20

<210> SEQ ID NO 650
<211> LENGTH: 21
<212> TYPE: PRT
<213> ORGANISM: Artificial Sequence
<220> FEATURE:
<223> OTHER INFORMATION: Description of Artificial Sequence: binding
peptide

<400> SEQUENCE: 650

Val Glu Phe Lys Ile Asp Ile Val Val Leu Ala Phe Gln Lys Ala Ser
1               5                   10                  15

Ser Ile Val Tyr Lys
            20

<210> SEQ ID NO 651
<211> LENGTH: 21
<212> TYPE: PRT
<213> ORGANISM: Artificial Sequence
<220> FEATURE:
<223> OTHER INFORMATION: Description of Artificial Sequence: binding
peptide

<400> SEQUENCE: 651

Glu Phe Lys Ile Asp Ile Val Val Leu Ala Phe Gln Lys Ala Ser Ser
1               5                   10                  15

Ile Val Tyr Lys Lys
            20

<210> SEQ ID NO 652
<211> LENGTH: 21
<212> TYPE: PRT
<213> ORGANISM: Artificial Sequence
<220> FEATURE:
<223> OTHER INFORMATION: Description of Artificial Sequence: binding
peptide

<400> SEQUENCE: 652

Phe Lys Ile Asp Ile Val Val Leu Ala Phe Gln Lys Ala Ser Ser Ile
1               5                   10                  15

```
Val Tyr Lys Lys Glu
            20
```

```
<210> SEQ ID NO 653
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 653

Lys Ile Asp Ile Val Val Leu Ala Phe Gln Lys Ala Ser Ser Ile Val
 1               5                  10                  15

Tyr Lys Lys Glu Gly
            20
```

```
<210> SEQ ID NO 654
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 654

Ile Asp Ile Val Val Leu Ala Phe Gln Lys Ala Ser Ser Ile Val Tyr
 1               5                  10                  15

Lys Lys Glu Gly Glu
            20
```

```
<210> SEQ ID NO 655
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 655

Asp Ile Val Val Leu Ala Phe Gln Lys Ala Ser Ser Ile Val Tyr Lys
 1               5                  10                  15

Lys Glu Gly Glu Gln
            20
```

```
<210> SEQ ID NO 656
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 656

Ile Val Val Leu Ala Phe Gln Lys Ala Ser Ser Ile Val Tyr Lys Lys
 1               5                  10                  15

Glu Gly Glu Gln Val
            20
```

```
<210> SEQ ID NO 657
<211> LENGTH: 21
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 657

Val Val Leu Ala Phe Gln Lys Ala Ser Ser Ile Val Tyr Lys Lys Glu
 1               5                  10                  15

Gly Glu Gln Val Glu
            20

<210> SEQ ID NO 658
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 658

Val Leu Ala Phe Gln Lys Ala Ser Ser Ile Val Tyr Lys Lys Glu Gly
 1               5                  10                  15

Glu Gln Val Glu Phe
            20

<210> SEQ ID NO 659
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 659

Leu Ala Phe Gln Lys Ala Ser Ser Ile Val Tyr Lys Lys Glu Gly Glu
 1               5                  10                  15

Gln Val Glu Phe Ser
            20

<210> SEQ ID NO 660
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 660

Ala Phe Gln Lys Ala Ser Ser Ile Val Tyr Lys Lys Glu Gly Glu Gln
 1               5                  10                  15

Val Glu Phe Ser Phe
            20

<210> SEQ ID NO 661
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 661

Phe Gln Lys Ala Ser Ser Ile Val Tyr Lys Lys Glu Gly Glu Gln Val
 1               5                  10                  15

Glu Phe Ser Phe Pro
            20

<210> SEQ ID NO 662
```

```
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 662

Gln Lys Ala Ser Ser Ile Val Tyr Lys Lys Glu Gly Glu Gln Val Glu
 1               5                  10                  15

Phe Ser Phe Pro Leu
             20

<210> SEQ ID NO 663
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 663

Lys Ala Ser Ser Ile Val Tyr Lys Lys Glu Gly Glu Gln Val Glu Phe
 1               5                  10                  15

Ser Phe Pro Leu Ala
             20

<210> SEQ ID NO 664
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 664

Ala Ser Ser Ile Val Tyr Lys Lys Glu Gly Glu Gln Val Glu Phe Ser
 1               5                  10                  15

Phe Pro Leu Ala Phe
             20

<210> SEQ ID NO 665
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 665

Ser Ser Ile Val Tyr Lys Lys Glu Gly Glu Gln Val Glu Phe Ser Phe
 1               5                  10                  15

Pro Leu Ala Phe Thr
             20

<210> SEQ ID NO 666
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 666

Ser Ile Val Tyr Lys Lys Glu Gly Glu Gln Val Glu Phe Ser Phe Pro
 1               5                  10                  15
```

```
Leu Ala Phe Thr Val
            20

<210> SEQ ID NO 667
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 667

Ile Val Tyr Lys Lys Glu Gly Glu Gln Val Glu Phe Ser Phe Pro Leu
  1               5                  10                  15

Ala Phe Thr Val Glu
            20

<210> SEQ ID NO 668
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 668

Val Tyr Lys Lys Glu Gly Glu Gln Val Glu Phe Ser Phe Pro Leu Ala
  1               5                  10                  15

Phe Thr Val Glu Lys
            20

<210> SEQ ID NO 669
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 669

Tyr Lys Lys Glu Gly Glu Gln Val Glu Phe Ser Phe Pro Leu Ala Phe
  1               5                  10                  15

Thr Val Glu Lys Leu
            20

<210> SEQ ID NO 670
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 670

Lys Lys Glu Gly Glu Gln Val Glu Phe Ser Phe Pro Leu Ala Phe Thr
  1               5                  10                  15

Val Glu Lys Leu Thr
            20

<210> SEQ ID NO 671
<211> LENGTH: 21
<212> TYPE: PRT
<213> ORGANISM: Artificial Sequence
<220> FEATURE:
<223> OTHER INFORMATION: Description of Artificial Sequence: binding
```

-continued peptide

<400> SEQUENCE: 671

Lys Glu Gly Glu Gln Val Glu Phe Ser Phe Pro Leu Ala Phe Thr Val
 1               5                  10                  15

Glu Lys Leu Thr Gly
            20

<210> SEQ ID NO 672
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 672

Glu Gly Glu Gln Val Glu Phe Ser Phe Pro Leu Ala Phe Thr Val Glu
 1               5                  10                  15

Lys Leu Thr Gly Ser
            20

<210> SEQ ID NO 673
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 673

Gly Glu Gln Val Glu Phe Ser Phe Pro Leu Ala Phe Thr Val Glu Lys
 1               5                  10                  15

Leu Thr Gly Ser Gly
            20

<210> SEQ ID NO 674
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 674

Glu Gln Val Glu Phe Ser Phe Pro Leu Ala Phe Thr Val Glu Lys Leu
 1               5                  10                  15

Thr Gly Ser Gly Glu
            20

<210> SEQ ID NO 675
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 675

Gln Val Glu Phe Ser Phe Pro Leu Ala Phe Thr Val Glu Lys Leu Thr
 1               5                  10                  15

Gly Ser Gly Glu Leu
            20

```
<210> SEQ ID NO 676
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 676

Val Glu Phe Ser Phe Pro Leu Ala Phe Thr Val Glu Lys Leu Thr Gly
 1               5                  10                  15

Ser Gly Glu Leu Trp
            20

<210> SEQ ID NO 677
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 677

Glu Phe Ser Phe Pro Leu Ala Phe Thr Val Glu Lys Leu Thr Gly Ser
 1               5                  10                  15

Gly Glu Leu Trp Trp
            20

<210> SEQ ID NO 678
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 678

Phe Ser Phe Pro Leu Ala Phe Thr Val Glu Lys Leu Thr Gly Ser Gly
 1               5                  10                  15

Glu Leu Trp Trp Gln
            20

<210> SEQ ID NO 679
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 679

Ser Phe Pro Leu Ala Phe Thr Val Glu Lys Leu Thr Gly Ser Gly Glu
 1               5                  10                  15

Leu Trp Trp Gln Ala
            20

<210> SEQ ID NO 680
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 680

Phe Pro Leu Ala Phe Thr Val Glu Lys Leu Thr Gly Ser Gly Glu Leu
```

-continued

```
                1               5              10              15

Trp Trp Gln Ala Glu
            20

<210> SEQ ID NO 681
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 681

Pro Leu Ala Phe Thr Val Glu Lys Leu Thr Gly Ser Gly Glu Leu Trp
  1               5                  10                  15

Trp Gln Ala Glu Arg
            20

<210> SEQ ID NO 682
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 682

Leu Ala Phe Thr Val Glu Lys Leu Thr Gly Ser Gly Glu Leu Trp Trp
  1               5                  10                  15

Gln Ala Glu Arg Ala
            20

<210> SEQ ID NO 683
<211> LENGTH: 21
<212> TYPE: PRT
<213> ORGANISM: Artificial Sequence
<220> FEATURE:
<223> OTHER INFORMATION: Description of Artificial Sequence: binding
      peptide

<400> SEQUENCE: 683

Ala Phe Thr Val Glu Lys Leu Thr Gly Ser Gly Glu Leu Trp Trp Gln
  1               5                  10                  15

Ala Glu Arg Ala Ser
            20

<210> SEQ ID NO 684
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 684

Leu Trp Asp Gln Gly Asn Phe Pro Leu Ile Ile Lys Asn Leu Lys
  1               5                  10                  15

<210> SEQ ID NO 685
<211> LENGTH: 15
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 685

Trp Asp Gln Gly Asn Phe Pro Leu Ile Ile Lys Asn Leu Lys Ile
 1               5                  10                  15

<210> SEQ ID NO 686
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 686

Asp Gln Gly Asn Phe Pro Leu Ile Ile Lys Asn Leu Lys Ile Glu
 1               5                  10                  15

<210> SEQ ID NO 687
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 687

Gln Gly Asn Phe Pro Leu Ile Ile Lys Asn Leu Lys Ile Glu Asp
 1               5                  10                  15

<210> SEQ ID NO 688
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 688

Gly Asn Phe Pro Leu Ile Ile Lys Asn Leu Lys Ile Glu Asp Ser
 1               5                  10                  15

<210> SEQ ID NO 689
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 689

Asn Phe Pro Leu Ile Ile Lys Asn Leu Lys Ile Glu Asp Ser Asp
 1               5                  10                  15

<210> SEQ ID NO 690
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 690

Phe Pro Leu Ile Ile Lys Asn Leu Lys Ile Glu Asp Ser Asp Thr
 1               5                  10                  15

<210> SEQ ID NO 691
<211> LENGTH: 15
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 691

Pro Leu Ile Ile Lys Asn Leu Lys Ile Glu Asp Ser Asp Thr Tyr
 1               5                  10                  15

<210> SEQ ID NO 692
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 692

Leu Ile Ile Lys Asn Leu Lys Ile Glu Asp Ser Asp Thr Tyr Ile
 1               5                  10                  15

<210> SEQ ID NO 693
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 693

Ile Ile Lys Asn Leu Lys Ile Glu Asp Ser Asp Thr Tyr Ile Cys
 1               5                  10                  15

<210> SEQ ID NO 694
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 694

Ile Lys Asn Leu Lys Ile Glu Asp Ser Asp Thr Tyr Ile Cys Glu
 1               5                  10                  15

<210> SEQ ID NO 695
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 695

Lys Asn Leu Lys Ile Glu Asp Ser Asp Thr Tyr Ile Cys Glu Val
 1               5                  10                  15

<210> SEQ ID NO 696
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 696

Asn Leu Lys Ile Glu Asp Ser Asp Thr Tyr Ile Cys Glu Val Glu
 1               5                  10                  15
```

```
<210> SEQ ID NO 697
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 697

Leu Lys Ile Glu Asp Ser Asp Thr Tyr Ile Cys Glu Val Glu Asp
 1               5                  10                  15

<210> SEQ ID NO 698
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 698

Lys Ile Glu Asp Ser Asp Thr Tyr Ile Cys Glu Val Glu Asp Gln
 1               5                  10                  15

<210> SEQ ID NO 699
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 699

Ile Glu Asp Ser Asp Thr Tyr Ile Cys Glu Val Glu Asp Gln Lys
 1               5                  10                  15

<210> SEQ ID NO 700
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 700

Glu Asp Ser Asp Thr Tyr Ile Cys Glu Val Glu Asp Gln Lys Glu
 1               5                  10                  15

<210> SEQ ID NO 701
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 701

Asp Ser Asp Thr Tyr Ile Cys Glu Val Glu Asp Gln Lys Glu Glu
 1               5                  10                  15

<210> SEQ ID NO 702
<211> LENGTH: 15
<212> TYPE: PRT
<213> ORGANISM: Artificial Sequence
<220> FEATURE:
<223> OTHER INFORMATION: Description of Artificial Sequence: binding
      peptide
```

-continued

<400> SEQUENCE: 702

Ser Asp Thr Tyr Ile Cys Glu Val Glu Asp Gln Lys Glu Glu Val
1               5                   10                  15

<210> SEQ ID NO 703
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 703

Asp Thr Tyr Ile Cys Glu Val Glu Asp Gln Lys Glu Glu Val Gln
1               5                   10                  15

<210> SEQ ID NO 704
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 704

Thr Tyr Ile Cys Glu Val Glu Asp Gln Lys Glu Glu Val Gln Leu
1               5                   10                  15

<210> SEQ ID NO 705
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 705

Tyr Ile Cys Glu Val Glu Asp Gln Lys Glu Glu Val Gln Leu Leu
1               5                   10                  15

<210> SEQ ID NO 706
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 706

Ile Cys Glu Val Glu Asp Gln Lys Glu Glu Val Gln Leu Leu Val
1               5                   10                  15

<210> SEQ ID NO 707
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 707

Cys Glu Val Glu Asp Gln Lys Glu Glu Val Gln Leu Leu Val Phe
1               5                   10                  15

<210> SEQ ID NO 708
<211> LENGTH: 15

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 708

Glu Val Glu Asp Gln Lys Glu Val Gln Leu Leu Val Phe Gly
1               5                   10                  15

<210> SEQ ID NO 709
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 709

Val Glu Asp Gln Lys Glu Val Gln Leu Leu Val Phe Gly Leu
1               5                   10                  15

<210> SEQ ID NO 710
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 710

Glu Asp Gln Lys Glu Val Gln Leu Leu Val Phe Gly Leu Thr
1               5                   10                  15

<210> SEQ ID NO 711
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 711

Asp Gln Lys Glu Val Gln Leu Leu Val Phe Gly Leu Thr Ala
1               5                   10                  15

<210> SEQ ID NO 712
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 712

Gln Lys Glu Val Gln Leu Leu Val Phe Gly Leu Thr Ala Asn
1               5                   10                  15

<210> SEQ ID NO 713
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 713

Lys Glu Val Gln Leu Leu Val Phe Gly Leu Thr Ala Asn Ser
```

-continued

```
<210> SEQ ID NO 714
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 714

Glu Glu Val Gln Leu Leu Val Phe Gly Leu Thr Ala Asn Ser Asp
  1               5                  10                  15

<210> SEQ ID NO 715
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 715

Glu Val Gln Leu Leu Val Phe Gly Leu Thr Ala Asn Ser Asp Thr
  1               5                  10                  15

<210> SEQ ID NO 716
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 716

Val Gln Leu Leu Val Phe Gly Leu Thr Ala Asn Ser Asp Thr His
  1               5                  10                  15

<210> SEQ ID NO 717
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 717

Gln Leu Leu Val Phe Gly Leu Thr Ala Asn Ser Asp Thr His Leu
  1               5                  10                  15

<210> SEQ ID NO 718
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 718

Leu Leu Val Phe Gly Leu Thr Ala Asn Ser Asp Thr His Leu Leu
  1               5                  10                  15

<210> SEQ ID NO 719
<211> LENGTH: 15
<212> TYPE: PRT
<213> ORGANISM: Artificial Sequence
<220> FEATURE:
<223> OTHER INFORMATION: Description of Artificial Sequence: binding
```

-continued

<400> SEQUENCE: 719

Leu Val Phe Gly Leu Thr Ala Asn Ser Asp Thr His Leu Leu Gln
 1               5                  10                  15

<210> SEQ ID NO 720
<211> LENGTH: 15
<212> TYPE: PRT
<213> ORGANISM: Artificial Sequence
<220> FEATURE:
<223> OTHER INFORMATION: Description of Artificial Sequence: binding
      peptide <400> SEQUENCE: 720

Val Phe Gly Leu Thr Ala Asn Ser Asp Thr His Leu Leu Gln Gly
 1               5                  10                  15

<210> SEQ ID NO 721
<211> LENGTH: 15
<212> TYPE: PRT
<213> ORGANISM: Artificial Sequence
<220> FEATURE:
<223> OTHER INFORMATION: Description of Artificial Sequence: binding
      peptide <400> SEQUENCE: 721

Phe Gly Leu Thr Ala Asn Ser Asp Thr His Leu Leu Gln Gly Gln
 1               5                  10                  15

<210> SEQ ID NO 722
<211> LENGTH: 15
<212> TYPE: PRT
<213> ORGANISM: Artificial Sequence
<220> FEATURE:
<223> OTHER INFORMATION: Description of Artificial Sequence: binding
      peptide <400> SEQUENCE: 722

Gly Leu Thr Ala Asn Ser Asp Thr His Leu Leu Gln Gly Gln Ser
 1               5                  10                  15

<210> SEQ ID NO 723
<211> LENGTH: 15
<212> TYPE: PRT
<213> ORGANISM: Artificial Sequence
<220> FEATURE:
<223> OTHER INFORMATION: Description of Artificial Sequence: binding
      peptide <400> SEQUENCE: 723

Leu Thr Ala Asn Ser Asp Thr His Leu Leu Gln Gly Gln Ser Leu
 1               5                  10                  15

<210> SEQ ID NO 724
<211> LENGTH: 15
<212> TYPE: PRT
<213> ORGANISM: Artificial Sequence
<220> FEATURE:
<223> OTHER INFORMATION: Description of Artificial Sequence: binding
      peptide <400> SEQUENCE: 724

Thr Ala Asn Ser Asp Thr His Leu Leu Gln Gly Gln Ser Leu Thr
 1               5                  10                  15

<210> SEQ ID NO 725

-continued

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 725

Ala Asn Ser Asp Thr His Leu Leu Gln Gly Gln Ser Leu Thr Leu
 1               5                  10                  15

<210> SEQ ID NO 726
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 726

Asn Ser Asp Thr His Leu Leu Gln Gly Gln Ser Leu Thr Leu Thr
 1               5                  10                  15

<210> SEQ ID NO 727
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 727

Ser Asp Thr His Leu Leu Gln Gly Gln Ser Leu Thr Leu Thr Leu
 1               5                  10                  15

<210> SEQ ID NO 728
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 728

Asp Thr His Leu Leu Gln Gly Gln Ser Leu Thr Leu Thr Leu Glu
 1               5                  10                  15

<210> SEQ ID NO 729
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 729

Thr His Leu Leu Gln Gly Gln Ser Leu Thr Leu Thr Leu Glu Ser
 1               5                  10                  15

<210> SEQ ID NO 730
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 730
```

```
His Leu Leu Gln Gly Gln Ser Leu Thr Leu Thr Leu Glu Ser Pro
  1               5                  10                  15

<210> SEQ ID NO 731
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 731

Leu Trp Asp Gln Gly Asn Phe Pro Leu Ile Ile Lys Asn Leu Lys Ile
  1               5                  10                  15

Glu Asp

<210> SEQ ID NO 732
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 732

Trp Asp Gln Gly Asn Phe Pro Leu Ile Ile Lys Asn Leu Lys Ile Glu
  1               5                  10                  15

Asp Ser

<210> SEQ ID NO 733
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 733

Asp Gln Gly Asn Phe Pro Leu Ile Ile Lys Asn Leu Lys Ile Glu Asp
  1               5                  10                  15

Ser Asp

<210> SEQ ID NO 734
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 734

Gln Gly Asn Phe Pro Leu Ile Ile Lys Asn Leu Lys Ile Glu Asp Ser
  1               5                  10                  15

Asp Thr

<210> SEQ ID NO 735
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 735

Gly Asn Phe Pro Leu Ile Ile Lys Asn Leu Lys Ile Glu Asp Ser Asp
```

```
                1               5                  10                 15
Thr Tyr

<210> SEQ ID NO 736
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 736

Asn Phe Pro Leu Ile Ile Lys Asn Leu Lys Ile Glu Asp Ser Asp Thr
  1               5                  10                 15
Tyr Ile

<210> SEQ ID NO 737
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 737

Phe Pro Leu Ile Ile Lys Asn Leu Lys Ile Glu Asp Ser Asp Thr Tyr
  1               5                  10                 15
Ile Cys

<210> SEQ ID NO 738
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 738

Pro Leu Ile Ile Lys Asn Leu Lys Ile Glu Asp Ser Asp Thr Tyr Ile
  1               5                  10                 15
Cys Glu

<210> SEQ ID NO 739
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 739

Leu Ile Ile Lys Asn Leu Lys Ile Glu Asp Ser Asp Thr Tyr Ile Cys
  1               5                  10                 15
Glu Val

<210> SEQ ID NO 740
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 740
```

-continued

Ile Ile Lys Asn Leu Lys Ile Glu Asp Ser Asp Thr Tyr Ile Cys Glu
1               5                   10                  15

Val Glu

<210> SEQ ID NO 741
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 741

Ile Lys Asn Leu Lys Ile Glu Asp Ser Asp Thr Tyr Ile Cys Glu Val
1               5                   10                  15

Glu Asp

<210> SEQ ID NO 742
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 742

Lys Asn Leu Lys Ile Glu Asp Ser Asp Thr Tyr Ile Cys Glu Val Glu
1               5                   10                  15

Asp Gln

<210> SEQ ID NO 743
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 743

Asn Leu Lys Ile Glu Asp Ser Asp Thr Tyr Ile Cys Glu Val Glu Asp
1               5                   10                  15

Gln Lys

<210> SEQ ID NO 744
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 744

Leu Lys Ile Glu Asp Ser Asp Thr Tyr Ile Cys Glu Val Glu Asp Gln
1               5                   10                  15

Lys Glu

<210> SEQ ID NO 745
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 745

Lys Ile Glu Asp Ser Asp Thr Tyr Ile Cys Glu Val Glu Asp Gln Lys
1               5                   10                  15

Glu Glu

<210> SEQ ID NO 746
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 746

Ile Glu Asp Ser Asp Thr Tyr Ile Cys Glu Val Glu Asp Gln Lys Glu
1               5                   10                  15

Glu Val

<210> SEQ ID NO 747
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 747

Glu Asp Ser Asp Thr Tyr Ile Cys Glu Val Glu Asp Gln Lys Glu Glu
1               5                   10                  15

Val Gln

<210> SEQ ID NO 748
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 748

Asp Ser Asp Thr Tyr Ile Cys Glu Val Glu Asp Gln Lys Glu Glu Val
1               5                   10                  15

Gln Leu

<210> SEQ ID NO 749
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 749

Ser Asp Thr Tyr Ile Cys Glu Val Glu Asp Gln Lys Glu Glu Val Gln
1               5                   10                  15

Leu Leu

<210> SEQ ID NO 750
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 750

Asp Thr Tyr Ile Cys Glu Val Glu Asp Gln Lys Glu Glu Val Gln Leu
 1               5                  10                  15

Leu Val

<210> SEQ ID NO 751
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 751

Thr Tyr Ile Cys Glu Val Glu Asp Gln Lys Glu Glu Val Gln Leu Leu
 1               5                  10                  15

Val Phe

<210> SEQ ID NO 752
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 752

Tyr Ile Cys Glu Val Glu Asp Gln Lys Glu Glu Val Gln Leu Leu Val
 1               5                  10                  15

Phe Gly

<210> SEQ ID NO 753
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 753

Ile Cys Glu Val Glu Asp Gln Lys Glu Glu Val Gln Leu Leu Val Phe
 1               5                  10                  15

Gly Leu

<210> SEQ ID NO 754
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 754

Cys Glu Val Glu Asp Gln Lys Glu Glu Val Gln Leu Leu Val Phe Gly
 1               5                  10                  15

Leu Thr

<210> SEQ ID NO 755
<211> LENGTH: 18
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 755

Glu Val Glu Asp Gln Lys Glu Glu Val Gln Leu Leu Val Phe Gly Leu
 1               5                  10                  15

Thr Ala

<210> SEQ ID NO 756
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 756

Val Glu Asp Gln Lys Glu Glu Val Gln Leu Leu Val Phe Gly Leu Thr
 1               5                  10                  15

Ala Asn

<210> SEQ ID NO 757
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 757

Glu Asp Gln Lys Glu Glu Val Gln Leu Leu Val Phe Gly Leu Thr Ala
 1               5                  10                  15

Asn Ser

<210> SEQ ID NO 758
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 758

Asp Gln Lys Glu Glu Val Gln Leu Leu Val Phe Gly Leu Thr Ala Asn
 1               5                  10                  15

Ser Asp

<210> SEQ ID NO 759
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 759

Gln Lys Glu Glu Val Gln Leu Leu Val Phe Gly Leu Thr Ala Asn Ser
 1               5                  10                  15

Asp Thr

<210> SEQ ID NO 760
<211> LENGTH: 18
<212> TYPE: PRT
<213> ORGANISM: Artificial Sequence
<220> FEATURE:
<223> OTHER INFORMATION: Description of Artificial Sequence: binding
``` peptide

<400> SEQUENCE: 760

Lys Glu Glu Val Gln Leu Leu Val Phe Gly Leu Thr Ala Asn Ser Asp
 1               5                  10                  15
Thr His

<210> SEQ ID NO 761
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 761

Glu Glu Val Gln Leu Leu Val Phe Gly Leu Thr Ala Asn Ser Asp Thr
 1               5                  10                  15
His Leu

<210> SEQ ID NO 762
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 762

Glu Val Gln Leu Leu Val Phe Gly Leu Thr Ala Asn Ser Asp Thr His
 1               5                  10                  15
Leu Leu

<210> SEQ ID NO 763
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 763

Val Gln Leu Leu Val Phe Gly Leu Thr Ala Asn Ser Asp Thr His Leu
 1               5                  10                  15
Leu Gln

<210> SEQ ID NO 764
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 764

Gln Leu Leu Val Phe Gly Leu Thr Ala Asn Ser Asp Thr His Leu Leu
 1               5                  10                  15
Gln Gly

<210> SEQ ID NO 765
<211> LENGTH: 18
<212> TYPE: PRT
<213> ORGANISM: Artificial Sequence
<220> FEATURE:

-continued

<223> OTHER INFORMATION: Description of Artificial Sequence: binding
      peptide

<400> SEQUENCE: 765

Leu Leu Val Phe Gly Leu Thr Ala Asn Ser Asp Thr His Leu Leu Gln
 1               5                  10                  15

Gly Gln

<210> SEQ ID NO 766
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 766

Leu Val Phe Gly Leu Thr Ala Asn Ser Asp Thr His Leu Leu Gln Gly
 1               5                  10                  15

Gln Ser

<210> SEQ ID NO 767
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 767

Val Phe Gly Leu Thr Ala Asn Ser Asp Thr His Leu Leu Gln Gly Gln
 1               5                  10                  15

Ser Leu

<210> SEQ ID NO 768
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 768

Phe Gly Leu Thr Ala Asn Ser Asp Thr His Leu Leu Gln Gly Gln Ser
 1               5                  10                  15

Leu Thr

<210> SEQ ID NO 769
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 769

Gly Leu Thr Ala Asn Ser Asp Thr His Leu Leu Gln Gly Gln Ser Leu
 1               5                  10                  15

Thr Leu

<210> SEQ ID NO 770
<211> LENGTH: 18
<212> TYPE: PRT
<213> ORGANISM: Artificial Sequence
<220> FEATURE:
<223> OTHER INFORMATION: Description of Artificial Sequence: binding
     peptide

<400> SEQUENCE: 770

Leu Thr Ala Asn Ser Asp Thr His Leu Leu Gln Gly Gln Ser Leu Thr
 1               5                  10                  15

Leu Thr

<210> SEQ ID NO 771
<211> LENGTH: 18
<212> TYPE: PRT
<213> ORGANISM: Artificial Sequence
<220> FEATURE:
<223> OTHER INFORMATION: Description of Artificial Sequence: binding
     peptide

<400> SEQUENCE: 771

Thr Ala Asn Ser Asp Thr His Leu Leu Gln Gly Gln Ser Leu Thr Leu
 1               5                  10                  15

Thr Leu

<210> SEQ ID NO 772
<211> LENGTH: 18
<212> TYPE: PRT
<213> ORGANISM: Artificial Sequence
<220> FEATURE:
<223> OTHER INFORMATION: Description of Artificial Sequence: binding
     peptide

<400> SEQUENCE: 772

Ala Asn Ser Asp Thr His Leu Leu Gln Gly Gln Ser Leu Thr Leu Thr
 1               5                  10                  15

Leu Glu

<210> SEQ ID NO 773
<211> LENGTH: 18
<212> TYPE: PRT
<213> ORGANISM: Artificial Sequence
<220> FEATURE:
<223> OTHER INFORMATION: Description of Artificial Sequence: binding
     peptide

<400> SEQUENCE: 773

Asn Ser Asp Thr His Leu Leu Gln Gly Gln Ser Leu Thr Leu Thr Leu
 1               5                  10                  15

Glu Ser

<210> SEQ ID NO 774
<211> LENGTH: 18
<212> TYPE: PRT
<213> ORGANISM: Artificial Sequence
<220> FEATURE:
<223> OTHER INFORMATION: Description of Artificial Sequence: binding
     peptide

<400> SEQUENCE: 774

Ser Asp Thr His Leu Leu Gln Gly Gln Ser Leu Thr Leu Thr Leu Glu
 1               5                  10                  15

Ser Pro

<210> SEQ ID NO 775
<211> LENGTH: 15
<212> TYPE: PRT

```
<213> ORGANISM: Artificial Sequence
<220> FEATURE:
<223> OTHER INFORMATION: Description of Artificial Sequence: binding
      peptide

<400> SEQUENCE: 775

Trp Thr Cys Thr Val Leu Gln Asn Gln Lys Lys Val Glu Phe Lys
 1               5                  10                  15

<210> SEQ ID NO 776
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 776

Thr Cys Thr Val Leu Gln Asn Gln Lys Lys Val Glu Phe Lys Ile
 1               5                  10                  15

<210> SEQ ID NO 777
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 777

Cys Thr Val Leu Gln Asn Gln Lys Lys Val Glu Phe Lys Ile Asp
 1               5                  10                  15

<210> SEQ ID NO 778
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 778

Thr Val Leu Gln Asn Gln Lys Lys Val Glu Phe Lys Ile Asp Ile
 1               5                  10                  15

<210> SEQ ID NO 779
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 779

Val Leu Gln Asn Gln Lys Lys Val Glu Phe Lys Ile Asp Ile Val
 1               5                  10                  15

<210> SEQ ID NO 780
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 780

Leu Gln Asn Gln Lys Lys Val Glu Phe Lys Ile Asp Ile Val Val
 1               5                  10                  15
```

<210> SEQ ID NO 781
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 781

Gln Asn Gln Lys Lys Val Glu Phe Lys Ile Asp Ile Val Val Leu
 1               5                  10                  15

<210> SEQ ID NO 782
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 782

Asn Gln Lys Lys Val Glu Phe Lys Ile Asp Ile Val Val Leu Ala
 1               5                  10                  15

<210> SEQ ID NO 783
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 783

Gln Lys Lys Val Glu Phe Lys Ile Asp Ile Val Val Leu Ala Phe
 1               5                  10                  15

<210> SEQ ID NO 784
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 784

Lys Lys Val Glu Phe Lys Ile Asp Ile Val Val Leu Ala Phe Gln
 1               5                  10                  15

<210> SEQ ID NO 785
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 785

Lys Val Glu Phe Lys Ile Asp Ile Val Val Leu Ala Phe Gln Lys
 1               5                  10                  15

<210> SEQ ID NO 786
<211> LENGTH: 15
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 786

Val Glu Phe Lys Ile Asp Ile Val Val Leu Ala Phe Gln Lys Ala
 1               5                  10                  15

<210> SEQ ID NO 787
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 787

Glu Phe Lys Ile Asp Ile Val Val Leu Ala Phe Gln Lys Ala Ser
 1               5                  10                  15

<210> SEQ ID NO 788
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 788

Phe Lys Ile Asp Ile Val Val Leu Ala Phe Gln Lys Ala Ser Ser
 1               5                  10                  15

<210> SEQ ID NO 789
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 789

Lys Ile Asp Ile Val Val Leu Ala Phe Gln Lys Ala Ser Ser Ile
 1               5                  10                  15

<210> SEQ ID NO 790
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 790

Ile Asp Ile Val Val Leu Ala Phe Gln Lys Ala Ser Ser Ile Val
 1               5                  10                  15

<210> SEQ ID NO 791
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 791

Asp Ile Val Val Leu Ala Phe Gln Lys Ala Ser Ser Ile Val Tyr
 1               5                  10                  15

<210> SEQ ID NO 792
<211> LENGTH: 15
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 792

Ile Val Val Leu Ala Phe Gln Lys Ala Ser Ser Ile Val Tyr Lys
 1               5                  10                  15

<210> SEQ ID NO 793
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 793

Val Val Leu Ala Phe Gln Lys Ala Ser Ser Ile Val Tyr Lys Lys
 1               5                  10                  15

<210> SEQ ID NO 794
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 794

Val Leu Ala Phe Gln Lys Ala Ser Ser Ile Val Tyr Lys Lys Glu
 1               5                  10                  15

<210> SEQ ID NO 795
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 795

Leu Ala Phe Gln Lys Ala Ser Ser Ile Val Tyr Lys Lys Glu Gly
 1               5                  10                  15

<210> SEQ ID NO 796
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 796

Ala Phe Gln Lys Ala Ser Ser Ile Val Tyr Lys Lys Glu Gly Glu
 1               5                  10                  15

<210> SEQ ID NO 797
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 797

Phe Gln Lys Ala Ser Ser Ile Val Tyr Lys Lys Glu Gly Glu Gln
```

```
                1               5              10              15
```

<210> SEQ ID NO 798
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 798

```
Gln Lys Ala Ser Ser Ile Val Tyr Lys Lys Glu Gly Glu Gln Val
1               5                  10                  15
```

<210> SEQ ID NO 799
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 799

```
Lys Ala Ser Ser Ile Val Tyr Lys Lys Glu Gly Glu Gln Val Glu
1               5                  10                  15
```

<210> SEQ ID NO 800
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 800

```
Ala Ser Ser Ile Val Tyr Lys Lys Glu Gly Glu Gln Val Glu Phe
1               5                  10                  15
```

<210> SEQ ID NO 801
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 801

```
Ser Ser Ile Val Tyr Lys Lys Glu Gly Glu Gln Val Glu Phe Ser
1               5                  10                  15
```

<210> SEQ ID NO 802
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 802

```
Ser Ile Val Tyr Lys Lys Glu Gly Glu Gln Val Glu Phe Ser Phe
1               5                  10                  15
```

<210> SEQ ID NO 803
<211> LENGTH: 15
<212> TYPE: PRT
<213> ORGANISM: Artificial Sequence
<220> FEATURE:
<223> OTHER INFORMATION: Description of Artificial Sequence: binding -continued

```
      peptide

<400> SEQUENCE: 803

Ile Val Tyr Lys Lys Glu Gly Glu Gln Val Glu Phe Ser Phe Pro
 1               5                  10                  15

<210> SEQ ID NO 804
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 804

Val Tyr Lys Lys Glu Gly Glu Gln Val Glu Phe Ser Phe Pro Leu
 1               5                  10                  15

<210> SEQ ID NO 805
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 805

Tyr Lys Lys Glu Gly Glu Gln Val Glu Phe Ser Phe Pro Leu Ala
 1               5                  10                  15

<210> SEQ ID NO 806
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 806

Lys Lys Glu Gly Glu Gln Val Glu Phe Ser Phe Pro Leu Ala Phe
 1               5                  10                  15

<210> SEQ ID NO 807
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 807

Lys Glu Gly Glu Gln Val Glu Phe Ser Phe Pro Leu Ala Phe Thr
 1               5                  10                  15

<210> SEQ ID NO 808
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 808

Glu Gly Glu Gln Val Glu Phe Ser Phe Pro Leu Ala Phe Thr Val
 1               5                  10                  15

<210> SEQ ID NO 809
```

-continued

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 809

Gly Glu Gln Val Glu Phe Ser Phe Pro Leu Ala Phe Thr Val Glu
 1               5                  10                  15

<210> SEQ ID NO 810
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 810

Glu Gln Val Glu Phe Ser Phe Pro Leu Ala Phe Thr Val Glu Lys
 1               5                  10                  15

<210> SEQ ID NO 811
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 811

Gln Val Glu Phe Ser Phe Pro Leu Ala Phe Thr Val Glu Lys Leu
 1               5                  10                  15

<210> SEQ ID NO 812
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 812

Val Glu Phe Ser Phe Pro Leu Ala Phe Thr Val Glu Lys Leu Thr
 1               5                  10                  15

<210> SEQ ID NO 813
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 813

Glu Phe Ser Phe Pro Leu Ala Phe Thr Val Glu Lys Leu Thr Gly
 1               5                  10                  15

<210> SEQ ID NO 814
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 814
```

```
Phe Ser Phe Pro Leu Ala Phe Thr Val Glu Lys Leu Thr Gly Ser
 1               5                  10                  15

<210> SEQ ID NO 815
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 815

Ser Phe Pro Leu Ala Phe Thr Val Glu Lys Leu Thr Gly Ser Gly
 1               5                  10                  15

<210> SEQ ID NO 816
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 816

Phe Pro Leu Ala Phe Thr Val Glu Lys Leu Thr Gly Ser Gly Glu
 1               5                  10                  15

<210> SEQ ID NO 817
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 817

Pro Leu Ala Phe Thr Val Glu Lys Leu Thr Gly Ser Gly Glu Leu
 1               5                  10                  15

<210> SEQ ID NO 818
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 818

Leu Ala Phe Thr Val Glu Lys Leu Thr Gly Ser Gly Glu Leu Trp
 1               5                  10                  15

<210> SEQ ID NO 819
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 819

Ala Phe Thr Val Glu Lys Leu Thr Gly Ser Gly Glu Leu Trp Trp
 1               5                  10                  15

<210> SEQ ID NO 820
<211> LENGTH: 15
<212> TYPE: PRT
<213> ORGANISM: Artificial Sequence
<220> FEATURE:
```

```
<223> OTHER INFORMATION: Description of Artificial Sequence: binding
      peptide

<400> SEQUENCE: 820

Phe Thr Val Glu Lys Leu Thr Gly Ser Gly Glu Leu Trp Trp Gln
 1               5                  10                  15

<210> SEQ ID NO 821
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 821

Thr Val Glu Lys Leu Thr Gly Ser Gly Glu Leu Trp Trp Gln Ala
 1               5                  10                  15

<210> SEQ ID NO 822
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 822

Val Glu Lys Leu Thr Gly Ser Gly Glu Leu Trp Trp Gln Ala Glu
 1               5                  10                  15

<210> SEQ ID NO 823
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 823

Glu Lys Leu Thr Gly Ser Gly Glu Leu Trp Trp Gln Ala Glu Arg
 1               5                  10                  15

<210> SEQ ID NO 824
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 824

Trp Thr Cys Thr Val Leu Gln Asn Gln Lys Lys Val Glu Phe Lys Ile
 1               5                  10                  15

Asp Ile

<210> SEQ ID NO 825
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 825

Thr Cys Thr Val Leu Gln Asn Gln Lys Lys Val Glu Phe Lys Ile Asp
 1               5                  10                  15
```

Ile Val

<210> SEQ ID NO 826
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 826

Cys Thr Val Leu Gln Asn Gln Lys Lys Val Glu Phe Lys Ile Asp Ile
 1               5                  10                  15

Val Val

<210> SEQ ID NO 827
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 827

Thr Val Leu Gln Asn Gln Lys Lys Val Glu Phe Lys Ile Asp Ile Val
 1               5                  10                  15

Val Leu

<210> SEQ ID NO 828
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 828

Val Leu Gln Asn Gln Lys Lys Val Glu Phe Lys Ile Asp Ile Val Val
 1               5                  10                  15

Leu Ala

<210> SEQ ID NO 829
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 829

Leu Gln Asn Gln Lys Lys Val Glu Phe Lys Ile Asp Ile Val Val Leu
 1               5                  10                  15

Ala Phe

<210> SEQ ID NO 830
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 830

Gln Asn Gln Lys Lys Val Glu Phe Lys Ile Asp Ile Val Val Leu Ala

```
                1               5                  10                 15
Phe Gln

<210> SEQ ID NO 831
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 831

Asn Gln Lys Lys Val Glu Phe Lys Ile Asp Ile Val Val Leu Ala Phe
  1               5                  10                 15
Gln Lys

<210> SEQ ID NO 832
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 832

Gln Lys Lys Val Glu Phe Lys Ile Asp Ile Val Val Leu Ala Phe Gln
  1               5                  10                 15
Lys Ala

<210> SEQ ID NO 833
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 833

Lys Lys Val Glu Phe Lys Ile Asp Ile Val Val Leu Ala Phe Gln Lys
  1               5                  10                 15
Ala Ser

<210> SEQ ID NO 834
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 834

Lys Val Glu Phe Lys Ile Asp Ile Val Val Leu Ala Phe Gln Lys Ala
  1               5                  10                 15
Ser Ser

<210> SEQ ID NO 835
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 835
```

```
Val Glu Phe Lys Ile Asp Ile Val Val Leu Ala Phe Gln Lys Ala Ser
 1               5                  10                  15

Ser Ile
```

<210> SEQ ID NO 836
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 836

```
Glu Phe Lys Ile Asp Ile Val Val Leu Ala Phe Gln Lys Ala Ser Ser
 1               5                  10                  15

Ile Val
```

<210> SEQ ID NO 837
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 837

```
Phe Lys Ile Asp Ile Val Val Leu Ala Phe Gln Lys Ala Ser Ser Ile
 1               5                  10                  15

Val Tyr
```

<210> SEQ ID NO 838
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 838

```
Lys Ile Asp Ile Val Val Leu Ala Phe Gln Lys Ala Ser Ser Ile Val
 1               5                  10                  15

Tyr Lys
```

<210> SEQ ID NO 839
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 839

```
Ile Asp Ile Val Val Leu Ala Phe Gln Lys Ala Ser Ser Ile Val Tyr
 1               5                  10                  15

Lys Lys
```

<210> SEQ ID NO 840
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 840

Asp Ile Val Val Leu Ala Phe Gln Lys Ala Ser Ser Ile Val Tyr Lys
 1               5                  10                  15

Lys Glu

<210> SEQ ID NO 841
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 841

Ile Val Val Leu Ala Phe Gln Lys Ala Ser Ser Ile Val Tyr Lys Lys
 1               5                  10                  15

Glu Gly

<210> SEQ ID NO 842
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 842

Val Val Leu Ala Phe Gln Lys Ala Ser Ser Ile Val Tyr Lys Lys Glu
 1               5                  10                  15

Gly Glu

<210> SEQ ID NO 843
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 843

Val Leu Ala Phe Gln Lys Ala Ser Ser Ile Val Tyr Lys Lys Glu Gly
 1               5                  10                  15

Glu Gln

<210> SEQ ID NO 844
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 844

Leu Ala Phe Gln Lys Ala Ser Ser Ile Val Tyr Lys Lys Glu Gly Glu
 1               5                  10                  15

Gln Val

<210> SEQ ID NO 845
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

<400> SEQUENCE: 845

Ala Phe Gln Lys Ala Ser Ser Ile Val Tyr Lys Lys Glu Gly Glu Gln
 1               5                  10                  15

Val Glu

<210> SEQ ID NO 846
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 846

Phe Gln Lys Ala Ser Ser Ile Val Tyr Lys Lys Glu Gly Glu Gln Val
 1               5                  10                  15

Glu Phe

<210> SEQ ID NO 847
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 847

Gln Lys Ala Ser Ser Ile Val Tyr Lys Lys Glu Gly Glu Gln Val Glu
 1               5                  10                  15

Phe Ser

<210> SEQ ID NO 848
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 848

Lys Ala Ser Ser Ile Val Tyr Lys Lys Glu Gly Glu Gln Val Glu Phe
 1               5                  10                  15

Ser Phe

<210> SEQ ID NO 849
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 849

Ala Ser Ser Ile Val Tyr Lys Lys Glu Gly Glu Gln Val Glu Phe Ser
 1               5                  10                  15

Phe Pro

<210> SEQ ID NO 850
<211> LENGTH: 18
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 850

Ser Ser Ile Val Tyr Lys Lys Glu Gly Glu Gln Val Glu Phe Ser Phe
1               5                   10                  15
Pro Leu

<210> SEQ ID NO 851
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 851

Ser Ile Val Tyr Lys Lys Glu Gly Glu Gln Val Glu Phe Ser Phe Pro
1               5                   10                  15
Leu Ala

<210> SEQ ID NO 852
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 852

Ile Val Tyr Lys Lys Glu Gly Glu Gln Val Glu Phe Ser Phe Pro Leu
1               5                   10                  15
Ala Phe

<210> SEQ ID NO 853
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 853

Val Tyr Lys Lys Glu Gly Glu Gln Val Glu Phe Ser Phe Pro Leu Ala
1               5                   10                  15
Phe Thr

<210> SEQ ID NO 854
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 854

Tyr Lys Lys Glu Gly Glu Gln Val Glu Phe Ser Phe Pro Leu Ala Phe
1               5                   10                  15
Thr Val

<210> SEQ ID NO 855
<211> LENGTH: 18
<212> TYPE: PRT
<213> ORGANISM: Artificial Sequence
<220> FEATURE:
<223> OTHER INFORMATION: Description of Artificial Sequence: binding
```

-continued

```
                peptide

<400> SEQUENCE: 855

Lys Lys Glu Gly Glu Gln Val Glu Phe Ser Phe Pro Leu Ala Phe Thr
 1               5                  10                  15

Val Glu

<210> SEQ ID NO 856
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 856

Lys Glu Gly Glu Gln Val Glu Phe Ser Phe Pro Leu Ala Phe Thr Val
 1               5                  10                  15

Glu Lys

<210> SEQ ID NO 857
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 857

Glu Gly Glu Gln Val Glu Phe Ser Phe Pro Leu Ala Phe Thr Val Glu
 1               5                  10                  15

Lys Leu

<210> SEQ ID NO 858
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 858

Gly Glu Gln Val Glu Phe Ser Phe Pro Leu Ala Phe Thr Val Glu Lys
 1               5                  10                  15

Leu Thr

<210> SEQ ID NO 859
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 859

Glu Gln Val Glu Phe Ser Phe Pro Leu Ala Phe Thr Val Glu Lys Leu
 1               5                  10                  15

Thr Gly

<210> SEQ ID NO 860
<211> LENGTH: 18
<212> TYPE: PRT
<213> ORGANISM: Artificial Sequence
<220> FEATURE:
```

```
<223> OTHER INFORMATION: Description of Artificial Sequence: binding
      peptide

<400> SEQUENCE: 860

Gln Val Glu Phe Ser Phe Pro Leu Ala Phe Thr Val Glu Lys Leu Thr
 1               5                  10                  15

Gly Ser

<210> SEQ ID NO 861
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 861

Val Glu Phe Ser Phe Pro Leu Ala Phe Thr Val Glu Lys Leu Thr Gly
 1               5                  10                  15

Ser Gly

<210> SEQ ID NO 862
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 862

Glu Phe Ser Phe Pro Leu Ala Phe Thr Val Glu Lys Leu Thr Gly Ser
 1               5                  10                  15

Gly Glu

<210> SEQ ID NO 863
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 863

Phe Ser Phe Pro Leu Ala Phe Thr Val Glu Lys Leu Thr Gly Ser Gly
 1               5                  10                  15

Glu Leu

<210> SEQ ID NO 864
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 864

Ser Phe Pro Leu Ala Phe Thr Val Glu Lys Leu Thr Gly Ser Gly Glu
 1               5                  10                  15

Leu Trp

<210> SEQ ID NO 865
<211> LENGTH: 18
<212> TYPE: PRT
<213> ORGANISM: Artificial Sequence
```

```
<220> FEATURE:
<223> OTHER INFORMATION: Description of Artificial Sequence: binding
      peptide

<400> SEQUENCE: 865

Phe Pro Leu Ala Phe Thr Val Glu Lys Leu Thr Gly Ser Gly Glu Leu
 1               5                  10                  15

Trp Trp

<210> SEQ ID NO 866
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 866

Pro Leu Ala Phe Thr Val Glu Lys Leu Thr Gly Ser Gly Glu Leu Trp
 1               5                  10                  15

Trp Gln

<210> SEQ ID NO 867
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 867

Leu Ala Phe Thr Val Glu Lys Leu Thr Gly Ser Gly Glu Leu Trp Trp
 1               5                  10                  15

Gln Ala

<210> SEQ ID NO 868
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 868

Ala Phe Thr Val Glu Lys Leu Thr Gly Ser Gly Glu Leu Trp Trp Gln
 1               5                  10                  15

Ala Glu

<210> SEQ ID NO 869
<211> LENGTH: 18
<212> TYPE: PRT
<213> ORGANISM: Artificial Sequence
<220> FEATURE:
<223> OTHER INFORMATION: Description of Artificial Sequence: binding
      peptide

<400> SEQUENCE: 869

Phe Thr Val Glu Lys Leu Thr Gly Ser Gly Glu Leu Trp Trp Gln Ala
 1               5                  10                  15

Glu Arg

<210> SEQ ID NO 870
<211> LENGTH: 9
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 870

Asp Gln Gly Asn Phe Pro Leu Ile Ile
 1               5

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 871

Gln Gly Asn Phe Pro Leu Ile Ile Lys
 1               5

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 872

Gly Asn Phe Pro Leu Ile Ile Lys Asn
 1               5

<210> SEQ ID NO 873
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 873

Asn Phe Pro Leu Ile Ile Lys Asn Leu
 1               5

<210> SEQ ID NO 874
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 874

Phe Pro Leu Ile Ile Lys Asn Leu Lys
 1               5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 875

Pro Leu Ile Ile Lys Asn Leu Lys Ile
 1               5
```

```
<210> SEQ ID NO 876
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 876

Leu Ile Ile Lys Asn Leu Lys Ile Glu
  1               5

<210> SEQ ID NO 877
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 877

Ile Ile Lys Asn Leu Lys Ile Glu Asp
  1               5

<210> SEQ ID NO 878
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 878

Ile Lys Asn Leu Lys Ile Glu Asp Ser
  1               5

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 879

Lys Asn Leu Lys Ile Glu Asp Ser Asp
  1               5

<210> SEQ ID NO 880
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 880

Asn Leu Lys Ile Glu Asp Ser Asp Thr
  1               5

<210> SEQ ID NO 881
<211> LENGTH: 9
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 881

Leu Lys Ile Glu Asp Ser Asp Thr Tyr
  1               5

<210> SEQ ID NO 882
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 882

Lys Ile Glu Asp Ser Asp Thr Tyr Ile
  1               5

<210> SEQ ID NO 883
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 883

Ile Glu Asp Ser Asp Thr Tyr Ile Cys
  1               5

<210> SEQ ID NO 884
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 884

Glu Asp Ser Asp Thr Tyr Ile Cys Glu
  1               5

<210> SEQ ID NO 885
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 885

Asp Ser Asp Thr Tyr Ile Cys Glu Val
  1               5

<210> SEQ ID NO 886
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 886

Ser Asp Thr Tyr Ile Cys Glu Val Glu
  1               5

<210> SEQ ID NO 887
<211> LENGTH: 9
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 887

Asp Thr Tyr Ile Cys Glu Val Glu Asp
 1               5

<210> SEQ ID NO 888
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 888

Thr Tyr Ile Cys Glu Val Glu Asp Gln
 1               5

<210> SEQ ID NO 889
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 889

Tyr Ile Cys Glu Val Glu Asp Gln Lys
 1               5

<210> SEQ ID NO 890
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 890

Ile Cys Glu Val Glu Asp Gln Lys Glu
 1               5

<210> SEQ ID NO 891
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 891

Cys Glu Val Glu Asp Gln Lys Glu Glu
 1               5

<210> SEQ ID NO 892
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 892

Glu Val Glu Asp Gln Lys Glu Glu Val
```

```
1               5
```

<210> SEQ ID NO 893
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 893

```
Val Glu Asp Gln Lys Glu Glu Val Gln
  1               5
```

<210> SEQ ID NO 894
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 894

```
Glu Asp Gln Lys Glu Glu Val Gln Leu
  1               5
```

<210> SEQ ID NO 895
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 895

```
Asp Gln Lys Glu Glu Val Gln Leu Leu
  1               5
```

<210> SEQ ID NO 896
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 896

```
Gln Lys Glu Glu Val Gln Leu Leu Val
  1               5
```

<210> SEQ ID NO 897
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 897

```
Lys Glu Glu Val Gln Leu Leu Val Phe
  1               5
```

<210> SEQ ID NO 898
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 898

Glu Glu Val Gln Leu Leu Val Phe Gly
  1               5

<210> SEQ ID NO 899
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 899

Glu Val Gln Leu Leu Val Phe Gly Leu
  1               5

<210> SEQ ID NO 900
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 900

Val Gln Leu Leu Val Phe Gly Leu Thr
  1               5

<210> SEQ ID NO 901
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 901

Gln Leu Leu Val Phe Gly Leu Thr Ala
  1               5

<210> SEQ ID NO 902
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 902

Leu Leu Val Phe Gly Leu Thr Ala Asn
  1               5

<210> SEQ ID NO 903
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 903

Leu Val Phe Gly Leu Thr Ala Asn Ser
  1               5

<210> SEQ ID NO 904

```
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 904

Val Phe Gly Leu Thr Ala Asn Ser Asp
 1               5

<210> SEQ ID NO 905
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 905

Phe Gly Leu Thr Ala Asn Ser Asp Thr
 1               5

<210> SEQ ID NO 906
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 906

Gly Leu Thr Ala Asn Ser Asp Thr His
 1               5

<210> SEQ ID NO 907
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 907

Leu Thr Ala Asn Ser Asp Thr His Leu
 1               5

<210> SEQ ID NO 908
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 908

Thr Ala Asn Ser Asp Thr His Leu Leu
 1               5

<210> SEQ ID NO 909
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 909
```

```
Ala Asn Ser Asp Thr His Leu Leu Gln
  1               5
```

<210> SEQ ID NO 910
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 910

```
Asn Ser Asp Thr His Leu Leu Gln Gly
  1               5
```

<210> SEQ ID NO 911
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 911

```
Ser Asp Thr His Leu Leu Gln Gly Gln
  1               5
```

<210> SEQ ID NO 912
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 912

```
Asp Thr His Leu Leu Gln Gly Gln Ser
  1               5
```

<210> SEQ ID NO 913
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 913

```
Thr His Leu Leu Gln Gly Gln Ser Leu
  1               5
```

<210> SEQ ID NO 914
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 914

```
His Leu Leu Gln Gly Gln Ser Leu Thr
  1               5
```

<210> SEQ ID NO 915
<211> LENGTH: 9
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 915

Leu Leu Gln Gly Gln Ser Leu Thr Leu
 1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 916

Leu Gln Gly Gln Ser Leu Thr Leu Thr
 1               5

<210> SEQ ID NO 917
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 917

Gln Gly Gln Ser Leu Thr Leu Thr Leu
 1               5

<210> SEQ ID NO 918
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 918

Gly Gln Ser Leu Thr Leu Thr Leu Glu
 1               5

<210> SEQ ID NO 919
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 919

Asp Gln Gly Asn Phe Pro Leu Ile Ile Lys Asn Leu
 1               5                  10

<210> SEQ ID NO 920
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 920

Gln Gly Asn Phe Pro Leu Ile Ile Lys Asn Leu Lys
 1               5                  10
```

<210> SEQ ID NO 921
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 921

Gly Asn Phe Pro Leu Ile Ile Lys Asn Leu Lys Ile
 1               5                  10

<210> SEQ ID NO 922
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 922

Asn Phe Pro Leu Ile Ile Lys Asn Leu Lys Ile Glu
 1               5                  10

<210> SEQ ID NO 923
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 923

Phe Pro Leu Ile Ile Lys Asn Leu Lys Ile Glu Asp
 1               5                  10

<210> SEQ ID NO 924
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 924

Pro Leu Ile Ile Lys Asn Leu Lys Ile Glu Asp Ser
 1               5                  10

<210> SEQ ID NO 925
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 925

Leu Ile Ile Lys Asn Leu Lys Ile Glu Asp Ser Asp
 1               5                  10

<210> SEQ ID NO 926
<211> LENGTH: 12
<212> TYPE: PRT
<213> ORGANISM: Artificial Sequence
<220> FEATURE:
<223> OTHER INFORMATION: Description of Artificial Sequence: binding peptide

<400> SEQUENCE: 926

```
Ile Ile Lys Asn Leu Lys Ile Glu Asp Ser Asp Thr
  1               5                  10
```

<210> SEQ ID NO 927
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 927

```
Ile Lys Asn Leu Lys Ile Glu Asp Ser Asp Thr Tyr
  1               5                  10
```

<210> SEQ ID NO 928
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 928

```
Lys Asn Leu Lys Ile Glu Asp Ser Asp Thr Tyr Ile
  1               5                  10
```

<210> SEQ ID NO 929
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 929

```
Asn Leu Lys Ile Glu Asp Ser Asp Thr Tyr Ile Cys
  1               5                  10
```

<210> SEQ ID NO 930
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 930

```
Leu Lys Ile Glu Asp Ser Asp Thr Tyr Ile Cys Glu
  1               5                  10
```

<210> SEQ ID NO 931
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 931

```
Lys Ile Glu Asp Ser Asp Thr Tyr Ile Cys Glu Val
  1               5                  10
```

<210> SEQ ID NO 932
<211> LENGTH: 12
<212> TYPE: PRT
<213> ORGANISM: Artificial Sequence

```
<220> FEATURE:
<223> OTHER INFORMATION: Description of Artificial Sequence: binding
      peptide

<400> SEQUENCE: 932

Ile Glu Asp Ser Asp Thr Tyr Ile Cys Glu Val Glu
 1               5                  10

<210> SEQ ID NO 933
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 933

Glu Asp Ser Asp Thr Tyr Ile Cys Glu Val Glu Asp
 1               5                  10

<210> SEQ ID NO 934
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 934

Asp Ser Asp Thr Tyr Ile Cys Glu Val Glu Asp Gln
 1               5                  10

<210> SEQ ID NO 935
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 935

Ser Asp Thr Tyr Ile Cys Glu Val Glu Asp Gln Lys
 1               5                  10

<210> SEQ ID NO 936
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 936

Asp Thr Tyr Ile Cys Glu Val Glu Asp Gln Lys Glu
 1               5                  10

<210> SEQ ID NO 937
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 937

Thr Tyr Ile Cys Glu Val Glu Asp Gln Lys Glu Glu
 1               5                  10
```

<210> SEQ ID NO 938
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 938

Tyr Ile Cys Glu Val Glu Asp Gln Lys Glu Glu Val
 1               5                  10

<210> SEQ ID NO 939
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 939

Ile Cys Glu Val Glu Asp Gln Lys Glu Glu Val Gln
 1               5                  10

<210> SEQ ID NO 940
<211> LENGTH: 11
<212> TYPE: PRT
<213> ORGANISM: Artificial Sequence
<220> FEATURE:
<223> OTHER INFORMATION: Description of Artificial Sequence: binding
      peptide

<400> SEQUENCE: 940

Cys Glu Val Glu Asp Gln Lys Glu Glu Val Gln
 1               5                  10

<210> SEQ ID NO 941
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 941

Glu Val Glu Asp Gln Lys Glu Glu Val Gln Leu Leu
 1               5                  10

<210> SEQ ID NO 942
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 942

Val Glu Asp Gln Lys Glu Glu Val Gln Leu Leu Val
 1               5                  10

<210> SEQ ID NO 943
<211> LENGTH: 12
<212> TYPE: PRT
<213> ORGANISM: Artificial Sequence
<220> FEATURE:
<223> OTHER INFORMATION: Description of Artificial Sequence: binding
      peptide -continued

```
<400> SEQUENCE: 943

Glu Asp Gln Lys Glu Glu Val Gln Leu Leu Val Phe
1               5                   10

<210> SEQ ID NO 944
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 944

Asp Gln Lys Glu Glu Val Gln Leu Leu Val Phe Gly
1               5                   10

<210> SEQ ID NO 945
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 945

Gln Lys Glu Glu Val Gln Leu Leu Val Phe Gly Leu
1               5                   10

<210> SEQ ID NO 946
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 946

Lys Glu Glu Val Gln Leu Leu Val Phe Gly Leu Thr
1               5                   10

<210> SEQ ID NO 947
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 947

Glu Glu Val Gln Leu Leu Val Phe Gly Leu Thr Ala
1               5                   10

<210> SEQ ID NO 948
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 948

Glu Val Gln Leu Leu Val Phe Gly Leu Thr Ala Asn
1               5                   10

<210> SEQ ID NO 949
<211> LENGTH: 12
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 949

Val Gln Leu Leu Val Phe Gly Leu Thr Ala Asn Ser
 1               5                  10

<210> SEQ ID NO 950
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 950

Gln Leu Leu Val Phe Gly Leu Thr Ala Asn Ser Asp
 1               5                  10

<210> SEQ ID NO 951
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 951

Leu Leu Val Phe Gly Leu Thr Ala Asn Ser Asp Thr
 1               5                  10

<210> SEQ ID NO 952
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 952

Leu Val Phe Gly Leu Thr Ala Asn Ser Asp Thr His
 1               5                  10

<210> SEQ ID NO 953
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 953

Val Phe Gly Leu Thr Ala Asn Ser Asp Thr His Leu
 1               5                  10

<210> SEQ ID NO 954
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 954

Phe Gly Leu Thr Ala Asn Ser Asp Thr His Leu Leu
 1               5                  10
```

<210> SEQ ID NO 955
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 955

Gly Leu Thr Ala Asn Ser Asp Thr His Leu Leu Gln
 1               5                  10

<210> SEQ ID NO 956
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 956

Leu Thr Ala Asn Ser Asp Thr His Leu Leu Gln Gly
 1               5                  10

<210> SEQ ID NO 957
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 957

Thr Ala Asn Ser Asp Thr His Leu Leu Gln Gly Gln
 1               5                  10

<210> SEQ ID NO 958
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 958

Ala Asn Ser Asp Thr His Leu Leu Gln Gly Gln Ser
 1               5                  10

<210> SEQ ID NO 959
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 959

Asn Ser Asp Thr His Leu Leu Gln Gly Gln Ser Leu
 1               5                  10

<210> SEQ ID NO 960
<211> LENGTH: 12
<212> TYPE: PRT
<213> ORGANISM: Artificial Sequence
<220> FEATURE:
<223> OTHER INFORMATION: Description of Artificial Sequence: binding
      peptide -continued

<400> SEQUENCE: 960

Ser Asp Thr His Leu Leu Gln Gly Gln Ser Leu Thr
1               5                   10

<210> SEQ ID NO 961
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 961

Asp Thr His Leu Leu Gln Gly Gln Ser Leu Thr Leu
1               5                   10

<210> SEQ ID NO 962
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 962

Thr His Leu Leu Gln Gly Gln Ser Leu Thr Leu Thr
1               5                   10

<210> SEQ ID NO 963
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 963

His Leu Leu Gln Gly Gln Ser Leu Thr Leu Thr Leu
1               5                   10

<210> SEQ ID NO 964
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 964

Leu Leu Gln Gly Gln Ser Leu Thr Leu Thr Leu Glu
1               5                   10

<210> SEQ ID NO 965
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 965

Thr Val Leu Gln Asn Gln Lys Lys Val
1               5

<210> SEQ ID NO 966
<211> LENGTH: 9

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 966

Val Leu Gln Asn Gln Lys Lys Val Glu
 1               5

<210> SEQ ID NO 967
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 967

Leu Gln Asn Gln Lys Lys Val Glu Phe
 1               5

<210> SEQ ID NO 968
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 968

Gln Asn Gln Lys Lys Val Glu Phe Lys
 1               5

<210> SEQ ID NO 969
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 969

Asn Gln Lys Lys Val Glu Phe Lys Ile
 1               5

<210> SEQ ID NO 970
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 970

Gln Lys Lys Val Glu Phe Lys Ile Asp
 1               5

<210> SEQ ID NO 971
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 971

Lys Lys Val Glu Phe Lys Ile Asp Ile
```

<210> SEQ ID NO 972
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 972

Lys Val Glu Phe Lys Ile Asp Ile Val
 1               5

<210> SEQ ID NO 973
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 973

Val Glu Phe Lys Ile Asp Ile Val Val
 1               5

<210> SEQ ID NO 974
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 974

Glu Phe Lys Ile Asp Ile Val Val Leu
 1               5

<210> SEQ ID NO 975
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 975

Phe Lys Ile Asp Ile Val Val Leu Ala
 1               5

<210> SEQ ID NO 976
<211> LENGTH: 9
<212> TYPE: PRT
<213> ORGANISM: Artificial Sequence
<220> FEATURE:
<223> OTHER INFORMATION: Description of Artificial Sequence: binding peptide

<400> SEQUENCE: 976

Lys Ile Asp Ile Val Val Leu Ala Phe
 1               5

<210> SEQ ID NO 977
<211> LENGTH: 9
<212> TYPE: PRT
<213> ORGANISM: Artificial Sequence
<220> FEATURE:
<223> OTHER INFORMATION: Description of Artificial Sequence: binding -continued

```
      peptide

<400> SEQUENCE: 977

Ile Asp Ile Val Val Leu Ala Phe Gln
 1               5

<210> SEQ ID NO 978
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 978

Asp Ile Val Val Leu Ala Phe Gln Lys
 1               5

<210> SEQ ID NO 979
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 979

Ile Val Val Leu Ala Phe Gln Lys Ala
 1               5

<210> SEQ ID NO 980
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 980

Val Val Leu Ala Phe Gln Lys Ala Ser
 1               5

<210> SEQ ID NO 981
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 981

Val Leu Ala Phe Gln Lys Ala Ser Ser
 1               5

<210> SEQ ID NO 982
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 982

Leu Ala Phe Gln Lys Ala Ser Ser Ile
 1               5

<210> SEQ ID NO 983
```

```
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 983

Ala Phe Gln Lys Ala Ser Ser Ile Val
  1               5

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 984

Phe Gln Lys Ala Ser Ser Ile Val Tyr
  1               5

<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 985

Gln Lys Ala Ser Ser Ile Val Tyr Lys
  1               5

<210> SEQ ID NO 986
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 986

Lys Ala Ser Ser Ile Val Tyr Lys Lys
  1               5

<210> SEQ ID NO 987
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 987

Ala Ser Ser Ile Val Tyr Lys Lys Glu
  1               5

<210> SEQ ID NO 988
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 988
```

Ser Ser Ile Val Tyr Lys Lys Glu Gly
1               5

<210> SEQ ID NO 989
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 989

Ser Ile Val Tyr Lys Lys Glu Gly Glu
1               5

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 990

Ile Val Tyr Lys Lys Glu Gly Glu Gln
1               5

<210> SEQ ID NO 991
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 991

Val Tyr Lys Lys Glu Gly Glu Gln Val
1               5

<210> SEQ ID NO 992
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 992

Tyr Lys Lys Glu Gly Glu Gln Val Glu
1               5

<210> SEQ ID NO 993
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 993

Lys Lys Glu Gly Glu Gln Val Glu Phe
1               5

<210> SEQ ID NO 994
<211> LENGTH: 9
<212> TYPE: PRT
<213> ORGANISM: Artificial Sequence
<220> FEATURE:

-continued

<223> OTHER INFORMATION: Description of Artificial Sequence: binding
      peptide

<400> SEQUENCE: 994

Lys Glu Gly Glu Gln Val Glu Phe Ser
 1               5

<210> SEQ ID NO 995
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 995

Glu Gly Glu Gln Val Glu Phe Ser Phe
 1               5

<210> SEQ ID NO 996
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 996

Gly Glu Gln Val Glu Phe Ser Phe Pro
 1               5

<210> SEQ ID NO 997
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 997

Glu Gln Val Glu Phe Ser Phe Pro Leu
 1               5

<210> SEQ ID NO 998
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 998

Gln Val Glu Phe Ser Phe Pro Leu Ala
 1               5

<210> SEQ ID NO 999
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 999

Val Glu Phe Ser Phe Pro Leu Ala Phe
 1               5

```
<210> SEQ ID NO 1000
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1000

Glu Phe Ser Phe Pro Leu Ala Phe Thr
 1               5

<210> SEQ ID NO 1001
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1001

Phe Ser Phe Pro Leu Ala Phe Thr Val
 1               5

<210> SEQ ID NO 1002
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1002

Ser Phe Pro Leu Ala Phe Thr Val Glu
 1               5

<210> SEQ ID NO 1003
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1003

Phe Pro Leu Ala Phe Thr Val Glu Lys
 1               5

<210> SEQ ID NO 1004
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1004

Pro Leu Ala Phe Thr Val Glu Lys Leu
 1               5

<210> SEQ ID NO 1005
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1005
```

```
Leu Ala Phe Thr Val Glu Lys Leu Thr
  1               5
```

<210> SEQ ID NO 1006
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1006

```
Ala Phe Thr Val Glu Lys Leu Thr Gly
  1               5
```

<210> SEQ ID NO 1007
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1007

```
Phe Thr Val Glu Lys Leu Thr Gly Ser
  1               5
```

<210> SEQ ID NO 1008
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1008

```
Thr Val Glu Lys Leu Thr Gly Ser Gly
  1               5
```

<210> SEQ ID NO 1009
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1009

```
Val Glu Lys Leu Thr Gly Ser Gly Glu
  1               5
```

<210> SEQ ID NO 1010
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1010

```
Glu Lys Leu Thr Gly Ser Gly Glu Leu
  1               5
```

<210> SEQ ID NO 1011
<211> LENGTH: 9
<212> TYPE: PRT
<213> ORGANISM: Artificial Sequence

```
<220> FEATURE:
<223> OTHER INFORMATION: Description of Artificial Sequence: binding
      peptide

<400> SEQUENCE: 1011

Lys Leu Thr Gly Ser Gly Glu Leu Trp
 1               5

<210> SEQ ID NO 1012
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1012

Leu Thr Gly Ser Gly Glu Leu Trp Trp
 1               5

<210> SEQ ID NO 1013
<211> LENGTH: 9
<212> TYPE: PRT
<213> ORGANISM: Artificial Sequence
<220> FEATURE:
<223> OTHER INFORMATION: Description of Artificial Sequence: binding
      peptide

<400> SEQUENCE: 1013

Thr Gly Ser Gly Glu Leu Trp Trp Gln
 1               5

<210> SEQ ID NO 1014
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1014

Thr Val Leu Gln Asn Gln Lys Lys Val Glu Phe Lys
 1               5                  10

<210> SEQ ID NO 1015
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1015

Val Leu Gln Asn Gln Lys Lys Val Glu Phe Lys Ile
 1               5                  10

<210> SEQ ID NO 1016
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1016

Leu Gln Asn Gln Lys Lys Val Glu Phe Lys Ile Asp
 1               5                  10
```

-continued

```
<210> SEQ ID NO 1017
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1017

Gln Asn Gln Lys Lys Val Glu Phe Lys Ile Asp Ile
 1               5                  10

<210> SEQ ID NO 1018
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1018

Asn Gln Lys Lys Val Glu Phe Lys Ile Asp Ile Val
 1               5                  10

<210> SEQ ID NO 1019
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1019

Gln Lys Lys Val Glu Phe Lys Ile Asp Ile Val Val
 1               5                  10

<210> SEQ ID NO 1020
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1020

Lys Lys Val Glu Phe Lys Ile Asp Ile Val Val Leu
 1               5                  10

<210> SEQ ID NO 1021
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1021

Lys Val Glu Phe Lys Ile Asp Ile Val Val Leu Ala
 1               5                  10

<210> SEQ ID NO 1022
<211> LENGTH: 12
<212> TYPE: PRT
<213> ORGANISM: Artificial Sequence
<220> FEATURE:
<223> OTHER INFORMATION: Description of Artificial Sequence: binding
      peptide
```

-continued

```
<400> SEQUENCE: 1022

Val Glu Phe Lys Ile Asp Ile Val Val Leu Ala Phe
 1               5                  10

<210> SEQ ID NO 1023
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1023

Glu Phe Lys Ile Asp Ile Val Val Leu Ala Phe Gln
 1               5                  10

<210> SEQ ID NO 1024
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1024

Phe Lys Ile Asp Ile Val Val Leu Ala Phe Gln Lys
 1               5                  10

<210> SEQ ID NO 1025
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1025

Lys Ile Asp Ile Val Val Leu Ala Phe Gln Lys Ala
 1               5                  10

<210> SEQ ID NO 1026
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1026

Ile Asp Ile Val Val Leu Ala Phe Gln Lys Ala Ser
 1               5                  10

<210> SEQ ID NO 1027
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1027

Asp Ile Val Val Leu Ala Phe Gln Lys Ala Ser Ser
 1               5                  10

<210> SEQ ID NO 1028
<211> LENGTH: 12
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 1028

Ile Val Val Leu Ala Phe Gln Lys Ala Ser Ser Ile
 1               5                  10

<210> SEQ ID NO 1029
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1029

Val Val Leu Ala Phe Gln Lys Ala Ser Ser Ile Val
 1               5                  10

<210> SEQ ID NO 1030
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1030

Val Leu Ala Phe Gln Lys Ala Ser Ser Ile Val Tyr
 1               5                  10

<210> SEQ ID NO 1031
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1031

Leu Ala Phe Gln Lys Ala Ser Ser Ile Val Tyr Lys
 1               5                  10

<210> SEQ ID NO 1032
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1032

Ala Phe Gln Lys Ala Ser Ser Ile Val Tyr Lys Lys
 1               5                  10

<210> SEQ ID NO 1033
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1033

Phe Gln Lys Ala Ser Ser Ile Val Tyr Lys Lys Glu
 1               5                  10
```

<210> SEQ ID NO 1034
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1034

Gln Lys Ala Ser Ser Ile Val Tyr Lys Lys Glu Gly
  1               5                  10

<210> SEQ ID NO 1035
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1035

Lys Ala Ser Ser Ile Val Tyr Lys Lys Glu Gly Glu
  1               5                  10

<210> SEQ ID NO 1036
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1036

Ala Ser Ser Ile Val Tyr Lys Lys Glu Gly Glu Gln
  1               5                  10

<210> SEQ ID NO 1037
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1037

Ser Ser Ile Val Tyr Lys Lys Glu Gly Glu Gln Val
  1               5                  10

<210> SEQ ID NO 1038
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1038

Ser Ile Val Tyr Lys Lys Glu Gly Glu Gln Val Glu
  1               5                  10

<210> SEQ ID NO 1039
<211> LENGTH: 12
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 1039

Ile Val Tyr Lys Lys Glu Gly Glu Gln Val Glu Phe
 1               5                  10

<210> SEQ ID NO 1040
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1040

Val Tyr Lys Lys Glu Gly Glu Gln Val Glu Phe Ser
 1               5                  10

<210> SEQ ID NO 1041
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1041

Tyr Lys Lys Glu Gly Glu Gln Val Glu Phe Ser Phe
 1               5                  10

<210> SEQ ID NO 1042
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1042

Lys Lys Glu Gly Glu Gln Val Glu Phe Ser Phe Pro
 1               5                  10

<210> SEQ ID NO 1043
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1043

Lys Glu Gly Glu Gln Val Glu Phe Ser Phe Pro Leu
 1               5                  10

<210> SEQ ID NO 1044
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1044

Glu Gly Glu Gln Val Glu Phe Ser Phe Pro Leu Ala
 1               5                  10

<210> SEQ ID NO 1045
<211> LENGTH: 12
```

-continued

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 1045

Gly Glu Gln Val Glu Phe Ser Phe Pro Leu Ala Phe
 1               5                  10

<210> SEQ ID NO 1046
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1046

Glu Gln Val Glu Phe Ser Phe Pro Leu Ala Phe Thr
 1               5                  10

<210> SEQ ID NO 1047
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1047

Gln Val Glu Phe Ser Phe Pro Leu Ala Phe Thr Val
 1               5                  10

<210> SEQ ID NO 1048
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1048

Val Glu Phe Ser Phe Pro Leu Ala Phe Thr Val Glu
 1               5                  10

<210> SEQ ID NO 1049
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1049

Glu Phe Ser Phe Pro Leu Ala Phe Thr Val Glu Lys
 1               5                  10

<210> SEQ ID NO 1050
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1050

Phe Ser Phe Pro Leu Ala Phe Thr Val Glu Lys Leu
```

-continued

```
<210> SEQ ID NO 1051
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1051

Ser Phe Pro Leu Ala Phe Thr Val Glu Lys Leu Thr
  1               5                  10

<210> SEQ ID NO 1052
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1052

Phe Pro Leu Ala Phe Thr Val Glu Lys Leu Thr Gly
  1               5                  10

<210> SEQ ID NO 1053
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1053

Pro Leu Ala Phe Thr Val Glu Lys Leu Thr Gly Ser
  1               5                  10

<210> SEQ ID NO 1054
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1054

Leu Ala Phe Thr Val Glu Lys Leu Thr Gly Ser Gly
  1               5                  10

<210> SEQ ID NO 1055
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1055

Ala Phe Thr Val Glu Lys Leu Thr Gly Ser Gly Glu
  1               5                  10

<210> SEQ ID NO 1056
<211> LENGTH: 12
<212> TYPE: PRT
<213> ORGANISM: Artificial Sequence
<220> FEATURE:
<223> OTHER INFORMATION: Description of Artificial Sequence: binding
```

```
      peptide

<400> SEQUENCE: 1056

Phe Thr Val Glu Lys Leu Thr Gly Ser Gly Glu Leu
 1               5                   10

<210> SEQ ID NO 1057
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1057

Thr Val Glu Lys Leu Thr Gly Ser Gly Glu Leu Trp
 1               5                   10

<210> SEQ ID NO 1058
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1058

Val Glu Lys Leu Thr Gly Ser Gly Glu Leu Trp Trp
 1               5                   10

<210> SEQ ID NO 1059
<211> LENGTH: 12
<212> TYPE: PRT
<213> ORGANISM: Artificial Sequence
<220> FEATURE:
<223> OTHER INFORMATION: Description of Artificial Sequence: binding
      peptide

<400> SEQUENCE: 1059

Glu Lys Leu Thr Gly Ser Gly Glu Leu Trp Trp Gln
 1               5                   10

<210> SEQ ID NO 1060
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1060

Glx Glx Glx Glx Glx Glx Asp Thr Tyr Ile Cys Glu Val Glu Asp
 1               5                   10                  15

<210> SEQ ID NO 1061
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1061

Glx Glx Glx Glx Glx Glx Ala Thr Tyr Ile Cys Glu Val Glu Asp
 1               5                   10                  15

<210> SEQ ID NO 1062
```

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1062

Glx Glx Glx Glx Glx Glx Asp Ala Tyr Ile Cys Glu Val Glu Asp
 1               5                  10                  15

<210> SEQ ID NO 1063
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1063

Glx Glx Glx Glx Glx Glx Asp Thr Ala Ile Cys Glu Val Glu Asp
 1               5                  10                  15

<210> SEQ ID NO 1064
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1064

Glx Glx Glx Glx Glx Glx Asp Thr Tyr Ala Cys Glu Val Glu Asp
 1               5                  10                  15

<210> SEQ ID NO 1065
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1065

Glx Glx Glx Glx Glx Glx Asp Thr Tyr Ile Ala Glu Val Glu Asp
 1               5                  10                  15

<210> SEQ ID NO 1066
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1066

Glx Glx Glx Glx Glx Glx Asp Thr Tyr Ile Cys Ala Val Glu Asp
 1               5                  10                  15

<210> SEQ ID NO 1067
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1067
```

Glx Glx Glx Glx Glx Glx Asp Thr Tyr Ile Cys Glu Ala Glu Asp
1               5                   10                  15

<210> SEQ ID NO 1068
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1068

Glx Glx Glx Glx Glx Glx Asp Thr Tyr Ile Cys Glu Val Ala Asp
1               5                   10                  15

<210> SEQ ID NO 1069
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1069

Glx Glx Glx Glx Glx Glx Asp Thr Tyr Ile Cys Glu Val Glu Ala
1               5                   10                  15

<210> SEQ ID NO 1070
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1070

Glx Glx Glx Glx Glx Glx Asp Thr Tyr Ile Cys Glu Val Glu Asp
1               5                   10                  15

<210> SEQ ID NO 1071
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1071

Glx Glx Glx Glx Glx Glx Asp Thr Tyr Ile Cys Glu Val Glu Asp
1               5                   10                  15

<210> SEQ ID NO 1072
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1072

Glx Glx Glx Glx Glx Glx Ala Thr Tyr Ile Cys Glu Val Glu Asp
1               5                   10                  15

<210> SEQ ID NO 1073
<211> LENGTH: 15
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 1073

Glx Glx Glx Glx Glx Glx Asp Ala Tyr Ile Cys Glu Val Glu Asp
 1               5                  10                  15

<210> SEQ ID NO 1074
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1074

Glx Glx Glx Glx Glx Glx Asp Thr Ala Ile Cys Glu Val Glu Asp
 1               5                  10                  15

<210> SEQ ID NO 1075
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1075

Glx Glx Glx Glx Glx Glx Asp Thr Tyr Ile Ala Glu Val Glu Asp
 1               5                  10                  15

<210> SEQ ID NO 1076
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1076

Glx Glx Glx Glx Glx Glx Asp Thr Tyr Ile Cys Ala Val Glu Asp
 1               5                  10                  15

<210> SEQ ID NO 1077
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1077

Glx Glx Glx Glx Glx Glx Asp Thr Tyr Ile Cys Glu Ala Glu Asp
 1               5                  10                  15

<210> SEQ ID NO 1078
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1078

Glx Glx Glx Glx Glx Glx Asp Thr Tyr Ile Cys Glu Val Ala Asp
 1               5                  10                  15
```

```
<210> SEQ ID NO 1079
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1079

Glx Glx Glx Glx Glx Glx Asp Thr Tyr Ile Cys Glu Val Glu Ala
 1               5                  10                  15

<210> SEQ ID NO 1080
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1080

Glx Glx Glx Glx Glx Glx Asp Thr Tyr Ile Cys Glu Val Glu Asp
 1               5                  10                  15

<210> SEQ ID NO 1081
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1081

Glu Glu Val Gln Leu Leu Val Phe Gly Leu Thr Ala Asn Ser Asp
 1               5                  10                  15

<210> SEQ ID NO 1082
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1082

Ala Glu Val Gln Leu Leu Val Phe Gly Leu Thr Ala Asn Ser Asp
 1               5                  10                  15

<210> SEQ ID NO 1083
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1083

Glu Ala Val Gln Leu Leu Val Phe Gly Leu Thr Ala Asn Ser Asp
 1               5                  10                  15

<210> SEQ ID NO 1084
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1084
```

Glu Glu Ala Gln Leu Leu Val Phe Gly Leu Thr Ala Asn Ser Asp
1               5                   10                  15

<210> SEQ ID NO 1085
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1085

Glu Glu Val Ala Leu Leu Val Phe Gly Leu Thr Ala Asn Ser Asp
1               5                   10                  15

<210> SEQ ID NO 1086
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1086

Glu Glu Val Gln Ala Leu Val Phe Gly Leu Thr Ala Asn Ser Asp
1               5                   10                  15

<210> SEQ ID NO 1087
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1087

Glu Glu Val Gln Leu Ala Val Phe Gly Leu Thr Ala Asn Ser Asp
1               5                   10                  15

<210> SEQ ID NO 1088
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1088

Glu Glu Val Gln Leu Leu Ala Phe Gly Leu Thr Ala Asn Ser Asp
1               5                   10                  15

<210> SEQ ID NO 1089
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1089

Glu Glu Val Gln Leu Leu Val Ala Gly Leu Thr Ala Asn Ser Asp
1               5                   10                  15

<210> SEQ ID NO 1090
<211> LENGTH: 15
<212> TYPE: PRT
<213> ORGANISM: Artificial Sequence

```
<220> FEATURE:
<223> OTHER INFORMATION: Description of Artificial Sequence: binding
      peptide

<400> SEQUENCE: 1090

Glu Glu Val Gln Leu Leu Val Phe Ala Leu Thr Ala Asn Ser Asp
1               5                   10                  15

<210> SEQ ID NO 1091
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1091

Glu Glu Val Gln Leu Leu Val Phe Gly Ala Thr Ala Asn Ser Asp
1               5                   10                  15

<210> SEQ ID NO 1092
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1092

Glu Glu Val Gln Leu Leu Val Phe Gly Leu Ala Ala Asn Ser Asp
1               5                   10                  15

<210> SEQ ID NO 1093
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1093

Glu Glu Val Gln Leu Leu Val Phe Gly Leu Thr Thr Asn Ser Asp
1               5                   10                  15

<210> SEQ ID NO 1094
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1094

Glu Glu Val Gln Leu Leu Val Phe Gly Leu Thr Ala Ala Ser Asp
1               5                   10                  15

<210> SEQ ID NO 1095
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1095

Glu Glu Val Gln Leu Leu Val Phe Gly Leu Thr Ala Asn Ala Asp
1               5                   10                  15
```

<210> SEQ ID NO 1096
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1096

Glu Glu Val Gln Leu Leu Val Phe Gly Leu Thr Ala Asn Ser Ala
 1               5                  10                  15

<210> SEQ ID NO 1097
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1097

Glu Glu Val Gln Leu Leu Val Phe Gly Leu Thr Ala Asn Ser Asp
 1               5                  10                  15

<210> SEQ ID NO 1098
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1098

Glu Glu Val Gln Leu Leu Val Phe Gly Leu Thr Ala Asn Ser Asp
 1               5                  10                  15

<210> SEQ ID NO 1099
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1099

Ala Glu Val Gln Leu Leu Val Phe Gly Leu Thr Ala Asn Ser Asp
 1               5                  10                  15

<210> SEQ ID NO 1100
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1100

Glu Ala Val Gln Leu Leu Val Phe Gly Leu Thr Ala Asn Ser Asp
 1               5                  10                  15

<210> SEQ ID NO 1101
<211> LENGTH: 15
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 1101

Glu Glu Ala Gln Leu Leu Val Phe Gly Leu Thr Ala Asn Ser Asp
 1               5                  10                  15

<210> SEQ ID NO 1102
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1102

Glu Glu Val Ala Leu Leu Val Phe Gly Leu Thr Ala Asn Ser Asp
 1               5                  10                  15

<210> SEQ ID NO 1103
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1103

Glu Glu Val Gln Ala Leu Val Phe Gly Leu Thr Ala Asn Ser Asp
 1               5                  10                  15

<210> SEQ ID NO 1104
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1104

Glu Glu Val Gln Leu Ala Val Phe Gly Leu Thr Ala Asn Ser Asp
 1               5                  10                  15

<210> SEQ ID NO 1105
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1105

Glu Glu Val Gln Leu Leu Ala Phe Gly Leu Thr Ala Asn Ser Asp
 1               5                  10                  15

<210> SEQ ID NO 1106
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1106

Glu Glu Val Gln Leu Leu Val Ala Gly Leu Thr Ala Asn Ser Asp
 1               5                  10                  15

<210> SEQ ID NO 1107
<211> LENGTH: 15
<212> TYPE: PRT
```

```
<213> ORGANISM: Artificial Sequence
<220> FEATURE:
<223> OTHER INFORMATION: Description of Artificial Sequence: binding
      peptide

<400> SEQUENCE: 1107

Glu Glu Val Gln Leu Leu Val Phe Ala Leu Thr Ala Asn Ser Asp
 1               5                  10                  15

<210> SEQ ID NO 1108
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1108

Glu Glu Val Gln Leu Leu Val Phe Gly Ala Thr Ala Asn Ser Asp
 1               5                  10                  15

<210> SEQ ID NO 1109
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1109

Glu Glu Val Gln Leu Leu Val Phe Gly Leu Ala Ala Asn Ser Asp
 1               5                  10                  15

<210> SEQ ID NO 1110
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1110

Glu Glu Val Gln Leu Leu Val Phe Gly Leu Thr Thr Asn Ser Asp
 1               5                  10                  15

<210> SEQ ID NO 1111
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1111

Glu Glu Val Gln Leu Leu Val Phe Gly Leu Thr Ala Ala Ser Asp
 1               5                  10                  15

<210> SEQ ID NO 1112
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1112

Glu Glu Val Gln Leu Leu Val Phe Gly Leu Thr Ala Asn Ala Asp
 1               5                  10                  15
```

<210> SEQ ID NO 1113
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1113

Glu Glu Val Gln Leu Leu Val Phe Gly Leu Thr Ala Asn Ser Ala
 1               5                  10                  15

<210> SEQ ID NO 1114
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1114

Glu Glu Val Gln Leu Leu Val Phe Gly Leu Thr Ala Asn Ser Asp
 1               5                  10                  15

<210> SEQ ID NO 1115
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1115

Thr His Leu Leu Gln Gly Gln Ser Leu Thr Leu Thr Leu Glu Ser
 1               5                  10                  15

<210> SEQ ID NO 1116
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1116

Ala His Leu Leu Gln Gly Gln Ser Leu Thr Leu Thr Leu Glu Ser
 1               5                  10                  15

<210> SEQ ID NO 1117
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1117

Thr Ala Leu Leu Gln Gly Gln Ser Leu Thr Leu Thr Leu Glu Ser
 1               5                  10                  15

<210> SEQ ID NO 1118
<211> LENGTH: 15
<212> TYPE: PRT
<213> ORGANISM: Artificial Sequence
<220> FEATURE:
<223> OTHER INFORMATION: Description of Artificial Sequence: binding
      peptide

```
<400> SEQUENCE: 1118

Thr His Ala Leu Gln Gly Gln Ser Leu Thr Leu Thr Leu Glu Ser
 1               5                  10                  15

<210> SEQ ID NO 1119
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1119

Thr His Leu Ala Gln Gly Gln Ser Leu Thr Leu Thr Leu Glu Ser
 1               5                  10                  15

<210> SEQ ID NO 1120
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1120

Thr His Leu Leu Ala Gly Gln Ser Leu Thr Leu Thr Leu Glu Ser
 1               5                  10                  15

<210> SEQ ID NO 1121
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1121

Thr His Leu Leu Gln Ala Gln Ser Leu Thr Leu Thr Leu Glu Ser
 1               5                  10                  15

<210> SEQ ID NO 1122
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1122

Thr His Leu Leu Gln Gly Gln Ala Leu Thr Leu Thr Leu Glu Ser
 1               5                  10                  15

<210> SEQ ID NO 1123
<211> LENGTH: 14
<212> TYPE: PRT
<213> ORGANISM: Artificial Sequence
<220> FEATURE:
<223> OTHER INFORMATION: Description of Artificial Sequence: binding
      peptide

<400> SEQUENCE: 1123

Thr His Leu Leu Gln Gly Gln Ala Leu Thr Leu Thr Leu Glu
 1               5                  10

<210> SEQ ID NO 1124
<211> LENGTH: 15
```

```
<212> TYPE: PRT
<213> ORGANISM: Artificial Sequence
<220> FEATURE:
<223> OTHER INFORMATION: Description of Artificial Sequence: binding
      peptide

<400> SEQUENCE: 1124

Thr His Leu Leu Gln Gly Gln Ser Ala Thr Leu Thr Leu Glu Ser
 1               5                  10                  15

<210> SEQ ID NO 1125
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1125

Thr His Leu Leu Gln Gly Gln Ser Leu Ala Leu Thr Leu Glu Ser
 1               5                  10                  15

<210> SEQ ID NO 1126
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1126

Thr His Leu Leu Gln Gly Gln Ser Leu Thr Ala Leu Glu Ser
 1               5                  10                  15

<210> SEQ ID NO 1127
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1127

Thr His Leu Leu Gln Gly Gln Ser Leu Thr Leu Ala Leu Glu Ser
 1               5                  10                  15

<210> SEQ ID NO 1128
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1128

Thr His Leu Leu Gln Gly Gln Ser Leu Thr Leu Thr Ala Glu Ser
 1               5                  10                  15

<210> SEQ ID NO 1129
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1129

Thr His Leu Leu Gln Gly Gln Ser Leu Thr Leu Thr Leu Ala Ser
```

```
                 1               5              10              15
```

<210> SEQ ID NO 1130
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1130

```
Thr His Leu Leu Gln Gly Gln Ser Leu Thr Leu Thr Leu Glu Ala
 1               5                  10                  15
```

<210> SEQ ID NO 1131
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1131

```
Thr His Leu Leu Gln Gly Gln Ser Leu Thr Leu Thr Leu Glu Ser
 1               5                  10                  15
```

<210> SEQ ID NO 1132
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1132

```
Thr His Leu Leu Gln Gly Gln Ser Leu Thr Leu Thr Leu Glu Ser
 1               5                  10                  15
```

<210> SEQ ID NO 1133
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1133

```
Ala His Leu Leu Gln Gly Gln Ser Leu Thr Leu Thr Leu Glu Ser
 1               5                  10                  15
```

<210> SEQ ID NO 1134
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1134

```
Thr Ala Leu Leu Gln Gly Gln Ser Leu Thr Leu Thr Leu Glu Ser
 1               5                  10                  15
```

<210> SEQ ID NO 1135
<211> LENGTH: 15
<212> TYPE: PRT
<213> ORGANISM: Artificial Sequence
<220> FEATURE:
<223> OTHER INFORMATION: Description of Artificial Sequence: binding -continued

```
<400> SEQUENCE: 1135

Thr His Ala Leu Gln Gly Gln Ser Leu Thr Leu Thr Leu Glu Ser
 1               5                  10                  15

<210> SEQ ID NO 1136
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1136

Thr His Leu Ala Gln Gly Gln Ser Leu Thr Leu Thr Leu Glu Ser
 1               5                  10                  15

<210> SEQ ID NO 1137
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1137

Thr His Leu Leu Ala Gly Gln Ser Leu Thr Leu Thr Leu Glu Ser
 1               5                  10                  15

<210> SEQ ID NO 1138
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1138

Thr His Leu Leu Gln Ala Gln Ser Leu Thr Leu Thr Leu Glu Ser
 1               5                  10                  15

<210> SEQ ID NO 1139
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1139

Thr His Leu Leu Gln Gly Ala Ser Leu Thr Leu Thr Leu Glu Ser
 1               5                  10                  15

<210> SEQ ID NO 1140
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1140

Thr His Leu Leu Gln Gly Gln Ala Leu Thr Leu Thr Leu Glu Ser
 1               5                  10                  15

<210> SEQ ID NO 1141
```

-continued

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1141

Thr His Leu Leu Gln Gly Gln Ser Ala Thr Leu Thr Leu Glu Ser
 1               5                  10                  15

<210> SEQ ID NO 1142
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1142

Thr His Leu Leu Gln Gly Gln Ser Leu Ala Leu Thr Leu Glu Ser
 1               5                  10                  15

<210> SEQ ID NO 1143
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1143

Thr His Leu Leu Gln Gly Gln Ser Leu Thr Ala Thr Leu Glu Ser
 1               5                  10                  15

<210> SEQ ID NO 1144
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1144

Thr His Leu Leu Gln Gly Gln Ser Leu Thr Leu Ala Leu Glu Ser
 1               5                  10                  15

<210> SEQ ID NO 1145
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1145

Thr His Leu Leu Gln Gly Gln Ser Leu Thr Leu Thr Ala Glu Ser
 1               5                  10                  15

<210> SEQ ID NO 1146
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1146
```

```
Thr His Leu Leu Gln Gly Gln Ser Leu Thr Leu Thr Leu Ala Ser
 1               5                  10                  15

<210> SEQ ID NO 1147
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1147

Thr His Leu Leu Gln Gly Gln Ser Leu Thr Leu Thr Leu Glu Ala
 1               5                  10                  15

<210> SEQ ID NO 1148
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1148

Thr His Leu Leu Gln Gly Gln Ser Leu Thr Leu Thr Leu Glu Ser
 1               5                  10                  15

<210> SEQ ID NO 1149
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1149

Gly Glu Gln Val Glu Phe Ser Phe Pro Leu Ala Phe Thr Val Glu
 1               5                  10                  15

<210> SEQ ID NO 1150
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1150

Ala Glu Gln Val Glu Phe Ser Phe Pro Leu Ala Phe Thr Val Glu
 1               5                  10                  15

<210> SEQ ID NO 1151
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1151

Gly Ala Gln Val Glu Phe Ser Phe Pro Leu Ala Phe Thr Val Glu
 1               5                  10                  15

<210> SEQ ID NO 1152
<211> LENGTH: 15
<212> TYPE: PRT
<213> ORGANISM: Artificial Sequence
<220> FEATURE:
```

-continued

<223> OTHER INFORMATION: Description of Artificial Sequence: binding
      peptide

<400> SEQUENCE: 1152

Gly Glu Ala Val Glu Phe Ser Phe Pro Leu Ala Phe Thr Val Glu
 1               5                  10                  15

<210> SEQ ID NO 1153
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1153

Gly Glu Gln Ala Glu Phe Ser Phe Pro Leu Ala Phe Thr Val Glu
 1               5                  10                  15

<210> SEQ ID NO 1154
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1154

Gly Glu Gln Val Ala Phe Ser Phe Pro Leu Ala Phe Thr Val Glu
 1               5                  10                  15

<210> SEQ ID NO 1155
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1155

Gly Glu Gln Val Glu Ala Ser Phe Pro Leu Ala Phe Thr Val Glu
 1               5                  10                  15

<210> SEQ ID NO 1156
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1156

Gly Glu Gln Val Glu Phe Ala Phe Pro Leu Ala Phe Thr Val Glu
 1               5                  10                  15

<210> SEQ ID NO 1157
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1157

Gly Glu Gln Val Glu Phe Ser Ala Pro Leu Ala Phe Thr Val Glu
 1               5                  10                  15

```
<210> SEQ ID NO 1158
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1158

Gly Glu Gln Val Glu Phe Ser Phe Ala Leu Ala Phe Thr Val Glu
 1               5                  10                  15

<210> SEQ ID NO 1159
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1159

Gly Glu Gln Val Glu Phe Ser Phe Pro Ala Ala Phe Thr Val Glu
 1               5                  10                  15

<210> SEQ ID NO 1160
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1160

Gly Glu Gln Val Glu Phe Ser Phe Pro Leu Thr Phe Thr Val Glu
 1               5                  10                  15

<210> SEQ ID NO 1161
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1161

Gly Glu Gln Val Glu Phe Ser Phe Pro Leu Ala Ala Thr Val Glu
 1               5                  10                  15

<210> SEQ ID NO 1162
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1162

Gly Glu Gln Val Glu Phe Ser Phe Pro Leu Ala Phe Ala Val Glu
 1               5                  10                  15

<210> SEQ ID NO 1163
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1163
```

```
Gly Glu Gln Val Glu Phe Ser Phe Pro Leu Ala Phe Thr Ala Glu
 1               5                  10                  15

<210> SEQ ID NO 1164
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1164

Gly Glu Gln Val Glu Phe Ser Phe Pro Leu Ala Phe Thr Val Ala
 1               5                  10                  15

<210> SEQ ID NO 1165
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1165

Gly Glu Gln Val Glu Phe Ser Phe Pro Leu Ala Phe Thr Val Glu
 1               5                  10                  15

<210> SEQ ID NO 1166
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1166

Gly Glu Gln Val Glu Phe Ser Phe Pro Leu Ala Phe Thr Val Glu
 1               5                  10                  15

<210> SEQ ID NO 1167
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1167

Ala Glu Gln Val Glu Phe Ser Phe Pro Leu Ala Phe Thr Val Glu
 1               5                  10                  15

<210> SEQ ID NO 1168
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1168

Gly Ala Gln Val Glu Phe Ser Phe Pro Leu Ala Phe Thr Val Glu
 1               5                  10                  15

<210> SEQ ID NO 1169
<211> LENGTH: 15
<212> TYPE: PRT
<213> ORGANISM: Artificial Sequence
```

-continued

```
<220> FEATURE:
<223> OTHER INFORMATION: Description of Artificial Sequence: binding
      peptide

<400> SEQUENCE: 1169

Gly Glu Ala Val Glu Phe Ser Phe Pro Leu Ala Phe Thr Val Glu
  1               5                  10                  15

<210> SEQ ID NO 1170
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1170

Gly Glu Gln Ala Glu Phe Ser Phe Pro Leu Ala Phe Thr Val Glu
  1               5                  10                  15

<210> SEQ ID NO 1171
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1171

Gly Glu Gln Val Ala Phe Ser Phe Pro Leu Ala Phe Thr Val Glu
  1               5                  10                  15

<210> SEQ ID NO 1172
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1172

Gly Glu Gln Val Glu Ala Ser Phe Pro Leu Ala Phe Thr Val Glu
  1               5                  10                  15

<210> SEQ ID NO 1173
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1173

Gly Glu Gln Val Glu Phe Ala Phe Pro Leu Ala Phe Thr Val Glu
  1               5                  10                  15

<210> SEQ ID NO 1174
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1174

Gly Glu Gln Val Glu Phe Ser Ala Pro Leu Ala Phe Thr Val Glu
  1               5                  10                  15
```

```
<210> SEQ ID NO 1175
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1175

Gly Glu Gln Val Glu Phe Ser Phe Ala Leu Ala Phe Thr Val Glu
1               5                   10                  15

<210> SEQ ID NO 1176
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1176

Gly Glu Gln Val Glu Phe Ser Phe Pro Ala Ala Phe Thr Val Glu
1               5                   10                  15

<210> SEQ ID NO 1177
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1177

Gly Glu Gln Val Glu Phe Ser Phe Pro Leu Thr Phe Thr Val Glu
1               5                   10                  15

<210> SEQ ID NO 1178
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1178

Gly Glu Gln Val Glu Phe Ser Phe Pro Leu Ala Ala Thr Val Glu
1               5                   10                  15

<210> SEQ ID NO 1179
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1179

Gly Glu Gln Val Glu Phe Ser Phe Pro Leu Ala Phe Ala Val Glu
1               5                   10                  15

<210> SEQ ID NO 1180
<211> LENGTH: 15
<212> TYPE: PRT
<213> ORGANISM: Artificial Sequence
<220> FEATURE:
<223> OTHER INFORMATION: Description of Artificial Sequence: binding
      peptide
```

```
<400> SEQUENCE: 1180

Gly Glu Gln Val Glu Phe Ser Phe Pro Leu Ala Phe Thr Ala Glu
 1               5                  10                  15

<210> SEQ ID NO 1181
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1181

Gly Glu Gln Val Glu Phe Ser Phe Pro Leu Ala Phe Thr Val Ala
 1               5                  10                  15

<210> SEQ ID NO 1182
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1182

Gly Glu Gln Val Glu Phe Ser Phe Pro Leu Ala Phe Thr Val Glu
 1               5                  10                  15

<210> SEQ ID NO 1183
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1183

Glx Glx Glx Glx Glx Glx Asp Thr Tyr Ile Cys Glu Val Glu Asp
 1               5                  10                  15

<210> SEQ ID NO 1184
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1184

Glx Glx Glx Glx Glx Glx Asp Thr Tyr Ile Cys Glu Val Glu Glx
 1               5                  10                  15

<210> SEQ ID NO 1185
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1185

Glx Glx Glx Glx Glx Glx Asp Thr Tyr Ile Cys Glu Val Glx Glx
 1               5                  10                  15

<210> SEQ ID NO 1186
<211> LENGTH: 15
<212> TYPE: PRT
```

-continued

```
<213> ORGANISM: Artificial Sequence
<220> FEATURE:
<223> OTHER INFORMATION: Description of Artificial Sequence: binding
      peptide

<400> SEQUENCE: 1186

Glx Glx Glx Glx Glx Glx Asp Thr Tyr Ile Cys Glu Glx Glx Glx
 1               5                  10                  15

<210> SEQ ID NO 1187
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1187

Glx Glx Glx Glx Glx Glx Asp Thr Tyr Ile Glx Glx Glx Glx Glx
 1               5                  10                  15

<210> SEQ ID NO 1188
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1188

Glx Glx Glx Glx Glx Glx Glx Thr Tyr Ile Cys Glu Val Glu Asp
 1               5                  10                  15

<210> SEQ ID NO 1189
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1189

Glu Glu Val Gln Leu Leu Val Phe Gly Leu Thr Ala Asn Ser Asp
 1               5                  10                  15

<210> SEQ ID NO 1190
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1190

Glu Glu Val Gln Leu Leu Val Phe Gly Leu Thr Ala Asn Ser Glx
 1               5                  10                  15

<210> SEQ ID NO 1191
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1191

Glu Glu Val Gln Leu Leu Val Phe Gly Leu Thr Ala Asn Glx Glx
 1               5                  10                  15
```

```
<210> SEQ ID NO 1192
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1192

Glu Glu Val Gln Leu Leu Val Phe Gly Leu Thr Ala Glx Glx Glx
 1               5                  10                  15

<210> SEQ ID NO 1193
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1193

Glu Glu Val Gln Leu Leu Val Phe Gly Leu Thr Glx Glx Glx Glx
 1               5                  10                  15

<210> SEQ ID NO 1194
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1194

Glu Glu Val Gln Leu Leu Val Phe Gly Leu Glx Glx Glx Glx Glx
 1               5                  10                  15

<210> SEQ ID NO 1195
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1195

Glu Glu Val Gln Leu Leu Val Phe Gly Glx Glx Glx Glx Glx Glx
 1               5                  10                  15

<210> SEQ ID NO 1196
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1196

Glu Glu Val Gln Leu Leu Val Phe Glx Glx Glx Glx Glx Glx Glx
 1               5                  10                  15

<210> SEQ ID NO 1197
<211> LENGTH: 15
<212> TYPE: PRT
<213> ORGANISM: Artificial Sequence
<220> FEATURE:
<223> OTHER INFORMATION: Description of Artificial Sequence: binding
      peptide
```

<400> SEQUENCE: 1197

Glu Glu Val Gln Leu Leu Val Glx Glx Glx Glx Glx Glx Glx Glx
 1               5                  10                  15

<210> SEQ ID NO 1198
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1198

Glx Glu Val Gln Leu Leu Val Phe Gly Leu Thr Ala Asn Ser Asp
 1               5                  10                  15

<210> SEQ ID NO 1199
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1199

Glx Glx Val Gln Leu Leu Val Phe Gly Leu Thr Ala Asn Ser Asp
 1               5                  10                  15

<210> SEQ ID NO 1200
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1200

Glx Glx Glx Gln Leu Leu Val Phe Gly Leu Thr Ala Asn Ser Asp
 1               5                  10                  15

<210> SEQ ID NO 1201
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1201

Glx Glx Glx Glx Leu Leu Val Phe Gly Leu Thr Ala Asn Ser Asp
 1               5                  10                  15

<210> SEQ ID NO 1202
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1202

Glx Glx Glx Glx Glx Leu Val Phe Gly Leu Thr Ala Asn Ser Asp
 1               5                  10                  15

<210> SEQ ID NO 1203
<211> LENGTH: 15

```
-continued

<212> TYPE: PRT
<213> ORGANISM: Artificial Sequence
<220> FEATURE:
<223> OTHER INFORMATION: Description of Artificial Sequence: binding
      peptide

<400> SEQUENCE: 1203

Glx Glx Glx Glx Glx Glx Val Phe Gly Leu Thr Ala Asn Ser Asp
 1               5                  10                  15

<210> SEQ ID NO 1204
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1204

Glx Glx Glx Glx Glx Glx Glx Phe Gly Leu Thr Ala Asn Ser Asp
 1               5                  10                  15

<210> SEQ ID NO 1205
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1205

Glx Glx Glx Glx Glx Glx Glx Glx Gly Leu Thr Ala Asn Ser Asp
 1               5                  10                  15

<210> SEQ ID NO 1206
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1206

Glu Glu Val Gln Leu Leu Val Phe Gly Leu Thr Ala Asn Ser Asp
 1               5                  10                  15

<210> SEQ ID NO 1207
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1207

Thr His Leu Leu Gln Gly Gln Ser Leu Thr Leu Thr Leu Glu Ser
 1               5                  10                  15

<210> SEQ ID NO 1208
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1208

Thr His Leu Leu Gln Gly Gln Ser Leu Thr Leu Thr Leu Glu Glx
```

```
<210> SEQ ID NO 1209
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1209

Thr His Leu Leu Gln Gly Gln Ser Leu Thr Leu Thr Leu Glx Glx
 1               5                  10                  15

<210> SEQ ID NO 1210
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1210

Thr His Leu Leu Gln Gly Gln Ser Leu Thr Leu Thr Glx Glx Glx
 1               5                  10                  15

<210> SEQ ID NO 1211
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1211

Thr His Leu Leu Gln Gly Gln Ser Leu Thr Leu Glx Glx Glx Glx
 1               5                  10                  15

<210> SEQ ID NO 1212
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1212

Thr His Leu Leu Gln Gly Gln Ser Leu Thr Glx Glx Glx Glx Glx
 1               5                  10                  15

<210> SEQ ID NO 1213
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1213

Thr His Leu Leu Gln Gly Gln Ser Leu Glx Glx Glx Glx Glx Glx
 1               5                  10                  15

<210> SEQ ID NO 1214
<211> LENGTH: 15
<212> TYPE: PRT
<213> ORGANISM: Artificial Sequence
<220> FEATURE:
<223> OTHER INFORMATION: Description of Artificial Sequence: binding
```

-continued peptide

<400> SEQUENCE: 1214

Thr His Leu Leu Gln Gly Gln Ser Glx Glx Glx Glx Glx Glx Glx
1               5                   10                  15

<210> SEQ ID NO 1215
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1215

Thr His Leu Leu Gln Gly Gln Glx Glx Glx Glx Glx Glx Glx Glx
1               5                   10                  15

<210> SEQ ID NO 1216
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1216

Glx His Leu Leu Gln Gly Gln Ser Leu Thr Leu Thr Leu Glu Ser
1               5                   10                  15

<210> SEQ ID NO 1217
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1217

Glx Glx Leu Leu Gln Gly Gln Ser Leu Thr Leu Thr Leu Glu Ser
1               5                   10                  15

<210> SEQ ID NO 1218
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1218

Glx Glx Glx Leu Gln Gly Gln Ser Leu Thr Leu Thr Leu Glu Ser
1               5                   10                  15

<210> SEQ ID NO 1219
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1219

Glx Glx Glx Glx Gln Gly Gln Ser Leu Thr Leu Thr Leu Glu Ser
1               5                   10                  15

<210> SEQ ID NO 1220

-continued

```
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1220

Glx Glx Glx Glx Glx Gly Gln Ser Leu Thr Leu Thr Leu Glu Ser
 1               5                  10                  15

<210> SEQ ID NO 1221
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1221

Glx Glx Glx Glx Glx Glx Gln Ser Leu Thr Leu Thr Leu Glu Ser
 1               5                  10                  15

<210> SEQ ID NO 1222
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1222

Glx Glx Glx Glx Glx Glx Glx Ser Leu Thr Leu Thr Leu Glu Ser
 1               5                  10                  15

<210> SEQ ID NO 1223
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1223

Glx Glx Glx Glx Glx Glx Glx Glx Leu Thr Leu Thr Leu Glu Ser
 1               5                  10                  15

<210> SEQ ID NO 1224
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1224

Thr His Leu Leu Gln Gly Gln Ser Leu Thr Leu Thr Leu Glu Ser
 1               5                  10                  15

<210> SEQ ID NO 1225
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1225
```

Gly Glu Gln Val Glu Phe Ser Phe Pro Leu Ala Phe Thr Val Glu
1               5                   10                  15

<210> SEQ ID NO 1226
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1226

Gly Glu Gln Val Glu Phe Ser Phe Pro Leu Ala Phe Thr Val Glx
1               5                   10                  15

<210> SEQ ID NO 1227
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1227

Gly Glu Gln Val Glu Phe Ser Phe Pro Leu Ala Phe Thr Glx Glx
1               5                   10                  15

<210> SEQ ID NO 1228
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1228

Gly Glu Gln Val Glu Phe Ser Phe Pro Leu Ala Phe Glx Glx Glx
1               5                   10                  15

<210> SEQ ID NO 1229
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1229

Gly Glu Gln Val Glu Phe Ser Phe Pro Leu Ala Glx Glx Glx Glx
1               5                   10                  15

<210> SEQ ID NO 1230
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1230

Gly Glu Gln Val Glu Phe Ser Phe Pro Leu Glx Glx Glx Glx Glx
1               5                   10                  15

<210> SEQ ID NO 1231
<211> LENGTH: 15
<212> TYPE: PRT
<213> ORGANISM: Artificial Sequence
<220> FEATURE:

```
<223> OTHER INFORMATION: Description of Artificial Sequence: binding
      peptide

<400> SEQUENCE: 1231

Gly Glu Gln Val Glu Phe Ser Phe Pro Glx Glx Glx Glx Glx
  1               5                  10                  15

<210> SEQ ID NO 1232
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1232

Gly Glu Gln Val Glu Phe Ser Glx Glx Glx Glx Glx Glx Glx
  1               5                  10                  15

<210> SEQ ID NO 1233
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1233

Gly Glu Gln Val Glu Phe Ser Glx Glx Glx Glx Glx Glx Glx
  1               5                  10                  15

<210> SEQ ID NO 1234
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1234

Glx Glu Gln Val Glu Phe Ser Phe Pro Leu Ala Phe Thr Val Glu
  1               5                  10                  15

<210> SEQ ID NO 1235
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1235

Glx Glx Gln Val Glu Phe Ser Phe Pro Leu Ala Phe Thr Val Glu
  1               5                  10                  15

<210> SEQ ID NO 1236
<211> LENGTH: 15
<212> TYPE: PRT
<213> ORGANISM: Artificial Sequence
<220> FEATURE:
<223> OTHER INFORMATION: Description of Artificial Sequence: binding
      peptide

<400> SEQUENCE: 1236

Glx Glx Glx Val Glu Phe Ser Phe Pro Leu Ala Phe Thr Val Glu
  1               5                  10                  15
```

<210> SEQ ID NO 1237
<211> LENGTH: 15
<212> TYPE: PRT
<213> ORGANISM: Artificial Sequence
<220> FEATURE:
<223> OTHER INFORMATION: Description of Artificial Sequence: binding peptide

<400> SEQUENCE: 1237

Glx Glx Glx Glx Glu Phe Ser Phe Pro Leu Ala Phe Thr Val Glu
 1               5                  10                  15

<210> SEQ ID NO 1238
<211> LENGTH: 15
<212> TYPE: PRT
<213> ORGANISM: Artificial Sequence
<220> FEATURE:
<223> OTHER INFORMATION: Description of Artificial Sequence: binding peptide

<400> SEQUENCE: 1238

Glx Glx Glx Glx Glx Phe Ser Phe Pro Leu Ala Phe Thr Val Glu
 1               5                  10                  15

<210> SEQ ID NO 1239
<211> LENGTH: 15
<212> TYPE: PRT
<213> ORGANISM: Artificial Sequence
<220> FEATURE:
<223> OTHER INFORMATION: Description of Artificial Sequence: binding peptide

<400> SEQUENCE: 1239

Glx Glx Glx Glx Glx Glx Ser Phe Pro Leu Ala Phe Thr Val Glu
 1               5                  10                  15

<210> SEQ ID NO 1240
<211> LENGTH: 15
<212> TYPE: PRT
<213> ORGANISM: Artificial Sequence
<220> FEATURE:
<223> OTHER INFORMATION: Description of Artificial Sequence: binding peptide

<400> SEQUENCE: 1240

Glx Glx Glx Glx Glx Glx Glx Phe Pro Leu Ala Phe Thr Val Glu
 1               5                  10                  15

<210> SEQ ID NO 1241
<211> LENGTH: 15
<212> TYPE: PRT
<213> ORGANISM: Artificial Sequence
<220> FEATURE:
<223> OTHER INFORMATION: Description of Artificial Sequence: binding peptide

<400> SEQUENCE: 1241

Glx Glx Glx Glx Glx Glx Glx Glx Pro Leu Ala Phe Thr Val Glu
 1               5                  10                  15

<210> SEQ ID NO 1242
<211> LENGTH: 15
<212> TYPE: PRT
<213> ORGANISM: Artificial Sequence
<220> FEATURE:
<223> OTHER INFORMATION: Description of Artificial Sequence: binding peptide -continued

```
<400> SEQUENCE: 1242

Gly Glu Gln Val Glu Phe Ser Phe Pro Leu Ala Phe Thr Val Glu
 1               5                  10                  15
```

US 7,304,127 B2

POLYPEPTIDES THAT BIND HIV GP120 AND RELATED NUCLEIC ACIDS, ANTIBODIES, COMPOSITIONS, AND METHODS OF USE

TECHNICAL FIELD OF THE INVENTION

The present invention relates to polypeptides with homology to regions of domains of the human chemokine receptors CCR5, CXCR4, and STRL33, as well as domains of CD4 that bind with human immunodeficiency virus (HIV), in particular HIV-1 glycoprotein 120 (gp120) envelope protein. The present invention also relates to nucleic acids encoding such polypeptides, antibodies, compositions comprising such polypeptides, nucleic acids or antibodies, and methods of using the same.

BACKGROUND OF THE INVENTION

There are seven transmembrane chemokine receptors that act as cofactors for HIV infection. The cofactors enable entry of HIV-1 into $CD4^+$ T cells and macrophages (Premack et al., Nature Medicine 2: 1174-78 (1996); and Zhang et al., Nature 383: 768 (1996)).

The presence of chemokines has an inhibitory effect on HIV-1 attachment to, and infection of, susceptible cells. Additionally, some mutations in chemokine receptors have been shown to result in resistance to HIV-1 infection. For example, a 32-nucleotide deletion within the CCR5 gene has been described in subjects who remained uninfected despite repeated exposures to HIV-1 (Huang et al., Nature Medicine 2: 1240-43 (1996)).

Evidence also exists for the physical association of a ternary complex between chemokine receptors, CD4, and HIV-1 gp120 envelope glycoprotein on cell membranes (Lapham et al., Science 274: 602-05 (1996)). Receptor signaling and cell activation are probably not required for the anti-HIV-1 effect of chemokines since a RANTES analog lacking the first eight amino-terminal amino acids, RANTES (9-68), lacked chemotactic and leukocyte-activating properties, but bound to multiple chemokine receptors and inhibited infection by macrophage-tropic HIV-1 (Arenzana-Seladedos et al., Nature 383: 400 (1996)). Cumulatively, the above described results suggest that the interaction between gp120, CD4, and at least one chemokine receptor is obligatory for HIV-1 infection. Accordingly, reagents that interfere with the binding of gp120 to chemokine receptors and to CD4 are used in the biological and medical arts. However, there presently exists a need for additional reagents that can compete with one or more proteins of the gp120-CD4-chemokine receptor complex to assist in basic biological or viral research, and to assist in medical intervention in the HIV-1 pandemic. It is an object of the present invention to provide such reagents. This and other objects and advantages, including additional inventive features, will be apparent from the description provided herein.

BRIEF SUMMARY OF THE INVENTION

The present invention provides a polypeptide that binds with HIV gp120 under physiological conditions. Multiple embodiments of the present inventive polypeptide are provided, and each embodiment possesses a degree of homology to at least one of the human CCR5, CXCR4 and STRL33 chemokine receptors, and the human CD4 cell-surface protein.

In a first embodiment, the present invention provides a polypeptide comprising the amino acid sequence YDIXYYXXE (SEQ ID NO: 1), wherein X is any synthetic or naturally occurring amino acid residue, and the polypeptide comprises less than about 100 contiguous amino acids that are identical to, or, in the alternative, substantially identical to, the amino acid sequence of the human CCR5 chemokine receptor. A preferred polypeptide of this first embodiment comprises the amino acid sequence YDIN*YYT*S*E (SEQ ID NO: 3). A more preferred polypeptide of this first embodiment comprises the amino acid sequence YDINYYTSE (SEQ ID NO: 3), wherein each letter is the standard one-letter abbreviation for an amino acid residue (i.e., for example, N denotes asparaginyl, T denotyes threoninyl, and S denotes serinyl). The polypeptide of the first embodiment can comprise the amino acid sequence M*D*YQ*V*S*SP*IYDIN*YYT*S*E (SEQ ID NO: 5). Preferably, the polypeptide comprises the amino acid sequence MDYQVSSPIYDINYYTSE (SEQ ID NO: 5).

In a second embodiment, the present invention provides a polypeptide comprising the amino acid sequence XEXIXIYXXXNYXXX (SEQ ID NO: 6), wherein X is any synthetic or naturally occurring amino acid and wherein said polypeptide comprises less than about 100 contiguous amino acid that are identical to or substantially identical to the amino acid sequence of the human CXCR4 chemokine receptor. The polypeptide can consist essentially of, or consist of, the sequence EXIXIYXXXNY (SEQ ID NO: 7). Preferably, the polypeptide comprises the sequence M*EG*IS*IYT*S*D*NYT*E*E*. Preferably, M*EG*IS*IYT*S*D*NYT*E*E* is M*EGISIYTSDNYT*E*E*.

In a third embodiment, the present invention provides a polypeptide comprising the amino acid sequence EHQAFLQFS (SEQ ID NO: 10), wherein said polypeptide comprises less than about 100 contiguous amino acids that are identical to or substantially identical to the amino acid sequence of the human STRL33 chemokine receptor. The polypeptide can consist essentially of, or consist of, the sequence EHQAFLQFS (SEQ ID NO: 10).

In a fourth embodiment, the present invention provides a polypeptide comprising at least a portion of an amino acid sequence selected from the group consisting of LPPLYSLVFIFGFVGNML (SEQ ID NO: 11), QWDFGNTMCQLLTGLYFIGFFS (SEQ ID NO: 12), SQYQFWKNFQTLKIVILG (SEQ ID NO: 13), APYNIVLLLNTFQEFFGLNNCS (SEQ ID NO: 14), and YAFVGEKFRNYLLVFFQK (SEQ ID NO: 15), wherein said polypeptide comprises less than about 100 contiguous amino acids that are identical to or substantially identical to the amino acid sequence of the human CCR5 chemokine receptor.

In a fifth embodiment, the present invention provides a polypeptide comprising at least a portion of an amino acid sequence selected from the group consisting of LLLTIPDFIFANVSEADD (SEQ ID NO: 16), VVFQFQHIMVGLILPGIV (SEQ ID NO: 17), and IDSFILLEIIKQGCEFEN (SEQ ID NO: 18), wherein said polypeptide comprises less than about 100 contiguous amino acids that are identical to or substantially identical to the amino acid sequence of the human CXCR4 chemokine receptor.

In a sixth embodiment, the present invention provides a polypeptide comprising at least a portion of an amino acid sequence selected from the group consisting of LVISIFYHKLQSLTDVFL (SEQ ID NO: 19), PFWAYAGIHEWVFGQVMC (SEQ ID NO: 20), EAISTVVLATQMTLGFFL (SEQ ID NO: 21), LTMIVCYSVIIKTLLHAG (SEQ ID NO: 22), MAVFLLTQMPFNLMKFIRSTHW (SEQ ID NO: 23), HWEYYAMTSFHYTIMVTE (SEQ ID NO: 24), ACLNPVLYAFVSLKFRKN (SEQ ID NO: 25) and SKTF-SASHNVEATSMFQL (SEQ ID NO: 26), wherein said polypeptide comprises less than about 100 contiguous amino acids that are identical to or substantially identical to the amino acid sequence of the human STRL33 chemokine receptor.

In a seventh embodiment, the present invention provides a polypeptide comprising at least a portion of an amino acid sequence selected from the group consisting of DTYICEVED (SEQ ID NO: 27), EEVQLLVFGLTANSD (SEQ ID NO: 28), THLLQGQSLTLTLES (SEQ ID NO: 29), and GEQVEFSFPLAFTVE (SEQ ID NO: 30), wherein said polypeptide comprises less than about 100 contiguous amino acids that are identical to or substantially identical to the amino acid sequence of the human CD4 cell-surface protein.

In the fourth to seventh embodiments, any selected portion of the polypeptide can comprise from 1 to about 6 conservative amino acid substitutions. In an alternative, the polypeptide can be partially defined by an absence of a polypeptide sequence, outside the region of the portion selected from the foregoing sequences, that has five, or ten, contiguous amino acid residues that have a sequence that consists of an amino acid sequence that is identical to or substantially identical to the protein to which the polypeptide has homology (i.e., CCR5, CXCR4, STRL33, or CD4). In yet another alternative, the polypeptide can lack a sequence of five or ten contiguous amino acids which are identical to or substantially identical to the sequence of the protein with which the sequence has homology except that one or more conservatively or neutrally substituted amino acids replace part of the sequence of the protein to which the polypeptide has homology. Additionally, any embodiment of the present inventive polypeptide can also comprise a pharmaceutically acceptable substituent.

Any embodiment of the present inventive polypeptide can be incorporated into a composition, which further comprises a carrier. Any suitable embodiment of the present inventive polypeptide can be encoded by a nucleic acid that can be expressed in a cell. In this regard, the present invention further provides a vector comprising such a nucleic acid. The nucleic acids and vectors also can be incorporated into a composition comprising a carrier.

Additionally, the present invention provides a method of making an antibody to a polypeptide of the present invention. The present invention also provides a method of prophylactically or therapeutically treating an HIV infection in a mammal.

Additionally, the present invention provides an anti-idiotypic antibody comprising an internal image of a portion of gp120, as well as a method of selecting such an antibody.

The present invention also provides a method of making an antibody to a portion of the gp120 protein that binds with a portion of CCR5, CXCR4, STRL33, or CD4, as well as the immunizing compound used to make the antibody, and the antibody itself. In another embodiment of the present invention, a method of removing HIV-1 from a bodily fluid is provided.

BRIEF DESCRIPTION OF THE DRAWINGS

FIGS. 1A-X depicts a listing of synthetic amino acids available (from Bachem, King of Prussia, Pa.) for incorporation into polypeptides of the present invention.

DETAILED DESCRIPTION OF THE INVENTION

The present invention provides a polypeptide that binds with gp120 of HIV, in particular HIV-1, more particularly HIV-$1_{LAI}$, under physiological conditions. The polypeptide has a number of uses including, but not limited to, the use of the polypeptide to elucidate the mechanism by which HIV, such as HIV-1, attaches to and/or infects a particular cell, to induce an immune response in a mammal, in particular a human, to HIV, in particular HIV-1, and to inhibit the replication of HIV, in particular HIV-1, in an infected mammal, in particular a human.

Multiple embodiments of the present inventive polypeptide are provided. Each embodiment of the polypeptide has a degree of homology to at least one of the human CCR5, CXCR4 and STRL33 chemokine receptors, or the human CD4 cell-surface protein. In each embodiment provided herein, a letter indicates the standard amino acid designated by that letter, and a letter followed directly by an asterisk (*) preferably represents the amino acid represented by the letter (e.g., N represents asparaginyl and T represents threoninyl), or a synthetic or naturally occurring conservative or neutral substitution therefor. Additionally, in accordance with convention, all amino acid sequences provided herein are given either from left to right, or top to bottom, such that the first amino acid is amino-terminal and the last is carboxyl-terminal. The synthesis of polypeptides, either synthetically (i.e., chemically) or biologically, is within the skill in the art.

It is within the skill of the ordinary artisan to select synthetic and naturally occurring amino acids that make conservative or neutral substitutions for any particular naturally occurring amino acids. The skilled artisan desirably will consider the context in which any particular amino acid substitution is made, in addition to considering the hydrophobicity or polarity of the side-chain, the general size of the side chain, and the pK value of side-chains with acidic or basic character under physiological conditions. For example, lysine, arginine, and histidine are often suitably substituted for each other, and more often arginine and lysine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the skilled artisan can readily group synthetic amino acids with naturally occurring amino acids.

In the context of the present invention, a polypeptide is "substantially identical" to another polypeptide if it comprises at least about 80% identical amino acids. Desirably, at least about 50% of the non-identical amino acids are conservative or neutral substitutions. Also, desirably, the polypeptides differ in length (i.e., due to deletion mutations) by no more than about 10%.

In a first embodiment, the present invention provides a polypeptide comprising the amino acid sequence YDIXYYXXE (SEQ ID NO: 1), wherein X is any synthetic or naturally occurring amino acid residue, and the polypeptide comprises less than about 100 contiguous amino acids, preferably less than about 50 amino acids, more preferably less than about 25 amino acids, and yet more preferably less than about 13 amino acids that are identical to, or, in the alternative, substantially identical to, the amino acid sequence of the human CCR5 chemokine receptor.

Preferably, the polypeptide of the first embodiment comprises YDIXYYXXE (SEQ ID NO: 1), wherein the amino moiety of the amino-terminal tyrosinyl residue is not bound to another amino acid residue via a peptidic bond, and the carboxyl moiety of the glutamyl residue is not bound to another amino acid residue via a peptidic bond. However, the polypeptide can consist essentially of YDIXYYXXE (SEQ ID NO: 1) and, optionally, can be modified by one or more pharmaceutically acceptable substituents, such as, for example, t-boc or a saccharide.

More particularly, the polypeptide comprises the amino acid sequence YDIN*YYT*S*E (SEQ ID NO: 3). Preferably, N* is asparaginyl, T* is threoninyl, and S* is serinyl.

The polypeptide of the first embodiment can comprise a dodecapeptide selected from the amino acid sequence M*D*YQ*V*S*SP*IYDIN*YYT*S*E (SEQ ID NO: 5). More preferably, the polypeptide of the first embodiment comprises the amino acid sequence MDYQVSSPIYDINYYTSE (SEQ ID NO: 5).

In a second embodiment, the present invention provides a polypeptide comprising the amino acid sequence XEXIXIYXXXNYXXX (SEQ ID NO: 6), wherein X is any synthetic or naturally occurring amino acid, and the polypeptide comprises less than about 100 contiguous amino acids, preferably less than about 50 amino acids, and more preferably less than about 25 amino acids, that are identical to or substantially identical to the amino acid sequence of the human CXCR4 chemokine receptor. Optionally, the polypeptide consists essentially of, or consists of, the sequence EXIXIYXXXNY (SEQ ID NO: 7).

In a preferred polypeptide of this second embodiment, the polypeptide comprises the amino acid sequence M*EG*IS*IYT*S*D*NYT*E*E*. Preferably, M*EG*IS*IYT*S*D*NYT*E*E* is M*EGISIYTSDNYT*E*E*.

In a third embodiment, the present invention provides a polypeptide comprising the amino acid sequence EHQAFLQFS, wherein the polypeptide comprises less than about 100 contiguous amino acid residues, preferably less than about 50 contiguous amino acid residues, more preferably less than about 25 contiguous amino acid residues, that are identical to or substantially identical to the amino acid sequence of the human STRL33 chemokine receptor. The polypeptide can consist essentially of, or consist of, the sequence EHQAFLQFS.

The first three embodiments of the present invention provide, among other things, polypeptides having substantial identity or identity to the amino-terminal regions of the chemokine receptors CCR5, CXCR4, and STRL33. These first three embodiments form a first group of embodiments of the present invention. The present invention also provides, in a second group of embodiments, polypeptides having substantial identity or identity to an internal region of the human chemokine receptors CCR5, CXCR4, and STRL33, as well as to the leukocyte cell-surface protein CD4.

This second group of embodiments provides a polypeptide that binds with HIV gp120 under physiological conditions and comprises at least a portion of or all of an amino acid sequence selected from the group consisting of LPPLYSLVFIFGFVGNML (SEQ ID NO: 11), QWDFGNTMCQLLTGLYFIGFFS (SEQ ID NO: 12), SQYQFWKNFQTLKIVILG (SEQ ID NO: 13), APYNIVLLLNTFQEFFGLNNCS (SEQ ID NO: 14), and YAFVGEKFRNYLLVFFQK (SEQ ID NO: 15), wherein the polypeptide comprises less than about 100 amino acids that are identical to or substantially identical to the amino acid sequence of the human CCR5 chemokine receptor; or selected from the group consisting of LLLTIPDFIFANVSEADD (SEQ ID NO: 16) (165-182), VVFQFQHIMVGLILPGIV (SEQ ID NO: 17) (197-214), and IDSFILLEIIKQGCEFEN (SEQ ID NO: 18) (261-278), wherein the polypeptide comprises less than about 100 amino acids that are identical to or substantially identical to the amino acid sequence of the human CXCR4 chemokine receptor; or selected from the group consisting of LVISIFYHKLQSLTDVFL (SEQ ID NO: 19) (53-70), PFWAYAGIHEWVFGQVMC (SEQ ID NO: 20) (85-102), EAISTVVLATQMTLGFFL (SEQ ID NO: 21) (185-202), LTMIVCYSVIIKTLLHAG (SEQ ID NO: 22) (205-222), MAVFLLTQMPFNLMKFIRSTHW (SEQ ID NO: 23) (237-258), HWEYYAMTSFHYTIMVTE (SEQ ID NO: 24) (257-274), ACLNPVLYAFVSLKFRKN (SEQ ID NO: 25) (281-298) and SKTFSASHNVEATSMFQL (SEQ ID NO: 26) (325-342), wherein the polypeptide comprises less than about 100 amino acids that are identical to a substantially identical to the amino acid sequence of the human STRL33 chemokine receptor; or selected from the group consisting of DTYICEVED (SEQ ID NO: 27), EEVQLLVFGLTANSD (SEQ ID NO: 28), THLLQGQSLTLTLES (SEQ ID NO: 29), and GEQVEFSFPLAFTVE (SEQ ID NO: 30), wherein the polypeptide binds with HIV gp120 under physiological conditions and comprises less than about 100 amino acids that are identical to or substantially identical to the amino acid sequence of the human CD4 cell-surface protein. Optionally, the recited amino acid sequences can comprise 1 to about 6 conservative or neutral amino acid substitutions.

The polypeptides of this second group of embodiments preferably comprise less than about 50 amino acid residues, and more preferably less than about 25 amino acid residues, and yet more preferably no additional amino acid residues, that are identical to a protein that naturally has the recited amino acid sequence. The polypeptide can be alternatively characterized by an absence of a region, outside the above-recited amino acid sequences, that has about five, or about ten, contiguous amino acid residues that have a sequence that consists of an amino identical and conservatively substituted residues as an amino acid sequence of the protein to which the polypeptide of the compound has homology.

Any embodiment of the present inventive polypeptide can also comprise a pharmaceutically acceptable substituent, attachment of which is within the skill in the art. The pharmaceutically acceptability of substituents are understood by those skilled in the art. For example, a pharmaceutically acceptable substituent can be a biopolymer, such as a polypeptide, an RNA, a DNA, or a polysaccharide. Suitable polypeptides comprise fusion proteins, an antibody or fragment thereof, a cell adhesion molecule or a fragment thereof, or a peptide hormone. Suitable polysaccharides comprise polyglucose moieties, such as starch and their derivatives, such as heparin. The pharmaceutically acceptable substituent also can be any suitable lipid or lipid-containing moiety, such as a lipid of a liposome or a vesicle, or even a lipophilic moiety, such as a prostaglandin, a steroid hormone, or a derivative thereof. Additionally, the pharmaceutically acceptable substituent can be a nucleotide or nucleoside, such as nicotine adenine dinucleotide or thymine, an amino acid residue, a saccharide or disaccharide, or the residue of another biomolecule naturally occurring in a cell, such as inositol, a vitamin, such as vitamin C, thiamine, or nicotinic acid. Synthetic organic moieties also can be pharmaceutically acceptable substituents, such as t-butyl carbonyl, an acetyl moiety, quinine, polystyrene and other biologically acceptable polymers. Optionally, a pharmaceutically acceptable substituent can be selected from the group consisting of a $C_1$-$C_{18}$ alkyl, a $C_2$-$C_{18}$ alkenyl, a $C_2$-$C_{18}$ alkynyl, a $C_6$-$C_{18}$ aryl, a $C_7$-$C_{18}$ alkaryl, a $C_7$-$C_{18}$ aralkyl, and a $C_3$-$C_{18}$ cycloalkyl, wherein any of the foregoing moieties that are cyclic comprise from 0 to 2 atoms per carbocyclic ring, which can be the same or different, and are selected from the group consisting of nitrogen, oxygen, and sulfur.

Any of the substituents from this group can be substituted by one to six substituent moieties, which can be the same or different, selected from the group consisting of an amino moiety, a carbamate moiety, a carbonate moiety, hydroxyl, a phosphamate moiety, a phosphate moiety, a phosphonate moiety, a pyrophosphate moiety, a triphosphate moiety, a sulfamate moiety, a sulfate moiety, a sulfonate moiety, a $C_1$-$C_8$ monoalkylamine moiety, a $C_1$-$C_8$ dialkylamine moiety, and a $C_1$-$C_8$ trialkylamine moiety.

Any embodiment of the present inventive polypeptide can be encoded by a nucleic acid and can be expressed in a cell. The skilled artisan will recognize that the encoded polypeptide as well as any pharmaceutically acceptable substituent to be incorporated into the polypeptide, e.g., a formyl or acetyl substituent on an amino-terminal methionine or a saccharide, will preferably be produced by a cell that can express the polypeptide of the present invention. Accordingly, the amino acids incorporated into the polypeptide encoded by the nucleic acid are preferably naturally occurring.

A nucleic acid as described above can be cloned into any suitable vector and can be used to transduce, transform, or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant, or animal) into which the vector is to be inserted, as appropriate and taking into consideration whether the vector is DNA or RNA. Preferably, the vector comprises regulatory sequences that are specific to the genus of the host. Most preferably, the vector comprises regulatory sequences that are specific to the species of the host and is optimized for the expression of an above-described polypeptide.

Constructs of vectors, which are circular or linear, can be prepared to contain an entire nucleic acid sequence as described above or a portion thereof ligated to a replication system that is functional in a prokaryotic or eukaryotic host cell. Replication systems can be derived from ColE1, 2 mμ plasmid, λ, SV40, bovine papilloma virus, and the like.

Suitable vectors include those designed for propagation and expansion, or for expression, or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Examples of animal expression vectors include pEUK-C1, pMAM and pMAM-neo (Clonetech, Palo Alto, Calif.).

An expression vector can comprise a native or normative promoter operably linked to a nucleic acid molecule encoding an above-described polypeptide. The selection of promoters, e.g., strong, weak, inducible, tissue-specific and developmental-specific, is within the skill in the art. Similarly, the combining of a nucleic acid molecule as described above with a promoter is also within the skill in the art.

The skilled artisan will also recognize that the polypeptide has ability to bind the gp120 protein, which is most often found outside of cells. Accordingly, the present inventive nucleic acid advantageously can comprise a nucleic acid sequence that encodes a signal sequence such that a signal sequence is translated as a fusion protein with the polypeptide of the present inventive polypeptide to form a signal sequence-polypeptide fusion. The signal sequence can cause secretion of the entire polypeptide, including the signal sequence (which is a pharmaceutically acceptable substituent), or can be cleaved from the polypeptide (i.e., the polypeptide of the compound) prior to, or during, secretion so that at least the present inventive polypeptide is secreted out of a cell in which the nucleic acid is expressed.

Alternatively, the nucleic acid comprises or encodes an antisense nucleic acid molecule or a ribozyme that is specific for a specified amino acid sequence of an above-described polypeptide. A nucleic acid sequence introduced in antisense suppression generally is substantially identical to at least a portion of the endogenous gene or gene to be repressed, but need not be identical. Thus, the vectors can be designed such that the inhibitory effect applies to other proteins within a family of genes exhibiting homology or substantial homology to the target gene. The introduced sequence also need not be full-length relative to either of the primary transcription product or the fully processed mRNA. Generally, higher homology can be used to compensate for the use of a shorter sequence. Furthermore, the introduced sequence need not have the same intron or exon pattern, and homology of non-coding segments will be equally effective.

Ribozymes also have been reported to have use as a means to inhibit expression of endogenous genes. It is possible to design ribozymes that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., Nature 334: 585-591 (1988).

Further provided by the present invention is a composition comprising an above-described polypeptide or nucleic acid and a carrier therefor. Another composition provided by the present invention is a composition comprising an antibody to an above-described polypeptide or an anti-antibody to an above-described polypeptide.

Any embodiment of the present invention including the present inventive polypeptide, nucleic acid, antibody, and anti-antibody, can be incorporated into a composition comprising a carrier. The carrier can serve any function. For example, the carrier can increase the solubility of the present inventive polypeptide, nucleic acid or antibody in aqueous solutions. Additionally, the carrier can protect the present inventive polypeptide, nucleic acid or antibody from environmental insults, such as dehydration, oxidation, and photolysis. Moreover, the carrier can serve as an adjuvant, or as a timed-release control means in a biological system.

Antibodies can be generated in accordance with methods known in the art. See, for example, Benjamin, In Immunology: a short course, Wiley-Liss, NY, 1996, pp. 436-437; Kuby, In Immunology, 3rd. ed., Freeman, NY, 1997, pp. 455-456; Greenspan et al., FASEB J. 7: 437-443 (1993); and Poskitt, Vaccine 9: 792-796 (1991). Anti-antibodies (i.e., anti-idiotypic antibodies) also can be generated in accordance with methods known in the art (see, for example, Benjamin, In Immunology: a short course, Wiley-Liss, NY, 1996, pp. 436-437; Kuby, In Immunology, 3rd. ed., Freeman, NY, 1997, pp. 455-456; Greenspan et al., *FASEB J.,* 7, 437-443, 1993; Poskitt, *Vaccine,* 9, 792-796, 1991; and Madiyalakan et al., Hybridonor 14: 199-203 (1995) ("Anti-idiotype induction therapy")). Such antibodies can be obtained and employed either in solution-phase or coupled to a desired solid-phase matrix. Having in hand such antibodies, one skilled in the art will further appreciate that such antibodies, using well-established procedures (e.g., such as described by Harlow and Lane (1988, supra), are useful in the detection, quantification, or purification of gp120 or HIV, particularly HIV-1, conjugates of each and host cells transformed to produce a gp120 receptor or a derivative thereof. Such antibodies are also useful in a method of prevention or treatment of a viral infection and in a method of inducing an immune response to HIV as provided herein.

In view of the above, an above-described polypeptide can be administered to an animal. The animal generates anti-polypeptide antibodies. Among the anti-polypeptide antibodies generated or induced in the animal are antibodies that have an internal image of gp120. In accordance with well-known methods, polyclonal or monoclonal antibodies can be obtained, isolated and selected. Selection of an anti-polypeptide antibody that has an internal image of gp120 can be based upon competition between the anti-polypeptide antibody and gp120 for binding to an above-described polypeptide, or upon the ability of the anti-polypeptide antibody to bind to a free polypeptide as opposed to a polypeptide bound to gp120. Such an anti-antibody can be administered to an animal to prevent or treat an HIV infection in accordance with methods provided herein.

Although nonhuman anti-idiotypic antibodies, such as an anti-polypeptide antibody that has an internal image of gp120 and, therefore, is anti-idiotypic to gp120, are useful for prophylaxis in humans, their favorable properties might, in certain instances, can be further enhanced and/or their adverse properties further diminished, through "humanization" strategies, such as those recently reviewed by Vaughan, *Nature Biotech.,* 16, 535-539, 1998.

Prior to administration to an animal, such as a mammal, in particular a human, an above-described polypeptide, nucleic acid, antibody or anti-antibody can be formulated into various compositions by combination with appropriate carriers, in particular, pharmaceutically acceptable carriers or diluents, and can be formulated to be appropriate for either human or veterinary applications.

The present invention also provides a method of making an antibody. The method comprises administering an immunogenic amount of an above-described polypeptide or nucleic acid to an animal, such as a mammal, in particular a human. Determining the quantity of a polypeptide or nucleic acid that is immunogenic will depend in part on the degree of similarity to a protein or other molecule of the inoculated animal, the route of administration of the polypeptide or nucleic acid, and the size of the polypeptide administered or encoded by the administered nucleic acid. If necessary, the polypeptide or nucleic acid can be mixed with or ligated to a substance (or an adjuvant) that enhances its immunogenicity. Such calculations and procedures are within the skill of the ordinary artisan. Additionally, the present inventive method preferably can be used to induce an immune response against HIV, particularly HIV-1, in a mammal, particularly a human.

In view of the above, the present invention further provides a method of prophylactically or therapeutically treating an HIV infection in a mammal, particularly a human, in need thereof. The method comprises administering to the mammal an HIV replication-inhibiting effective amount of an above-described polypeptide, nucleic acid, or an anti-antibody to an above-described polypeptide or a nucleic acid encoding such a polypeptide.

The present invention also provides a method of prophylactically or therapeutically treating HIV infection in a mammal. The method comprises administering to the mammal an effective amount of an above-described polypeptide or nucleic acid. Prior to administration to an animal, such as a mammal, in particular a human, an above-described polypeptide or nucleic acid can be formulated into various compositions by combination with appropriate carriers, in particular, pharmaceutically acceptable carriers or diluents, and can be formulated to be appropriate for either human or veterinary applications.

Thus, a composition for use in the method of the present invention can comprise one or more of the polypeptides, nucleic acids, antibodies or anti-antibodies described herein, preferably in combination with a pharmaceutically acceptable carrier. Pharmaceutically acceptable carriers are well-known to those skilled in the art, as are suitable methods of administration. The choice of carrier will be determined, in part, by whether a polypeptide or a nucleic acid is to be administered, as well as by the particular method used to administer the composition. Optionally, the carrier can be selected to increase the solubility of the composition or mixture, e.g., a liposome or polysaccharide. One skilled in the art will also appreciate that various routes of administering a composition are available, and, although more than one route can be used for administration, a particular route can provide a more immediate and more effective reaction than another route. Accordingly, there are a wide variety of suitable formulations of compositions that can be used in the present inventive methods.

A composition in accordance with the present invention, alone or in further combination with one or more other active agents, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Similarly, a formulation suitable for oral administration can include lozenge forms, which can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

An aerosol formulation suitable for administration via inhalation also can be made. The aerosol formulation can be placed into a pressurized acceptable propellant, such as dichlorodifluoromethane, propane, nitrogen, and the like.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

Important general considerations for design of delivery systems and compositions, and for routes of administration, for polypeptide drugs also apply (Eppstein, *CRC Crit. Rev. Therapeutic Drug Carrier Systems* 5, 99-139, 1988; Siddiqui et al., *CRC Crit. Rev. Therapeutic Drug Carrier Systems* 3, 195-208, 1987); Banga et al., *Int. J. Pharmaceutics* 48, 15-50, 1988; Sanders, *Eur. J. Drug Metab. Pharmacokinetics* 15, 95-102, 1990; Verhoef, *Eur. J. Drug Metab. Pharmacokinetics* 15, 83-93, 1990). The appropriate delivery system for a given polypeptide will depend upon its particular nature, the particular clinical application, and the site of drug action. As with any protein drug, oral delivery will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given polypeptide. A wide variety of absorption-enhancing agents have been investigated and/or applied in combination with protein drugs for oral delivery and for delivery by other routes (Verhoef, 1990, supra; van Hoogdalem, *Pharmac. Ther.* 44, 407-43, 1989; Davis, *J. Pharm. Pharmacol.* 44(Suppl. 1), 186-90, 1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides, and diglycerides, (e) non-surfactants, such as unsaturated cyclic ureas, (f) saponins, (g) cyclodextrins, and (h) phospholipids.

Other approaches to enhancing oral delivery of protein drugs can include the aforementioned chemical modifications to enhance stability to gastrointestinal enzymes and/or increased lipophilicity. Alternatively, the protein drug can be administered in combination with other drugs or substances that directly inhibit proteases and/or other potential sources of enzymatic degradation of proteins. Yet another alternative approach to prevent or delay gastrointestinal absorption of protein drugs is to incorporate them into a delivery system that is designed to protect the protein from contact with the proteolytic enzymes in the intestinal lumen and to release the intact protein only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes*, Swarbrick, ed., Marcell Dekker, Inc.: New York, 1984, pp. 1-60, 88-89, 208-11). Microcapsules also can provide a useful way to effect a prolonged delivery of a protein drug after injection (Maulding, *J. Controlled Release* 6, 167-76, 1987).

The dose administered to an animal, such as a mammal, particularly a human, in the context of the present invention should be sufficient to effect a therapeutic or prophylactic response in the individual over a reasonable time frame. The dose will be determined by the particular polypeptide, nucleic acid, antibody, or anti-antibody administered, the severity of any existing disease state, as well as the body weight and age of the individual. The size of the dose also will be determined by the existence of any adverse side effects that may accompany the use of the particular polypeptide, nucleic acid, antibody or anti-antibody employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a vector, alone or in combination with other active agents, calculated in an amount sufficient to produce the desired effect in association with a pharmaceutically acceptable diluent, carrier, or vehicle. The specifications for the unit dosage forms of the present invention depend on the particular embodiment employed and the effect to be achieved, as well as the pharmacodynamics associated with each polypeptide, nucleic acid or anti-antibody in the host. The dose administered should be an "HIV infection inhibiting amount" of an above-described polypeptide or nucleic acid or an "immune response-inducing effective amount" of an above-described polypeptide, an above-described nucleic acid, or an antibody as appropriate.

Another composition provided by the present invention is a composition comprising a solid support matrix to which is attached an above-described polypeptide, or an anti-antibody to an above-described polypeptide. The solid matrix can comprise other functional reagents including, for example, polyethylene glycol, dextran, albumin and the like, whose intended effector functions may include one or more of the following: to improve stability of the conjugate; to increase the half-life of the conjugate; to increase resistance of the conjugate to proteolysis; to decrease the immunogenicity of the conjugate; to provide a means to attach or immobilize a functional polypeptide or anti-antibody onto a solid support matrix (e.g., see, for example, Harris, in *Poly(Ethylene Glycol) Chemistry: Biotechnical and Biomedical Applications*, Harris, ed., Plenum Press: New York (1992), pp. 1-14). Conjugates furthermore may comprise a polypeptide or anti-antibody coupled to an effector molecule, each of which, optionally, may have different functions (e.g., such as a toxin molecule (or an immunological reagent) and a polyethylene glycol (or dextran or albumin) molecule). Diverse applications and uses of functional proteins and polypeptides, attached to or immobilized on a solid support matrix, are exemplified more specifically for poly (ethylene glycol) conjugated proteins or peptides in a review by Holmberg et al. (In *Poly(Ethylene Glycol) Chemistry: Biotechnical and Biomedical Applications*, Harris, ed., Plenum Press: New York, 1992, pp. 303-324).

In addition, the present invention provides a method of removing HIV from a bodily fluid of an animal. The method comprises extracorporeally contacting the bodily fluid of the animal with a solid-support matrix to which is attached an above-described polypeptide or an anti-antibody to an above-described polypeptide. Alternatively, the bodily fluid can be contacted with the polypeptide or anti-antibody in solution and then the solution can be contacted with a solid support matrix to which is attached a means to remove the polypeptide or anti-antibody to which is bound HIV gp120 from the bodily fluid.

Methods of attaching an herein-described polypeptide, or an anti-antibody to a solid support matrix are known in the art. "Attached" is used herein to refer to attachment to (or coupling to) and immobilization in or on a solid support matrix. See, for example, Harris, in *Poly(Ethylene Glycol) Chemistry: Biotechnical and Biomedical Applications*, Harris, ed., Plenum Press: New York (1992), pp. 1-14) and international patent application WO 91/02714 (Saxinger). Diverse applications and uses of functional polypeptides attached to or immobilized on a solid support matrix are exemplified more specifically for poly(ethylene glycol) conjugated proteins or peptides in a review by Holmberg et al. (In *Poly(Ethylene Glycol) Chemistry: Biotechnical and Biomedical Applications*, Harris, ed., Plenum Press: New York, 1992, pp. 303-324).

The present invention also provides a method of making an antibody that binds to gp120 of HIV under physiological conditions. The method comprises labeling an embodiment of the present inventive compound to obtain a labeled compound. Labeling compounds are within the skill of the ordinary artisan. For example, the present inventive compound can be labeled with radioactive atom, such as $^{125}I$ in the same or a similar manner as was performed in the examples provided below. Alternatively, an enzyme, such as horseradish peroxidase, can be attached to or incorporated into the present inventive compound. Then by exposing a chromogenic or photogenic compound to the compound, a signal indicative of the presence and quantity of the compound present can be generated. In another alternative, a polyhistidinyl moiety can be attached to, or incorporated into, the present inventive moiety so that the present inventive compound will react with high affinity to transition metal ions such as nickel, copper, or zinc ions; this reaction can be used as the basis to quantify the amount of the present inventive compound present at a particular location. In yet another alternative, the present inventive compound can be used as antigen to a standard antibody that specifically recognizes an antigenic epitope of the present inventive compound. As is well-known, the standard antibody can itself be labeled or used in conjunction with an additional antibody that is labeled with an enzyme, radioisotope, or other suitable means. The skilled artisan will recognize that there is a plethora of other suitable means and methods to label the present inventive compound.

This present inventive method of making an antibody that binds to a gp120 envelope protein of HIV further comprises providing a library of synthetic peptides. The library consists of a multiplicity of synthetically-produced polypeptides that are homologous, and preferably essentially identical (i.e., having the same primary amino acid residue sequence, ignoring blocking groups, phosphorylation of serinyl, threoninyl, and tyrosinyl residues, hydroxylation of prolinyl residues, and the like) or identical, to a continuous region of an HIV gp120 envelope protein. The polypeptides of the library can be any suitable length. While larger regions allow faster scanning and tend to preserve non-linear epitopes, shorter length polypeptides allow more sensitive screening of the primary sequence of the gp120 protein. However, polypeptides that are too short can lose essential secondary structure or cleave reactive sites into one or more pieces. Preferably, a mixture of short and long polypeptides are incorporated into the library, however, the library can consist of polypeptides of a single length (measured in amino acid residues). For the sake of convenience the library can be split into multiple parts, and screened by parts. Typically, the polypeptides of the library will be between about 6 and about 45 amino acid residues in length.

Typically, the library will comprise a series of polypeptides each having an identical sequence to that of gp120 but having an amino-terminus a particular number of amino acids downstream of the amino-terminus of the prior polypeptide (see, examples section below). The distance, measured in amino acid residues, is referred to as the offset. Preferably, libraries that are characterized by the existence of an offset, the offset is not greater than the product of length of the longest polypeptide measured in amino acid residues and 1.5, preferably 1.0, and more preferably 0.5. The library can be alternatively characterized by the existence of an offset not greater than 30, preferably 15, and more preferably 4.

Each polypeptide of the library is substantially isolated from every other polypeptide of said library and is located in a known position. For example, each polypeptide can be bound to a solid support and that is in a vessel or that can be placed in a vessel. The vessel preferably enables each polypeptide to be covered in a liquid that does not contact any other oligonucleotide of the library. By way of example, each polypeptide can be bound to a bead that is placed in a vessel (or tube) or can be bound to the well of a multi-well assay plate. Alternatively, an array of polypeptides can be fashioned, for example on a microchip device (as is presently used in some DNA sequencing devices and methods), and the entire array can be bathed in a single solution.

Each polypeptide is then individually contacted with the labeled compound such that a portion of the labeled compound can bind with the polypeptide of the library. In this way, a bound population of each labeled compound of the present invention and an unbound population of the labeled compound is generated. The phrase individually contacted means that each polypeptide has the opportunity to bind with the labeled compound and the quantity of labeled compound bound by each can be determined.

The method then comprises removing substantially all of the unbound labeled compound from the position occupied by each polypeptide. That is, the solution comprising the labeled compound is separated from the polypeptides of the library and the bound population of the labeled compound. This can be done by any suitable method, e.g., by aspiration and one or more washing steps comprising adding a quantity of liquid sufficient to cover all the surfaces that were contacted by the labeled compound and aspirating away substantially all of the wash liquid.

The amount of labeled compound that remains co-localized with each polypeptide of the library is then measured to determine the quantity of labeled compound bound by each polypeptide. The amount of the present inventive compound bound by each polypeptide can be directly evaluated to identify a portion of the HIV gp120 envelope protein that binds to an (HIV)-receptor selected from the group consisting of CCR5, CXCR4, STRL33, and CD4. This information is then used to identify and provide an immunizing compound. The immunizing compound comprises a polypeptide comprising an amino acid sequence that is homologous to, or preferably is essentially identical to, or identical to, the portion of the HIV-1 gp120 envelope protein that binds with CD4, CCR5, CXCR4, and/or STRL33. The immunizing protein can be provided by processing gp120, e.g., proteolytically digesting gp120 that has been isolated from a preparation of HIV-1. Preferably, however, the immunizing compound is prepared synthetically, or by genetic engineering, or by a combination of genetic engineering and synthetic methods. The immunizing compound can comprise a pharmaceutically acceptable substituent, can be encoded by a nucleic acid that can be expressed in a cell, can be mixed with a carrier, and is an inventive aspect of the present invention.

An immunogenic quantity of the immunizing compound is then inserted into an animal (e.g., a human, or a rodent, a canine, a feline, or a ruminant) in a manner consistent with the discussion of a method of raising an antibody to the present inventive compounds that are homologous to portions of CCR5, CXCR4, STRL33, and CD4, above. The insertion of the immunizing compound causes the inoculated animal to produce an antibody that binds with said portion of the HIV gp120 envelope protein. Thus the present invention also provides an antibody that binds to an HIV gp120 envelope protein, as well as an antigen binding protein comprising one or more complementarity determining regions of the antibody (e.g., a Fab, a $Fab_{2'}$, an Fv, a single-chain antibody, a diabody, and humanized variants of all of the above, all of which are within the skill in the art).

The antibody or variant thereof is preferably useful in detecting or diagnosing the presence of HIV gp120 envelope protein, and thus HIV, in an animal. The antibody is also preferably prevents or attenuates infection of an animal exposed to HIV, to whom an effective quantity of the antibody or a variant thereof, has been administered or produced in response to inoculation with the immunizing compound. The antibody preferably also is useful in treating or preventing (i.e., inhibiting) HIV infection in an animal to whom a suitable dose has been administered or in which a suitable quantity of antibody has been produced. The antibody is also useful in the study of HIV infection of mammalian cells, the host range specificities of HIV infection, and preferably, the mechanism by which antibodies neutralize infectious viruses.

EXAMPLES

The following examples further illustrate the present invention but, of course, should not be construed as limiting the scope of the claimed invention in any way.

Synthetic peptide arrays were constructed in 96-well microtiter plates in accordance with the method set forth in WO 91/02714 (Saxinger), and used to test the binding of $HIV\text{-}1_{LAI}$ envelope gp120 that had been labeled with radioactive iodine (radiolabeling by standard methods). After incubating the radiolabeled gp120 in a well with each synthetic peptide, a washing step was performed to remove unbound label, and the relative level of radioactivity remaining in each well of the plate was evaluated to determine the relative affinity of each peptide for the gp120. The synthesis of the peptides and the quantity of binding between the synthetic peptides and the gp120 were found to be suitably reproducible, precise, and sensitive. Initial screening of the entire primary sequence of the chemokine and CD4 receptor molecules was taken 18 amino acid residues at a time.

The authenticity of the binding signals generated by this technique has been repeatedly demonstrated by showing that antibodies to CCR5 and CXCR4 are able to inhibit the binding of radiolabeled gp120 to the polypeptides derived from CCR5 and CXCR4 that show a high affinity for binding with gp120. Additionally, the accuracy of the binding assay used hereinbelow is demonstrated by Example 7.

Example 1

This example identifies segments of the CCR5 co-receptor that bind with gp120.

The first column in the table below indicates the number of the amino acid in the wild-type CCR5 receptor. The second column explicitly identifies the peptide sequence. The third column indicates the radioactive counts recorded in twenty minutes (i.e., the cpm×20) after the background or non-specific counts had been subtracted. The fourth column contains an X in each row for which the listed polypeptide bound with high affinity to gp120. The fifth and final column contains an X in each row wherein the listed sequence binds with substantial affinity but is weak in comparison to other samples, particularly adjacent samples.

| SEQ SEG | PEPTIDE | Counts per 20' Average-back-ground | Peak Activity | Non-Peak Activity | SEQ ID NO: |
|---|---|---|---|---|---|
| | empty (control) | 7 | | | |
| 1--18 | MDYQVSSPIYDINYYTSE | 735 | X | | 31 |
| 5--22 | VSSPIYDINYYTSEPCQK | 383 | | X | 32 |
| 9--26 | IYDINYYTSEPCQKINVK | 228 | | X | 33 |
| 13—30 | NYYTSEPCQKINVKQIAA | 6 | | | 34 |
| 17—34 | SEPCQKINVKQIAARLLP | -44 | | | 35 |
| 21—38 | QKINVKQIAARLLPPLYS | 20 | | | 36 |

-continued

| SEQ SEG | PEPTIDE | Counts per 20' Average-background | Peak Activity | Non-Peak Activity | SEQ ID NO: |
|---|---|---|---|---|---|
| 25-42 | VKQIAARLLPPLYSLVFI | 18 | | | 37 |
| 29-46 | AARLLPPLYSLVFIFGFV | 33 | | | 38 |
| 33-50 | LPPLYSLVFIFGFVGNML | 705 | X | | 39 |
| 37-54 | YSLVFIFGFVGNMlVILI | 347 | | X | 40 |
| 41-58 | FIFGFVGNMLVILILINC | 343 | | X | 41 |
| 45-62 | FVGNMLVILILINCKRLK | 62 | | | 42 |
| 49-66 | MLVILILINCKRLKSMTD | 84 | | | 43 |
| 53-70 | LILINCKRLKSMTDIYLL | 2 | | | 44 |
| 57-74 | NCKRLKSMTDIYLLNLAI | 25 | | | 45 |
| 61-78 | LKSMTDIYLLNLAISDLF | 210 | | | 46 |
| 65-82 | TDIYLLNLAISDLFFLLT | 38 | | | 47 |
| 69-86 | LLNLAISDLFFLLTVPFW | 144 | | | 48 |
| 73-90 | AISDLFFLLTVPFWAHYA | 41 | | | 49 |
| 77-94 | LFFLLTVPFWAHYAAAQW | 173 | | | 50 |
| 81-98 | LTVPFWAHYAAAQWDFGN | 306 | | | 51 |
| 85- | FWAHYAAAQWDFGNTMCQ | 212 | | | 52 |
| 89- | YAAAQWDFGNTMCQLLTG | 494 | | X | 53 |
| 93- | QWDFGNTMCQLLTGLYFI | 1019 | X | | 54 |
| 97- | GNTMCQLLTGLYFIGFFS | 941 | X | | 55 |
| 101- | CQLLTGLYFIGFFSGIFF | 489 | | X | 56 |
| 105- | TGLYFIGFFSGIFFIILL | 80 | | | 57 |
| 109- | FIGFFSGIFFIILLTIDR | 76 | | | 58 |
| 113- | FSGIFFIILLTIDRYLAV | 83 | | | 59 |
| 117- | FFIILLTIDRYLAVVHAV | 77 | | | 60 |
| 121- | LLTIDRYLAVVHAVFALK | 31 | | | 61 |
| 125- | DRYLAVVHAVFALKARTV | 62 | | | 62 |
| 129- | AVVHAVFALKARTVTFGV | 34 | | | 63 |
| 133- | AVFALKARTVTFGVVTSV | 63 | | | 64 |
| 137- | LKARTVTFGVWDSVITWV | 74 | | | 65 |
| 141- | TVTFGVVTSVITWVVAVF | -25 | | | 66 |
| 145- | GVVTSVITWVVAVFASLP | 69 | | | 67 |
| 149- | SVITWVVAVFASLPGIIF | 46 | | | 68 |
| 153- | WVVAVFASLPGIIFTRSQ | 87 | | | 69 |
| 157- | VFASLPGIIFTRSQKEGL | 54 | | | 70 |
| 161- | LPGIIFTRSQKEGLHYTC | 118 | | | 71 |
| 165- | IFTRSQKEGLHYTCSSHF | 98 | | | 72 |
| 169- | SQKEGLHYTCSSHFPYSQ | 304 | | X | 73 |
| 173- | GLHYTCSSEFPYSQYQFW | 301 | | X | 74 |
| 177- | TCSSHFPYSQYQFWKNFQ | 367 | | X | 75 |
| 181- | HFPYSQYQFWKNFQTLKI | 1008 | | X | 76 |
| 185- | SQYQFWKNFQTLKIVILG | 1572 | X | | 77 |
| 189- | FWKNFQTLKIVILGLVLP | 40 | | | 78 |
| 193- | FQTLKIVILGLVLPLLVM | 45 | | | 79 |
| 197- | KIVILGLVLPLLVMVICY | 65 | | | 80 |
| 201- | LGLVLPLLVMVICYSGIL | 180 | | | 81 |
| 205- | LPLLVMVICYSGILKTLL | 68 | | | 82 |
| 209- | VMVICYSGILKTLLRCRN | -8 | | | 83 |
| 213- | CYSGILKTLLRCRNEKKR | 70 | | | 84 |
| 217- | ILKTLLRCRNEKKRHRAV | 19 | | | 85 |
| 221- | LLRCRNEKKRHRAVRLIF | 102 | | | 86 |
| 225- | RNEKKRHRAVRLIFTIMI | 23 | | | 87 |
| 229- | KRHRAVRLIFTIMIVYFL | 36 | | | 88 |
| 233- | AVRLIFTIMTVYFLFWAP | 62 | | | 89 |
| 237- | IFTIMIVYFLFWAPYNIV | 121 | | | 90 |
| 241- | MIVYFLFWAPYNIVLLLN | 214 | | | 91 |
| 245- | FLFWAPYNIVLLLNTFQE | 616 | | X | 92 |
| 249- | APYNIVLLLNTFQEFFGL | 1962 | X | | 93 |
| 253- | IVLLLNTFQEFFGLNNCS | 2134 | X | | 94 |
| 257- | LNTFQEFFGLNNCSSSNR | 293 | | X | 95 |
| 261- | QEFFGLNNCSSSNRLDQA | 63 | | | 96 |
| 265- | GLNNCSSSNRLDQAMQVT | -31 | | | 97 |
| 269- | CSSSNRLDQAMQVTETLG | 90 | | | 98 |
| 273- | NRLDQAMQVTETLGMTHC | 10 | | | 99 |
| 277- | QAMQVTETLGMTHCCINP | 81 | | | 100 |
| 281- | VTETLGMTHCCINPIIYA | 15 | | | 101 |
| 285- | LGMTHCCINPIIYAFVGE | 282 | | X | 102 |
| 289- | HCCINPIIYAFVGEKFRN | 200 | | X | 103 |
| 293- | NPIIYAFVGEKFRNYLLV | 162 | | X | 104 |
| 297- | YAFVGEKFRNYLLVFFQK | 596 | X | | 105 |
| 301- | GEKFRNYLLVFFQKHIAK | 69 | | | 106 |
| 305- | RNYLLVFFQKHIAKRFCK | 65 | | | 107 |
| 309- | LVFFQKHIAKRFCKCCSI | 76 | | | 108 |
| 313- | QKHIAKRFCKCCSIFQQE | 23 | | | 109 |

-continued

| SEQ SEG | PEPTIDE | Counts per 20' Average-background | Peak Activity | Non-Peak Activity | SEQ ID NO: |
|---|---|---|---|---|---|
| 317- | AKRFCKCCSIFQQEAPER | 64 | | | 110 |
| 321- | CKCCSIFQQEAPERASSV | 53 | | | 111 |
| 325- | SIFQQEAPERASSVYTRS | 100 | | | 112 |
| 329- | QEAPERASSVYTRSTGEQ | 84 | | | 113 |
| 333- | ERASSVYTRSTGEQEISV | 84 | | | 114 |
| 337- | SVYTRSTGEQEISVGL | 47 | | | 115 |

These data indicate that, in addition to polypeptide sequences derived from positions 1-18 of the CCR5 receptor, the polypeptide sequences LPPLYSLVFIFGFVGNML (SEQ ID NO: 11), QWDFGNTMCQLLTGLYFIGFFS (SEQ ID NO: 12), SQYQFWKNFQTLKIVILG (SEQ ID NO: 13), APYNIVLLLNTFQEFFGLNNCS (SEQ ID NO: 14), and YAFVGEKFRNYLLVFFQK (SEQ ID NO: 15) comprise multiple subsequences, each which is capable of binding to HIV-1 envelope gp120.

Example 2

This example identifies segments of the CXCR4 co-receptor that bind with gp120.

The first column in the table below indicates the number of the amino acid in the wild-type CXCR4 receptor. The second column explicitly identifies the peptide sequence. The third and fourth columns indicate the radioactive counts recorded in twenty minutes (i.e., the cpm×20) after the background or non-specific counts had been subtracted. The fifth column contains an X in each row for which the listed polypeptide bound with high affinity to gp120. The sixth and final column contains an X in each row wherein the listed sequence binds with substantial affinity but is weak in comparison to other samples, particularly adjacent samples.

| SEQ SEG | PEPTIDE | | | Major Activity Peak | Minor Activity Peak | SEQ ID NO: |
|---|---|---|---|---|---|---|
| | empty (control) | 412 | 0 | | | |
| 1-18 | MEGISIYTSDNYTEEMGS | 3003 | 2591 | X | | 116 |
| 5-22 | SIYTSDNYTEEMGSGDYD | 483 | 71 | | | 117 |
| 9-26 | SDNYTEEMGSGDYDSMKE | 455 | 43 | | | 118 |
| 13-30 | TEEMGSGDYDSMKEPCFR | 453 | 41 | | | 119 |
| 17-34 | GSGDYDSMKEPCFREENA | 384 | -28 | | | 120 |
| 21-38 | YDSMKEPCFREENANFNK | 465 | 53 | | | 121 |
| 25-42 | KEPCFREENANFNKIFLP | 664 | 252 | | | 122 |
| 29-46 | FREENANFNKIFLPTIYS | 463 | 51 | | | 123 |
| 33-50 | NANFNKIFLPTIYSIIFL | 585 | 173 | | | 124 |
| 37-54 | NKIFLPTIYSIIFLTGIV | 550 | 138 | | | 125 |
| 41-58 | LPTIYSIIFLTGIVGNGL | 530 | 118 | | | 126 |
| 45-62 | YSIIFLTGIVGNGLVILV | 535 | 123 | | | 127 |
| 49-66 | FLTGIVGNGLVILVMGYQ | 658 | 246 | | | 128 |
| 53-70 | IVGNGLVILVMGYQKKLR | 650 | 238 | | | 129 |
| 57-74 | GLVILVMGYQKKLRSMTD | 569 | 157 | | | 130 |
| 61-78 | LVMGYQKKLRSMTDKYRL | 517 | 105 | | | 131 |
| 65-82 | YQKKLRSMTDKYRLHLSV | 511 | 99 | | | 132 |
| 69-86 | LRSMTDKYRLHLSVADLL | 572 | 160 | | | 133 |
| 73-90 | TDKYRLHLSVADLLFVIT | 504 | 92 | | | 134 |
| 77-94 | RLHLSVADLLFVITLPFW | 548 | 136 | | | 135 |
| 81-98 | SVADLLFVITLPFWAVDA | 665 | 253 | | | 136 |
| 85-102 | LLFVITLPFWAVDAVANW | 475 | 63 | | | 137 |
| 89-106 | ITLPFWAVDAVANWYFGN | 542 | 130 | | | 138 |
| 93-110 | FWAVDAVANWYFGNFLCK | 478 | 66 | | | 139 |
| 97-114 | DAVANWYFGNFLCKAVHV | 524 | 112 | | | 140 |
| 101-118 | NWYFGNFLCKAVHVIYTV | 508 | 96 | | | 141 |
| 105-122 | GNFLCKAVHVIYTVNLYS | 643 | 231 | | | 142 |
| 109-126 | CKAVHVIYTVNLYSSVLI | 655 | 243 | | | 143 |
| 113-130 | HVIYTVNLYSSVLILAFI | 530 | 118 | | | 144 |
| 117-134 | TVNLYSSVLILAFISLDR | 654 | 242 | | | 145 |
| 121-138 | YSSVLILAFISLDRYLAI | 569 | 157 | | | 146 |
| 125-142 | LILAFISLDRYLAIVHAT | 519 | 107 | | | 147 |
| 129-146 | FISLDRYLAIVHATNSQR | 503 | 91 | | | 148 |
| 133-150 | DRYLAIVHATNSQRPRKL | 580 | 168 | | | 149 |
| 137-154 | AIVHATNSQRPRKLLAEK | 485 | 73 | | | 150 |
| 141-158 | ATNSQRPRKLLAEKVVYV | 490 | 78 | | | 151 |

-continued

| SEQ SEG | PEPTIDE | Major Activity Peak | Minor Activity Peak | | SEQ ID NO: |
|---|---|---|---|---|---|
| 145–162 | QRPRKLLAEKVVYVGVWI | 539 | 127 | | 152 |
| 149–166 | KLLAEKVVYVGVWIPALL | 501 | 89 | | 153 |
| 153–170 | EKVVYVGVWIPALLLTIP | 559 | 147 | | 154 |
| 157–174 | YVGVWIPALLLTIPDFIF | 536 | 124 | | 155 |
| 161–178 | WIPALLLTIPDFIFANVS | 594 | 182 | | 156 |
| 165–182 | LLLTIPDFIFANVSEADD | 1418 | 1006 | X | 157 |
| 169–186 | IPDFIFANVSEADDRYIC | 850 | 438 | | X | 158 |
| 173–190 | IFANVSEADDRYICDRFY | 679 | 267 | | 159 |
| 177–194 | VSEADDRYICDRFYPNDL | 569 | 157 | | 160 |
| 181–198 | DDRYICDRFYPNDLWVVV | 537 | 125 | | 161 |
| 185–202 | ICDRFYPNDLWVVVFQFQ | 718 | 306 | | 162 |
| 189–206 | FYPNDLWVVVFQFQHIMV | 828 | 416 | | X | 163 |
| 193–210 | DLWVVVFQFQHIMVGLIL | 834 | 422 | X | 164 |
| 197–214 | VVFQFQHIMVGLILPGIV | 1001 | 589 | | X | 165 |
| 201–218 | FQHIMVGLILPGIVILSC | 582 | 170 | | 166 |
| 205–222 | MVGLILPGIVILSCYCII | 579 | 167 | | 167 |
| 209–226 | ILPGIVILSCYCIIISKL | 604 | 192 | | 168 |
| 213–230 | IVILSCYCIIISKLSHSK | 689 | 277 | | 169 |
| 217–234 | SCYCIIISKLSHSKGHQK | 671 | 259 | | 170 |
| 221–238 | IIISKLSHSKGHQKRKAL | 569 | 157 | | 171 |
| 225–242 | KLSHSKGHQKRKALKTTV | 542 | 130 | | 172 |
| 229–246 | SKGHQKRKALKTTVILIL | 552 | 140 | | 173 |
| 233–250 | QKRKALKTTVILILAFFA | 695 | 283 | | 174 |
| 237–254 | ALKTTVILILAFFACWLP | 673 | 261 | | 175 |
| 241–258 | TVILILAFFACWLPYYIG | 735 | 323 | | 176 |
| 245–262 | ILAFFACWLPYYIGISID | 596 | 184 | | 177 |
| 249–266 | FACWLPYYIGISIDSFIL | 614 | 202 | | 178 |
| 253–270 | LPYYIGISIDSFILLEII | 851 | 439 | | 179 |
| 257–274 | IGISIDSFILLEIIKQGC | 1146 | 734 | | X | 180 |
| 261–278 | IDSFILLEIIKQGCEFEN | 3884 | 3472 | X | 181 |
| 265–282 | ILLEIIKQGCEFENTVHK | 529 | 117 | | 182 |
| 269–286 | IIKQGCEFENTVEKWISI | 518 | 106 | | 183 |
| 273–290 | GCEFENTVHKWISITEAL | 676 | 264 | | 184 |
| 277–294 | ENTVHKWISITEALAFFH | 727 | 315 | | 185 |
| 281–298 | HKWISITEALAFFHCCLN | 575 | 163 | | 186 |
| 285–302 | SITEALAFFHCCLNPILY | 600 | 188 | | 187 |
| 289–306 | ALAFFHCCLNPILYAFLG | 593 | 181 | | 188 |
| 293–310 | FHCCLNPILYAFLGAKFK | 535 | 123 | | 189 |
| 297–314 | LNPILYAFLGAKFKTSAQ | 686 | 274 | | 190 |
| 301–318 | LYAFLGAKFKTSAQHALT | 568 | 156 | | 191 |
| 305–322 | LGAKFKTSAQHALTSVSR | 612 | 200 | | 192 |
| 309–326 | FKTSAQHALTSVSRGSSL | 585 | 173 | | 193 |
| 313–330 | AQNALTSVSRGSSLKILS | 559 | 147 | | 194 |
| 317–334 | LTSVSRGSSLKILSKGKR | 595 | 183 | | 195 |
| 321–338 | SRGSSLKILSKGKRGGHS | 581 | 169 | | 196 |
| 325–342 | SLKILSKGKRGGHSSVST | 697 | 285 | | 197 |
| 329–346 | LSKGKRGGHSSVSTESES | 597 | 185 | | 198 |
| 333–350 | KRGGHSSVSTESESSSFH | 579 | 167 | | 199 |
| 337–352 | HSSVSTESESSSFHSS | 515 | 103 | | 200 |

These data indicate that, in addition to polypeptide sequences derived from positions 1-18 of the CXCR4 receptor, the polypeptide sequences LLLTIPDFIFANVSEADD (SEQ ID NO: 16)(165-182), VVFQFQHIMVGLILPGIV (SEQ ID NO: 17) (197-214), and IDSFILLEIIKQGCEFEN (SEQ ID NO: 18) (261-278) comprise multiple subsequences, which is capable of binding to HIV-1 envelope gp120.

Example 3

This example identifies segments of the STRL33 coreceptor that bind with gp120.

The first column in the table below indicates the number of the amino acid in the wild-type STRL33 receptor. The second column explicitly identifies the peptide sequence. The third and fourth columns indicate the radioactive counts recorded in twenty minutes (i.e., the cpm×20) after the background or non-specific counts had been subtracted. The fifth column contains an X in each row for which the listed polypeptide bound with high affinity to gp120. The sixth and final column contains an X in each row wherein the listed sequence binds with substantial affinity but is weak in comparison to other samples, particularly adjacent samples.

| SEQ SEG | PEPTIDE | | Major Activity Peak | Minor Activity Peak | SEQ ID NO: |
|---|---|---|---|---|---|
| | empty (control) | −34.5 | 34.5 | | |
| 1--18 | MAEHDYHEDYGFSSFNDS | 1178.5 | 1320.5 | X | 201 |
| 5--22 | DYHEDYGFSSFNDSSQEE | 3357.5 | 3689.5 | X | 202 |
| 9--26 | DYGFSSFNDSSQEEHQAF | 8579.5 | 8909.5 | X | 203 |
| 13--30 | SSFNDSSQEEHQAFLQFS | 2689.5 | 2757.5 | | X | 204 |
| 17--34 | DSSQEEHQAFLQFSKVFL | 869.5 | 2152.5 | | X | 205 |
| 21--38 | EEHQAFLQFSKVFLPCMY | 2316.5 | 1819.5 | | X | 206 |
| 25--42 | AFLQFSKVFLPCMYLVVF | 1421.5 | 1359.5 | | X | 207 |
| 29--46 | FSKVFLPCMYLVVFVCGL | 534.5 | 633.5 | | | 208 |
| 33--50 | FLPCMYLVVFVCGLVGNS | 605.5 | 372.5 | | | 209 |
| 37--54 | MYLVVFVCGLVGNSLVLV | 168.5 | 235.5 | | | 210 |
| 41--58 | VFVCGLVGNSLVLVISIF | 570.5 | 284.5 | | | 211 |
| 45--62 | GLVGNSLVLVISIFYHKL | 164.5 | 95.5 | | | 212 |
| 49--66 | NSIYLVISIFYHKLQSLT | 1255.5 | 1378.5 | | X | 213 |
| 53--70 | LVISIFYHKLQSLTDVFL | 1620.5 | 1780.5 | X | | 214 |
| 57--74 | IFYHKLQSLTDVFLVNLP | 1275.5 | 1256.5 | | X | 215 |
| 61--78 | KLQSLTDVFLVNLPLADL | 412.5 | 348.5 | | | 216 |
| 65--82 | LTDVFLVNLPLADLVFVC | 233.5 | 336.5 | | | 217 |
| 69--86 | FLVNLPLADLVFVCTLPF | 70.5 | 51.5 | | | 218 |
| 73--90 | LPLADLVFVCTLPFWAYA | 557.5 | 960.5 | | X | 219 |
| 77--94 | DLVFVCTLPFWAYAGIHE | 1116.5 | 1063.5 | | X | 220 |
| 81--98 | VCTLPFWAYAGIHEWVFG | 1819.5 | 1754.5 | | X | 221 |
| 85--102 | PFWAYAGIHEWVFGQVMC | 7262.5 | 7537.5 | X | | 222 |
| 89--106 | YAGIHEWVFGQVMCKSLL | 5911.5 | 6245.5 | | X | 223 |
| 93--110 | HEWVFGQVMCKSLLGIYT | 3391.5 | 3466.5 | | X | 224 |
| 97--114 | FGQVMCKSLLGIYTINFY | 1257.5 | 1354.5 | | X | 225 |
| 101--118 | MCKSLLGIYTINFYTSML | 1505.5 | 1283.5 | | | 226 |
| 105--122 | LLGIYTINFYTSMLILTC | 499.5 | 408.5 | | | 227 |
| 109--126 | YTINFYTSMLILTCITVD | 351.5 | 510.5 | | | 228 |
| 113--130 | FYTSMLILTCITVDRFIV | 744.5 | 907.5 | | | 229 |
| 117--134 | MLILTCITVDRFIVVVKA | 298.5 | 228.5 | | | 230 |
| 121--138 | TCITVDRFIVVVKATKAY | 89.5 | 346.5 | | | 231 |
| 125--142 | VDRFIVVVKATKAYNQQA | 103.5 | 53.5 | | | 232 |
| 129--146 | IVVVKATKAYNQQAKRMT | 166.5 | 43.5 | | | 233 |
| 133--150 | KATKAYNQQAKRMTWGKV | 701.5 | 568.5 | | | 234 |
| 137--154 | AYNQQAKRMTWGKVTSLL | 55.5 | 4.5 | | | 235 |
| 141--158 | QAKRMTWGKVTSLLIWVI | −71.5 | −31.5 | | | 236 |
| 145--162 | MTWGKVTSLLIWVISLLV | −0.5 | −26.5 | | | 237 |
| 149--166 | KVTSLLIWVISLLVSLPQ | −39.5 | −118.5 | | | 238 |
| 153--170 | LLIWVISLLVSLPQIIYG | 42.5 | 75.5 | | | 239 |
| 157--174 | VISLLVSLPQIIYGNVFN | −60.5 | −127.5 | | | 240 |
| 161--178 | LVSLPQIIYGNVFNLDKL | 91.5 | −15.5 | | | 241 |
| 165--182 | PQIIYGNVFNLDKLICGY | −18.5 | −37.5 | | | 242 |
| 169--186 | YGNVFNLDKLICGYHDEA | −41.5 | −20.5 | | | 243 |
| 173--190 | FNLDKLICGYHDEAISTV | 1072.5 | 1078.5 | | X | 244 |
| 177--194 | KLICGYHDEAISTVVLAT | 1363.5 | 1604.5 | | X | 245 |
| 181--198 | GYHDEAISTVVLATQMTL | 754.5 | 1181.5 | | X | 246 |
| 185--202 | EAISTVVLATQMTLGFFL | 3973.5 | 3745.5 | X | | 247 |
| 189--206 | TVVLATQMTLGFFLPLLT | 2327.5 | 2389.5 | | X | 248 |
| 193--210 | ATQMTLGFFLPLLTMIVC | 2365.5 | 2444.5 | | X | 249 |
| 197--214 | TLGFFLPLLTMIVCYSVI | 2387.5 | 479.5 | | | 250 |
| 201--218 | FLPLLTMIVCYSVIIKTL | 1270.5 | 1195.5 | | X | 251 |
| 205--222 | LTMIVCYSVIIKTLLHAG | 2787.5 | 2654.5 | X | | 252 |
| 209--226 | VCYSVIIKTLLHAGGFQK | 1334.5 | 1143.5 | | X | 253 |
| 213--230 | VIIKTLLHAGGFQKERSL | 961.5 | 682.5 | | | 254 |
| 217--234 | TLLHAGGFQKHRSLKIIF | 1041.5 | 999.5 | | | 255 |
| 221--238 | AGGFQKHRSLKIIFLVMA | 340.5 | 260.5 | | | 256 |
| 225--242 | QKHRSLKIIFLVMAVFLL | 810.5 | 814.5 | | | 257 |
| 229--246 | SLKIIFLVMAVFLLTQMP | 612.5 | 853.5 | | | 258 |
| 233--250 | IFLVMAVFLLTQMPFNLM | 386.5 | 772.5 | | | 259 |
| 237--254 | MAVFLLTQMPFNLMKFIR | 2263.5 | 2842.5 | X | | 260 |
| 241--258 | LLTQMPFNLMKFIRSTHW | 2513.5 | 3154.5 | X | | 261 |
| 245--262 | MPFNLMKFIRSTHWEYYA | 2171.5 | 2182.5 | | X | 262 |
| 249--266 | LMKFIRSTHWEYYAMTSF | 934.5 | 949.5 | | | 263 |
| 253--270 | IRSTHWEYYAMTSFHYTI | 1571.5 | 1807.5 | | X | 264 |
| 257--274 | HWEYYAMTSFHYTIMVTE | 2040.5 | 3065.5 | X | | 265 |
| 261--278 | YAMTSFHYTIMVTEAIAY | 2688.5 | 2359.5 | | X | 266 |
| 265--282 | SFHYTIMVTEAIAYLRAC | 761.5 | 1033.5 | | | 267 |
| 269--286 | TIMVTEAIAYLRACLNPV | 140.5 | 272.5 | | | 268 |
| 273--290 | TEAIAYLRACLNPVLYAF | 604.5 | 480.5 | | | 269 |
| 277--294 | AYLRACLNPVLYAFVSLK | 1802.5 | 1849.5 | | X | 270 |
| 281--298 | ACLNPVLYAFVSLKFRKN | 4173.5 | 4515.5 | X | | 271 |

-continued

| SEQ SEG | PEPTIDE | Major Activity Peak | Minor Activity Peak | SEQ ID NO: |
|---|---|---|---|---|
| 285–302 | PVLYAFVSLKFRKNFWKL | 1852157.5 | X | 272 |
| 289–306 | AFVSLKFRKNFWKLVKDI | 808050.5 |  | 273 |
| 293–310 | LKFRKNFWKLVKDIGCLP | 920957.5 |  | 274 |
| 297–314 | KNFWKLVKDIGCLPYLGV | 143.52.5 |  | 275 |
| 301–318 | KLVKDIGCLPYLGVSHQW | −2.57.5 |  | 276 |
| 305–322 | DIGCLPYLGVSHQWKSSE | 17.58.5 |  | 277 |
| 309–326 | LPYLGVSHQWKSSEDNSK | 111152.5 |  | 278 |
| 313–330 | GVSNQWKSSEDNSKTFSA | 208356.5 |  | 279 |
| 317–334 | QWKSSEDNSKTFSASHNV | 464553.5 |  | 280 |
| 321–338 | SEDNSKTFSASHNVEATS | 524.5 | .434.5 | 281 |
| 325–342 | SKTFSASHNVEATSMFQL | 1524259.5 | X | 282 |

These data indicate that, in addition to polypeptide sequences derived from positions 9-26 of the STRL33 receptor, the polypeptide sequences LVISIFYHKLQSLTD-VFL (SEQ ID NO: 19) (53-70), PFWAYAGIHEWVF-GQVMC (SEQ ID NO: 20)(85-102), EAISTVV-LATQMTLGFFL (SEQ ID NO: 21)(185-202), LTMIVCYSVIIKTLLHAG (SEQ ID NO: 22)(205-222), MAVFLLTQMPFNLMKFIRSTHW (SEQ ID NO: 23)(237-258), HWEYYAMTSFHYTIMVTE (SEQ ID NO: 24)(257-274), ACLNPVLYAFVSLKFRKN (SEQ ID NO: 25)(281-298) and SKTFSASHNVEATSMFQL (SEQ ID NO: 26) (325-342) comprise multiple subsequences, which is capable of binding to HIV-1 envelope gp120.

Example 4

This example identifies segments of the human CD4 protein that bind with gp120.

The second column in the in the table below identifies the amino acid residue sequence of the polypeptide employed in the assay. The first column identifies the sequence coordinates of human CD4 that have an identical amino acid sequence. The third column indicates the number of radioactive decays (i.e., counts) that were counted, which is indicative of the affinity of the synthetic polypeptide for the gp120 protein. In the table below, polypeptides retaining more than 4,000 counts identify fragments that have a substantial capability to bind with gp120. Polypeptides retaining more than 6,000 counts have more substantial binding affinity. Polypeptides retaining at least about 10,000 counts have a substantial and strong capacity to bind to gp120. Of course, fragments corresponding to amino acid coordinates 101-121 and 106-126 have a substantial, strong, and dominant capacity to bind to gp120.

|  |  |  |  |  | SEQ ID NO: |
|---|---|---|---|---|---|
| B1 | (1) | 1–21 | MNRGVPFRRLLLVLQLALLPA | 3587 | 283 |
| C1 | (2) | 16–26 | PFRELLLVLQLALLPAATQGK | 4356 | 284 |
| D1 | (3) | 11–31 | LLVLQLALLPAATQGKKVVLG | 1785 | 285 |
| E1 | (4) | 16–36 | LALLPAATQGKKVVLGKKGDT | 1759 | 286 |
| F1 | (5) | 21–41 | AATQGKKVVLGKKGDTVELTC | 1562 | 287 |
| G1 | (6) | 26–46 | KKVVLGKKGDTVELTCTASQK | 1910 | 288 |
| H1 | (7) | 31–51 | GKKGDTVELTCTASQKKSIQF | 1831 | 289 |
| A2 | (8) | 36–56 | TVELTCTASQKKSIQFHWKNS | 1732 | 290 |
| B2 | (9) | 41–61 | CTASQKKSIQFHWKNSNQIKI | 1717 | 291 |
| C2 | (10) | 46–66 | KKSIQFHWKNSNQIKILGNQG | 2182 | 292 |
| D2 | (11) | 51–71 | FHWKNSNQIKILGNQGSFLTK | 1835 | 293 |
| E2 | (12) | 56–76 | SNQIKILGNQGSFLTKGPSKL | 1487 | 294 |
| F2 | (13) | 61–81 | ILGNQGSFLTKGPSKLNDRAD | 1467 | 295 |
| G2 | (14) | 66–86 | GSFLTKGPSKLNDRADSRRSL | 1844 | 296 |
| H2 | (15) | 71–91 | KGPSKLNDRADSRRSLWDQGN | 1912 | 297 |
| A3 | (16) | 76–96 | LNDRADSRRSLWDQGNFPLII | 1753 | 298 |
| B3 | (17) | 81–101 | DSRRSLWDQGNFPLIIKNLKI | 2224 | 299 |
| C3 | (18) | 86–106 | LWDQGNFPLIIKNLKIEDSDT | 3264 | 300 |
| D3 | (19) | 91–111 | NFPLIIKNLKIEDSDTYICEV | 11646 | 301 |
| E3 | (20) | 96–116 | IKNLKIEDSDTYICEVEDQKE | 8439 | 302 |
| F3 | (21) | 101–121 | IEDSDTYICEVEDQKEEVQLL | 6803 | 303 |
| G3 | (22) | 106–126 | TYICEVEDQKEEVQLLVFGLT | 44965 | 304 |
| H3 | (23) | 111–131 | VEDQKEEVQLLVFGLTANSDT | 36249 | 305 |
| A4 | (24) | 116–136 | EEVQLLVFGLTANSDTHLLQG | 14171 | 306 |
| B4 | (25) | 121–141 | LVFGLTANSDTHLLQGQSLTL | 3683 | 307 |
| C4 | (26) | 126–146 | TANSDTHLLQGQSLTLTLESP | 6114 | 308 |
| D4 | (27) | 131–151 | THLLQGQSLTLTLESPPGSSP | 2552 | 309 |
| E4 | (28) | 136–156 | GQSLTLTLESPPGSSPSVQCR | 1538 | 310 |
| F4 | (29) | 141–161 | LTLESPPGSSPSVQCRSPRGK | 1476 | 311 |

-continued

| | | | | | SEQ ID NO: |
|---|---|---|---|---|---|
| G4 | (30) | 146-166 | PPGSSPSVQCRSPRGKNIQGG | 1496 | 312 |
| H4 | (31) | 151-171 | PSVQCRSPRGKNIQGGKTLSV | 1400 | 313 |
| A5 | (32) | 156-176 | RSPRGKNIQGGKTLSVSQLEL | 2066 | 314 |
| B5 | (33) | 161-181 | KNIQGGKTLSVSQLELQDSGT | 3078 | 315 |
| C5 | (34) | 166-186 | GKTLSVSQLELQDSGTWTCTV | 2618 | 316 |
| D5 | (35) | 171-191 | VSQLELQDSGTWTCTVLQNQK | 3879 | 317 |
| E5 | (36) | 176-196 | LQDSGTWTCTVLQNQKKVEFK | 2456 | 318 |
| F5 | (37) | 181-201 | TWTCTVLQNQKKVEFKIDIVV | 4030 | 319 |
| G5 | (38) | 186-206 | VLQNQKKVEFKIDIVVLAFQK | 9737 | 320 |
| H5 | (39) | 191-211 | KKVEFKIDIVVLAFQKASSIV | 6313 | 321 |
| A6 | (40) | 196-216 | KIDIVVLAFQKASSIVYKKEG | 3681 | 322 |
| B6 | (41) | 201-221 | VLAFQKASSIVYKKEGEQVEF | 3566 | 323 |
| C6 | (42) | 206-226 | KASSIVYKKEGEQVEFSFPLA | 14347 | 324 |
| D6 | (43) | 211-231 | VYKKEGEQVEFSFPLAFTVEK | 14740 | 325 |
| E6 | (44) | 216-236 | GEQVEFSFPLAFTVEKLTGSG | 18549 | 326 |
| F6 | (45) | 221-241 | FSFPLAFTVEKLTGSGELWWQ | 9673 | 327 |
| G6 | (46) | 226-246 | AFTVEKLTGSGELWWQAERAS | 3992 | 328 |
| H6 | (47) | 231-251 | KLTGSGELWWQAERASSSKSW | 1878 | 329 |
| A7 | (48) | 236-256 | GELWWQAERASSSKSWITFDL | 2730 | 330 |
| B7 | (49) | 241-261 | QAERASSSKSWITFDLINKEV | 2588 | 331 |
| C7 | (50) | 246-266 | SSSKSWITFDLKNKEVSVKRV | 1761 | 332 |
| D7 | (51) | 251-271 | WITFDLKNKEVSVKRVTQDPK | 2126 | 333 |
| E7 | (52) | 256-276 | LKNKEVSVKRVTQDPKLQMGK | 2288 | 334 |
| F7 | (53) | 261-281 | VSVKRVTQDPKLQMGKKLPLH | 1848 | 335 |
| G7 | (54) | 266-286 | VTQDPKLQMGKKLPLHLTLPQ | 2075 | 336 |
| H7 | (55) | 271-291 | KLQMGKKLPLHLTLPQALPQY | 1949 | 337 |
| A8 | (56) | 276-296 | KKLPLHLTLPQALPQYAGSGN | 1922 | 338 |
| B8 | (57) | 281-301 | HLTLPQALPQYAGSGNLTLAL | 2394 | 339 |
| C8 | (58) | 286-306 | QALPQYAGSGNLTLALEAKTG | 2364 | 340 |
| D8 | (59) | 291-311 | YAGSGNLTLALEAKTGKLHQE | 1830 | 341 |
| E8 | (60) | 296-316 | NLTLALEAKTGKLHQEVNLVV | 1676 | 342 |
| F8 | (61) | 301-321 | LEAKTGKLHQEVNLVVMRATQ | 1729 | 343 |
| G8 | (62) | 306-326 | GKLHQEVNLVVMRATQLQKNL | 1776 | 344 |
| ES | (63) | 311-331 | EVNLVVMRATQLQKNLTCEVW | 2183 | 345 |
| A9 | (64) | 316-336 | VMRATQLQKNLTCEVWGPTSP | 2144 | 346 |
| B9 | (65) | 321-341 | QLQKNLTCEVWGPTSPKLMLS | 1856 | 347 |
| C9 | (66) | 326-346 | LTCEVWGPTSPKLMLSLKLEN | 2412 | 348 |
| D9 | (67) | 331-351 | WGPTSPKLMLSLKLENKEAKV | 2414 | 349 |
| E9 | (68) | 336-356 | PKLMLSLKLENKEAKVSKREK | 1656 | 350 |
| F9 | (69) | 341-361 | SLKLENKEAKVSKREKAVWVL | 1663 | 351 |
| G9 | (70) | 346-366 | NKEAKVSKREKAVWVLNPEAG | 1735 | 352 |
| H9 | (71) | 351-371 | VSKREKAVWVLNPEAGMWQCL | 2034 | 353 |
| A10 | (72) | 356-376 | KAVWVLNPEAGMWQCLLSDSG | 3133 | 354 |
| B10 | (73) | 361-381 | LNPEAGMWQCLLSDSGQVLLE | 6316 | 355 |
| C10 | (74) | 366-386 | GMWQCLLSDSGQVLLESNIKV | 4185 | 356 |
| D10 | (75) | 371-391 | LLSDSGQVLLESNIKVLPTWS | 2375 | 357 |
| E10 | (76) | 376-396 | GQVLLESNIKVLPTWSTPVQP | 2089 | 358 |
| F10 | (77) | 381-401 | ESNIKVLPTWSTPVQPMALIV | 1992 | 359 |
| G10 | (78) | 386-406 | VLPTWSTPVQPMALIVLGGVA | 2197 | 360 |
| E10 | (79) | 391-411 | STPVQPMALIVLGGVAGLLLF | 2527 | 361 |
| A11 | (80) | 396-416 | PMALIVLGGVAGLLLFIGLGI | 3067 | 362 |
| B11 | (81) | 401-421 | VLGGVAGLLLFIGLGIFFCVR | 3738 | 363 |
| C11 | (82) | 406-426 | AGLLLFIGLGIFFCVRCRHRR | 2099 | 364 |
| D11 | (83) | 411-431 | FIGLGIFFCVRCRHRRRQAER | 1900 | 365 |
| E11 | (84) | 416-436 | IFFCVRCRHRRRQAERMSQIK | 2085 | 366 |
| F11 | (85) | 421-441 | RCRHRRRQAERMSQIKRLLSE | 2075 | 367 |
| G11 | (86) | 42E-446 | RRQAERMSQLKRLLSEKKTCQ | 1607 | 368 |
| H11 | (87) | 431-451 | RMSQIKRLLSEKKTCQCPHRF | 2020 | 369 |
| A12 | (88) | 436-456 | KRLLSEKKTCQCPERFQKTCS | 1674 | 370 |
| B12 | (89) | 441-458 | EKKTCQCPHRFQKTCSPI | 2006 | 371 |
| A1 | ( 0) | | empty (control) | 2075 | |

Example 5

This example shows the binding of $^{125}$I-HIV-1$_{LAI}$ gp120 to the amino termini of CCR5, CXCR4, and STRL33 as a function of the dependence on position and length. Synthetic peptide arrays of nonapeptides, dodecapeptides, pentadecapeptides and octadecapeptides derived from CCR5 (panel A), CXCR4 (panel B) and STRL33 (panel C) amino terminal domains were prepared and utilized to test the binding of $^{125}$I-HIV-1$_{LAI}$ envelope gp120. Ordinal sequence position numbers are given in accordance with the sequence data provided by the Genbank database for CCR5 (accession No. gi1457946, gi|1457946), CXCR4 (accession No. g539677, gi|400654, sp|P30991) and STRL33 (accession No. g2209288, gi|2209288). The counts shown are the counts detected in each well minus the background counts (i.e., counts observed in the assay when no polypeptide was bound to the well of the 96-well assay plate).

| Panel A CCR5 Initial Sequence # | Peptide Sequence Scanning Windows (In each sequence row 9-, 12-, 15-, isomers share the same initial starting point.) | Binding Results For Window Length (counts bound-background (no peptide)) | | | | SEQ ID NO: |
|---|---|---|---|---|---|---|
| | XXXXXXXXX 9 | 9 | | | | |
| | XXXXXXXXXXXX 12 | | 12 | | | |
| | XXXXXXXXXXXXXXX 15 | | | 15 | | |
| | XXXXXXXXXXXXXXXXXX 18 | | | | 18 | |
| 1 | MDYQVSSPIYDINYYTSE | 543 | 2682 | 4976 | 5880 | 372 |
| 2 | DYQVSSPIYDINYYTSEP | 1552 | 3089 | 5401 | 6363 | 373 |
| 3 | YQVSSPIYDINYYTSEPC | 2533 | 5305 | 5415 | 6119 | 374 |
| 4 | QVSSPIYDINYYTSEPCQ | 490 | 1959 | 4594 | 5645 | 375 |
| 5 | VSSPIYDINYYTSEPCQK | 509 | 1629 | 3280 | 3521 | 376 |
| 6 | SSPIYDINYYTSEPCQKI | 671 | 1739 | 3498 | 3285 | 377 |
| 7 | SPIYDINYYTSEPCQKIN | 1503 | 3463 | 4575 | 3234 | 378 |
| 8 | PIYDINYYTSEPCQKINV | 1186 | 2285 | 2682 | 2036 | 379 |
| 9 | IYDINYYTSEPCQKTNVK | 1359 | 2702 | 2516 | 1261 | 380 |
| 10 | YDINYYTSEPCQKINVKQ | 4379 | 5245 | 3052 | 1913 | 381 |
| 11 | DINYYTSEPCQKINVKQI | 1396 | 1361 | 1144 | 712 | 382 |
| 12 | INYYTSEPCQKINVKQIA | 1384 | 1190 | 707 | 684 | 383 |
| 13 | NYYTSEPGQKINVKQIAA | 1548 | 977 | 760 | 595 | 384 |
| 14 | YYTSEPCQKINVKQIAAR | 1029 | 1052 | 847 | 638 | 385 |
| 15 | YTSEPCQKINVKQIA | 567 | 507 | 459 | | 386 |
| 16 | TSEPCQKINVKQIAA | 440 | 427 | 509 | | 387 |
| 17 | SEPCQKINVKQIAAR | 434 | 430 | 426 | | 388 |
| 18 | BPCQKINVKQIA | 397 | 432 | | | 389 |
| 19 | PCQKINVKQIAA | 386 | 385 | | | 390 |
| 20 | CQKINVKQIAAR | 435 | 581 | | | 391 |
| 21 | QKINVKQIA | 453 | | | | 392 |
| 22 | KINVKQIAA | 487 | | | | 393 |
| 23 | INVKQIAAR | 474 | | | | 394 |

| Panel B CXCR4 Initial Sequence # | Peptide Sequence Scanning Windows (In each sequence row 9-, 12-, 15-, 18-mers share the same initial starting point.) | Binding Results For Window Length (counts bound-background) | | | | SEQ ID NO: |
|---|---|---|---|---|---|---|
| | XXXXXXXXX 9 | 9 | | | | |
| | XXXXXXXXXXXX 12 | | 12 | | | |
| | XXXXXXXXXXXXXXX 15 | | | 15 | | |
| | XXXXXXXXXXXXXXXXXX 18 | | | | 18 | |
| 1 | MEGISIYTSDNYTEEMGS | 591 | 334 | 3275 | 2079 | 395 |
| 2 | EGISJYTSDNYTEEMGSG | a | 886 | 7255 | 1548 | 396 |
| 3 | GISIYTSDNYTEEMGSGD | 454 | 2644 | 3274 | 1217 | 397 |
| 4 | ISIYTSDNYTEEMGSGDY | 466 | 3973 | 2202 | 861 | 398 |
| 5 | SLYTSDNYTEEMGSGDYD | a | 288 | 168 | 239 | 399 |
| 6 | IYTSDNYTEEMGSGDYDS | 332 | 335 | 195 | 173 | 400 |
| 7 | YTSDNYTEEMGSGDYDSM | 181 | 161 | 201 | 103 | 401 |
| 8 | TSDNYTEEMGSGDYDSMK | a | 54 | 119 | 38 | 402 |
| 9 | SDNYTEEMGSODYDSMKE | 151 | 149 | 124 | 161 | 403 |
| 10 | DNYTEEMGSGDYDSMKEP | 67 | 121 | 57 | 102 | 404 |
| 11 | NYTEEMGSGDYDSMKEPC | a | 100 | 30 | 134 | 405 |
| 12 | YTEEMGSGDYDSMKEPCF | 68 | 213 | 70 | 103 | 406 |
| 13 | TEEMGSGDYDSMKEPCFR | 146 | 67 | 23 | 47 | 407 |
| 14 | EEMGSGDYDSMKEPCFRB | a | 61 | 121 | 130 | 408 |
| 15 | EMGSGDYDSMKEPCFREE | 64 | 36 | 69 | 64 | 409 |
| 16 | MGSGDYDSMKEPCFREEN | 57 | 68 | 64 | 129 | 410 |
| 17 | GSGDYDSMKEPCFREENA | a | 155 | 172 | 155 | 411 |
| 18 | SGDYDSMKEPCFREENAN | 100 | 118 | 186 | 89 | 412 |
| 19 | GDYDSMKEPCFREENANF | 53 | 167 | 198 | 134 | 413 |
| 20 | DYDSMKEPCFREENANFN | a | 167 | 146 | 75 | 414 |
| 21 | YDSMKEPCFREENANFNK | 171 | 144 | 80 | 89 | 415 |
| 22 | DSMKEPCFREENANFNKI | 85 | 144 | 146 | 40 | 416 |
| 23 | SMKEPCFREENANFN | a | 119 | 55 | | 417 |
| 24 | MKEPCFREBNANFNK | 188 | 133 | 74 | | 418 |
| 25 | KEPCFREENANFNKI | 165 | 105 | 93 | | 419 |
| 26 | EPCFREENANFN | a | 69 | | | 420 |

-continued

| | | | | | |
|---|---|---|---|---|---|
| 27 | PCFREENANFNK | 104 | 108 | | 421 |
| 28 | CFREENANFNKI | 103 | 66 | | 422 |
| 29 | REENANFNK | 58 | | | 423 |

[a]Not done

| Panel C STRL33 Initial Sequence # | Peptide Sequence Scanning Windows (In each sequence row 9-, 12-, 15-, 18-mers share the same initial starting point.) | Binding Results For Window Length (counts bound-background) | | | SEQ ID NO: |
|---|---|---|---|---|---|
| | XXXXXXXXX 9<br>XXXXXXXXXXXX 12<br>XXXXXXXXXXXXXXX 15<br>XXXXXXXXXXXXXXXXXX 18 | 9 | 12 | 15 | 18 |
| 1 | MAEHDYHEDYGFSSFNDS | 160 | 625 | 1239 | 1386 | 424 |
| 2 | AEHDYHEDYGFSSFNDSS | 354 | 697 | 1095 | | 425 |
| 3 | EHDYHEDYGFSSFNDSSQ | 509 | 937 | 2235<br>1014 | | 426 |
| 4 | HDYHEDYGFSSFNDSSQE | 708 | 1427 | 1772<br>1219 | | 427 |
| 5 | DYHEDYGFSSFNDSSQEE | 851 | 1554 | 1240<br>1500 | | 428 |
| 6 | YHEDYGFSSFNDSSQEEH | 728 | 1950 | 1357<br>1191 | | 429 |
| 7 | HEDYGFSSFNDSSQEEHQ | 729 | 1077 | 947 | 537 | 430 |
| 8 | EDYGFSSFNDSSQEEHQA | 953 | 817 | 1152 | 548 | 431 |
| 9 | DYGFSSFNDSSQEEHQAF | 701 | 573 | 595 | 440 | 432 |
| 10 | YGFSSFNDSSQEEHQAFL | 345 | 745 | 645<br>1138 | 433 | |
| 11 | GFSSFNDSSQEEEQAFLQ | 171 | 480 | 270<br>1639 | 434 | |
| 12 | FSSFNDSSQEEHQAFLQF | 249 | 403 | 361<br>3608 | 435 | |
| 13 | SSFNDSSQEEHQAFLQFS | 243 | 277 | 902<br>6038 | 436 | |
| 14 | SFWDSSQEEEQAFLQFSK | 304 | 303 | 969<br>4537 | 437 | |
| 15 | FNDSSQEEEQAFLQFSKV | 246 | 470 | 4089<br>4678 | 438 | |
| 16 | NDSSQEEHQAFLQFS | 180 | 497 | 6160 | | 439 |
| 17 | DSSQEEHQAFLQFSK | 147 | 882 | 4588 | | 440 |
| 18 | SSQEEEQAFLQFSKV | 287 | 4455 | 4732 | | 441 |
| 19 | SQEEHQAFLQFS | 647 | 7512 | | | 442 |
| 20 | QEEHQAFLQFSK | 1109 | 5672 | | | 443 |
| 21 | EEHQAFLQFSKV | 6060 | 5598 | | | 444 |
| 22 | EHQAFLQFS | 7505 | | | | 445 |
| 23 | HQAFLQFSK | 2761 | | | | 446 |
| 24 | QAFLQFSKV | 2600 | | | | 447 |

Example 6

This example shows $^{125}$I-HIV-1$_{LAI}$ gp120 binding to N-terminal peptide variants of CCR5, CXCR4 and STRL33.

Octadecapeptide alanine replacement variants of maximum gp120 binding activity peaks were synthesized and tested for $^{125}$I-HIV-1$_{LAI}$ gp120 binding. Each binding value presented is the average of two separate synthesis and binding experiments. Relative percentage of Control={[(mean counts/Control counts)]×100%}±average deviation. Background counts (no peptide, see Example 7) were subtracted from all values. Data for CCR5 are presented in Panel A; data for CXCR4 are presented in Panel B; and data for STRL33 are presented in Panel C.

Panel A. $^{125}$I-HIV-1$_{LAI}$ gp120 binding to N-terminal peptide variants of CCR5

| CCR5 variant peptides (1–18) | | Relative % of Control[a] | SEQ ID NO: |
|---|---|---|---|
| Control | MDYQVSSPIYDINYYTSE | 100 | 448 |
| M1A | ADYQVSSPIYDINYYTSE | 167 ± 4 | 449 |
| D2A | MAYQVSSPIYDINYYTSE | 125 ± 8 | 450 |
| Y3A | MDAQVSSPIYDINYYTSE | 51 ± 2 | 451 |
| Q4A | MDYAVSSPIYDINYYTSE | 104 ± 7 | 452 |
| V5A | MDYQASSPIYDINYYTSE | 82 ± 3 | 453 |
| S6A | MDYQVASPIYDINYYTSE | 124 ± 3 | 454 |
| S7A | MDYQVSAPIYDINYYTSE | 56 ± 2 | 455 |

-continued

Panel A. $^{125}$I-HIV-1$_{LAI}$ gp120 binding to N-terminal peptide variants of CCR5

| CCR5 variant peptides (1–18) | | Relative % of Control[a] | SEQ ID NO: |
|---|---|---|---|
| P8A | MDYQVSSAIYDINYYTSE | 157 ± 2 | 456 |
| 19A | MDYQVSSPAYDINYYTSE | 24 ± 7 | 457 |
| Y10A | MDYQVSSPIADINYYTSE | 19 ± 6 | 458 |
| D11A | MDYQVSSPIYAINYYTSE | 63 ± 22 | 459 |
| I12A | MDYQVSSPIYDANYYTSE | 14 ± 1 | 460 |
| N13A | MDYQVSSPIYDIAYYTSE | 253 ± 19 | 461 |
| Y14A | MDYQVSSPIYDINAYTSE | 15 ± 0.3 | 462 |
| Y15A | MDYQVSSPIYDINYATSE | 21 ± 5 | 463 |
| T16A | MDYQVSSPIYDINYYASE | 78 ± 34 | 464 |
| S17A | MDYQVSSPIYDINYYTAE | 64 ± 6 | 465 |
| E18A | MDYQVSSPIYDINYYTSA | 4 ± 2 | 466 |

[a]The percent binding for the wild-type peptide was defined as 100%.

Panel B $^{125}$I-HIV-1$_{LAI}$gp120 binding to N-terminal peptide variants of CXCR4

| CXCR4 variant peptides (1–18) | | Relative % of Control[a] | SEQ ID NO: |
|---|---|---|---|
| Control | MEGISIYTSDNYTEEMGS | 100 | 467 |
| M1A | AEGISIYTSDNYTEEMGS | 118 ± 18 | 468 |
| E2A | MAGISIYTSDNYTEEMGS | 36 ± 0.3 | 469 |
| G3A | MEAISIYTSDNYTEEMGS | 101 ± 3 | 470 |
| I4A | MEGASIYTSDNYTEEMGS | 6 ± 0.3 | 471 |
| S5A | MEGIAIYTSDNYTEEMGS | 133 ± 5 | 472 |
| I6A | MEGISAYTSDNYTEEMGS | 2 ± 1 | 473 |
| Y7A | MEGISIATSDNYTEEMGS | 7 ± 0.4 | 474 |
| T8A | MEGISIYASDNYTEEDGS | 97 ± 10 | 475 |
| S9A | MEGISIYTADNYTEEMGS | 70 ± 4 | 476 |
| D10A | MEGISIYTSANYTEEMGS | 71 ± 8 | 477 |
| N11A | MEGISIYTSDAYTEEMGS | 38 ± 0.4 | 478 |
| Y12A | MEGISIYTSDNATEEMGS | 28 ± 2 | 479 |
| T13A | MEGISIYTSDNYAEEMGS | 70 ± 6 | 480 |
| E14A | MEGISIYTSDNYTAEMGS | 72 ± 1 | 481 |
| E15A | MEGISIYTSDNYTEAMGS | 56 ± 7 | 482 |
| M16A | MEGISIYTSDNYTEEAGS | 88 ± 4 | 483 |
| G17A | MEGISIYTSDNYTEEMAS | 68 ± 8 | 484 |
| S18A | MEGISIYTSDNYTEEMGA | 79 ± 1 | 485 |

[a]The percent binding for the wild-type peptide was defined as 100%.

Panel C $^{125}$I-HIV-1$_{LAI}$gp120 binding to N-terminal peptide variants of STRL33

| STRL33 variant peptides (21–38) | | Relative % of Control[a] | SEQ ID NO: |
|---|---|---|---|
| Control | EEHQAFLQFSKVFLPCMY | 100 | 486 |
| E21A | AEHQAFLQFSKVFLPCMY | 81 ± 2 | 487 |
| E22A | EAHQAFLQFSKVFLPCMY | 70 ± 1 | 488 |
| H23A | EEAQAFLQFSKVFLPCMY | 99 ± 1 | 489 |
| Q24A | EEHAAFLQFSKVFLPCMY | 72 ± 1 | 490 |
| A25A | EEHQAFLQFSKVFLPCMY | 101 ± 1 | 491 |
| F26A | EEHQAALQFSKVFLPCMY | 32 ± 0.1 | 492 |
| L27A | EEHQAFAQFSKVFLPCMY | 37 ± 2 | 493 |
| Q28A | EEEQAFLAFSKVFLPCMY | 44 ± 0.4 | 494 |
| F29A | EEHQAFLQASKVFLPCMY | 20 ± 1 | 495 |
| S30A | EEHQAFLQFAKVFLPCMY | 92 ± 2 | 496 |
| K31A | EEHQAFLQFSAVFLPCMY | 162 ± 2 | 497 |
| V32A | EEHQAFLQFSKAFLPCMY | 51 ± 3 | 498 |
| F33A | EEHQAFLQFSKVALPCMY | 45 ± 2 | 499 |
| L34A | EEHQAFLQFSKVFAPCMY | 76 ± 1 | 500 |
| P35A | EEHQAFLQFSKVFLACMY | 82 ± 3 | 501 |
| C36A | EEHQAFLQFSKVFLPAMY | 53 ± 5 | 502 |
| M37A | EEHQAFLQFSKVFLPCAY | 112 ± 4 | 503 |
| Y38A | EEHQAFLQFSKVFLPCMA | 83 ± 2 | 504 |

[a]The percent binding for the wild-type peptide was defined as 100%.

Example 7

This example demonstrates that the binding of HIV-1 gp120 envelope protein to the polypeptides of the present invention and to the chemokine receptors from which the present inventive polypeptides were originally derived or inspired is conserved across the various species of HIV-1. This example also demonstrates that a step subsequent to initial binding of gp120 to CCR5, CXCR4, STRL33, and CD4 is the most likely source of the phenomenon of host-range selectivity. Additionally, this example demonstrates that the underlying method is accurate in that receptor variants that are predicted to have an altered affinity for binding with gp120, do in fact have a statistically similar alteration in affinity where comparable changes in the receptors have been identified in other work and the affinity for binding of gp120/effect on infectivity has been measured.

This example examines the effect of particular mutations of CCR5 that were studied in the work underlying the present invention and that were also studied by other artisans in the field.

The following table identifies a mutation in the first column. The first letter designates the wild-type amino acid present at the position indicated by the number, and the letter A which terminates all entries in the first column indicates that the amino acid residue present in that position in the mutant polypeptide is alaninyl. For example, the first data row (i.e., the second row of the table) contains the entry Y3A in the first column, which indicates that the tyrosine residue at position 3 of the wild-type CCR5 is substituted by an alanine residue.

The second column provides the percentage of binding exhibited by a mutant polypeptide compared to a wild-type polypeptide, when the methods used to elucidate the present invention are used in conjunction with radiolabeled HIV-1$_{LAI}$ gp120 envelope protein. The third through seventh columns provide similar data that have been extracted from the work of others in the field using a strain of HIV-1 virus indicated at the top of each column. For example, row 2 of the following table indicates that when the mutation Y3A is effected in the human CCR5 chemokine receptor, then the resulting CCR5 polypeptide has 51.4% of the ability to bind HIV-1$_{LAI}$ gp120 envelope protein in comparison to an equivalent wild-type peptide. Similarly, HIV-1$_{ADA}$ binds to the mutant polypeptide with 79% of the affinity of a non-mutated CCR5 chemokine receptor.

| | gp120 | YU2 | ADA | JF-RL | 89.6 | DH123 |
|---|---|---|---|---|---|---|
| Y3A | 51.4 | n/a | 79 | 82 | n/a | 42 |
| Q4A | 104 | 85 | 132 | 111 | 67 | 105 |

-continued

|      | gp120 | YU2 | ADA | JF-RL | 89.6 | DH123 |
|------|-------|-----|-----|-------|------|-------|
| Y10A | 19.2  | 2   | 50  | 26    | 10   | 3     |
| D11A | 62.8  | 2   | 27  | 22    | 6    | 3     |
| Y14A | 14.6  | 12  | 47  | 25    | 6    | 0     |
| Y15A | 21    | 30  | 3   | 3     | 1    | 0     |
| E18A | 4.1   | 45  | 12  | 12    | 3    | 10    |

Statistical analysis of these data indicates that the similarity between the binding affinity of each mutant peptide for gp120 elucidated in this study is not more than about 25% likely to be causally unrelated to the effects observed for YU2, and not more than about 4% likely to be causally unrelated to the effects observed for each of the other viruses listed in the table above.

Additionally, the affinity measurements generated by the underlying technique has been demonstrated to be accurate by (repetitively) showing that antibodies that specifically bind to radiolabeled gp120 are capable of preventing the binding of gp120 to polypeptides that have shown high affinity for binding with gp120 in the experiments upon which the present invention is predicated. Thus, this example shows that the binding with chemokine receptors HIV-1 can be inhibited by the present inventive polypeptides, irrespective of the strain of HIV-1 from which the gp120 protein is obtained.

Example 8

This example provides a characterization of the critical amino acids in the amino-terminal segments of CCR5, CXCR4, and STRL33 that are essential for the ability of these polypeptides to bind with gp120.

In this example, the effect on binding that occurs to due successive replacement of each amino acid with alanine is indicated, wherein a (+) signifies a decrease in binding affinity and a (>) signifies an enhancement in binding affinity. As is clear from inspection, the sequences are shown with that amino-terminus at top and the carboxyl-terminus at bottom.

| CCR5 (1–18) | CXCR4 (1–18) | STRL33 (21–38) |
|-------------|--------------|----------------|
| M>          | M            | E              |
| D           | E+           | E              |
| Y++         | G            | H              |
| Q           | I+++++       | Q              |
| V           | S>           | A              |
| S           | I++++++      | F+++           |
| S+          | Y+++++       | L++            |
| P>          | T            | Q+             |
| I+++        | S+           | F+++           |
| Y+++        | D+           | S              |
| D+          | N++          | K>             |
| I++++       | Y++          | V+             |
| N>          | T            | F+             |
| Y++++       | E            | L              |
| Y+++        | E++          | P              |
| T           | M            | C+             |
| S+          | G            | M              |
| E+++++      | S            | Y              |

Example 9

This example employs the same technique as Example 4 and provides information similar to that available from Example 4.

The data below compares the ability of synthetic fragments of CD4 to bind to labeled gp120. 9-mer, 12-mer, 15-mer, 18-mer, and 21-mers were selected based on the data from Examples 4. The relative binding affinities of each group of polypeptides can be determined by inspection of the number of counts of radiolabeled gp120 that were retained by each N-mer. Data supporting these conclusions are provided by Examples 10 and 11.

| Peptide starting position # | Active Peptides | Gp120 Bound (counts) | SEQ ID NO: |
|---|---|---|---|
| ACTIVE 9-MERS | | | |
| 105 | DTYICEVED | 1043 | 505 |
| 115 | KEEVQLLVF | 1273 | 506 |
| 116 | EEVQLLVFG | 3170 | 507 |
| 117 | EVQLLVFGL | 2146 | 508 |
| 217 | EQVEFSFPL | 1032 | 509 |
| 218 | QVEFSFPLLA | 1205 | 510 |
| 219 | VEFSFPLAF | 1064 | 511 |
| ACTIVE 15-MERS | | | |
| 109 | CEVEDQKEEVQLLVF | 1729 | 512 |
| 110 | EVEDQKEEVQLLVFG | 2805 | 513 |
| 111 | VEDQKEEVQLLVFGL | 3816 | 514 |
| 112 | EDQKEEVQLLVFGLT | 3633 | 515 |
| 113 | DQKEEVQLLVFGLTA | 3905 | 516 |
| 114 | QKEEVQLLVFGLTAN | 3770 | 517 |
| 115 | KEEVQLLVFGLTANS | 3485 | 518 |
| 116 | EEVQLLVFGLTANSD | 6423 | 519 |
| 117 | EVQLLVFGLTANSDT | 2689 | 520 |
| 130 | DTHLLQGQSLTLTLE | 1622 | 521 |
| 131 | THLLQGQSLTLTLES | 1874 | 522 |
| 132 | HLLQGQSLTLTLESP | 1277 | 523 |
| 213 | KKEGEQVEFSFPLAF | 1921 | 524 |
| 214 | KEGEQVEFSFPLAFT | 3253 | 525 |
| 215 | EGEQVEFSFPLAFTV | 3270 | 526 |
| 216 | GEQVEFSFPLAFTVE | 4656 | 527 |
| 217 | EQVEFSFPLAFTVEK | 4135 | 528 |
| 218 | QVEFSFPLAFTVEKL | 2047 | 529 |
| ACTIVE 21-MERS | | | |
| 90 | GNFPLIIKNLKIEDSDTYICE | 5248 | 562 |
| 91 | NFPLIIKNLKIEDSDTYICEV | 7803 | 563 |
| 92 | FPLIIKNLKIEDSDTYICEVE | 13919 | 564 |

| Peptide starting position # | Active Peptides | Gp120 Bound (counts) | SEQ ID NO: |
|---|---|---|---|
| 93 | PLIIKNLKIEDSDTYICEVED | 20145 | 565 |
| 94 | LIIKNLKIEDSDTYICEVEDQ | 17108 | 566 |
| 95 | IIKNLKIEDSDTYICEVEDQK | 11892 | 567 |
| 96 | IKNLKIEDSDTYICEVEDQKE | 15073 | 568 |
| 97 | KNLKIEDSDTYICEVEDQKEE | 8789 | 569 |
| 99 | LKIEDSDTYICEVEDQKEEVQ | 5519 | 570 |
| 100 | KIEDSDTYICEVEDQKEEVQL | 6325 | 571 |
| 101 | IEDSDTYICEVEDQKEEVQLL | 12064 | 572 |
| 102 | EDSDTYICEVEDQKEEVQLLV | 4933 | 573 |
| 103 | DSDTYICEVEDQKEEVQLLVF | 30277 | 574 |
| 104 | SDTYICEVEDQKEEVQLLVFG | 30319 | 575 |
| 105 | DTYICEVEDQKEEVQLLVFGL | 25424 | 576 |
| 106 | TYICEVEDQKEEVQLLVFGLT | 20191 | 577 |
| 107 | YICEVEDQKEEVQLLVFGLTA | 22884 | 578 |
| 108 | ICEVEDQKEEVQLLVFGLTAN | 7276 | 579 |
| 109 | CEVEDQKEEVQLLVFGLTANS | 3517 | 580 |
| 123 | FGLTANSDTHLLQGQSLTLTL | 11529 | 581 |
| 124 | GLTANSDTHLLQGQSLTLTLE | 14065 | 582 |
| 125 | LTANSDTHLLQGQSLTLTLES | 17113 | 583 |
| 126 | TANSDTHLLQGQSLTLTLESP | 23595 | 584 |
| 204 | FQKASSIVYKKEGEQVEFSFP | 9382 | 585 |
| 205 | QKASSIVYKKEGEQVEFSFPL | 24959 | 586 |
| 206 | KASSIVYKKEGEQVEFSFPLA | 30873 | 587 |
| 207 | ASSIVYKKEGEQVEFSFPLAF | 25146 | 588 |
| 208 | SSIVYKKEGEQVEFSFPLAFT | 28068 | 589 |
| 209 | SIVYKKEGEQVEFSFPLAFTV | 8165 | 590 |
| 210 | IVYKKEGEQVEFSFPLAFTVE | 15620 | 591 |
| 221 | FSFPLAFTVEKLTGSGELWWQ | 4163 | 592 |
| 222 | SFPLAFTVEKLTGSGELWWQA | 2284 | 593 |
| 223 | FPLAFTVEKLTGSGELWWQAE | 6276 | 594 |
| 224 | PLAFTVEKLTGSGELWWQAER | 2647 | 595 |
| 225 | LAFTVEKLTGSGELWWQAERA | 3577 | 596 |
| ACTIVE 12-MERS | | | |
| 101 | IEDSDTYICEVE | 1107 | 530 |
| 112 | EDQKEEVQLLVF | 1379 | 531 |
| 113 | DQKEEVQLLVFG | 1624 | 532 |
| 114 | QKEEVQLLVFGL | 1785 | 533 |
| 115 | KEEVQLLVFGLT | 1774 | 534 |
| 116 | EEVQLLVFGLTA | 3261 | 535 |
| 117 | EVQLLVFGLTAN | 1838 | 536 |
| 133 | LLQGQSLTLTLE | 1320 | 537 |
| 215 | EGEQVEFSFPLA | 1456 | 538 |
| 216 | GEQVEFSFPLAF | 1729 | 539 |
| 217 | EQVEFSFPLAFT | 1556 | 540 |
| 218 | QVEFSFPLAFTV | 1636 | 541 |
| ACTIVE 18-MERS | | | |
| 105 | DTYICEVEDQKEEVQLLV | 1648 | 542 |
| 106 | TYICEVEDQKEEVQLLVF | 3794 | 543 |
| 107 | YICEVEDQKEEVQLLVFG | 4611 | 544 |
| 108 | ICEVEDQKEEVQLLVFGL | 3898 | 545 |
| 109 | CEVEDQKEEVQLLVFGLT | 3797 | 546 |
| 110 | EVEDQKEEVQLLVFGLTA | 3647 | 547 |
| 111 | VEDQKEEVQLLVFGLTAN | 3913 | 548 |
| 112 | EDQKEEVQLLVFGLTANS | 3416 | 549 |

| Peptide starting position # | Active Peptides | Gp120 Bound (counts) | SEQ ID NO: |
|---|---|---|---|
| 113 | DQKEEVQLLVFGLTANSD | 3317 | 550 |
| 114 | QKEEVQLLVFGLTANSDT | 3671 | 551 |
| 127 | ANSDTHLLQGQSLTLTLE | 1540 | 552 |
| 128 | NSDTHLLQGQSLTLTLES | 1726 | 553 |
| 129 | SDTHLLQGQSLTLTLESP | 1260 | 554 |
| 210 | IVYKKEGEQVEFSFPLAF | 5382 | 555 |
| 211 | VYKKEGEQVEFSFPLAFT | 4307 | 556 |
| 212 | YKKEGEQVEFSFPLAFTV | 4839 | 557 |
| 213 | KKEGEQVEFSFPLAFTVE | 4683 | 558 |
| 214 | KEGEQVEFSFPLAFTVEK | 3117 | 559 |
| 215 | EGEQVEFSFPLAFTVEKL | 2164 | 560 |
| 216 | GEQVEFSFPLAFTVEKLT | 1643 | 561 |

Example 10

This example provides data which enables those skilled in the art to arrive at the conclusions indicated in Examples 9 and 12. In this example, the counts of radiolabeled gp-120 retained by each peptide indicated in the left hand column are given in the right hand column. The first panel (panel A) provides data for 21-mers of CD4.

| Panel A | | |
|---|---|---|
| PEPTIDE | COUNTS | SEQ ID NO: |
| LWDQGNFPLIIKNLKIEDSDT | 731 | 597 |
| WDQGNFPLIIKNLKIEDSDTY | 889 | 598 |
| DQGNFPLIIKNLKIEDSDTYI | 1138 | 599 |
| QGNFPLIIKNLKIEDSDTYIC | 2242 | 600 |
| GNFPLIIKNLKIEDSDTYICE | 5248 | 601 |
| NFPLIIKNLKIEDSDTYICEV | 7803 | 602 |
| FPLIIKNLKIEDSDTYICEVE | 13919 | 603 |
| PLIIKLNKIEDSDTYICEVED | 20145 | 604 |
| LIIKNLKIEDSDTYICEVEDQ | 17108 | 605 |
| IIKNLKIEDSDTYICEVEDQK | 11892 | 606 |
| IKNLKIEDSDTYICEVEDQKE | 15073 | 607 |
| KNLKIEDSDTYICEVEDQKEE | 8789 | 608 |
| NLKIEDSDTYICEVEDQKEEV | 2016 | 609 |
| LKIEDSDTYICEVEDQKEEVQ | 5519 | 610 |
| KIEDSDTYICEVEDQKEEVQL | 6325 | 611 |
| IEDSDTYICEVEDQKEEVQLL | 12064 | 612 |
| EDSDTYICEVEDQKEEVQLLV | 4933 | 613 |
| DSDTYICEVEDQKEEVQLLVF | 30277 | 614 |
| SDTYICEVEDQKEEVQLLVFG | 30319 | 615 |
| DTYICEVEDQKEEVQLLVFGL | 25424 | 616 |
| TYICEVEDQKEEVQLLVFGLT | 20191 | 617 |
| YICEVEDQKEEVQLLVFGLTA | 22884 | 618 |
| ICEVEDQKEEVQLLVFGLTAN | 7276 | 619 |
| CEVEDQKEEVQLLVFGLTANS | 3517 | 620 |
| EVEDQKEEVQLLVFGLTANSD | 1687 | 621 |
| VEDQKEEVQLLVFGLTANSDT | 646 | 622 |
| EDQKEEVQLLVFGLTANSDTH | 562 | 623 |
| DQKEEVQLLVFGLTANSDTHL | 599 | 624 |
| QKEEVQLLVFGLTANSDTHLL | 573 | 625 |
| KEEVQLLVFGLTANSDTHLLQ | 682 | 626 |
| EEVQLLVFGLTANSDTHLLQG | 690 | 627 |
| EVQLLVFGLTANSDTHLLQGQ | 589 | 628 |
| VQLLVFGLTANSDTHLLQGQS | 1099 | 629 |
| QLLVFGLTANSDTHLLQGQSL | 2057 | 630 |
| LLVFGLTANSDTHLLQGQSLT | 860 | 631 |
| LVFGLTANSDTHLLQGQSLTL | 4677 | 632 |
| VFGLTANSDTHLLQGQSLTLT | 2762 | 633 |
| FGLTANSDTHLLQGQSLTLTL | 11529 | 634 |
| GLTANSDTHLLQGQSLTLTLE | 14065 | 635 |
| LTANSDTHLLQGQSLTLTLES | 17113 | 636 |
| TANSDTHLLQGQSLTLTLESP | 23595 | 637 |
| Empty (Control) | 515 | |
| TWTCTVLQNQKKVEFKIDIVV | 1430 | 638 |
| WTCTVLQNQKKVEFKIDIVVL | 1616 | 639 |
| TCTVLQNQKKVEFKIDIVVLA | 1092 | 640 |

Panel A

| PEPTIDE | COUNTS | SEQ ID NO: |
|---|---|---|
| CTVLQNQKKVEFKIDIVVLAF | 2909 | 641 |
| TVLQNQKKVEFKIDIVVLAFQ | 3273 | 642 |
| VLQNQKKVEFKIDIVVLAFQK | 1323 | 643 |
| LQNQKKVEFKIDIVVLAFQKA | 1256 | 644 |
| QNQKKVEFKIDIVVLAFQKAS | 1808 | 645 |
| NQKKVEFKIDIVVLAFQKASS | 1507 | 646 |
| QKKVEFKIDIVVLAFQKASSI | 759 | 647 |
| KKVEFKIDIVVLAFQKASSIV | 782 | 648 |
| KVEFKIDIVVLAFQKASSIVY | 635 | 649 |
| VEFKIDIVVLAFQKASSIVYK | 725 | 650 |
| EFKIDIVVLAFQKASSIVYKK | 649 | 651 |
| FKIDIVVLAFQKASSIVYKKE | 593 | 652 |
| KIDIVVLAFQKASSIVYKKEG | 1394 | 653 |
| IDIVVLAFQKASSIVYKKEGE | 962 | 654 |
| DIVVLAFQKASSIVYKKEGEQ | 788 | 655 |
| IVVLAFQKASSIVYKKEGEQV | 646 | 656 |
| VVLAFQKASSIVYKKEGEQVE | 772 | 657 |
| VLAFQKASSIVYKKEGEQVEF | 1793 | 658 |
| LAFQKASSIVYKKEGEQVEFS | 1410 | 659 |
| AFQKASSIVYKKEGEQVEFSF | 3775 | 660 |
| FQKASSIVYKKEGEQVEFSFP | 9382 | 661 |
| QKASSIVYKKEGEQVEFSFPL | 24959 | 662 |
| KASSIVYKKEGEQVEFSFPLA | 30873 | 663 |
| ASSIVYKKEGEQVEFSFPLAF | 25146 | 664 |
| SSIVYKKEGEQVEFSFPLAFT | 28068 | 665 |
| SIVYKKEGEQVEFSFPLAFTV | 8165 | 666 |
| IVYKKEGEQVEFSFPLAFTVE | 15620 | 667 |
| VYKKEGEQVEFSFPLAFTVEK | 2429 | 668 |
| YKKEGEQVEFSFPLAFTVEKL | 735 | 669 |
| KKEGEQVEFSFPLAFTVEKLT | 1847 | 670 |
| KEGEQVEFSFPLAFTVEKLTG | 972 | 671 |
| EGEQVEFSFPLAFTVEKLTGS | 739 | 672 |
| GEQVEFSFPLAFTVEKLTGSG | 652 | 673 |
| EQVEFSFPLAFTVEKLTGSGE | 765 | 674 |
| QVEFSFPLAFTVEKLTGSGEL | 741 | 675 |
| VEFSFPLAFTVEKLTGSGELW | 633 | 676 |
| EFSFPLAFTVEKLTGSGELWW | 681 | 677 |
| FSFPLAFTVEKLTGSGELWWQ | 4163 | 678 |
| SFPLAFTVEKLTGSGELWWQA | 2284 | 679 |
| FPLAFTVEKLTGSGELWWQAE | 6276 | 680 |
| PLAFTVEKLTGSGELWWQAER | 2647 | 681 |
| LAFTVEKLTGSGELWWQAERA | 3577 | 682 |
| AFTVEKLTGSGELWWQAERAS | 1739 | 683 |
| Empty (control) | 617 | |

These second and third panels (panels B and C) provide data for 18-mers of a small region of CD4.

Panel B

| PEPTIDE | COUNTS | SEQ ID NO: |
|---|---|---|
| LWDQGNFPLIIKNLK | 502 | 684 |
| WDQGNFPLIIKNLKI | 534 | 685 |
| DQGNFPLIIKNLKIE | 635 | 686 |
| QGNFPLIIKNLKIED | 509 | 687 |
| GNFPLIIKNLKIEDS | 624 | 688 |
| NFPLIIKNLKIEDSD | 654 | 689 |
| FPLIIKNLKIEDSDT | 539 | 690 |
| PLIIKNLKIEDSDTY | 661 | 691 |
| LIIKNLKIEDSDTYI | 542 | 692 |
| IIKNLKIEDSDTYIC | 664 | 693 |
| IKNLKIEDSDTYICE | 568 | 694 |
| KNLKIEDSDTYICEV | 562 | 695 |
| NLKIEDSDTYICEVE | 1160 | 696 |
| LKIEDSDTYICEVED | 846 | 697 |
| KIEDSDTYICEVEDQ | 1088 | 698 |
| IEDSDTYICEVEDQK | 1143 | 699 |
| EDSDTYICEVEDQKE | 815 | 700 |
| DSDTYICEVEDQKEE | 973 | 701 |
| SDTYICEVEDQKEEV | 993 | 702 |
| DTYICEVEDQKEEVQ | 1071 | 703 |
| TYICEVEDQKEEVQL | 956 | 704 |
| YICEVEDQKEEVQLL | 1064 | 705 |
| ICEVEDQKEEVQLLV | 1084 | 706 |
| CEVEDQKEEVQLLVF | 1729 | 707 |

Panel B

| PEPTIDE | COUNTS | SEQ ID NO: |
|---|---|---|
| EVEDQKEEVQLLVFG | 2805 | 708 |
| VEDQKEEVQLLVFGL | 3816 | 709 |
| EDQKEEVQLLVFGLT | 3633 | 710 |
| DQKEEVQLLVFGLTA | 3905 | 711 |
| QKEEVQLLVFGLTAN | 3770 | 712 |
| KEEVQLLVFGLTANS | 3485 | 713 |
| EEVQLLVFGLTANSD | 6423 | 714 |
| EVQLLVFGLTANSDT | 2689 | 715 |
| VQLLVFGLTANSDTH | 1006 | 716 |
| QLLVFGLTANSDTHL | 865 | 717 |
| LLVFGLTANSDTHLL | 599 | 718 |
| LVFGLTANSDTHLLQ | 609 | 719 |
| VFGLTANSDTHLLQG | 532 | 720 |
| FGLTANSDTHLLQGQ | 625 | 721 |
| GLTANSDTHLLQGQS | 532 | 722 |
| LTANSDTHLLQGQSL | 634 | 723 |
| TANSDTHLLQGQSLT | 513 | 724 |
| ANSDTHLLQGQSLTL | 542 | 725 |
| NSDTHLLQGQSLTLT | 631 | 726 |
| SDTHLLQGQSLTLTL | 747 | 727 |
| DTHLLQGQSLTLTLE | 1622 | 728 |
| THLLQGQSLTLTLES | 1874 | 729 |
| HLLQGQSLTLTLESP | 1277 | 730 |
| LWDQGNFPLIIKNLKIED | 582 | 731 |
| WDQGNFPLIIKNLKIEDS | 626 | 732 |
| DQGNFPLIIKNLKIEDSD | 598 | 733 |
| QGNFPLIIKNLKIEDSDT | 564 | 734 |
| GNFPLIIKNLKIEDSDTY | 557 | 735 |
| NFPLIIKNLKIEDSDTYI | 627 | 736 |
| FPLIIKNLKIEDSDTYIC | 509 | 737 |
| PLIIKNLKIEDSDTYICE | 624 | 738 |
| LIIKNLKIEDSDTYICEV | 634 | 739 |
| IIKNLKIEDSDTYICEVE | 751 | 740 |
| IKNLKIEDSDTYICEVED | 699 | 741 |
| KNLKIEDSDTYICEVEDQ | 708 | 742 |
| NLKIEDSDTYICEVEDQK | 863 | 743 |
| LKIEDSDTYICEVEDQKE | 872 | 744 |
| KIEDSDTYICEVEDQKEE | 858 | 745 |
| IEDSDTYICEVEDQKEEV | 1230 | 746 |
| EDSDTYICEVEDQKEEVQ | 788 | 747 |
| DSDTYICEVEDQKEEVQL | 961 | 748 |
| SDTYICEVEDQKEEVQLL | 870 | 749 |
| DTYICEVEDQKEEVQLLV | 1648 | 750 |
| TYICEVEDQKEEVQLLVF | 3794 | 751 |
| YICEVEDQKEEVQLLVFG | 4611 | 752 |
| ICEVEDQKEEVQLLVFGL | 3898 | 753 |
| CEVEDQKEEVQLLVFGLT | 3797 | 754 |
| EVEDQKEEVQLLVFGLTA | 3647 | 755 |
| VEDQKEEVQLLVFGLTAN | 3913 | 756 |
| EDQKEEVQLLVFGLTANS | 3416 | 757 |
| DQKEEVQLLVFGLTANSD | 3317 | 758 |
| QKEEVQLLVFGLTANSDT | 3671 | 759 |
| KEEVQLLVFGLTANSDTH | 1271 | 760 |
| EEVQLLVFGLTANSDTHL | 783 | 761 |
| EVQLLVFGLTANSDTHLL | 667 | 762 |
| VQLLVFGLTANSDTHLLQ | 673 | 763 |
| QLLVFGLTANSDTHLLQG | 574 | 764 |
| LLVFGLTANSDTHLLQGQ | 568 | 765 |
| LVFGLTANSDTHLLQGQS | 564 | 766 |
| VFGLTANSDTHLLQGQSL | 531 | 767 |
| FGLTANSDTHLLQGQSLT | 591 | 768 |
| GLTANSDTHLLQGQSLTL | 572 | 769 |
| LTANSDTHLLQGQSLTLT | 528 | 770 |
| TANSDTHLLQGQSLTLTL | 891 | 771 |
| ANSDTHLLQGQSLTLTLE | 1540 | 772 |
| NSDTHLLQGQSLTLTLES | 1726 | 773 |
| SDTHLLQGQSLTLTLESP | 1260 | 774 |
| Empty (control) | 575 | |

Panel C

| PEPTIDE | COUNTS | SEQ ID NO: |
|---|---|---|
| WTCTVLQNQKKVEFK | 566 | 775 |
| TCTVLQNQKKVEFKI | 510 | 776 |
| CTVLQNQKKVEFKID | 608 | 777 |
| TVLQNQKKVEFKIDI | 587 | 778 |
| VLQNQKKVEFKIDIV | 605 | 779 |
| LQNQKKVEFKIDIVV | 644 | 780 |
| QNQKKVEFKIDIVVL | 636 | 781 |
| NQKKVEFKIDIVVLA | 860 | 782 |
| QKKVEFKIDIVVLAF | 1333 | 783 |
| KKVEFKIDIVVLAFQ | 951 | 784 |
| KVEFKIDIVVLAFQK | 1051 | 785 |
| VEFKIDIVVLAFQKA | 1005 | 786 |
| EFKIDIVVLAFQKAS | 1188 | 787 |
| FKIDIVVLAFQKASS | 1001 | 788 |
| KIDIVVLAFQKASSI | 956 | 789 |
| IDIVVLAFQKASSIV | 865 | 790 |
| DIVVLAFQKASSIVY | 776 | 791 |
| IVVLAFQKASSIVYK | 783 | 792 |
| VVLAFQKASSIVYKK | 577 | 793 |
| VLAFQKASSIVYKKE | 634 | 794 |
| LAFQKASSIVYKKEG | 593 | 795 |
| AFQKASSIVYKKEGE | 544 | 796 |
| FQKASSIVYKKEGEQ | 637 | 797 |
| QKASSIVYKKEGEQV | 519 | 798 |
| KASSIVYKKEGEQVE | 563 | 799 |
| ASSIVYKKEGEQVEF | 589 | 800 |
| SSIVYKKEGEQVEFS | 558 | 801 |
| SIVYKKEGEQVEFSF | 651 | 802 |
| IVYKKEGEQVEFSFP | 615 | 803 |
| VYKKEGEQVEFSFPL | 714 | 804 |
| YKKEGEQVEFSFPLA | 687 | 805 |
| KKEGEQVEFSFPLAF | 1921 | 806 |
| KEGEQVEFSFPLAFT | 3253 | 807 |
| EGEQVEFSFPLAFTV | 3270 | 808 |
| GEQVEFSFPLAFTVE | 4656 | 809 |
| EQVEFSFPLAFTVEK | 4135 | 810 |
| QVEFSFPLAFTVEKL | 2047 | 811 |
| VEFSFPLAFTVEKLT | 899 | 812 |
| EFSFPLAFTVEKLTG | 920 | 813 |
| FSFPLAFTVEKLTGS | 672 | 814 |
| SFPLAFTVEKLTGSG | 565 | 815 |
| FPLAFTVEKLTGSGE | 556 | 816 |
| PLAFTVEKLTGSGEL | 612 | 817 |
| LAFTVEKLTGSGELW | 579 | 818 |
| AFTVEKLTGSGELWW | 586 | 819 |
| FTVEKLTGSGELWWQ | 625 | 820 |
| TVEKLTGSGELWWQA | 550 | 821 |
| VEKLTGSGELWWQAE | 735 | 822 |
| EKLTGSGELWWQAER | 683 | 823 |
| WTCTVLQNQKKVEFKIDI | 588 | 824 |
| TCTVLQNQKKVEFKIDIV | 571 | 825 |
| CTVLQNQKKVEFKIDIVV | 553 | 826 |
| TVLQNQKKVEFKIDIVVL | 655 | 827 |
| VLQNQKKVEFKIDIVVLA | 724 | 828 |
| LQNQKKVEFKIDIVVLAF | 938 | 829 |
| QNQKKVEFKIDIVVLAFQ | 917 | 830 |
| NQKKVEFKIDIVVLAFQK | 889 | 831 |
| QKKVEFKIDIVVLAFQKA | 1013 | 832 |
| KKVEFKIDIVVLAFQKAS | 912 | 833 |
| KVEFKIDIVVLAFQKASS | 1011 | 834 |
| VEFKIDIVVLAFQKASSI | 819 | 835 |
| EFKIDIVVLAFQKASSIV | 799 | 836 |
| FKIDIVVLAFQKASSIVY | 843 | 837 |
| KIDIVVLAFQKASSIVYK | 779 | 838 |
| IDIVVLAFQKASSIVYKK | 711 | 839 |
| DIVVLAFQKASSIVYKKE | 660 | 840 |
| IVVLAFQKASSIVYKKEG | 531 | 841 |
| VVLAFQKASSIVYKKEGE | 560 | 842 |
| VLAFQKASSIVYKKEGEQ | 549 | 843 |
| LAFQKASSIVYKKEGEQV | 665 | 844 |
| AFQKASSIVYKKEGEQVE | 514 | 845 |
| FQKASSIVYKKEGEQVEF | 528 | 846 |
| QKASSIVYKKEGEQVEFS | 602 | 847 |
| KASSIVYKKEGEQVEFSF | 536 | 848 |

-continued

Panel C

| PEPTIDE | COUNTS | SEQ ID NO: |
|---|---|---|
| ASSIVYKKEGEQVEFSFP | 701 | 849 |
| SSIVYKKEGEQVEFSFPL | 756 | 850 |
| SIVYKKEGEQVEFSFPLA | 771 | 851 |
| IVYKKEGEQVEFSFPLAF | 5382 | 852 |
| VYKKEGEQVEFSFPLAFT | 4307 | 853 |
| YKKEGEQVEFSFPLAFTV | 4839 | 854 |
| KKEGEQVEFSFPLAFTVE | 4683 | 855 |
| KEGEQVEFSFPLAFTVEK | 3117 | 856 |
| EGEQVEFSFPLAFTVEKL | 2164 | 857 |
| GEQVEFSFPLAFTVEKLT | 1643 | 858 |
| EQVEFSFPLAFTVEKLTG | 798 | 859 |
| QVEFSFPLAFTVEKLTGS | 736 | 860 |
| VEFSFPLAFTVEKLTGSG | 533 | 861 |
| EFSFPLAFTVEKLTGSGE | 668 | 862 |
| FSFPLAFTVEKLTGSGEL | 613 | 863 |
| SFPLAFTVEKLTGSGELW | 656 | 864 |
| FPLAFTVEKLTGSGELWW | 586 | 865 |
| PLAFTVEKLTGSGELWWQ | 650 | 866 |
| LAFTVEKLTGSGELWWQA | 866 | 867 |
| AFTVEKLTGSGELWWQAE | 788 | 868 |
| FTVEKLTGSGELWWQAER | 1143 | 869 |
| Empty (control) | 556 | |

The fourth and fifth panels (Panels D and E) provide data for select 9-mers and 12-mers of CD4.

Panel D

| PEPTIDE | COUNTS | SEQ ID NO: |
|---|---|---|
| DQGNFPLII | 662 | 870 |
| QGNFPLIIK | 508 | 871 |
| GNFPLIIKN | 600 | 872 |
| NFPLIIKNL | 561 | 873 |
| FPLIIKNLK | 601 | 874 |
| PLIIKNLKI | 697 | 875 |
| LIIKNLKIE | 515 | 876 |
| IIKNLKIED | 658 | 877 |
| IKNLKIEDS | 557 | 878 |

-continued

Panel D

| PEPTIDE | COUNTS | SEQ ID NO: |
|---|---|---|
| KNLKIEDSD | 612 | 879 |
| NLKIEDSDT | 512 | 880 |
| LKIEDSDTY | 492 | 881 |
| KIEDSDTYI | 603 | 882 |
| IEDSDTYIC | 567 | 883 |
| EDSDTYICE | 650 | 884 |
| DSDTYICEV | 712 | 885 |
| SDTYICEVE | 819 | 886 |
| DTYICEVED | 1043 | 887 |
| TYICEVEDQ | 805 | 888 |
| YICEVEDQK | 728 | 889 |
| ICEVEDQKE | 596 | 890 |
| CEVEDQKEE | 555 | 891 |
| EVEDQKEEV | 587 | 892 |
| VEDQKEEVQ | 521 | 893 |
| EDQKEEVQL | 564 | 894 |
| DQKEEVQLL | 589 | 895 |
| QKEEVQLLV | 636 | 896 |
| KEEVQLLVF | 1273 | 897 |
| EEVQLLVFG | 3170 | 898 |
| EVQLLVFGL | 2146 | 899 |
| VQLLVFGLT | 815 | 900 |
| QLLVFGLTA | 822 | 901 |
| LLVFGLTAN | 576 | 902 |
| LVFGLTANS | 522 | 903 |
| VFGLTANSD | 549 | 904 |
| FGLTANSDT | 563 | 905 |
| GLTANSDTH | 481 | 906 |
| LTANSDTHL | 596 | 907 |
| TANSDTHLL | 554 | 908 |
| ANSDTHLLQ | 642 | 909 |
| NSDTHLLQG | 561 | 910 |
| SDTHLLQGQ | 526 | 911 |
| DTHLLQGQS | 578 | 912 |
| THLLQGQSL | 512 | 913 |
| HLLQGQSLT | 564 | 914 |
| LLQGQSLTL | 568 | 915 |

-continued

Panel D

| PEPTIDE | COUNTS | SEQ ID NO: |
|---|---|---|
| LQGQSLTLT | 501 | 916 |
| QGQSLTLTL | 594 | 917 |
| GQSLTLTLE | 777 | 918 |
| DQGNFPLIIKNL | 604 | 919 |
| QGNFPLIIKNLK | 533 | 920 |
| GNFPLIIKNLKI | 547 | 921 |
| NFPLIIKNLKIE | 647 | 922 |
| FPLIIKNLKIED | 511 | 923 |
| PLIIKNLKIEDS | 565 | 924 |
| LIIKNLKIEDSD | 619 | 925 |
| IIKNLKIEDSDT | 511 | 926 |
| IKNLKIEDSDTY | 574 | 927 |
| KNLKIEDSDTYI | 523 | 928 |
| NLKIEDSDTYIC | 639 | 929 |
| LKIEDSDTYICE | 635 | 930 |
| KIEDSDTYICEV | 601 | 931 |
| IEDSDTYICEVE | 1107 | 932 |
| EDSDTYICEVED | 956 | 933 |
| DSDTYICEVEDQ | 937 | 934 |
| SDTYICEVEDQK | 846 | 935 |
| DTYICEVEDQKE | 720 | 936 |
| TYICEVEDQKEE | 818 | 937 |
| YICEVEDQKEEV | 734 | 938 |
| ICEVEDQKEEVQ | 585 | 939 |
| CEVEDQKEEVQL | 561 | 940 |
| EVEDQKEEVQLL | 508 | 941 |
| VEDQKEEVQLLV | 657 | 942 |
| EDQKEEVQLLVF | 1379 | 943 |
| DQKEEVQLLVFG | 1624 | 944 |
| QKEEVQLLVFGL | 1785 | 945 |
| KEEVQLLVFGLT | 1774 | 946 |
| EEVQLLVFGLTA | 3261 | 947 |
| EVQLLVFGLTAN | 1838 | 948 |
| VQLLVFGLTANS | 747 | 949 |
| QLLVFGLTANSD | 721 | 950 |
| LLVFGLTANSDT | 533 | 951 |
| LVFGLTANSDTH | 586 | 952 |

-continued

Panel D

| PEPTIDE | COUNTS | SEQ ID NO: |
|---|---|---|
| VFGLTANSDTHL | 548 | 953 |
| FGLTANSDTHLL | 571 | 954 |
| GLTANSDTHLLQ | 574 | 955 |
| LTANSDTHLLQG | 534 | 956 |
| TANSDTHLLQGQ | 549 | 957 |
| ANSDTHLLQGQS | 559 | 958 |
| NSDTHLLQGQSL | 585 | 959 |
| SDTHLLQGQSLT | 540 | 960 |
| DTHLLQGQSLTL | 527 | 961 |
| THLLQGQSLTLT | 646 | 962 |
| HLLQGQSLTLTL | 701 | 963 |
| LLQGQSLTLTLE | 1320 | 964 |
| Empty (control) | 581 | |

Panel E

| PEPTIDE | COUNTS | SEQ ID NO: |
|---|---|---|
| TVLQNQKKV | 534 | 965 |
| VLQNQKKVE | 556 | 966 |
| LQNQKKVEF | 565 | 967 |
| QNQKKVEFK | 537 | 968 |
| NQKKVEFKI | 597 | 969 |
| QKKVEFKID | 575 | 970 |
| KKVEFKIDI | 501 | 971 |
| KVEFKIDIV | 555 | 972 |
| VEFKIDIVV | 548 | 973 |
| EFKIDIVVL | 665 | 974 |
| FKIDIVVLA | 568 | 975 |
| KIDIVVLAF | 665 | 976 |
| IDIVVLAFQ | 691 | 977 |
| DIVVLAFQK | 686 | 978 |
| IVVLAFQKA | 602 | 979 |
| VVLAFQKAS | 600 | 980 |
| VLAFQKASS | 466 | 981 |
| LAFQKASSI | 592 | 982 |
| AFQKASSIV | 595 | 983 |

-continued

Panel E

| PEPTIDE | COUNTS | SEQ ID NO: |
|---|---|---|
| FQKASSIVY | 568 | 984 |
| QKASSIVYK | 494 | 985 |
| KASSIVYKK | 498 | 986 |
| ASSIVYKKE | 600 | 987 |
| SSIVYKKEG | 515 | 988 |
| SIVYKKEGE | 566 | 989 |
| IVYKKEGEQ | 534 | 990 |
| VYKKEGEQV | 490 | 991 |
| YKKEGEQVE | 518 | 992 |
| KKEGEQVEF | 546 | 993 |
| KEGEQVEFS | 595 | 994 |
| EGEQVEFSF | 735 | 995 |
| GEQVEFSFP | 697 | 996 |
| EQVEFSFPL | 1032 | 997 |
| QVEFSFPLA | 1205 | 998 |
| VEFSFPLAF | 1064 | 999 |
| EFSFPLAFT | 658 | 1000 |
| FSFPLAFTV | 472 | 1001 |
| SFPLAFTVE | 619 | 1002 |
| FPLAFTVEK | 569 | 1003 |
| PLAFTVEKL | 597 | 1004 |
| LAFTVEKLT | 501 | 1005 |
| AFTVEKLTG | 517 | 1006 |
| FTVEKLTGS | 574 | 1007 |
| TVEKLTGSG | 487 | 1008 |
| VEKLTGSGE | 585 | 1009 |
| EKLTGSGEL | 541 | 1010 |
| KLTGSGELW | 491 | 1011 |
| LTGSGELWW | 550 | 1012 |
| TGSGELWWQ | 507 | 1013 |
| TVLQNQKKVEFK | 563 | 1014 |
| VLQNQKKVEFKI | 503 | 1015 |
| LQNQKKVEFKID | 508 | 1016 |
| QNQKKVEFKIDI | 559 | 1017 |
| NQKKVEFKIDIV | 532 | 1018 |
| QKKVEFKIDIVV | 595 | 1019 |
| KKVEFKIDIVVL | 597 | 1020 |

-continued

Panel E

| PEPTIDE | COUNTS | SEQ ID NO: |
|---|---|---|
| KVEFKIDVVLA | 560 | 1021 |
| VEFKIDIVVLAF | 681 | 1022 |
| EFKIDIVVLAFQ | 659 | 1023 |
| FKIDIVVLAFQK | 736 | 1024 |
| KIDIVVLAFQKA | 689 | 1025 |
| IDIVVLAFQKAS | 630 | 1026 |
| DIVVLAFQKASS | 746 | 1027 |
| IVVLAFQKASSI | 548 | 1028 |
| VVLAFQKASSIV | 567 | 1029 |
| VLAFQKASSIVY | 548 | 1030 |
| LAFQKASSIVYK | 465 | 1031 |
| AFQKASSIVYKK | 597 | 1032 |
| FQKASSIVYKKE | 577 | 1033 |
| QKASSIVYKKEG | 596 | 1034 |
| KASSIVYKKEGE | 559 | 1035 |
| ASSIVYKKEGEQ | 523 | 1036 |
| SSIVYKKEGEQV | 615 | 1037 |
| SIVYKKEGEQVE | 543 | 1038 |
| IVYKKEGEQVEF | 533 | 1039 |
| VYKKEGEQVEFS | 584 | 1040 |
| YKKEGEQVEFSF | 548 | 1041 |
| KKEGEQVEFSFP | 598 | 1042 |
| KEGEQVEFSFPL | 710 | 1043 |
| EGEQVEFSFPLA | 1456 | 1044 |
| GEQVEFSFPLAF | 1729 | 1045 |
| EQVEFSFPLAFT | 1556 | 1046 |
| QVEFSFPLAFTV | 1636 | 1047 |
| VEFSFPLAFTVE | 518 | 1048 |
| EFSFPLAFTVEK | 585 | 1049 |
| FSFPLAFTVEKL | 573 | 1050 |
| SFPLAFTVEKLT | 528 | 1051 |
| FPLAFTVEKLTG | 622 | 1052 |
| PLAFTVEKLTGS | 528 | 1053 |
| LAFTVEKLTGSG | 608 | 1054 |
| AFTVEKLTGSGE | 511 | 1055 |
| FTVEKLTGSGEL | 530 | 1056 |
| TVEKLTGSGELW | 573 | 1057 |

Panel E

| PEPTIDE | COUNTS | SEQ ID NO: |
|---|---|---|
| VEKLTGSGELWW | 477 | 1058 |
| EKLTGSGELWWQ | 543 | 1059 |
| Empty (control) | 571 | |

Panels F and G provide data on sequential alanine replacements for selected CD4 polypeptides.

Panel F

| PEPTIDE | COUNTS | SEQ ID NO: |
|---|---|---|
| ZZZZZZZDTYICEVED | 5844 | 1060 |
| ZZZZZZZATYICEVED | 5921 | 1061 |
| ZZZZZZZDAYICEVED | 6362 | 1062 |
| ZZZZZZZDTAICEVED | 1301 | 1063 |
| ZZZZZZZDTYACEVED | 2583 | 1064 |
| ZZZZZZZDTYIAEVED | 4483 | 1065 |
| ZZZZZZZDTYICAVED | 3154 | 1066 |
| ZZZZZZZDTYICEAED | 3432 | 1067 |
| ZZZZZZZDTYICEVAD | 3595 | 1068 |
| ZZZZZZZDTYICEVEA | 5942 | 1069 |
| ZZZZZZZDTYICEVED | 4973 | 1070 |
| ZZZZZZZDTYICEVED | 4775 | 1070 |
| ZZZZZZZATYICEVED | 4962 | 1071 |
| ZZZZZZZDAYICEVED | 4163 | 1072 |
| ZZZZZZZDTAICEVED | 1384 | 1073 |
| ZZZZZZZDTYACEVED | 3085 | 1074 |
| ZZZZZZZDTYIAEVED | 5128 | 1075 |
| ZZZZZZZDTYICAVED | 2587 | 1076 |
| ZZZZZZZDTYICEAED | 2499 | 1077 |
| ZZZZZZZDTYICEVAD | 2706 | 1078 |
| ZZZZZZZDTYICEVEA | 6345 | 1079 |
| ZZZZZZZDTYICEVED | 5564 | 1080 |
| EEVQLLVFGLTANSD | 18582 | 1081 |
| AEVQLLVFGLTANSD | 16220 | 1082 |
| EAVQLLVFGLTANSD | 14220 | 1083 |
| EEAQLLVFGLTANSD | 18124 | 1084 |
| EEVALLVFGLTANSD | 10890 | 1085 |
| EEVQALVFGLTANSD | 11258 | 1086 |
| EEVQLAVFGLTANSD | 11954 | 1087 |
| EEVQLLAFGLTANSD | 13317 | 1088 |
| EEVQLLVAGLTANSD | 9573 | 1089 |
| EEVQLLVFALTANSD | 19348 | 1090 |
| EEVQLLVFGATANSD | 10408 | 1091 |
| EEVQLLVFGLAANSD | 19973 | 1092 |
| EEVQLLVFGLTTNSD | 20100 | 1093 |
| EEVQLLVFGLTAASD | 19390 | 1094 |
| EEVQLLVFGLTANAD | 17684 | 1095 |
| EEVQLLVFGLTANSA | 18227 | 1096 |
| EEVQLLVFGLTANSD | 19738 | 1097 |
| EEVQLLVFGLTANSD | 21338 | 1098 |
| AEVQLLVFGLTANSD | 14590 | 1099 |
| EAVQLLVFGLTANSD | 13213 | 1100 |
| EEAQLLVFGLTANSD | 16296 | 1101 |
| EEVALLVFGLTANSD | 13415 | 1102 |
| EEVQALVFGLTANSD | 12603 | 1103 |
| EEVQLAVFGLTANSD | 13690 | 1104 |
| EEVQLLAFGLTANSD | 16286 | 1105 |
| EEVQLLVAGLTANSD | 11480 | 1106 |
| EEVQLLVFALTANSD | 18254 | 1107 |
| EEVQLLVFGATANSD | 19978 | 1108 |
| EEVQLLVFGLAANSD | 18863 | 1109 |
| EEVQLLVFGLTTNSD | 20021 | 1110 |
| EEVQLLVFGLTAASD | 19200 | 1111 |
| EEVQLLVFGLTANAD | 17928 | 1112 |
| EEVQLLVFGLTANSA | 22206 | 1113 |
| EEVQLLVFGLTANSD | 18721 | 1114 |
| THLLQGQSLTLTLES | 7756 | 1115 |
| AHLLQGQSLTLTLES | 8602 | 1116 |
| TALLQGQSLTLTLES | 6931 | 1117 |
| THALQGQSLTLTLES | 7683 | 1118 |
| THLAQGQSLTLTLES | 7701 | 1119 |
| THLLAGQSLTLTLES | 4578 | 1120 |
| THLLQAQSLTLTLES | 8471 | 1121 |
| TELLQGASLTLTLES | 4238 | 1122 |

Panel F

| PEPTIDE | COUNTS | SEQ ID NO: |
|---|---|---|
| THLLQGQALTLTLES | 8659 | 1123 |
| THLLQGQSATLTLES | 4430 | 1124 |
| THLLQGQSLALTLES | 8158 | 1125 |
| THLLQGQSLTATLES | 4380 | 1126 |
| THLLQGQSLTLALES | 11699 | 1127 |
| THLLQGQSLTLTAES | 862 | 1128 |
| THLLQGQSLTLTLAS | 2596 | 1129 |
| THLLQGQSLTLTLEA | 5849 | 1130 |
| THLLQGQSLTLTLES | 6545 | 1131 |
| THLLQGQSLTLTLES | 4787 | 1132 |
| AHLLQGQSLTLTLES | 5826 | 1133 |
| TALLQGQSLTLTLES | 5012 | 1134 |
| THALQGQSLTLTLES | 5059 | 1135 |
| THLAQGQSLTLTLES | 5120 | 1136 |
| THLLAGQSLTLTLES | 2956 | 1137 |
| THLLQAQSLTLTLES | 6393 | 1138 |
| THLLQGASLTLTLES | 1933 | 1139 |
| THLLQGQALTLTLES | 5151 | 1140 |
| THLLQGQSATLTLES | 1391 | 1141 |
| THLLQGQSLALTLES | 4749 | 1142 |
| THLLQGQSLTATLES | 813 | 1143 |
| THLLQGQSLTLALES | 8147 | 1144 |
| THLLQGQSLTLTAES | 797 | 1145 |
| THLLQGQSLTLTLAS | 2193 | 1146 |
| THLLQGQSLTLTLEA | 7984 | 1147 |
| THLLQGQSLTLTLES | 5947 | 1148 |
| Empty (control) | 569 | |

Panel G

| PEPTIDE | COUNTS | SEQ ID NO: |
|---|---|---|
| GEQVEFSFPLAFTVE | 20691 | 1149 |
| AEQVEFSFPLAFTVE | 18546 | 1150 |
| GAQVEFSFPLAFTVE | 17733 | 1151 |
| GEAVEFSFPLAFTVE | 17500 | 1152 |
| GEQAEFSFPLAFTVE | 14764 | 1153 |
| GEQVAFSFPLAFTVE | 16668 | 1154 |
| GEQVEASFPLAFTVE | 6793 | 1155 |
| GEQVEFAFPLAFTVE | 21681 | 1156 |
| GEQVEFSAPLAFTVE | 7767 | 1157 |
| GEQVEFSFALAFTVE | 20480 | 1158 |
| GEQVEFSFPAAFTVE | 10024 | 1159 |
| GEQVEFSFPLTFTVE | 17397 | 1160 |
| GEQVEFSFPLAATVE | 10130 | 1161 |
| GEQVEFSFPLAFAVE | 20627 | 1162 |
| GEQVEFSFPLAFTAE | 18797 | 1163 |
| GEQVEFSFPLAFTVA | 18371 | 1164 |
| GEQVEFSFPLAFTVE | 17662 | 1165 |
| GEQVEFSFPLAFTVE | 19190 | 1166 |
| AEQVEFSFPLAFTVE | 18042 | 1167 |
| GAQVEFSFPLAFTVE | 18079 | 1168 |
| GEAVEFSFPLAFTVE | 19756 | 1169 |
| GEQAEFSFPLAFTVE | 13000 | 1170 |
| GEQVAFSFPLAFTVE | 13930 | 1171 |
| GEQVEASFPLAFTVE | 6533 | 1172 |
| GEQVEFAFPLAFTVE | 20072 | 1173 |
| GEQVEFSAPLAFTVE | 7378 | 1174 |
| GEQVEFSFALAFTVE | 19480 | 1175 |
| GEQVEFSFPAAFTVE | 10589 | 1176 |
| GEQVEFSFPLTFTVE | 18318 | 1177 |
| GEQVEFSFPLAATVE | 9572 | 1178 |
| GEQVEFSFPLAFAVE | 19516 | 1179 |
| GEQVEFSFPLAFTAE | 16765 | 1180 |
| GEQVEFSFPLAFTVA | 18187 | 1181 |
| GEQVEFSFPLAFTVE | 18219 | 1182 |
| ZZZZZZZDTYICEVED | 5017 | 1183 |
| ZZZZZZZDTYICEVEZ | 5421 | 1184 |
| ZZZZZZZDTYICEVZZ | 2166 | 1185 |
| ZZZZZZZDTYICEZZZ | 922 | 1186 |
| ZZZZZZZDTYIZZZZZ | 564 | 1187 |
| ZZZZZZZZTYICEVED | 3031 | 1188 |
| EEVQLLVFGLTANSD | 23357 | 1189 |
| EEVQLLVFGLTANSZ | 15808 | 1190 |

Panel G

| PEPTIDE | COUNTS | SEQ ID NO: |
|---|---|---|
| EEVQLLVFGLTANZZ | 16496 | 1191 |
| EEVQLLVFGLTAZZZ | 14097 | 1192 |
| EEVQLLVFGLTZZZZ | 16473 | 1193 |
| EEVQLLVFGLZZZZZ | 10516 | 1194 |
| EEVQLLVFGZZZZZZ | 10372 | 1195 |
| EEVQLLVFZZZZZZZ | 7333 | 1196 |
| EEVQLLVZZZZZZZZ | 1098 | 1197 |
| ZEVQLLVFGLTANSD | 16716 | 1198 |
| ZZVQLLVFGLTANSD | 5281 | 1199 |
| ZZZQLLVFGLTANSD | 4310 | 1200 |
| ZZZZLLVFGLTANSD | 1026 | 1201 |
| ZZZZZLVFGLTANSD | 664 | 1202 |
| ZZZZZZVFGLTANSD | 779 | 1203 |
| ZZZZZZZFGLTANSD | 760 | 1204 |
| ZZZZZZZZGLTANSD | 657 | 1205 |
| EEVQLLVFGLTANSD | 18040 | 1206 |
| THLLQGQSLTLTLES | 10850 | 1207 |
| THLLQGQSLTLTLEZ | 10269 | 1208 |
| THLLQGQSLTLTLZZ | 4668 | 1209 |
| THLLQGQSLTLTZZZ | 908 | 1210 |
| THLLQGQSLTLZZZZ | 844 | 1211 |
| THLLQGQSLTZZZZZ | 475 | 1212 |
| THLLQGQSLZZZZZZ | 548 | 1213 |
| THLLQGQSZZZZZZZ | 570 | 1214 |
| THLLQGQZZZZZZZZ | 442 | 1215 |
| ZHLLQGQSLTLTLES | 11445 | 1216 |
| ZZLLQGQSLTLTLES | 11631 | 1217 |
| ZZZLQGQSLTLTLES | 7993 | 1218 |
| ZZZZQGQSLTLTLES | 6887 | 1219 |
| ZZZZZGQSLTLTLES | 3305 | 1220 |
| ZZZZZZQSLTLTLES | 4453 | 1221 |
| ZZZZZZZSLTLTLES | 1086 | 1222 |
| ZZZZZZZZLTLTLES | 1201 | 1223 |
| THLLQGQSLTLTLES | 9756 | 1224 |
| GEQVEFSFPLAFTVE | 18856 | 1225 |
| GEQVEFSFPLAFTVZ | 16222 | 1226 |
| GEQVEFSFPLAFTZZ | 12535 | 1227 |
| GEQVEFSFPLAFZZZ | 11384 | 1228 |
| GEQVEFSFPLAZZZZ | 5846 | 1229 |
| GEQVEFSFPLZZZZZ | 4749 | 1230 |
| GEQVEFSFPZZZZZZ | 2208 | 1231 |
| GEQVEFSFZZZZZZZ | 3277 | 1232 |
| GEQVEFSZZZZZZZZ | 742 | 1233 |
| ZEQVEFSFPLAFTVE | 19736 | 1234 |
| ZZQVEFSFPLAFTVE | 18684 | 1235 |
| ZZZVEFSFPLAFTVE | 12892 | 1236 |
| ZZZZEFSFPLAFTVE | 12166 | 1237 |
| ZZZZZFSFPLAFTVE | 2134 | 1238 |
| ZZZZZZSFPLAFTVE | 1454 | 1239 |
| ZZZZZZZFPLAFTVE | 1391 | 1240 |
| ZZZZZZZZPLAFTVE | 1489 | 1241 |
| GEQVEFSFPLAFTVE | 18867 | 1242 |
| empty (control) | 580 | |

Example 11

This example characterizes CD4 receptor sequences found to have HIV gp120 binding activity in screening tests. Panel A displays information obtained from sequential replacement of amino acid residues by alaninyl residues. In panel A, a (+) signifies a decrease in binding affinity whereas a (>) indicates that replacement of the residue by an alaninyl residue yields an increase in binding affinity. Sequences are shown with amino-terminus at the top and the carboxyl-terminus at the bottom. Right and left sides are from independent assays.

Panel A.

| 105–113 | 116–130 | 131–145 | 216–229 |
|---|---|---|---|
| D | E | T | G |
| T | E | H | E |
| ++Y++ | V | L | Q |
| +I+ | +Q+ | L | +V+ |
| C | +L+ | +Q+ | +E+ |
| +E+ | +L+ | G | ++F++ |
| +V+ | +V+ | +Q+ | S |
| +E+ | +F+ | S | ++F++ |
| D | G | +L+ | P |
| | +L | T | ++L++ |
| | T | +L+ | A |
| | A | >T> | ++F++ |
| | N | +++L+++ | T |
| | S | ++E++ | V |
| | D | S | E |

Panel B indicates the effect on binding affinity when successive amino acid residues are deleted, either from the amino-terminus (right side-symbols) or the carboxyl-terminus from the bottom (left side-symbol). A (+) signifies a decrease in binding affinity, and the underlined residues indicate which residue was the last residue to be serially deleted.

Panel B.

| 105–113 | 116–130 | 131–145 | 216–229 |
|---|---|---|---|
| D+ | E | T | G |
| T | E+ | H | E |
| Y | V+ | L+ | Q+ |
| I | Q++ | L+ | V+ |
| C | L+++ | Q++ | E+++ |
| +++E | L+++ | G++ | F+++ |
| ++V | V+++ | Q+++ | S++++ |
| +E | ++++E++++ | +++S+++ | ++++F++++ |
| D | ++G | +++L | +++P |
| | +L | +++T | +++L |
| | T | +++L | ++A |
| | A | ++T | ++F |
| | N | ++L | +T |
| | S | +E | +V |
| | D | S | E |

All publications cited herein are hereby incorporated by reference to the same extent as if each publication were individually and specifically indicated to be incorporated by reference and were set forth in its entirety herein.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A polypeptide comprising an amino acid sequence selected from the group consisting of QWDFGNTMCQLLTGLYFIGFFS (SEQ ID NO: 12), SQYQFWKNFQTLKIVILG (SEQ ID NO: 13), APYNIVLLLNTFQEFFGLNNCS (SEQ ID NO: 14), YAFVGEKFRNYLLVFFQK (SEQ ID NO: 15), and SEQ ID NOs: 12-15 with up to one conservative or neutral amino acid substitution, wherein the polypeptide binds with HIV gp120 under physiological conditions and comprises less than 100 contiguous amino acid residues that are identical to the amino acid sequence of the human CCR5 chemokine receptor.

2. A composition comprising the polypeptide of claim 1 and a carrier.

3. The polypeptide of claim 1, wherein the polypeptide comprises QWDFGNTMCQLLTGLYFIGFFS (SEQ ID NO: 12).

4. The polypeptide of claim 1, wherein the polypeptide comprises SQYQFWKNFQTLKIVILG (SEQ ID NO: 13).

5. The polypeptide of claim 1, wherein the polypeptide comprises APYNIVLLLNTFQEFFGLNNCS (SEQ ID NO: 14).

6. The polypeptide of claim 1, wherein the polypeptide comprises YAFVGEKFRNYLLVFFQK (SEQ ID NO: 15).

7. The polypeptide of claim 1, wherein the polypeptide comprises QWDFGNTMCQLLTGLYFIGFFS (SEQ ID NO: 12) with up to one conservative or neutral amino acid substitution.

8. The polypeptide of claim 1, wherein the polypeptide comprises SQYQFWKNFQTLKIVILG (SEQ ID NO: 13) with up to one conservative or neutral amino acid substitution.

9. The polypeptide of claim 1, wherein the polypeptide comprises APYNIVLLLNTFQEFFGLNNCS (SEQ ID NO: 14) with up to one conservative or neutral amino acid substitution.

10. The polypeptide of claim 1, wherein the polypeptide comprises YAFVGEKFRNYLLVFFQK (SEQ ID NO: 15) with up to one conservative or neutral amino acid substitution.

11. A composition comprising the polypeptide of claim 3 and a carrier.

12. A composition comprising the polypeptide of claim 4 and a carrier.

13. A composition comprising the polypeptide of claim 5 and a carrier.

14. A composition comprising the polypeptide of claim 6 and a carrier.

15. A composition comprising the polypeptide of claim 7 and a carrier.

16. A composition comprising the polypeptide of claim 8 and a carrier.

17. A composition comprising the polypeptide of claim 9 and a carrier.

18. A composition comprising the polypeptide of claim 10 and a carrier.

* * * * *